(12) United States Patent
Osterkamp et al.

(10) Patent No.: US 9,745,344 B2
(45) Date of Patent: *Aug. 29, 2017

(54) NPR-B AGONISTS

(71) Applicant: Shire Orphan Therapies GmbH, Berlin (DE)

(72) Inventors: Frank Osterkamp, Berlin (DE); Heiko Hawlisch, Berlin (DE); Gerd Hummel, Berlin (DE); Tobias Knaute, Berlin (DE); Ulf Reimer, Berlin (DE); Ulrich Reineke, Berlin (DE); Bernadett Simon, Bonn (DE); Uwe Richter, Berlin (DE); Edgar Specker, Berlin (DE); Markus Woischnik, Berlin (DE); Mark R. Hellberg, Arlington, TX (US)

(73) Assignee: Shire Orphan Therapies GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/824,353

(22) Filed: Aug. 12, 2015

(65) Prior Publication Data

US 2016/0194357 A1 Jul. 7, 2016

Related U.S. Application Data

(62) Division of application No. 14/011,855, filed on Aug. 28, 2013, now Pat. No. 9,169,293, which is a division of application No. 12/888,556, filed on Sep. 23, 2010, now Pat. No. 8,546,523.

(60) Provisional application No. 61/245,960, filed on Sep. 25, 2009.

(51) Int. Cl.
*C07K 7/06* (2006.01)
*C07K 7/02* (2006.01)
*C07K 7/08* (2006.01)

(52) U.S. Cl.
CPC .............. *C07K 7/06* (2013.01); *C07K 7/02* (2013.01); *C07K 7/08* (2013.01)

(58) Field of Classification Search
None
See application file for complete search history.

(56) References Cited

U.S. PATENT DOCUMENTS

| 4,757,048 | A | 7/1988 | Lewicki et al. |
| 5,449,662 | A | 9/1995 | Scarborough |
| 6,833,358 | B1 | 12/2004 | Nakata et al. |
| 6,995,186 | B2 | 2/2006 | Castillo et al. |
| 7,276,481 | B2 | 10/2007 | Golembo et al. |
| 7,297,709 | B2 | 11/2007 | Dai et al. |
| 8,546,523 | B2 | 10/2013 | Osterkamp et al. |
| 8,551,938 | B2 | 10/2013 | Hellberg et al. |
| 9,169,293 | B2 | 10/2015 | Osterkamp et al. |
| 9,187,525 | B2 | 11/2015 | Hellberg et al. |
| 2003/0055102 | A1 | 3/2003 | Castillo et al. |
| 2005/0158387 | A1 | 7/2005 | Castillo et al. |
| 2005/0196754 | A1 | 9/2005 | Drmanac et al. |
| 2006/0074009 | A1 | 4/2006 | James et al. |
| 2006/0189608 | A1 | 8/2006 | Bingaman |
| 2007/0232546 | A1 | 10/2007 | Sharma et al. |
| 2008/0153747 | A1 | 6/2008 | Alewood et al. |
| 2008/0199532 | A1 | 8/2008 | Bakis et al. |
| 2009/0035287 | A1 | 2/2009 | Levine et al. |

FOREIGN PATENT DOCUMENTS

| JP | 2003/503048 A | 1/2003 |
| JP | 2009/532384 A | 9/2009 |
| RU | 2388765 C2 | 5/2010 |
| WO | WO 2007/047504 A2 | 4/2007 |
| WO | WO 2009/067639 A2 | 5/2009 |
| WO | WO 2011/038061 A2 | 3/2011 |
| WO | WO 2011/038061 A3 | 7/2011 |

OTHER PUBLICATIONS

U.S. Appl. No. 14/939,293, filed Nov. 12, 2015, Hellberg et al.
Abdelalim et al.; Distribution of natriuretic peptide receptor-C immunoreactivity in the rat brainstem and its relationship to cholinergic and catecholaminergic neurons; Neuroscience; vol. 155; pp. 192-202 (2008).
Ahluwalia et al.; Vascular actions of natriuretic peptides Basic Res. Cardiol; vol. 99; pp. 83-89 (2004).
Anand-Srivastava; Natriuretic peptide receptor-C signaling and regulation; Peptides; vol. 26; pp. 1044-1059 (2005).
Ardaillou et al.; Mesangial cells from diabetic NOD mice constitutively express increased density of atrial natriuretic peptide C receptors; Kidney International; vol. 55; pp. 1293-1302 (1999).
Barber et al.; Atrial natriuretic peptide preserves endothelial function during intimal hyperplasia; Vascular Research; vol. 42; pp. 101-110 (2005).
Bartels et al.; Mutations in the transmembrane natriuretic peptide receptor NPR-B impair skeletal growth and cause acromesomelic dysplasia, type maroteaux; Am. J. Hum. Genet.; vol. 75; pp. 27-34 (2004).
Beaulieu et al.; Positive chronotropic and inotropic effects of c-type natriuretic peptide in dogs; Am. J. Physiol; vol. 73; pp. H1933-H1940 (1997).
Becker; Topical 8-bromo-cyclic GMP lowers intraocular pressure in rabbits; Investigative Ophthalmology & Visual Science; vol. 31; No. 8; pp. 1647-1649 (1990).
Beltowski et al.; Regulation of renal tubular sodium transport by cardiac natriuretic peptides: two decades of research; Med. Sci. Monit; vol. 8; No. 2; pp. RA39-RA52 (2002).
Bianciotti et al.; Centrally applied atrial natriuretic factor diminishes bile secretion in the rat; Regulatory Peptides; vol. 102; pp. 127-133 (2001).
Brenard et al.; Hemodynamic and sympathetic responses to human atrial natriuretic peptide infusion in patients with cirrhosis; Journal of Hepatology; vol. 14; pp. 347-356 (1992).

(Continued)

*Primary Examiner* — Thomas S Heard
(74) *Attorney, Agent, or Firm* — Proskauer Rose LLP; Fangli Chen

(57) ABSTRACT

Disclosed are novel compounds having NPR-B agonistic activity. Preferred compounds are linear peptides containing 8-13 conventional or non-conventional L- or D-amino acid residues connected to one another via peptide bonds.

8 Claims, 3 Drawing Sheets

(56) References Cited

OTHER PUBLICATIONS

Buschhausen et al.; Regulation of mesangial cell function by vasodilatory signaling molecules; Cardiovascular Research; vol. 51; pp. 463-469 (2001).
Canaan-Kuhl et al.; C-type natriuretic peptide inhibits mesangial cell proliferation and matrix accumulation in vivo;Kidney International; vol. 53; pp. 1143-1151 (1998).
Cataliotti et al.; CNP production in the kidney and effects of protein intake restriction in nephrotic syndrome; Am. J. Physiol. Renal Physiol.; vol. 283; pp. F464-F472 (2002).
Chang et al.; Differential activation by atrial and brain natriuretic peptides of two different receptor guanylate cyclases; Letters to Nature; Nature; vol. 341; pp. 6872 (1989).
Chen et al.; C-type natriuretic peptide: the endothelial component of the natriuretic peptide system; Journal of Cardiovascular Pharmacology; vol. 32 (Suppl. 3); pp. 823-828 (1998).
Chinkers et al.; A membrane form of guanylate cyclase is an atrial natriuretic peptide receptor; Letters to Nature; Nature: vol. 338; pp. 78-83 (1989).
Cho et al.; Natriuretic peptides and their therapeutic potential; Natriuretic Peptides, Heart Disease; vol. 5; pp. 305-328 (1999).
Chrisman et al.; Reciprocal antagonism coordinates c-type natriuretic peptide and mitogen-signaling pathways in fibroblasts; The Journal of Biological Chemistry; vol. 274; No. 7; pp. 4293-4299 (1999).
Chrisman et al.; Seminal plasma factors that cause large elevations in cellular cyclic GMP are c-type natriuretic peptides; The Journal of Biological Chemistry; vol. 268; No. 5; pp. 3698-3703 (1993).
Chusho et al.; Dwarfism and early death in mice lacking c-type natriuretic peptide; Proc. Natl. Acad. Sci.; vol. 98; No. 7; pp. 4016-4021 (2001).
Collin et al.; Atrial natriuretic peptide, brain natriuretic peptide and c-type natriuretic peptide: effects on testicular microcirculation and immunohistochemical localization; International Journal of Andrology; vol. 20; pp. 55-60 (1997).
Dean et al.; Synthesis and localization of c-type natriuretic peptide in mammalian kidney; Am. J. Physiol; 266; F491 F496 (1994).
Debold et al.; A rapid and potent natriuretic response to intravenous injection of atrial myocardial extract in rats; Life Sciences; vol. 28; pp. 89-94 (1981).
Del Ry et al.; C-type natriuretic peptide plasma levels increase in patients with chronic heart failure as a function of clinical severity; The European Journal of Heart Failure; vol. 7; pp. 1145-1148 (2005).
Del Ry et al.; Increased levels of c-type natriuretic peptide in patients with idiopathic left ventricular dysfunction; Peptides; vol. 28; pp. 1068-1073 (2007).
Dickey et al.; Differential regulation of membrane guanylyl cyclases in congestive heart failure: Natriuretic peptide receptor (NPR)-B, not NPR-A, is the predominant natriuretic peptide receptor in the failing heart; Endocrinology; vol. 148; No. 7; pp. 3518-3522 (2007).
Diestelhorst et al.; The intraocular pressure response of human atrial natriuretic factor in glaucoma; International Ophthalmology; vol. 13; pp. 99-101 (1989).
Ding et al.; Actions of c-type natriuretic peptide and sodium nitroprusside on carbachol-stimulated inositol phosphate format and contraction in ciliary and iris sphincter smooth muscles; Investigative Ophthalmology and Visual Science; vol. 38; No. 12; pp. 2629-2638 (1997).
Dos Reis et al.; Characterization and distribution of natriuretic peptide receptors in the rat uterus; Endocrinology; vol. 136; No. 10; pp. 4247-4253 (1995).
Drewett et al.; Natriuretic peptide receptor-B (guanylyl cyclase-B) mediates c-type natriuretic peptide relaxation of precontracted rat aorta; The Journal of Biological Chemistry; vol. 270; No. 9; pp. 4668-4674 (1995).
D'Souza et al., Autocrine and paracrine actions of natriuretic peptides in the heart, Pharmacology and Therapeutics, 101:113-129 (2004).

Eguchi et al.; Effects of three distinct natriuretic peptides on receptor binding and guanylate cyclase activities in rat glioma cells; European Journal of Pharmacology—Molecular Pharmacology Section; vol. 225; pp. 79-82 (1992).
Endlich et al.; Natriuretic peptide receptors mediate different responses in rat renal microvessels; Kidney International; vol. 52; pp. 202-207 (1997).
European Patent Office, Supplementary European Search Report, Application No. 10819424.2, Publication No. 2480247, dated Aug. 1, 2012, 7 pages.
Fenrick et al.; Cloning and functional expression of the bovine natriuretic peptide receptor-B (Natriuretic factor R1c subtype); Molecular and Cellular Biochemistry; vol. 137; pp. 173-182 (1994).
Fernandez-Durango et al.; Type B and type C natriuretic peptide receptors modulate intraocular pressure in the rabbit eye; European Journal of Pharmacology; vol. 364; pp. 107-113 (1999).
Fernandez-Durango et al., Messenger RNAs encoding the natriuretic peptides and their receptors are expressed in the eye, Experimental Eye Research, 61:723-729 (1995).
Fluge et al.; Bronchodilating effects of natriuretic and vasorelaxant peptides compared to salbutamol in asthmatics; Regulatory Peptides; vol. 59; pp. 357-370 (1995).
Foresta et al.; Stimulatory effects of α-hANP on testosterone secretion in man; Journal of Clinical Endocrinology and Metabolism; vol. 2; No. 2; pp. 392-295 (1991).
Foster et al.; The prevalence of glaucoma in Chinese residents of Singapore; Epidemiology and Biostatistics; vol. 18; pp. 1105-1111 (2000).
Friedman; Seminars in medicine of the Beth Israel Hospital, Boston: The cellular basis of hepatic fibrosis—mechanisms and treatment strategies; The New England Journal of Medicine; vol. 328; No. 24; pp. 1828-1835; [Ovid: Seminars in medicine of the Beth Israel Hospital, Boston; https://ovidsp.tx.ovid.com/sp-3.2.4b/ovidweb.cgi; p. 1-24].
Fuller et al.; Atrial natriuretic peptide clearance receptor; The Journal of Biological Chemistry; vol. 263; No. 19; pp. 9395-9401 (1988).
Furuya et al.; C-type natriuretic peptide inhibits intimal thickening after vascular injury; Ann NY Acad. Sci. vol. 748; pp. 517-523 (1995).
Furuya et al.; C-type natriuretic peptide is a growth inhibitor of rat vascular smooth muscle cells; Biochemical and Biophysical Research Communications; vol. 177; No. 3; pp. 927-931 (Jun. 28, 1991).
Gaspari et al.; Type-C natriuretic peptide prevents development of experimental atherosclerosis in rabbits; Clinical and Experimental Pharmacology and Physiology; vol. 27; pp. 653-655 (2000).
Gilkes et al.; Characterization of natriuretic peptide receptor subtypes in the AtT-20 pituitary tumour cell line; Biochem. J.; vol. 299; pp. 481-487 (1994).
Gower et al.; Four peptides decrease human colon adenocarcinoma cell number and DNA synthesis via cyclic GMP; International Journal of Gastrointestinal Cancer; vol. 36; No. 2; pp. 77-88 (2005).
Gulberg et al.; Increased renal production of c-type natriuretic peptide (CNP) in patients with cirrhosis and functional renal failure; Gut.; vol. 47; pp. 852-857 (2000).
Horio et al.; Gene expression, secretion, and autocrine action of c-type natriuretic peptide in cultured adult rat cardiac fibroblasts; Endocrinology; vol. 144; No. 6; pp. 2279-2284 (2003).
Horl; Natriuretic peptides in acute and chronic kidney disease and during renal replacement therapy; Journal of Investigative Medicine; vol. 53; No. 7; pp. 366-370 (2005).
Hosang et al.; cDNA cloning identified a calmodulin-binding protein in bovine seminal plasma and bovine c-type natriuretic peptide; DNA and Cell Biology; vol. 13; No. 4; pp. 409-417 (1994).
Huang et al.; Isolation, mapping, and regulated expression of the gene encoding mouse c-type natriuretic peptide; American Physiological Society; vol. 271; pp. H1565-H1575 (1996).
Hutchinson et al. Mechanisms of natriuretic-peptide-induced growth inhibition of vascular smooth muscle cells; Cardiovascular Research; vol. 35; pp. 158-167 (1997).

(56) References Cited

OTHER PUBLICATIONS

Ikeda et al.; Natriuretic peptide family as a novel antimigration factor of vascular smooth muscle cells; Arterioscler Thromb Vasc. Biol.; vol. 17; pp. 731-736 (1997).
International Search Report for PCT/US10/049917, dated Mar. 23, 2011, 3 pages.
International Search Report for PCT/US2010/049912, dated Jun. 2, 2011, 5 pages.
Written Opinion of the International Searching Authority for PCT/US2010/049912, dated Jun. 2, 2011, 7 pages.
Written Opinion of the International Searching Authority for PCT/US10/049917, dated Mar. 23, 2011, 6 pages.
Itoh et al.; C-type natriuretic peptide ameliorates monocrotaline-induced pulmonary hypertension in rats; Am. J. Respir. Grit. Care Med.; vol. 170; pp. 1204-1211 (2004).
Itoh et al.; Expression of biologically active receptors for natriuretic peptides in the human uterus during pregnancy; Biochemical and Biophysical Research Communications; vol. 203; No. 1; pp. 602-607 (1994).
Khurana et al.; Receptor-mediated stimulatory effect of atrial natriuretic factor, brain natriuretic peptide, and c-type natriuretic peptide on testosterone production in purified mouse leydig cells: activation of cholesterol side- chain cleavage enzyme; Endocrinology; vol. 133; No. 5; pp. 2141-2149 (1993).
Kim et al.; Presence and biological activity of c-type natriuretic peptide-dependent guanylate cyclase-coupled receptor in the penile corpus cavernosum; The Journal of Urology; vol. 159; pp. 1741-1746 (1998).
Koller et al.; Selective activation of the B natriuretic peptide receptor by c-type natriuretic peptide (CNP); Science; vol. 252; pp. 120-123 (1991).
Komeichi et al.; Blunted natriuresis and abnormal systemic hemodynamic responses to c-type and brain natriuretic peptides in rats with cirrhosis; Journal of Hepatology; vol. 22; pp. 319-325 (1995).
Korenfeld et al.; Atrial natriuretic peptides; effects on intraocular pressure; cGMP, and aqueous flow; Investigative Ophthalmology & Visual Science; vol. 30; No. 11; pp. 2385-2392 (1989).
Krejci et al.; Interaction of fibroblast growth factor and C-natriuretic peptide signaling in regulation of chondrocyte proliferation and extracellular matrix homeostatis; Journal of Cell Science; vol. 118; pp. 5089-5100 (2005).
Kuhn; Structure, regulation, and function of mammalian membrane guanylyl cyclase receptors, with a focus on guanylyl cyclase-a; Review; Circulation Research; DOI: 10.1161/01.RES.0000094745.28948.40; pp. 700-709.
Kuthe et al.; Expression of guanylyl cyclase B in the human corpus cavernosum penis and the possible involvement of it ligand c-type natriuretic polypeptide in the induction of penile erection; Journal of Urology; vol. 169; Issue 5; pp. 1918-1922 (2003).
Kyriakides et al.; Atrial natriuretic peptide augments coronary collateral blood flow: a study during coronary angioplasty; Clin. Cardiol. vol.; 21; pp. 737-742 (1998).
Langenickel et al.; Cardiac hypertrophy in transgenic rats expressing a dominant-negative mutant of the natriuretic peptide receptor B; Proc. Natl. Acad. Sci.; vol. 103; No. 12; pp. 4735-4740 (2006).
Leske; Open-angle glaucoma—an epidemiologic overview; Ophthalmic Epidemiology; Reviews; vol. 14; pp. 166-172 (2007).
Lohe et al.; Natriuretic peptide B receptor and c-type natriuretic peptide in the rat kidney; J. Am. Soc. Nephrol.; vol. 6; pp. 1552-1558 (1995).
Maack et al.; Physiological role of silent receptors of atrial natriuretic factor; Science; vol. 238; pp. 675-678 (1987).
Madhani et al.; Vascular natriuretic peptide receptor-linked particulate guanylate cyclases are modulated by nitric oxide-cyclic GMP signalling; British Journal of Pharmacology; vol. 139; pp. 1289-1296 (2003).
Makino et al.; Transgenic overexpression of brain natriuretic peptide prevents the progression of diabetic nephropathy in mice; Diabetologia; vol. 49; pp. 2514-2524 (2006).
Mantyh et al.; Localization of specific binding sites for atrial natriuretic factor in peripheral tissues of the guinea pig, rat, and human; Hypertension; vol. 8; pp. 712-721 (1986).
Marton et al.; NEP inhibitors enhance c-type natriuretic peptide-induced relaxation in porcine isolated coronary artery; Vascular Pharmacology; vol. 43; pp. 207-212 (2005).
Marumo et al.; Natriuretic peptide-augmented induction of nitric oxide synthase through cyclic guanosine 3',5'—monophosphate elevation in vascular smooth muscle cells; Endocrinology; vol. 136; No. 5; pp. 2135-2142 (1995).
Matiingly et al.; Presence of c-type natriuretic peptide in human kidney and urine; Kidney International; vol. 46; pp. 744-747 (1994).
Middendorff; Natriuretic peptides in the human testis: evidence for a potential role of c-type natriuretic peptide in leydig cells; Journal of Clinical Endocrinology and Metabolism; vol. 81; No. 12; pp. 4324-4328 (1996).
Millar et al.; Atriopeptin lowers aqueous humor formation and intraocular pressure and elevates ciliary cyclic GMP but lacks uveal vascular effects in the bovine perfused eye; Journal of Ocular Pharmacology and Therapeutics; vol. 13; No. 1; pp. 1-11 (1997).
Minamino et al.; Characterization of immunoreactive human c-type natriuretic peptide in brain and heart; Biochemical and Biophysical Research Communications; vol. 179; No. 1; pp. 535-542 (1991).
Misono et al.; Structural studies of the natriuretic peptide receptor: a novel hormone-induced rotation mechanism for transmembrane signal transduction; Peptides; vol. 26; pp. 957-968 (2005).
Mittag et al.; Atrial natriuretic peptide (ANP), guanylate cyclase, and intraocular pressure in the rabbit eye; Current Eye Research; vol. 6; No. 10; pp. 1189-1196 (1987).
Miyazawa et al.; Cyclic GMP-dependent protein kinase II plays a critical role in c-type natriuretic peptide-mediated endochondral ossification; Endocrinology; vol. 143; No. 9; pp. 3604-3610 (2002).
Moffatt et al.; Osteocrin is a specific ligand of the natriuretic peptide clearance receptor that modulates bone growth; The Journal of Biological Chemistry; vol. 282; No. 5; pp. 36454-36462 (Dec. 14, 2007).
Morishige et al.; Local adenovirus mediated transfer of c-type natriuretic peptide suppresses vascular remodeling in porcine coronary arteries in vivo; Journal of American College of Cardiology; vol. 35; No. 4; pp. 1040-1047 (2000).
Mukoyama et al.; Brain natriuretic peptide as a novel cardiac hormone in humans; J. Clin. Invest.; vol. 87; pp. 1402-1412 (Apr. 1991).
Murakami et al.; C-type natriuretic peptide attenuates bleomycin-induced pulmonary fibrosis in mice; Am. J. Physiol Lung Cell Mol. Physiol; vol. 287; pp. L1172-L1177 (2004).
Murthy et al.; Identification of the G protein-activating domain of the natriuretic peptide clearance receptor (NPR-C); The Journal of Biological Chemistry; vol. 274; No. 25; pp. 17587-17592 (Jun. 18, 1999).
Nakamura et al.; vasodilatory effects of c-type natriuretic peptide on forearm resistance vessels are distinct from those of artial natriuretic peptide in chronic heart failure; Circulation; vol. 90; pp. 1210-1214 (1994).
Nathanson; Atriopeptin-activated guanylate cyclase in the anterior segment; Invest. Ophthalmol. Vis Sci; vol. 28 pp. 1357-1364; (1987).
Nathanson; Direct application of a guanylate cyclase activator lowers intraocular pressure; European Journal of Pharmacology; vol. 147; pp. 155-156 (1988).
Nathanson; Nitrovasodilators as a new class of ocular hypotensive agents; The Journal of Pharmacology and Experimental Therapeutics; vol. 260; No. 3; pp. 956-965 (1992).
Noubani et al.; B-type natriuretic peptide receptor expression and activity are hormonally regulated in rat ovarian cells; Endocrinology; vol. 141; No. 2; pp. 551-559 (2000).
Obata et al.; CNP infusion attenuates cardiac dysfunction and inflammation in myocarditis; Biochemical and Biophysical Research Communications; vol. 356; pp. 60-66 (2007).
Ohbayashi et al.; Compared effects of natriuretic peptides on ovalbumin-induced asthmatic model; European Journal of Pharmacology; vol. 346; pp. 55-64 (1998).

(56) References Cited

OTHER PUBLICATIONS

Ohno et al.; Accelerated reendothelialization with suppressed thrombogenic property and neointimal hyperplasia of rabbit jugular vein grafts by adenovirus mediated gene transfer of c-type natriuretic peptide; Circulation; vol. 105; pp. 1623-1626 (2002).
Olney; C-type natriuretic peptide in growth: a new paradigm; Growth Hormone & IGF Research; vol. 16; pp. 86-814 (2006).
Osawa et al.; C-type natriuretic peptide inhibits proliferation and monocyte chemoattractant protein-1 secretion in cultured human mesangial cells; Nephron; vol. 86; pp. 467-472 (2000).
Ozasa et al.; complementary antagonistic actions between C-type natriuretic peptide and the MAPK pathway through FGFR-3 in ATDC5 cells; Bone; vol. 36; pp. 1056-1064 (2005).
Pandey; Biology of natriuretic peptides and their receptors; Peptides; vol. 26; pp. 901-932 (2005).
Pang et al.; Presence of functional type B natriuretic peptide receptor in human ocular cells; Investigative Ophthalmology and Visual Science; vol. 37; No. 9; pp. 1724-1731 (1996).
Pelisek et al.; C-type natriuretic peptide for reduction of restenosis: gene transfer is superior over single peptide administration; The Journal of Gene Medicine; vol. 8; pp. 835-944 (2006).
Pfeifer et al.; Intestinal secretory defects and dwarfism in mice lacking cGMP-dependent protein kinase II; Science; vol. 274; pp. 2082-2086 (1996).
Potter et al.; Dephosphorylation of the guanylyl cyclase-A receptor causes desensitization; The Journal of Biological Chemistry; vol. 267; No. 21; pp. 1 4531-14534 (1992).
Puurunen et al.; Vagal-dependent stimulation of gastric acid secretion by intracerebroventricularly administered atrial natriuretic peptide in anaesthetized rats; European Journal of Pharmacology; vol. 141; pp. 493-495 (1987).
Qian et al.; Local expression of c-type natriuretic peptide suppresses inflammation, eliminates shear stress-induced thrombosis, and prevents neointima formation through enhanced nitric oxide production in rabbit injured carotid arteries; Circulation Research; vol. 91; pp. 1063-1069 (2002).
Quigley et al.; The number of people with glaucoma worldwide in 2010; Br. J. Ophthalmol; vol. 90; pp. 262-267 (2006).
Quigley; European glaucoma prevention study; Ophthalmology; vol. 112; No. 9; pp. 1642-1643 (Sep. 2005).
Resnik et al.; Evaluation of b-type natriuretic peptide (BNP) levels in normal and preeclamptic women; American Journal of Obstertrics & Gynecology; vol. 193; pp. 450-454 (2005).
Rosenkranz et al.; Antihypertrophic actions of the natriuretic peptides in adult rat cardiomyocytes: importance of cyclic GMP; Cardiovascular Research; vol. 57; pp. 515-522 (2003).
Royen et al.; Stimulation of arteriogenesis; a new concept for the treatment of arterial occlusive disease; Cardiovascular Research; vol. 49; pp. 543-553 (2001).
Sabbatini et al.; C-type natriuretic peptide applied to the brain enhances exocrine pancreatic secretion through a vagal pathway; European Journal of Pharmacology; vol. 524; pp. 67-74 (2005).
Sabbatini et al.; C-type natriuretic peptide stimulates pancreatic exocrine secretion in the rat: role of vagal afferent and efferent pathways; European Journal of Pharmacology; vol. 577; pp. 192-202 (2007).
Schulz; C-type natriuretic peptide and guanylyl cyclase B receptor; Peptides; vol. 26; pp. 1024-1034 (2005).
Scotland et al.; C-type natriuretic peptide inhibits leukocyte recruitment and platelet-leukocyte interactions via suppression of P-selectin expression; Proc. Natl. Acad. Sci.; vol. 102; No. 40; pp. 14452-14457 (2005).
Shahidullah et al.; Atriopeptin, sodium azide and cyclic GMP reduce secretion of aqueous humour and inhibit intracellular calcium release in bovine cultured ciliary epithelium; British Journal of Pharmacology; vol. 127; pp. 1438-1446 (1999).
Shin et al.; Increased c-type natriuretic peptice mRNA expression in the kidney of diabetic rats; Journal of Endocrinology; vol. 158; pp. 35-42 (1998).
Shinomiya et al.; C-type natriuretic peptide inhibits intimal thickening of rabbit carotid artery after balloon catheter injury; Biochemical and Biophysical Research Communications; vol. 205; No. 2; pp. 1051-1056 (1994).
Soeki et al.; C-type natriuretic peptide, a novel antifibrotic and antihypertrophic agent, prevents cardiac remodeling after myocardial infarction; Journal of the American College of Cardiology; vol. 45; No. 4; pp. 608-616 (2005).
Stein et al.; Topical application of a cyclic GMP analog lowers IOP in normal and ocular hypertensive rabbits; Investigative Ophthalmology & Visual Science; vol. 35; No. 6; pp. 2765-2768 (1994).
Stepan et al.; Expression of c-type natriuretic peptide in human placenta and myometrium in normal pregnancies complicated by intrauterine growth retardation; Fetal Diagnosis Therapy; vol. 17; pp. 37-41 (2002).
Stepan et al.; Gestational regulation of the gene expression of c-type natriuretic peptide in mouse reproductive and embryonic tissue; Regulatory Peptides; vol. 102; pp. 9-13 (2001).
Stingo et al.; Presence of c-type natriuretic peptide in cultured human endothelial cells and plasma; Am. J. Physiol; vol. 263; pp. H1318-H-1321 (1992).
Stoupakis et al.; Natriuretic peptides: biochemistry, physiology, and therapeutic role in heart failure; Heart Disease; vol. 5; No. 3; pp. 215-223 (2003).
Stumpff et al.; Regulation of trabecular meshwork contractility; Ophthalmologica; vol. 214; pp. 33-53 (2000).
Suda et al.; Skeletal overgrowth in transgenic mice that overexpress brain natriuretic peptide; Proc. Natl. Acad. Sci.; vol. 95; pp. 2337-2342 (1998).
Sudoh et al.; A new natriuretic peptide in porcine brain; Letters to Nature; Nature; vol. 332; pp. 78-81 (1988).
Sudoh et al.; C-type natriuretic peptide (CNP): A new member of natriuretic peptide family identified in porcine brain; Biochemical and Biophysical Research Communications; vol. 168; No. 2; pp. 863-870 (1990).
Suga et al.; Characterization of natriuretic peptide receptors in cultured cells; Hypertension; vol. 19; pp. 762-765 (1992).
Suga et al.; Phenotype-related alteration in expression of natriuretic peptide receptors in aortic smooth muscle cells; Circulation Research; vol. 71; pp. 34-39 (1992).
Suganami et al.; Overexpression of brain natriuretic peptide in mice ameliorates immune-mediated renal injury; J. Am. Soc. Nephrol.; vol. 12; pp. 2652-2663 (2001).
Sugrue et al.; Synthetic atrial natriuretic factor lowers rabbit intraocular pressure; European Journal of Pharmacology; vol. 130; pp. 349-350 (1986).
Takashima et al.; Ocular hypotension induced by intravitreally injected c-type natriuretic peptide; Exp. Eye Research; vol. 66; pp. 89-96 (1998).
Takashima et al.; Ocular hypotensive mechanism of intravitreally injected brain natriuretic peptide in rabbit; Investigative Ophthalmology & Visual Science; vol. 37; No. 13; pp. 2671-2677 (1996).
Tamura et al.; Cardiac fibrosis in mice lacking brain natriuretic peptide; Proc. Natl. Acad. Sci.; vol. 97; No. 8; pp. 4239-4244 (2000).
Tamura et al.; Critical roles of the guanylyl cyclase B receptor in endochondral ossification and development of female reproductive organs; Proc. Natl. Acad. Sci.; vol. 101; No. 49; pp. 17300-17305 (2004).
Tao et al. Biological effects of c-type natriuretic peptide in human myofibroblastic hepatic stellate cells; Journal of Biological Chemistry; vol. 274; No. 34; pp. 23761-23769 (1999).
Terada et al.; PCR localization of c-type natriuretic peptide and b-type receptor mRNAs in rat nephron segments; Am. J. Physiol; vol. 267; pp. F215-F222 (1994).
Thomas et al.; Osteocrin, a novel bone-specific secreted protein that modulates the osteoblast phenotype; The Journal of Biological Chemistry; vol. 278; No. 50; pp. 50563-50571 (2003).
Thylefors et al.; The global impact of glaucoma; Clin. Chem.; vol. 38; No. 10; pp. 2136-2139 (1992).
Togashi et al.; Concentrations and molecular forms of c-type natriuretic peptide in brain and cerebrospinal fluid; Clin. Chem.; vol. 38; No. 10; pp. 2136-2139 (1992).

(56) References Cited

OTHER PUBLICATIONS

Tokudome et al.; Inhibitory effect of c-type natriuretic peptide (CNP) on cultured cardiac myocyte hypertrophy: interference between CNP and endothelin-1 signaling pathways; Endocrinology; vol. 145; pp. 2131-2140 (2004).

Totsune et al.; C-type natriuretic peptide in the human central nervous system: distribution and molecular form; Peptides; vol. 15; No. 1; pp. 37-40 (1994).

Tsuji et al.; Hypomorphic mutation in mouse Nppc gene causes retarded bone growth due to impaired endochondral ossification; Biochemical and Biophysical Research Communications; vol. 376; pp. 186-190 (2008).

Tsukahara et al.; Effect of alpha-human atrial natriuretic peptides on intraocular pressure in normal albino rabbits; Ophthalmologica; vol. 197; pp. 104-109 (1988).

Ueno et al.; Local expression of c-type natriuretic peptide markedly suppresses neointimal formation in rat injured arteries through an autocrine/paracrine loop; Circulation; vol. 96; pp. 2272-2279 (1997).

Van Den Akker; Structural insights into the ligand binding domains of membrane bound guanylyl cyclases and natriuretic peptide receptors; J. Mol. Biol.; vol. 311; pp. 923-937 (2001).

Vesely et al.; Five cardiac hormones decrease the number of human small-cell lung cancer cells; European Journal of Clinical Investigation; vol. 35; pp. 388-398 (2005).

Vesely et al.; Novel therapeutic approach for cancer using four cardiovascular hormones; European Journal of Clinical Investigation; vol. 34; pp. 674-682 (2004).

Vesely et al.; Urodilatin and four cardiac hormones decrease human renal carcinoma cell numbers; European Journal of Clinical Investigation; vol. 36; pp. 810-819 (2006).

Vlachopoulos et al.; Amino-terminal pro-c-type natriuretic peptide is associated with the presence, severity, and duration of vasculogenic erectile dysfunction; European Association of Urology; vol. 56; pp. 552-558 (2009).

Vollmar et al.; Differential gene expression of the three natriuretic peptides and natriuretic peptide receptor subtypes in human liver; Gut.; vol. 40; pp. 145-150; (1997).

Waldman et al.; Differential effects of natriuretic peptide stimulation on tissue-engineered cartilage; Tissue Engineering; vol. 14; No. 3; pp. 441-449 (2008).

Walther et al.; Opposite regulation of brain and c-type natriuretic peptides in the streptozotocin-diabetic cardiopathy; Journal of Molecular Endocrinology; vol. 24; pp. 391-395 (2000).

Wang et al.; Cardiomyocyte-restricted over-expression of c-type natriuretic peptide prevents cardiac hypertrophy induced by myocardial infarction in mice; European Journal of Heart Failure; vol. 9; pp. 548-557 (2007).

Wei et al.; Action of c-type natriuretic peptide in isolated canine arteries and veins; Am. J. Physiol.; vol. 264; pp. H71-H73 (1993).

Woods et al.; Atrial, b-type and c-type natriuretic peptides cause mesenteric vasoconstriction in conscious dogs; Am. J. Physiol.; vol. 276; pp. R1443-R1452 (1999).

Wright et al.; Amino-terminal pro-c-type natriuretic peptide in heart failure; Hypertension; Journal of the American Heart Association; vol. 43; pp. 94-100 (2004).

Yamashita et al.; Opposite regulation of gax homeobox expression by angiotensin II and c-type natriuretic peptide; Hypertension; vol. 29; pp. 381-385 (1997).

Yan et al.; Corin, a transmembrane cardiac serine protease, acts as a pro-atrial natriuretic peptide-converting enzyme; Proc. Natl. Acad. Sci.; vol. 97; No. 15; pp. 8525-8529 (2000).

Yang et al.; An experimental study on effect of atrial natriuretic peptide on intraocular pressure of white rabbits; Chinese Journal of Ophthalmology; vol. 33; pp. 149-151 (1997) [Abstract in English].

Yasoda et al.; Natriuretic peptide regulation of endochondral ossification; The Journal of Biological Chemistry; vol. 273; No. 19; pp. 11695-11700 (1998).

Yasoda et al.; Overexpression of CNP in chondrocytes rescues achondroplasia through a MAPK-dependent pathway; Nature Medicine; vol. 10; No. 1; pp. 80-86 (Jan. 2004).

Yoder et al.; Reduced ability of c-type natriuretic peptide (CNP) to activate natriuretic peptide receptor B (NPR-B) causes dwarfism in Ibab -/- mice; Peptides; vol. 29; pp. 1575-1581 (2008).

Zhao et al.; Characterization of c-type natriuretic peptide receptors in human mesangial cells; Kidney International; vol. 46; pp. 717-725 (1994).

NPR-B AGONISTS

The present application is a divisional application of U.S. patent application Ser. No. 14/011,855, filed Aug. 28, 2013, and which issued as U.S. Pat. No. 9,169,293, issued on Oct. 27, 2015, which is a divisional application of U.S. patent application Ser. No. 12/888,556 filed Sep. 23, 2010, and which issued as U.S. Pat. No. 8,546,523, issued on Oct. 1, 2013, which claims priority to U.S. provisional application Ser. No. 61/245,960 filed Sep. 25, 2009, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Mar. 16, 2016, is named 2006685_1199_ST25 and is 392,326 bytes in size.

BACKGROUND OF THE INVENTION

1. Field of the Invention

The present invention generally relates to novel compounds which are useful in the treatment and prevention of disorders mediated by natriuretic peptides or proteins. More particularly, the present invention relates to novel peptides, pharmaceutical compositions comprising one or more novel peptides described herein, and their use in methods of treating or preventing ocular disorders, such as glaucoma, ocular hypertension, and optic neuropathies, cardiovascular disease, kidney disease, lung disease, and other disorders mediated by natriuretic peptides or proteins.

2. Description of Related Art

The natriuretic peptides (NP's) are a family of cyclic peptide hormones that have first been described by their involvement in the regulation of natriuresis, diuresis and blood pressure control. To date, four natriuretic peptides have been discovered in man, i.e. atrial natriuretic peptide (ANP; SEQ ID NO:1), B-type or brain natriuretic peptide (BNP; SEQ ID NO:2), C-type natriuretic peptide (CNP; SEQ ID NO:3) and urodilatin (SEQ ID NO:4) (see FIG. 1; and Cho et al., 1999, *Heart Dis.* 1:305-328). All NP's are synthesized as prepro-hormones which are activated by proteolytic cleavage before their release into the circulation. The NP's bind to natriuretic peptide receptors (NPR), a group of 3 different membrane bound receptors with guanylyl cyclase activity (Pandey 2005, *Peptides* 26:901-932).

ANP was first discovered as a blood pressure decreasing factor in rat atrial homogenates in 1981 (de Bold 1981, *Life Sci* 28:89-94). Human pre-pro-ANP (SEQ ID NO: 5) contains 151 amino acids and is stored after N-terminal cleavage as 126 amino acid pro-ANP (SEQ ID NO:6), predominantly in atrial granules. Cardiac stretch, due to systemic volume overload induces the rapid release of ANP from these stores. Upon secretion into the circulation, the C-terminal part of pro-ANP is cleaved by the atrial peptidase corin to the biologically active 28 amino acid form of ANP (SEQ ID NO:1) (Yan 2000, *Proc Natl Acad Sci* 97:8525-8529). The remaining N-terminal part can be further cleaved into 3 different hormones. i.e. Long Acting Natriuretic Peptide (LANP, amino acids 1-30; SEQ ID NO:7), Vessel Dilator (VSDL, amino acids 31-67; SEQ ID NO:8) and Kaliuretic Peptide (KP, amino acids 79-98; SEQ ID NO:9) (Vesely 2004, *Eur J Clin Invest* 34:674-682).

After BNP was discovered in porcine brain as a factor that showed smooth muscle relaxing activity (Sudoh T, 1988, *Nature* 332:78), a much greater tissue expression was found in preparations of cardiac ventricles (Mukoyama 1991, *J Clin Invest* 87:1402-1412), which led to the conclusion that BNP is, similarly to ANP, a cardiac peptide hormone. Although BNP can be found in storage granules in the atria, the expression in ventricles is transcriptionally regulated (Tamura 2000, *Proc Natl Acad Sci* 93:4239-4244). Synthesis of pre-pro-BNP is induced through cardiac wall stretch and leads to a 134 amino acid long peptide (SEQ ID NO:10) which is further cleaved by an unknown protease to yield the 108 amino acid long pro-BNP (SEQ ID NO:11). Additional cleavage liberates the active 32 amino acid C-terminal fragment of BNP (SEQ ID NO:2) and the inactive 76 amino acid N-terminal fragment also referred to as NT-pro-BNP (SEQ ID NO:12). To date, no known splice variants of human BNP exists.

CNP was first isolated from porcine brain almost 10 years after the discovery of ANP (Sudoh 1990, *Biochem Biophys Res Comm* 168:863-870). It is primarily expressed in the central nervous system and endothelial cells. Unlike other NP's, CNP is nearly not present in cardiac tissue, which suggest a more paracrine function on vascular tone and muscle cell growth. The 126 amino acid precursor molecule pro-CNP (SEQ ID NO: 13) is processed by the intracellular endoprotease furin into the mature 53 amino acid peptide CNP-53 (SEQ ID NO:14), which is the most abundant form in the brain (Totsune 1994, *Peptides* 15:37-40), endothelial cells (Stingo, 1992, *Am J Phys* 263:H1318-H1321) and the heart (Minamino 1991, *Biochem Biophys Res Comm* 179: 535-542). In both, cerebral spinal fluid (Togashi 1992, *Clin Chem* 38:2136-2139) and human plasma (Stingo 1992, *Am J Phys* 263:H1318-H1321) the most common form is CNP-22 (SEQ ID NO:3), which is generated from CNP-53 by an unknown extracellular protease. Unlike the other NP's CNP-22 lacks the C-terminal extension of the 17 amino acid ring (see FIG. 1).

ANP (SEQ ID NO:1), BNP (SEQ ID NO:2) and CNP (SEQ ID NO:3) show a highly conserved amino acid sequence among different vertebrate species (see FIG. 1; and Cho 1999, *Heart Dis.* 1:305-328). The NP's are inactivated by two distinct mechanisms, i.e. enzymatic cleavage through neutral endopeptidases and binding to the NP clearance receptor (NPR-C; SEQ ID NO:15), which is followed by internalization and intracellular degradation of the NP (Stoupakis 2003, *Heart Dis.* 5:215-223).

The discovery of the natriuretic peptides ANP, BNP and CNP was followed by the description and cloning of their specific receptors, natriuretic peptide receptor-A, -B and -C (NPR-A, -B, -C) (Fuller 1988, *J Biol Chem.* 263:9395-9401; Chang 1989 *Nature* 341:68-72; Chinkers 1989, *Nature* 338: 78-83). NPR-A (SEQ ID NO:16) preferentially binds ANP and BNP, while NPR-B (SEQ ID NO:17) is most specific for CNP and NPR-C(SEQ ID NO:15) binds all natriuretic peptides (Koller 1991, *Science* 252:120-123).

The primary structure of NPR-A and NPR-B contain an extracellular ligand binding domain, transmembrane domain, intracellular kinase homology domain containing phosphorylation sites and a C-terminal guanylate cyclase domain (reviewed in Misono 2005, *Peptides* 26:957-68). The latter classifies NPR-A and NPR-B as particulate guanylate cyclases, also known as GC-A and GC-B (E.C.4.6.1.2). In contrast, NPR-C is lacking intracellular homology domains, but evidence is increasing for NPR-C's role not only as a scavenger receptor for natriuretic peptides, but for its' functional coupling to inhibitory G-proteins and phosphoinositide turnover (Maack 1987, *Science* 238:675-678; Murthy and Makhlouf 1999, *J Biol Chem* 274:17587-

17592; Anand-Srivastava 2005, *Peptides* 26:1044-1059). Reflecting the grade of sequence homology in natriuretic peptides, natriuretic peptide receptors show a high degree of homology in their extracellular ligand binding domains, with the calculated similarities being 41% between NPR-A and NPR-B and 29% between NPR-A and NPR-C (van den Akker 2001, *J Mol Biol.* 311:923-937).

Ligand binding to NPRs requires a dimer of glycosylated receptor subunits (Fenrick et al. 1994, *Mol Cell Biochem.* 137:173-182; Kuhn 2003, *Circ Res.* 93:700-709) and is followed by a conformational change leading to activation of the guanylate cyclase domains. Subsequently, activity of particulate guanylate cyclases is regulated through phosphorylation (reviewed in Kuhn 2003, *Circ Res.* 93:700-709). Phosphorylation of NPRs is maximal in the basal state, while ligand binding is followed by dephosphorylation and subsequent desensitization of the receptor.

Natriuretic receptors are expressed in many tissues throughout the organism. NPR-A, NPR-B and NPR-C are present in the cardiovascular system and the kidney, with NPR-C being the most abundant receptor subtype accounting for 80% of NPR-expression in some tissues. NPR-B is present in a particularly high level in rat pineal gland, testis and ovaries. NPR-A and NPR-B ligands both induce endothelium-independent vasorelaxation, where ANP and BNP mainly act on arterial vasculature. In contrast, CNP mainly targets the venous system; with the exception of coronary arteries, that relax in response to CNP stimulation (Marton et al. 2005, *Vascul Pharmacol* 43:207-212). Importantly, induction of hypotension via NPR-B activation requires 10-fold higher concentrations of ligand compared to blood pressure reduction in response to NPR-A activation (Wei et al. 1993, *Am J Physiol.* 264:H71-H73; Woods and Jones 1999, *Am J Physiol.* 276:R1443-R1452). Relaxation of smooth muscle by activation of NPR-B has been shown in a variety of tissues, including blood vessels, seminiferous tubules and uterus. Also contraction of the ocular trabecular meshwork tissue is reduced by activation of natriuretic peptide receptors, confirming functional similarities of trabecular meshwork and smooth muscle cells (Stumpff and Wiederholt 2000, *Ophthalmologica* 214:33-53).

Another main target organ of natriuretic peptides is the kidney. Ligands of NPR-A induce natriuresis and diuresis by a dual mechanism (reviewed in Beltowski and Wojcicka 2002, *Med Sci Monit.* 8:RA39-RA52): (1) increased excretion of sodium by a reduced re-uptake of sodium ions in the distal tubulus, subsequently leading also to higher retention of water in the final urine: and (2) dilation of the affluent and concomitant contraction of the effluent glomerular capillary, increasing glomerular filtration rate, at the cost of reduction of renal perfusion (Endlich and Steinhausen 1997, *Kidney Int.* 52:202-207). In contrast to NPR-A-specific ligands, NPR-B-specific ligands do not induce significant natri- and diuresis, and in addition, show a peculiarity regarding glomerular flow regulation: CNP was shown to dilate both affluent and effluent capillaries in the glomerulus, thus increasing renal blood flow, but not glomerular filtration (Endlich and Steinhausen 1997, *Kidney Int.* 52:202-207).

In addition to effects of NP-receptor (NPR) activation on blood pressure and kidney function, powerful effects of natriuretic peptides on proliferative processes in a variety of cell types have been documented in the literature. Antiproliferative properties of NPR activation are documented for vascular smooth muscle cells, fibroblasts of different origins, mesangial cells, cancer cells and chondrocytes (reviewed in Schulz 2005, *Peptides* 26:1024-1034). At least for VSMC, evidence for the involvement of the transcription factor GAX in the regulation of proliferation has given an indication as to which intracellular mechanisms might be involved in growth regulation through NPR (Yamashita et al. 1997, *Hypertension* 29:381-387). Though tissue growth is mainly regulated by proliferative activity, some organs feature variations in cell size to influence tissue mass. This might be a physiological process, as during endochondral ossification, when chondrocytes mature by undergoing hypertrophy, or a pathological event, as in cardiac hypertrophy, which often precedes chronic heart failure. Both of the above-mentioned events of hypertrophy are regulated by NPR-B. NPR-B deficiency causes dwarfism due to abnormal endochondral ossification, characterized by size reduction of the hypertrophic zone of the epiphyseal growth plate (Bartels et al. 2004, *Am J Hum Genet.* 75:27-34; Tamura et al. 2004, *Proc Natl Acad Sci.* 101:17300-17305).

Quite different, a partial knock out of NPR-B in rats promoted cardiac hypertrophy, i.e. hypertrophy of cardiomyocytes (Langenickel et al. 2006, *Proc Natl Acad Sci.* 103:4735-4740).

Natriuretic peptides, having activity at the natriuretic receptors, were later discovered in various tissues, as well. For example, ANP was discovered in the early 1980s as an endogenous diuretic and vasorelaxant peptide, whose principle circulating form consists of 28 amino acids (SEQ ID NO:1). Subsequently, other natriuretic peptides, such as BNP (SEQ ID NO:2) and CNP (SEQ ID NO:3), were discovered. The presence of natriuretic peptides and their receptors in ocular tissues, especially those involved in the regulation of IOP, have been demonstrated. For example, in rat and rabbit eyes, ANP, BNP, and CNP, as well as NPR-A, NPR-B, and NPR-C mRNA were found in the ciliary processes, retina, and choroid (Mittag et al. 1987, *Curr Eye Res.* 6:1189-1196; Nathanson 1987, *Invest Ophthalmol Vis Sci.* 28:1357-1364; Fernandez-Durango et al. 1995, *Exp Eye Res.* 61:723-729). Similar results were found in bovine ciliary processes and cultured bovine ciliary epithelial cells. (Millar et al. 1997, *J Ocul Pharmacol Ther.* 13:1-11; Shahidullah and Wilson 1999, *Br J Pharmacol.* 127:1438-1446). The presence of the peptides and their receptors in the ciliary epithelium suggests that they may play a role in the production of aqueous humor.

In addition to the ciliary processes, natriuretic peptide receptors were also found in tissues associated with the outflow of aqueous humor. ANP binding sites were localized in the longitudinal ciliary muscle of the guinea pig. (Mantyh et al. 1986, *Hypertension.* 8:712-721). In cultured human TM and ciliary muscle cells, CNP is the most potent and efficacious in stimulating the production of cyclic GMP, indicating the presence of functional NPR-B. Activation of this receptor reduces carbachol-induced calcium influx. (Pang et al. 1996, *Invest Ophthalmol Vis Sci.* 37:1724-1731). This result predicts that activation of NPR-B should cause relaxation of these tissues. Indeed, CNP significantly decreases the carbachol-induced contraction of monkey and human ciliary muscles. (Ding and Abdel-Latif, 1997, *Invest Ophthalmol Vis Sci.* 38:2629-2638). Change in contractility in TM and ciliary muscle may affect the outflow facility of aqueous humor.

Cyclic GMP and compounds that increase cyclic GMP in ocular tissues, such as nitric oxide donors, have been shown to lower IOP. (Nathanson 1988, *Eur J Pharmacol.* 147:155-156; Becker 1990, *Invest Ophthalmol Vis Sci.* 31:1647-1649; Nathanson 1992, *J Pharmacol Exp Ther.* 260:956-965; Stein and Clack 1994, *Invest Ophthalmol Vis Sci.* 35:2765-2768). Since natriuretic peptides potently increase cyclic GMP production, they were predicted to lower IOP, too. In the past 20 years, the natriuretic peptides have been shown to be highly effective as IOP-lowering agents. For example, various researchers have independently shown that intravitreal injection of ANP in rabbits consistently and significantly lowers IOP. This effect lasts for many hours. (Sugrue and Viader, 1986, *Eur J Pharmacol.* 130:349-350; Mittag et al. 1987, *Curr Eye Res.* 6:1189-1196; Nathanson 1987 *Invest Ophthalmol Vis Sci.* 28:1357-1364; Korenfeld and Becker 1989, *Invest Ophthalmol Vis Sci.* 30:2385-2392; Takashima et al. 1996, *Invest Ophthalmol Vis Sci.* 37:2671-2677). The IOP effect of ANP correlates with an increase in cyclic GMP production in the iris-ciliary body. (Korenfeld and Becker 1989, *Invest Ophthalmol Vis Sci.* 30:2385-2392). Intravitreal injection of BNP (Takashima et al. 1996, *Invest Ophthalmol Vis Sci.* 37:2671-2677) or CNP (Takashima et al. 1998, *Exp Eye Res.* 66:89-96) is also highly efficacious in lowering IOP. In addition to intravitreal injection, subconjunctival (Yang et al. 1997, *Chin J Ophthalmol.* 33:149-151) or intracameral (Sugrue and Viader 1986, *Eur J Pharmacol.* 130:349-350; Fernandez-Durango et al. 1999, *Eur J Pharmacol.* 364:107-113) injection of the natriuretic peptides have been shown to be ocular hypotensive as well. Systemic administration of ANP in the rabbit, (Tsukahara et al. 1988, *Ophthalmologica.* 197:104-109) or human (Diestelhorst and Krieglstein 1989, *Int Ophthalmol.* 13:99-101) also lowers IOP. Unfortunately, it has not been possible to deliver these peptides topically due to their inability to penetrate the cornea. Therefore, these potent and efficacious IOP-lowering compounds have not been developed for such use.

There is a need for novel NPR-B agonists having improved bioavailability, as compared to isolated or synthesized natriuretic peptides, that can be used in the treatment of natriuretic peptide-mediated disorders, such as ocular disorders, diabetes-related disorders, vascular disorders, cardiac and cardiovascular pathologies, inflammation and other disorders described herein. The novel NPR-B agonists, compositions and methods of the present invention meet these needs.

SUMMARY OF THE INVENTION

The present invention provides novel NPR-B agonists, also referred to herein as natriuretic peptide mimics or similars, that are therapeutically useful for lowering intraocular pressure (IOP) and treating other disorders where activation of the type B natriuretic peptide receptor will be beneficial. Specifically, the invention provides novel NPR-B agonists that activate the type B natriuretic peptide receptor (NPR-B). The invention further provides compositions containing such novel NPR-B agonists. The compositions provided herein may be ophthalmic compositions for use in methods of treating or preventing particular ophthalmic diseases such as glaucoma, preferably by lowering intraocular pressure, using such novel NPR-B agonists. Alternatively, the compositions provided herein may be used in methods of treating or preventing cardiovascular disorders, kidney disease, lung disease, skeletal disorders, infertility, and other disorders mediated by natriuretic peptides or proteins.

The invention is in part based on the inventors' finding that the novel NPR-B agonists described herein can provide improved bioavailability, increased chemical stability, and increased metabolic stability in body fluids or tissues, due to their significantly reduced molecular size as compared to the known natriuretic peptides. Certain embodiments of the present application generally pertain to novel peptides containing modified amino acids and that bind to and activate NPR-B with high specificity, as described in more detail herein.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

As used herein, the term "NPR-B agonist" refers to the novel molecules described herein that activate the NPR-B with high potency.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention is in part based on the finding that novel NPR-B agonists having improved bioavailability as compared to known natriuretic peptides are useful for lowering elevated intraocular pressure and treating glaucoma. Thus, the present invention is generally directed to novel NPR-B agonists and their use in methods of treating or preventing disorders mediated by natriuretic peptides or proteins. In one particularly preferred embodiment, the novel NPR-B agonists described herein are formulated for the treatment of ophthalmic diseases such as glaucoma, preferably by lowering the elevated intraocular pressure often associated with glaucoma, using a pharmaceutical composition that comprises one or more novel NPR-B agonists, as described herein. In other preferred embodiments, the novel NPR-B agonists described herein are formulated for the treatment of other natriuretic peptide- or protein-mediated disorders such as cardiovascular disorders, kidney disorders, lung disorders, skeletal disorders, fertility disorders, and fibrosis.

Figure 1:
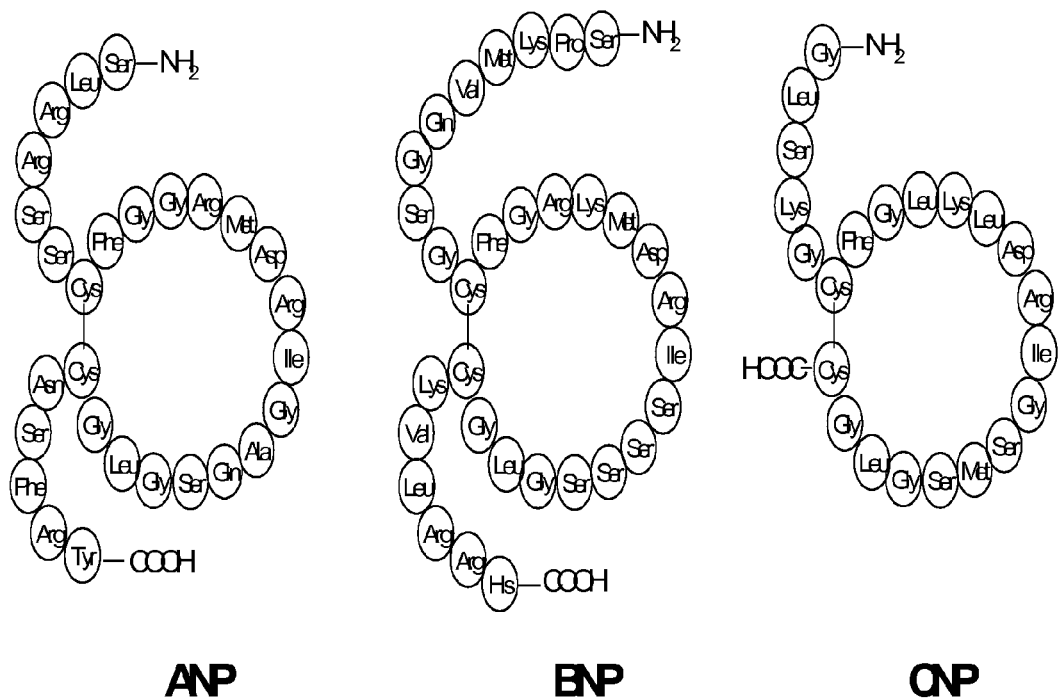
FIG. 1. Illustrates the amino acid sequence of ANP (SEQ ID NO:1), BNP (SEQ ID NO:2) and CNP (SEQ ID NO:3).
Figure 2:
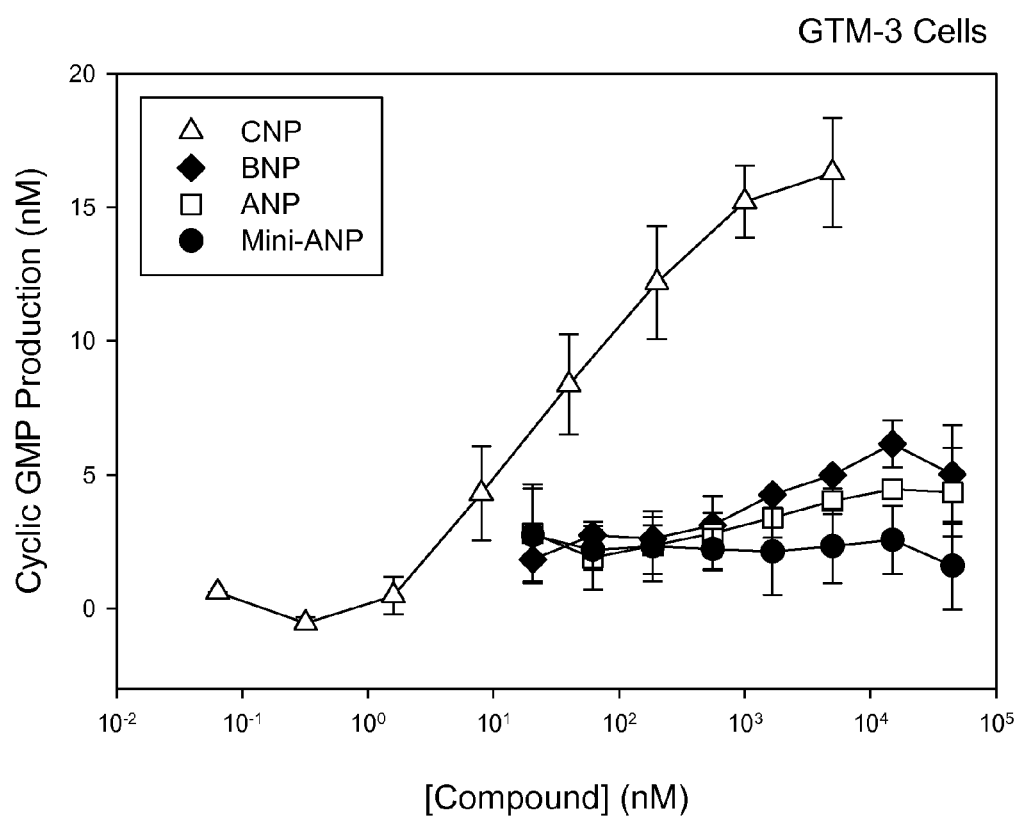
FIG. 2. Illustrates the effects of CNP, ANP, BNP and mini-ANP (SEQ ID NO:18) on cyclic GMP production in GTM-3 cells. GTM-3 cells have been shown to express NPR-B (Pang et al. 1996, Invest Ophthalmol Vis Sci. 37:1724-1731). The cells were treated with CNP (triangles), ANP (squares), BNP (diamonds) and mini-ANP (circles). The symbols represent mean values and standard deviations. The highest concentration of compounds used was 45 µM for ANP, BNP and mini-ANP and 5 µM for CNP. EC50 values were determined using the 4-Parameter Logistic Equation. CNP EC50=38.8 nM, ANP EC50=1.63 µM, BNP EC50=1.18 µM, mini-ANP EC50>45 µM. The Emax (maximum activation) of each compound was determined relative to the maximum activation of CNP, i.e. CNP Emax=100%, ANP Emax=15%, BNP Emax=20% and mini-ANP Emax=0%.
Figure 3:
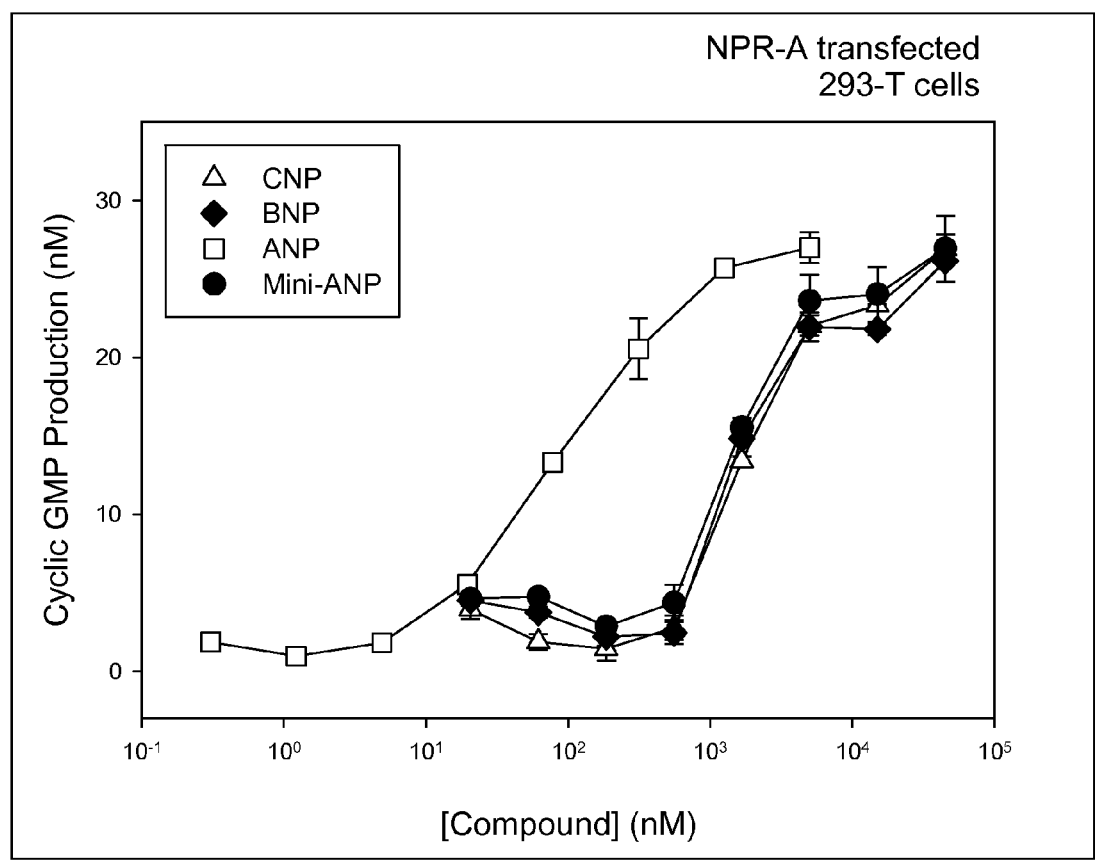
FIG. 3. Illustrates the effects of CNP, ANP, BNP and mini-ANP on cyclic GMP production in NPR-A transfected 293-T cells. NPR-A transfected 293-T cells were treated with CNP (triangles), ANP (squares), BNP (diamonds), and mini-ANP (circles). The symbols represent mean values and standard deviations. $EC_{50}$ was determined using the 4-Parameter Logistic Equation. $EC_{50}$ of ANP=73.0 nM, $EC_{50}$ of CNP=1.60 µM, $EC_{50}$ of BNP=1.85 µM, $EC_{50}$ of mini-ANP=1.54 µM.

The hallmark feature of all known NP's is the 17 amino acid ring which is formed by an intramolecular cysteine bridge (see FIG. 1). The integrity of the cyclic structure of NP's is believed to be critical for the functional activity, i.e. NP receptor transduced cGMP production. The present inventors have discovered that certain linear peptides, such as the novel peptides described herein, having increased chemical and metabolic stability and the improved bioavailability as compared to known NP's, are useful in the treatment of natriuretic peptide- or protein-mediated disorders.

A. Novel Peptides

The present invention provides novel NPR-B agonists having biological activity that is improved in certain aspects as compared to that of the known natriuretic peptides. The novel peptides of the invention include conventional and non-conventional amino acids. Conventional amino acids are identified according to their standard, three-letter codes, as set forth in Table 1, below.

TABLE 1

| For conventional amino acids the 3-letter codes were used: | | | |
|---|---|---|---|
| 3-letter codes | Amino acids | 3-letter codes | Amino acids |
| Ala | Alanine | Met | Methionine |
| Cys | Cysteine | Asn | Asparagine |
| Asp | Aspartic acid | Pro | Proline |
| Glu | Glutamic acid | Gln | Glutamine |
| Phe | Phenylalanine | Arg | Arginine |
| Gly | Glycine | Ser | Serine |
| His | Histidine | Thr | Threonine |
| Ile | Isoleucine | Val | Valine |
| Lys | Lysine | Trp | Tryptophane |
| Leu | Leucine | Tyr | Tyrosine |

Non-conventional amino acids are identified according to a three-letter code, or other abbreviation, when present in the novel NPR-B agonists of the invention. Table 2, below, provides the full name, three-letter code or abbreviation, and structure of each non-conventional amino acid appearing in the sequences of the novel peptides described herein.

TABLE 2

| List of abbreviations of non-conventional amino acids and other chemical structures. | | |
|---|---|---|
| Name | Abbr | Structure |
| (S)-2-((S)-3-amino-2,5-dioxopyrrolidin-1-yl)-5-guanidinopentanoic acid | Dim-Arg | [structure] |
| rac-2-amino-4-morpholinobutanoic acid | AR-385-017 | [structure] |
| (S)-2-amino-3-(2H-tetrazol-5-yl)propanoic acid | AR-314-145 | [structure] |

TABLE 2-continued

List of abbreviations of non-conventional amino acids and other chemical structures.

| Name | Abbr | Structure |
| --- | --- | --- |
| rac (1S,2S)-2-(octylcarbamoyl)cyclohexane carboxylic acid | AR-314-171 | 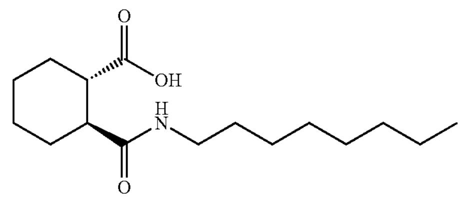 [SMILES: CCCCCCCCNC(=O)[C@H]1CCCC[C@@H]1C(=O)O] |
| rac (1S,2S)-2-(hexylcarbamoyl)cyclohexane carboxylic acid | AR-314-170 | 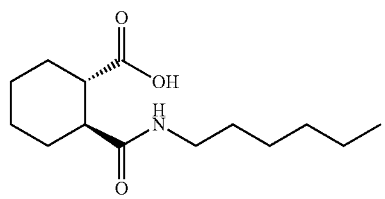 [SMILES: CCCCCCNC(=O)[C@H]1CCCC[C@@H]1C(=O)O] |
| rac (1R,2S)-2-octylcarbamoyl)cyclohexane carboxylic acid | AR-314-169 | 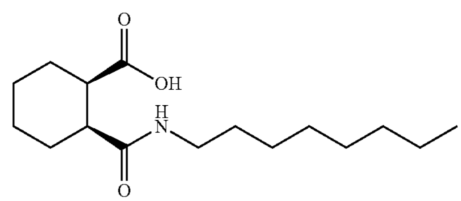 [SMILES: CCCCCCCCNC(=O)[C@H]1CCCC[C@H]1C(=O)O] |
| (S)-2-(6-hexanamido-1-oxoisoindolin-2-yl)-3-phenylpropanoic acid | AR-385-008 | 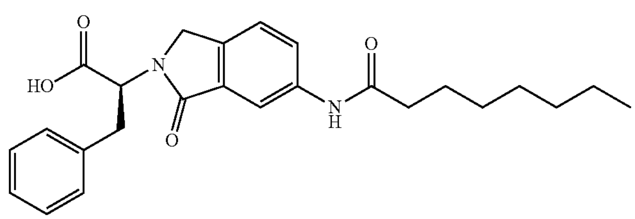 [SMILES: CCCCCCCC(=O)Nc1ccc2c(c1)C(=O)N([C@@H](Cc1ccccc1)C(=O)O)C2] |
| (S)-2-(4-octanamido-1,3-dioxoisoindolin-2-yl)-3-phenylpropanoic acid | AR-314-172 | 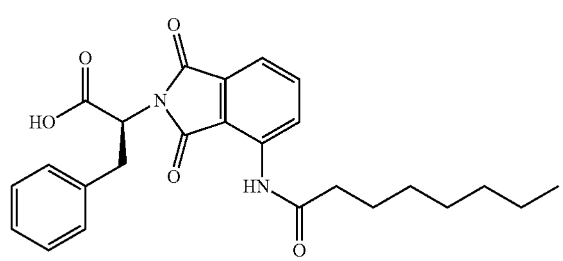 [SMILES: CCCCCCCC(=O)Nc1cccc2c1C(=O)N([C@@H](Cc1ccccc1)C(=O)O)C2=O] |
| (S)-2-(5-hexanamido-1,3-dioxoisoindolin-2-yl)-3-phenylpropanoic acid | AR-385-042 | 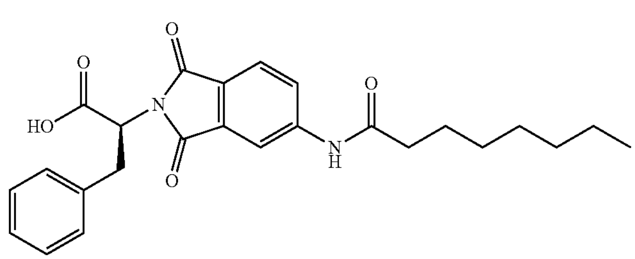 [SMILES: CCCCCCCC(=O)Nc1ccc2c(c1)C(=O)N([C@@H](Cc1ccccc1)C(=O)O)C2=O] |

TABLE 2-continued

List of abbreviations of non-conventional amino acids and other chemical structures.

| Name | Abbr | Structure |
| --- | --- | --- |
| (S,S)-2-(3-methyl-3-octanoylamino-2-oxo-pyrrolidin-1-yl)-3-phenyl-propionic acid | AR-314-102 | 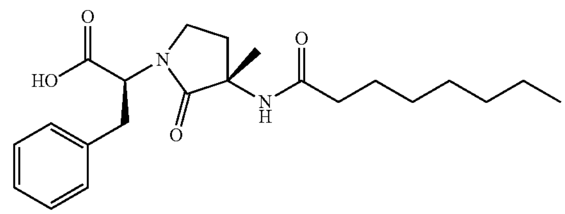 [SMILES: CCCCCCCC(=O)N[C@@]1(C)CCN([C@@H](Cc2ccccc2)C(=O)O)C1=O] |
| 2-(7-Octanoyl-1-oxo-2,7-diaza-spiro[4.5]dec-2-yl)-3-phenyl-propionic acid | AR-314-087 | 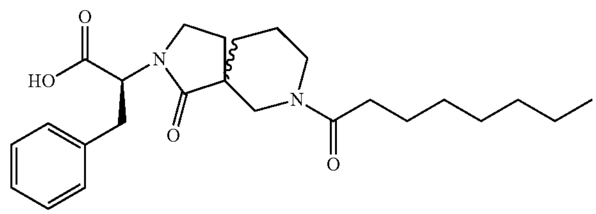 [SMILES: CCCCCCCC(=O)N1CCCC2(CCN([C@@H](Cc3ccccc3)C(=O)O)C2=O)C1] |
| 1-(3-Methyl-butyl)-piperazine | AR-201-124 | 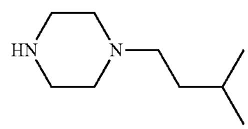 |
| Cycloheptyl-pyrrolidin-2-ylmethyl-amine | ES-283-049 | 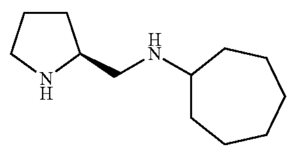 [SMILES: C1CCCC(NC[C@@H]2CCCN2)CC1] |
| (S)-Amino-thiophen-2-yl-acetic acid | BB727 | 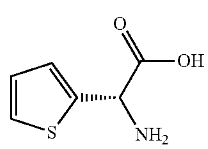 |
| (R)-Amino-thiophen-2-yl-acetic acid | BB726 | 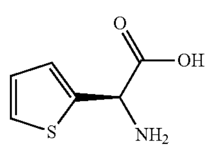 |
| 2-Octylsulfanyl-propionic acid | AR-201-073 | 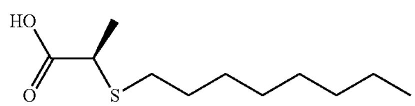 |
| 5-Pentylsulfanylmethyl-oxazole-2-carboxylic acid | AR-201-072 | 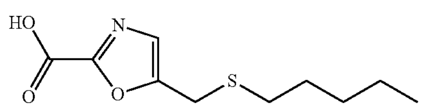 |
| 4-(4-Butyl-thiazol-2-ylamino)-benzoic acid | AR-201-069 | 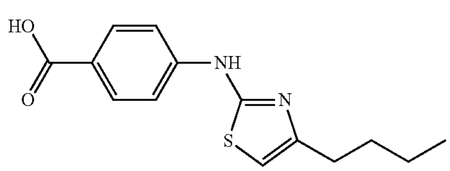 [SMILES: CCCCc1csc(Nc2ccc(C(=O)O)cc2)n1] |

TABLE 2-continued

List of abbreviations of non-conventional amino acids and other chemical structures.

| Name | Abbr | Structure |
|---|---|---|
| 4-(5-Butyl-thiazol-2-ylamino)-benzoic acid | AR-201-068 | 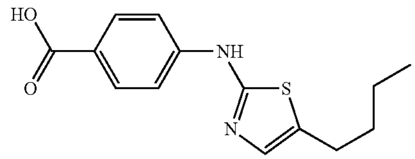 [SMILES: CCCCc1cnc(Nc2ccc(C(=O)O)cc2)s1] |
| 2-Hexylamino-oxazole-4-carboxylic acid | AR-201-062 | 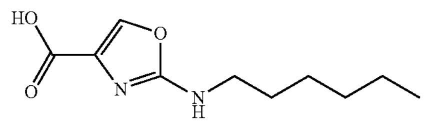 |
| 2-Hexanoylamino-oxazole-4-carboxylic acid | AR-201-059 | 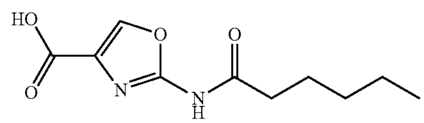 [SMILES: CCCCCC(=O)Nc1nc(C(=O)O)co1] |
| 3-Hexyloxy-isoxazole-5-carboxylic acid | AR-201-058 | 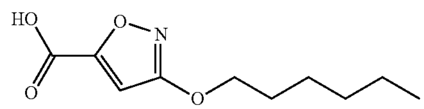 |
| 2-Hexanoylamino-isonicotinic acid | AR-201-054 | 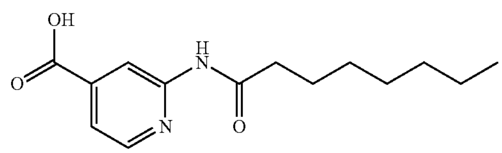 [SMILES: CCCCCCCC(=O)Nc1cc(C(=O)O)ccn1] |
| Octanoic acid 1-carboxy-ethyl ester | AR-201-049 | 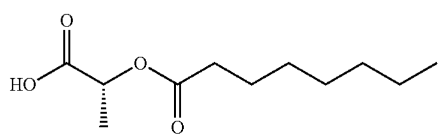 |
| Dodecanoic acid 1-carboxy-2-phenyl-ethyl ester | AR-201-048 | 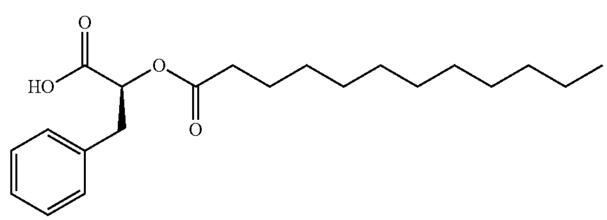 [SMILES: CCCCCCCCCCCC(=O)O[C@@H](Cc1ccccc1)C(=O)O] |
| (R)-2-Amino-4-(piperidin-1-yl)butanoic acid | abu(pip) | 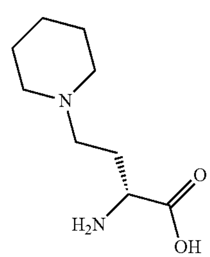 [SMILES: N[C@H](CCN1CCCCC1)C(=O)O] |
| 8-amino-3,6-dioxaoctanoic acid | Adx | 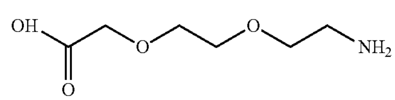 [SMILES: NCCOCCOCC(=O)O] |
| (2,3,4,5,6-Pentahydroxy-hexylidenaminooxy)-acetic acid | Gluc-Aoa | 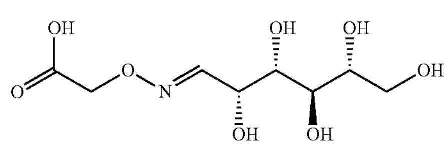 [SMILES: O=C(O)CO/N=C/[C@@H](O)[C@H](O)[C@H](O)[C@H](O)CO] |

TABLE 2-continued

List of abbreviations of non-conventional amino acids and other chemical structures.

| Name | Abbr | Structure |
| --- | --- | --- |
| 5-((4S)-2-oxohexahydro-1H-thieno[3,4-d]imidazol-4-yl)pentanoic acid | 74 | 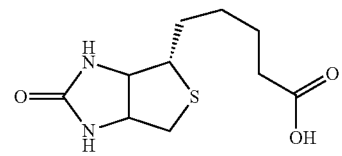 [SMILES: O=C(O)CCCC[C@@H]1SCC2NC(=O)NC21] |
| Adamantan-2-yl-amine | 504 | 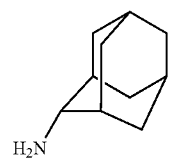 |
| Cyclohexylamine | 558 | 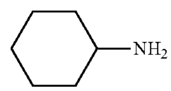 |
| Cyclopentylamine | 559 | 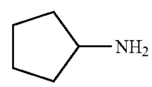 |
| 2-((1S,2R,4R)-bicyclo[2.2.1]heptan-2-yl)acetic acid | 779 | 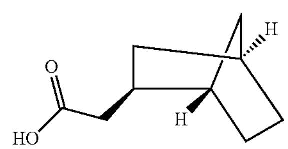 [SMILES: O=C(O)C[C@H]1C[C@@H]2CC[C@H]1C2] |
| 2-Phenethyl-benzoic acid | 785 | 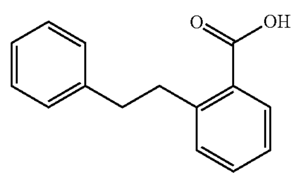 [SMILES: O=C(O)c1ccccc1CCc1ccccc1] |
| Dodecanoic acid | 832 | 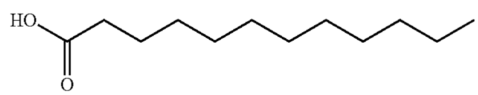 |
| Aniline | 873 | 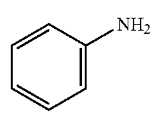 |
| Octanesulfonyl chloride | 933 | 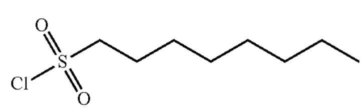 |
| Hexyl chloroformate | 1270 | 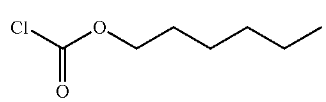 |
| 3-Phenyl-propionic acid | 1281 | 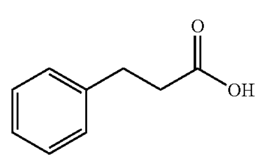 [SMILES: O=C(O)CCc1ccccc1] |

TABLE 2-continued

List of abbreviations of non-conventional amino acids and other chemical structures.

| Name | Abbr | Structure |
| --- | --- | --- |
| 4-Phenyl-butyric acid | 1319 | 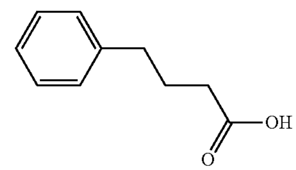 [SMILES: O=C(O)CCCc1ccccc1] |
| 5-Phenyl-pentanoic acid | 1320 | 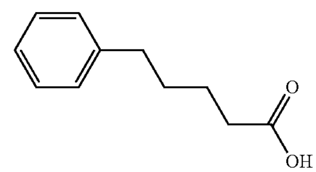 [SMILES: O=C(O)CCCCc1ccccc1] |
| 4-Cyclohexyl-butyric acid | 1339 | 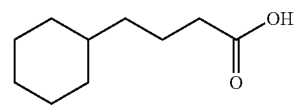 [SMILES: O=C(O)CCCC1CCCCC1] |
| 3-Cyclohexyl-propionic acid | 1340 | 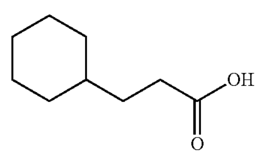 [SMILES: O=C(O)CCC1CCCCC1] |
| (S)-3,3-dimethylbutan-2-amine | 1381 | 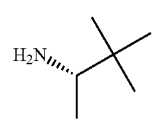 |
| 2-(hexylamino)acetic acid | 1625-Ac | 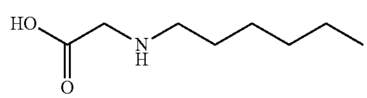 |
| Piperidine-1,2-dicarboxylic acid 1-benzyl ester | 1695 | 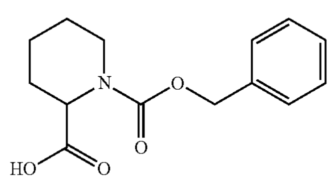 [SMILES: O=C(O)C1CCCCN1C(=O)OCc1ccccc1] |
| 4-Methyl-cyclohexyl-amine | 1859 | 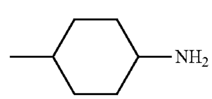 |
| (1R,2R)-2-methyl-cyclohexanamine | 1860 | 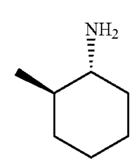 |
| 2-(2-Methoxy-ethoxy)-ethoxy]-acetic acid | 1888 | 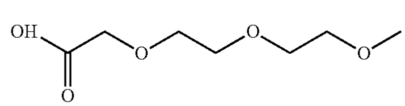 |

TABLE 2-continued

List of abbreviations of non-conventional amino acids and other chemical structures.

| Name | Abbr | Structure |
| --- | --- | --- |
| (1R,2R,4R)-bicyclo[2.2.1]heptan-2-amine | 1906 | 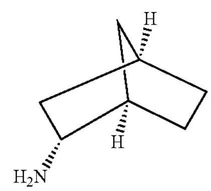 |
| (2-Methoxy-ethoxy)-acetyl chloride | 1913 | 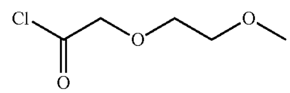 |
| (1R,2R)-2-(benzyloxy)cyclohexanamine | 1934 | 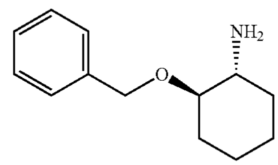 [SMILES: N[C@@H]1CCCC[C@H]1OCc1ccccc1] |
| (S)-1,2,3,4-tetrahydro-naphthalen-1-amine | 2118 | 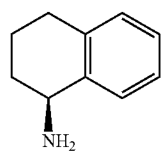 [SMILES: N[C@H]1CCCc2ccccc21] |
| (S)-3-methylpiperidine | 2137 | 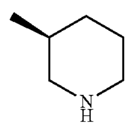 |
| 4-(4-Methoxy-phenyl)-butyric acid | 2553 | 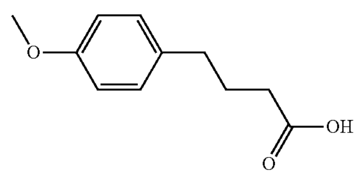 |
| (1R,2R,4R)-1,7,7-trimethylbicyclo[2.2.1]heptan-2-amine | 2797 | 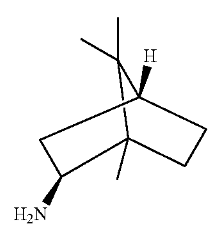 |
| 2-((2S,3R,4R,5R)-2,3,4,5,6-pentahydroxyhexylamino)acetic acid | 2857-Ac | 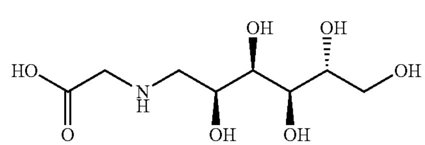 [SMILES: O=C(O)CNC[C@H](O)[C@@H](O)[C@H](O)[C@H](O)CO] |
| Cyclobutyl-amine | 2906 | 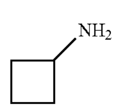 |

TABLE 2-continued

List of abbreviations of non-conventional amino acids and other chemical structures.

| Name | Abbr | Structure |
|---|---|---|
| (S)-2-cyclopentylhexanoic acid | 3218 | 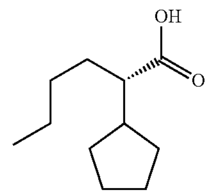 |
| 3-Amino-4-hydroxy-benzoic acid | 3421 | 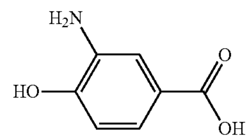 [SMILES: Nc1cc(C(=O)O)ccc1O] |
| 1-Ethyl-propyl-amine | 3791 | 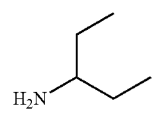 |
| (R)-2-methylbutan-1-amine | 3806 | 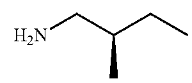 |
| 2-Ethyl-butyl-amine | 3816 | 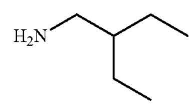 |
| 3-(4-Bromo-phenyl)-propionic acid | 4703 | 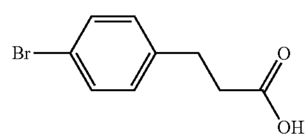 [SMILES: O=C(O)CCc1ccc(Br)cc1] |
| (4-Butoxy-phenyl)-acetic acid | 4734 | 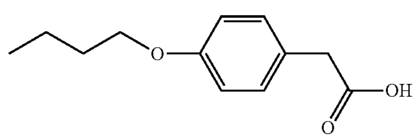 |
| (1S,2R)-2-aminocyclo-hexanecarboxamide | 5116 | 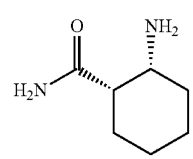 |
| (1R,2S)-ethyl 2-amino-cyclohexanecarboxylate | 5118 | 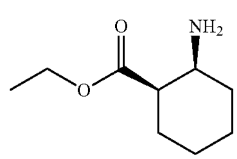 |
| (1R,2R)-ethyl 2-amino-cyclohexanecarboxylate | 5119 | 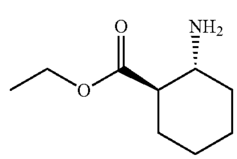 |
| 1-Propyl-butyl-amine | 5121 | 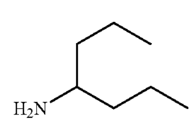 |

TABLE 2-continued

List of abbreviations of non-conventional amino acids and other chemical structures.

| Name | Abbr | Structure |
|---|---|---|
| (S)-3-amino-1-ethyl-azepan-2-one | 5164 | 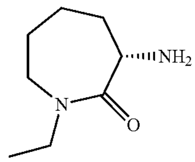 |
| Decanoic acid | 5587 | 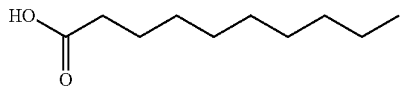 |
| (2-Butoxy-ethoxy)-acetic acid | 6013 | 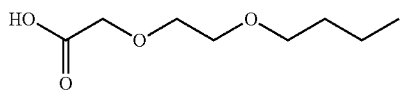 |
| (E)-dodec-2-enoic acid | 6014 | 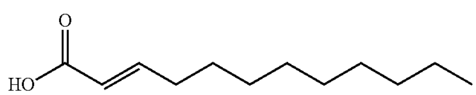 |
| (Z)-dodec-5-enoic acid | 6015 | 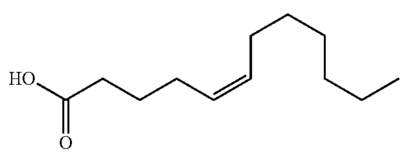 |
| (2S)-2-octylcyclopropane-carboxylic acid | 6056 | 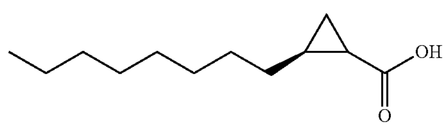 |
| 3-Octylsulfanyl-propionic acid | 6057 | 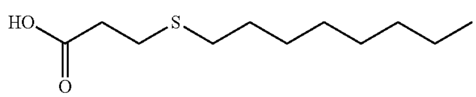 |
| 7-Butylsulfanyl-heptanoic acid | 6058 | 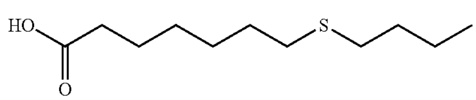 |
| 3-(Octane-1-sulfinyl)-propionic acid | 6059 | 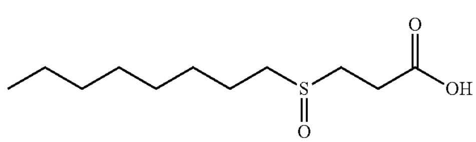 |
| 3-(Octane-1-sulfonyl)-propionic acid | 6059(O) | 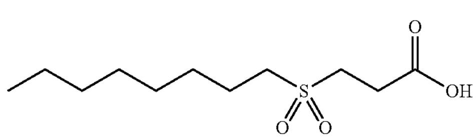 [SMILES: CCCCCCCCS(=O)(=O)CCC(=O)O] |
| rac-6-Hydroxy-decanoic acid | (6071-OH) | 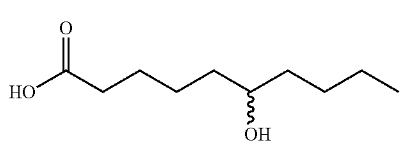 |
| rac-7-Hydroxy-dodecanoic acid | (6072-OH) | 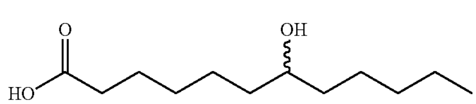 |

TABLE 2-continued

List of abbreviations of non-conventional amino acids and other chemical structures.

| Name | Abbr | Structure |
|---|---|---|
| 5-Butyl-2H-pyrrazole-3-carboxylic acid | 6182 | 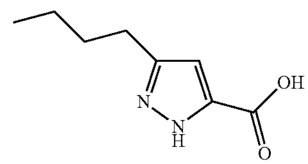 |
| 2-Pentyl-benzooxazole-5-carboxylic acid | 6988 | 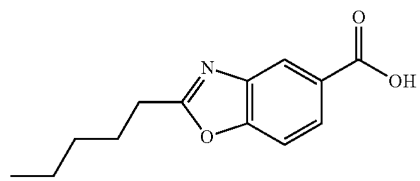 [SMILES: CCCCCc1nc2cc(C(=O)O)ccc2o1] |
| (R)-2-aminobutanoic acid | abu | 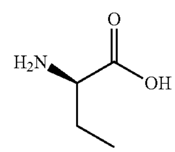 |
| 3-Amino-1-carboxymethyl-pyridin-2-one | Acp | 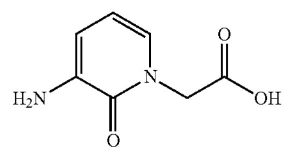 [SMILES: Nc1cccn(CC(=O)O)c1=O] |
| (S)-2-((S)-3-amino-2-oxopyrrollidin-1-yl)-3-phenylpropanoic acid | AFL | 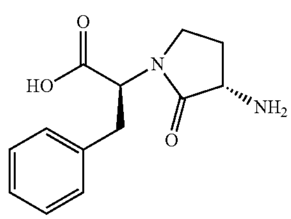 [SMILES: N[C@H]1CCN([C@@H](Cc2ccccc2)C(=O)O)C1=O] |
| (S)-2-((R)-3-amino-2-oxopyrrollidin-1-yl)-3-phenylpropanoic acid | aFL | 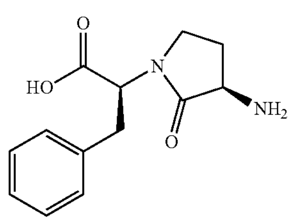 [SMILES: N[C@@H]1CCN([C@@H](Cc2ccccc2)C(=O)O)C1=O] |
| (R)-2-((R)-3-amino-2-oxopyrrolidin-1-yl)-3-phenylpropanoic acid | afL | 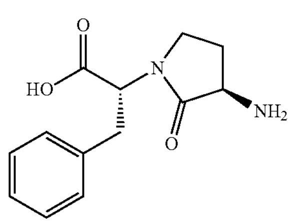 [SMILES: N[C@@H]1CCN([C@H](Cc2ccccc2)C(=O)O)C1=O] |
| 2-Aminoisobutyric acid | Aib | 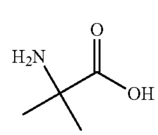 |

TABLE 2-continued

List of abbreviations of non-conventional amino acids and other chemical structures.

| Name | Abbr | Structure |
| --- | --- | --- |
| 2-Aminoindan-2-carboxylic acid | Aic | 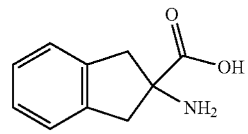 [SMILES: NC1(C(=O)O)Cc2ccccc2C1] |
| rac-α-Methyl-leucine | Aml | 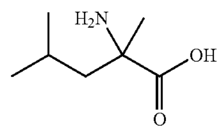 |
| (R)-α-methyl-proline | Amp | 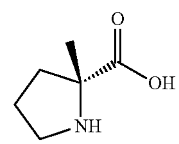 |
| 1-Aminomethyl-cyclopropanecarboxylic acid | Amcp | 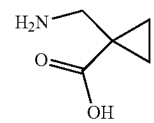 |
| 4-Amino-piperdine-4-carboxylic acid | Apc | 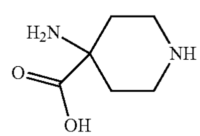 |
| 4-Amino-1-(2-amino-ethyl)-piperidine-4-carboxylic acid | Apc(Ae) | 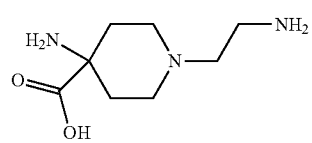 [SMILES: NCCN1CCC(N)(C(=O)O)CC1] |
| 4-Amino-1-ethyl-piperidine-4-carboxylic acid | Apc(Et) | 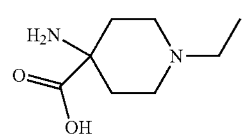 |
| 4-Amino-1-methyl-piperidine-4-carboxylic acid | Apc(Me) | 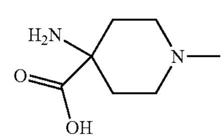 |
| (2S,4S)-4-aminopyrrolidine-2-carboxylic acid | Apr | 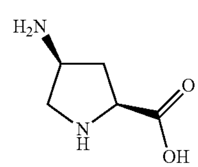 |
| Azetidine-3-carboxylic acid | Az3 | 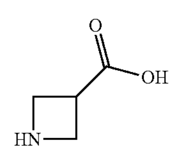 |
| (S)-azetidin-2-carboxylic acid | Aze | 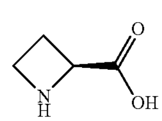 |

TABLE 2-continued

List of abbreviations of non-conventional amino acids and other chemical structures.

| Name | Abbr | Structure |
| --- | --- | --- |
| (R)-azetidin-2-carboxylic acid | aze | 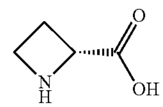 |
| β-Alanine | Bal | 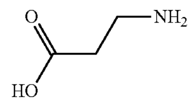 |
| (S)-β-Homolysine | Bhk | 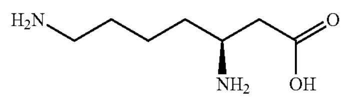 [SMILES: NCCCC[C@H](N)CC(=O)O] |
| (2S,4R)-4-(benzyloxy)pyrrolidine-2-carboxylic acid | Bhp | 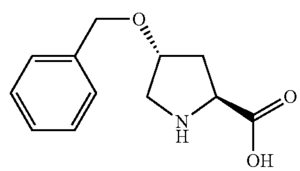 [SMILES: O=C(O)[C@@H]1C[C@@H](OCc2ccccc2)CN1] |
| (R)-β-homoleucine | Ble | 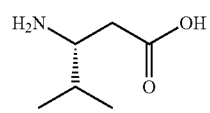 |
| rac-2-amino-3-phenyl-butyric acid | Bmf | 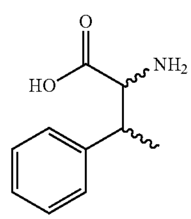 |
| (S)-2-((S)-3-(carboxy-methyl)-2-oxopiperazin-1-yl)-5-guanidinopentanoic acid | cDR | 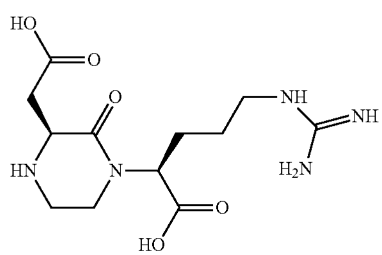 [SMILES: N=C(N)NCCC[C@@H](C(=O)O)N1CCN[C@@H](CC(=O)O)C1=O] |
| (S)-β-cyclohexylalanine | Cha | 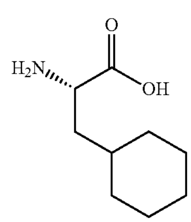 [SMILES: N[C@@H](CC1CCCCC1)C(=O)O] |
| Cycloheptyl-amine | Che | 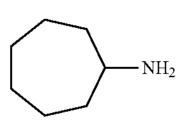 |

TABLE 2-continued

List of abbreviations of non-conventional amino acids and other chemical structures.

| Name | Abbr | Structure |
|---|---|---|
| (S)-Cyclohexylglycine | Chg | 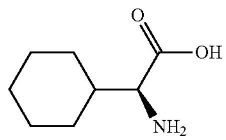 [SMILES: N[C@H](C(=O)O)C1CCCCC1] |
| (2S,4S)-4-hydroxy-pyrrolidine-2-carboxylic acid | Chy | 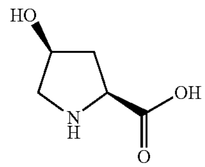 |
| (S)-2-amino-2-cyclopropyl-acetic acid | Cpa | 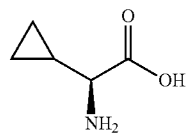 |
| (S)-2-amino-2-cyclopentyl-acetic acid | Cpg | 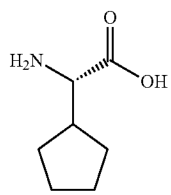 |
| rac-(3R,4S)-cis-methano-proline | Cpp | 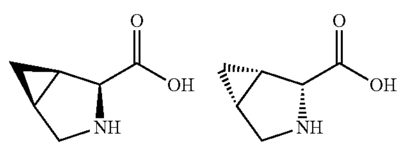 |
| (S)-2-amino-3-(tert-butylthio) propanoic acid | ctb | 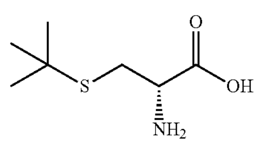 |
| (S)-2-Amino-3-sulfo-propanoic acid | Cya | 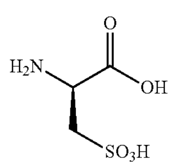 |
| (R)-2,4-diaminobutanoic acid | dab | 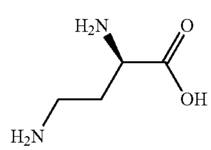 |
| (R)-2-amino-3-(neopentylamino) propanoic acid | dap(1464) | 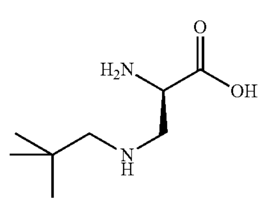 |

TABLE 2-continued

List of abbreviations of non-conventional amino acids and other chemical structures.

| Name | Abbr | Structure |
| --- | --- | --- |
| (R)-2-amino-3-(bis(2-aminoethyl)amino)propanoic acid | dap(6263)2 | 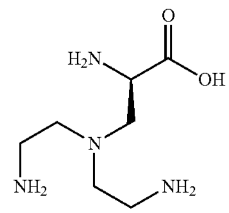 [SMILES: NCCN(CCN)C[C@@H](N)C(=O)O] |
| (R)-2-amino-3-(bis((1H-imidazol-2-yl)methyl)amino)propanoic acid | dap(3846)2 | 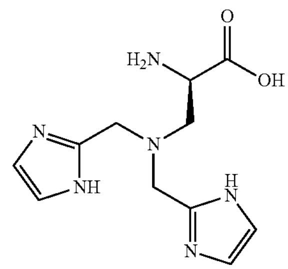 [SMILES: N[C@H](CN(Cc1ncc[nH]1)Cc1ncc[nH]1)C(=O)O] |
| (R)-2-amino-3-(piperidin-4-ylmethylamino)propanoic acid | dap(6238) | 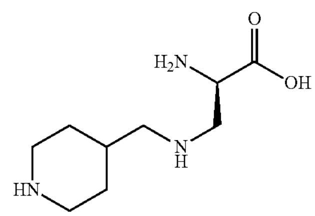 [SMILES: N[C@H](CNCC1CCNCC1)C(=O)O] |
| ((R)-2-amino-4-(dimethylamino)butanoic acid | dab(Me2) | 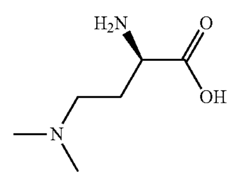 |
| (R)-2,3-diaminopropanoic acid | dap | 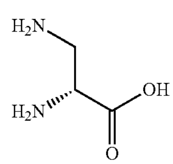 |
| (S)-2-amino-3-(dimethylamino)propanoic acid | Dap(Me2) | 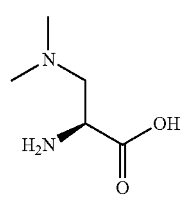 |
| (R)-2-amino-3-(dimethylamino)propanoic acid | dap(Me2) | 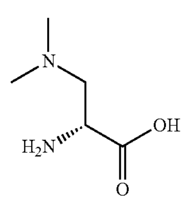 |

TABLE 2-continued

List of abbreviations of non-conventional amino acids and other chemical structures.

| Name | Abbr | Structure |
| --- | --- | --- |
| 2-Amino-2-ethyl-butyric acid | Deg | 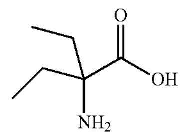 |
| 2-Aminoacrylic acid | Dha | 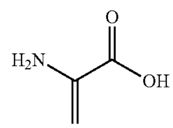 |
| (S)-2,5-dihydro-1H-pyrrole-2-carboxylic acid | Dhp | 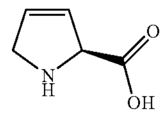 |
| (R)-2,2-dimethyl-thiazolidine-4-carboxylic acid | Dtp | 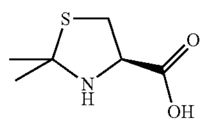 |
| (S)-3,4-dichloro-phenylalanine | Eaa | 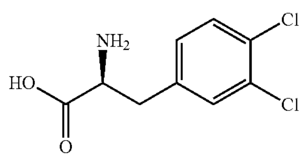 [SMILES: N[C@@H](Cc1ccc(Cl)c(Cl)c1)C(=O)O] |
| (S)-2-(3-amino-2-oxoazepan-1-yl) acetic acid | Eah | 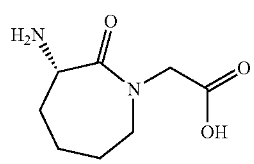 [SMILES: N[C@H]1CCCCN(CC(=O)O)C1=O] |
| rac-Imidazolidine-2-carboxylic acid | Eal | 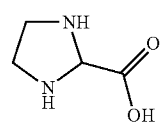 |
| (S)-4-methyl-2-((S)-6-oxo-1,7-diazaspiro[4.4]nonan-7-yl) pentanoic acid | Eam | 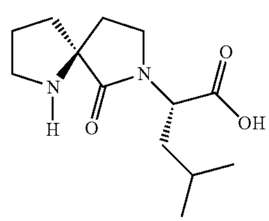 [SMILES: CC(C)C[C@@H](C(=O)O)N1CC[C@@]2(CCCN2)C1=O] |
| rac-1-amino-2,3-dihydro-1H-indene-1-carboxylic acid | Eao | 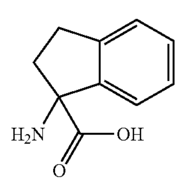 [SMILES: NC1(C(=O)O)CCc2ccccc21] |
| 2,3-Dihydro-1H-indole-2-carboxylic acid | Eat | 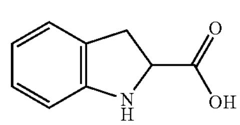 [SMILES: O=C(O)C1Cc2ccccc2N1] |

TABLE 2-continued

List of abbreviations of non-conventional amino acids and other chemical structures.

| Name | Abbr | Structure |
| --- | --- | --- |
| (2S,4S)-4-phenyl-pyrrolidine-2-carboxylic acid | Eay | 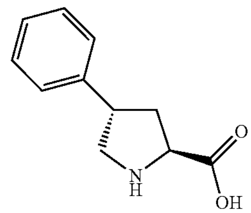 [SMILES: O=C(O)[C@@H]1C[C@@H](c2ccccc2)CN1] |
| (R)-thiazolidine-4-carboxylic acid | Eaz | 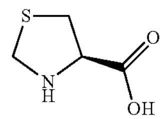 |
| 1-Aminocyclopropane-carboxylic acid | Ebc | 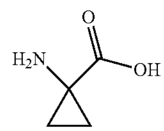 |
| (R)-2-amino-3-(methylsulfanyl)propanoic acid | Ebe | 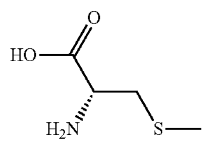 |
| 1-Amino-cyclopentane-carboxylic acid | Eca | 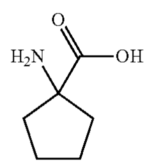 |
| 2-Amino-3-piperidin-4-yl-propionic acid | Egg | 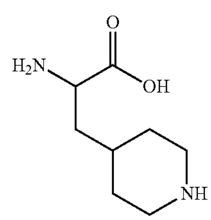 |
| 1-aminocyclohexane-carboxylic acid | Egz | 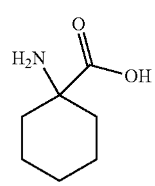 |
| (1S,3R)-3-amino-cyclohexane carboxylic acid | Fio | 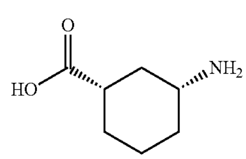 |
| trans-4-(aminomethyl)cyclohexane carboxylic acid | Fir | 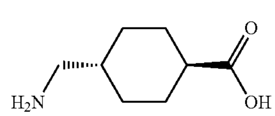 |

TABLE 2-continued

List of abbreviations of non-conventional amino acids and other chemical structures.

| Name | Abbr | Structure |
| --- | --- | --- |
| Amino-piperidin-3-yl-acetic acid | Fhy | 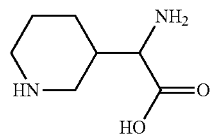 [SMILES: NC(C(=O)O)C1CCCNC1] |
| (S)-2-amino-2-(piperidin-4-yl)acetic acid | Fhz | 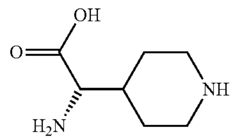 |
| (2S,4S)-4-fluoropyrrolidine-2-carboxylic acid | Fpr | 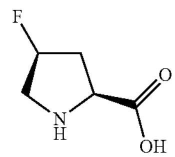 |
| 4-aminobutyric acid | Gab | 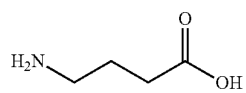 |
| (R)-2-amino-3-guanidinopropanoic acid | gdp | 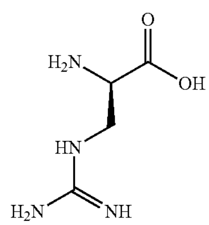 |
| (2S,4R)-4-guanidino-pyrrolidine-2-carboxylic acid | Gup | 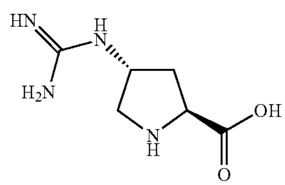 [SMILES: N=C(N)N[C@H]1CN[C@H](C(=O)O)C1] |
| (2S,3S)-3-hydroxypyrrolidine-2-carboxylic acid | H3p | 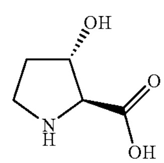 |
| Hexanoic acid | Hex | 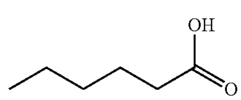 |
| (S)-homo-phenylalanine | Hfe | 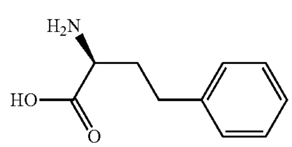 [SMILES: N[C@@H](CCc1ccccc1)C(=O)O] |
| (S)-2-aminooctanoic acid | Hgl | 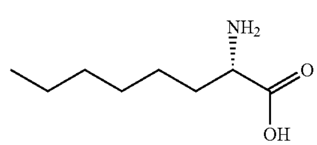 |

TABLE 2-continued

List of abbreviations of non-conventional amino acids and other chemical structures.

| Name | Abbr | Structure |
|---|---|---|
| (R)-2-aminooctanoic acid | hgl | 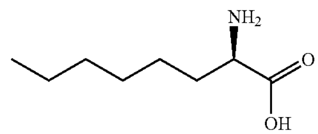 |
| (S)-2-amino-5-methylhexanoic acid | Hle | 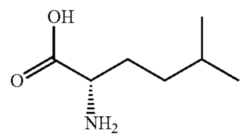 |
| (S)-homo-serine | Hse | 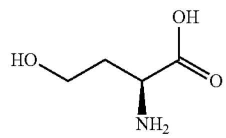 |
| (R)-homo-serine | hse | 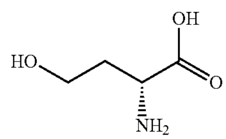 |
| (2S,4R)-4-hydroxypyrrolidine-2-carboxylic acid | Hyp | 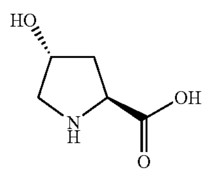 |
| Piperidine-4-carboxylic acid | Inp | 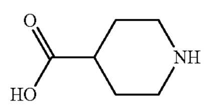 |
| Dodecane | Lau | 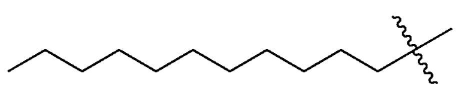 [SMILES: *CCCCCCCCCCC] |
| (R)-2-amino-6-(dimethylamino)hexanoic acid | lys(Me2) | 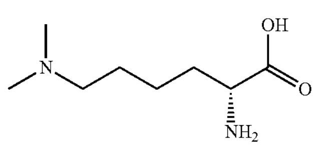 |
| 3-Aminomethyl-benzoic acid | Mam | 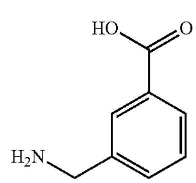 |
| (R)-2-amino-4-(methylsulfonyl)butanoic acid | metO$_2$ | 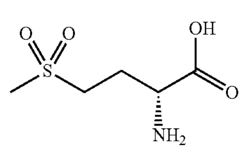 |

TABLE 2-continued

List of abbreviations of non-conventional amino acids and other chemical structures.

| Name | Abbr | Structure |
|---|---|---|
| (S)-meta-chloro-phenylalanine | Mcf | 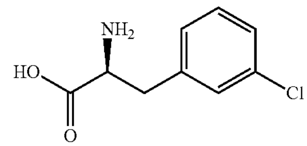 [SMILES: N[C@@H](Cc1cccc(Cl)c1)C(=O)O] |
| (S)-4-hydroxy-3-Iodo-phenylalanine | Miy | 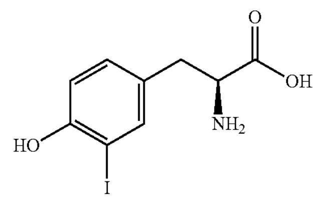 [SMILES: N[C@@H](Cc1ccc(O)c(I)c1)C(=O)O] |
| (S)-meta-methyl-phenylalanine | Mmf | 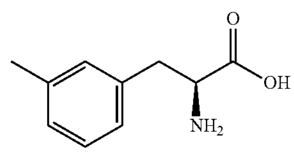 |
| (S)-3-(3-Pyridyl)-alanine | Mpa | 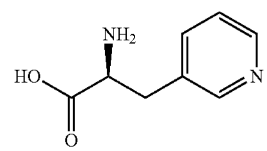 [SMILES: N[C@@H](Cc1cccnc1)C(=O)O] |
| (3-Amino-phenyl)-acetic acid | Mpe | 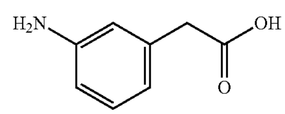 [SMILES: Nc1cccc(CC(=O)O)c1] |
| (S)-meta-trifluoromethyl-phenylalanine | Mtf | 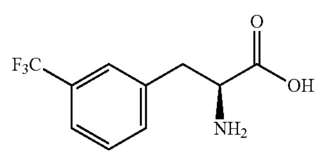 [SMILES: N[C@@H](Cc1cccc(C(F)(F)F)c1)C(=O)O] |
| (R)-2-amino-4-guanidinobutanoic acid | nar | 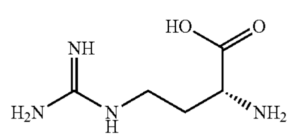 [SMILES: N=C(N)NCC[C@@H](N)C(=O)O] |
| rac-(2,3-Dihydroxy-propylamino)-acetic acid | Nbhp | 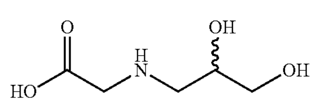 |
| 4-Butyl-thiazole | Nbt | 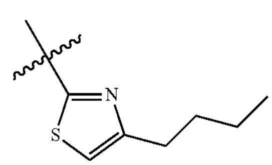 [SMILES: *c1nc(CCCC)cs1] |
| (3-Hydroxy-propylamino)acetic acid | Nhpr | 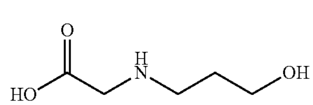 |

TABLE 2-continued

List of abbreviations of non-conventional amino acids and other chemical structures.

| Name | Abbr | Structure |
| --- | --- | --- |
| Phenethylamino-acetic acid | NHfe | 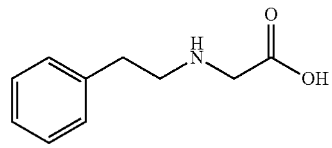 [SMILES: O=C(O)CNCCc1ccccc1] |
| (S)-para-nitro-phenylalanine | Nif | 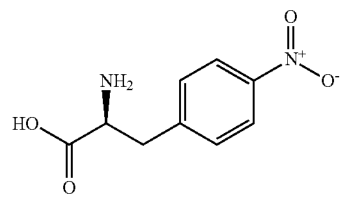 [SMILES: N[C@@H](Cc1ccc([N+](=O)[O-])cc1)C(=O)O] |
| rac-Nipecotic acid | Nip | 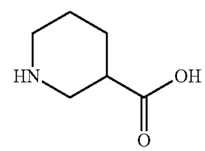 |
| (S)-Norleucine | Nle | 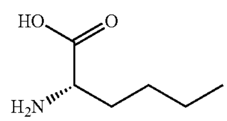 |
| (R)-Norleucine | nle | 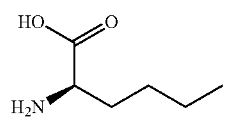 |
| (S)-N-methyl-alanine | Nma | 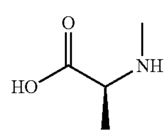 |
| (S)-N-methyl-aspartic acid | Nmd | 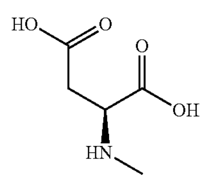 |
| (S)-N-methyl-phenylalanine | Nmf | 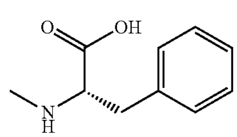 |
| (S)-N-methyl-isoleucine | Nmi | 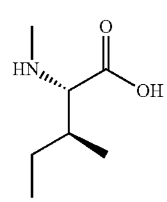 |
| (S)-N-methyl-lysine | Nmk | 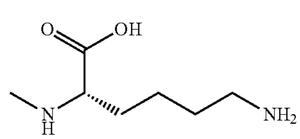 |

TABLE 2-continued

List of abbreviations of non-conventional amino acids and other chemical structures.

| Name | Abbr | Structure |
| --- | --- | --- |
| (S)-N-methyl-leucine | Nml | 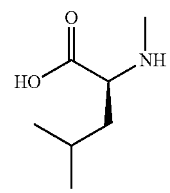 |
| (S)-N-methyl-arginine | Nmr | 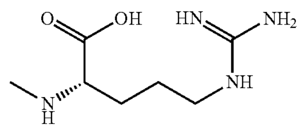 |
| (S)-2-amino-4,4-dimethyl-pentanoic acid | Npg | 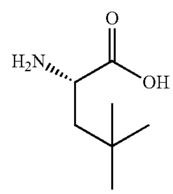 |
| 4,4-Dimethyl-2-methylamino-pentanoic acid | SH-112-158 | 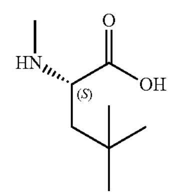 |
| Benzylamino-acetic acid | NPhe | 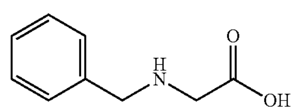 [SMILES: O=C(O)CNCc1ccccc1] |
| (S)-4-methyl-2-(propylamino)pentanoic acid | Npl | 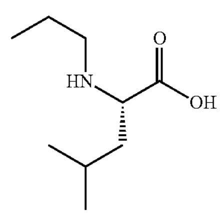 |
| (S)-norvaline | Nva | 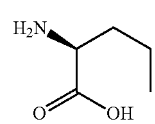 |
| (R)-norvaline | nva | 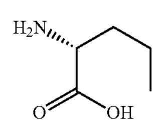 |
| Octanoic acid | Occ | 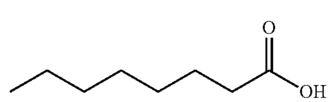 |
| octane | Oct | 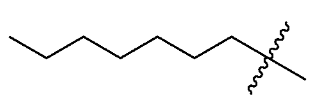 [SMILES: *CCCCCCC] |

TABLE 2-continued

List of abbreviations of non-conventional amino acids and other chemical structures.

| Name | Abbr | Structure |
| --- | --- | --- |
| (2S,3aS,7aS)-octahydro-1H-indole-2-carboxylic acid | Oic | 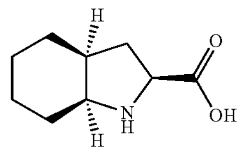 [SMILES: O=C(O)[C@@H]1C[C@@H]2CCCC[C@@H]2N1] |
| (S)-3-(2-pyridyl)-alanine | Opa | 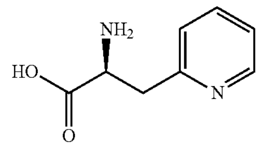 [SMILES: N[C@@H](Cc1ccccn1)C(=O)O] |
| (S)-ornithine | Orn | 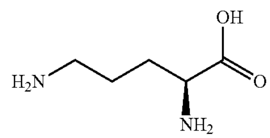 |
| (R)-ornithine | orn | 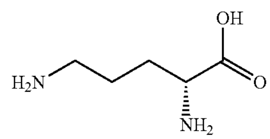 |
| (R)-2-amino-5-(dimethylamino) pentanoic acid | orn(Me2) | 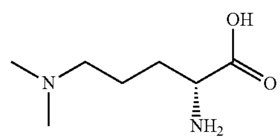 |
| (S)-ortho-trifluoro-phenylalanine | Otf | 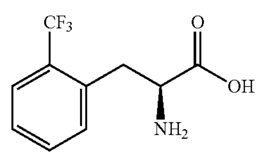 [SMILES: N[C@@H](Cc1ccccc1C(F)(F)F)C(=O)O] |
| Piperazin-1-yl-acetic acid | Paa | 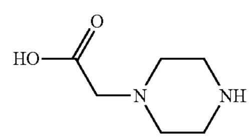 |
| (S)-para-amino-phenylalanine | Paf | 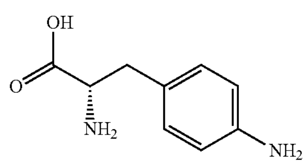 [SMILES: Nc1ccc(C[C@H](N)C(=O)O)cc1] |
| (4-Aminomethyl)-benzoic acid | Pam | 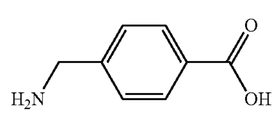 |
| (S)-para-bromo-phenylalanine | Pbf | 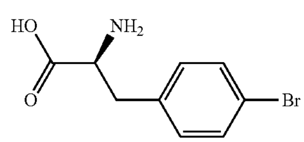 [SMILES: N[C@@H](Cc1ccc(Br)cc1)C(=O)O] |

TABLE 2-continued

List of abbreviations of non-conventional amino acids and other chemical structures.

| Name | Abbr | Structure |
| --- | --- | --- |
| (2S,3R)-3-aminopyrrolidine-2-carboxylic acid | Pca | 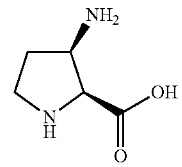 |
| (S)-para-chloro-phenylalanine | Pcf | 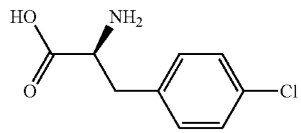 [SMILES: N[C@@H](Cc1ccc(Cl)cc1)C(=O)O] |
| (S)-para-fluoro-phenylalanine | Pff | 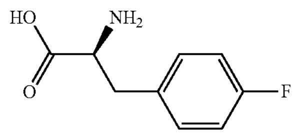 [SMILES: N[C@@H](Cc1ccc(F)cc1)C(=O)O] |
| (S)-phenylglycine | Phg | 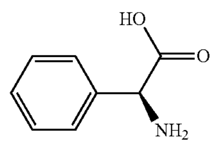 |
| (S)-pipecolinic acid | Pip | 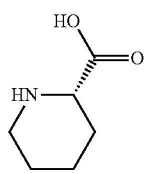 |
| (R)-pipecolinic acid | pip | 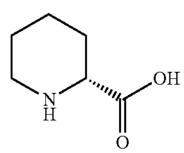 |
| (S)-para-methyl-phenylalanine | Pmf | 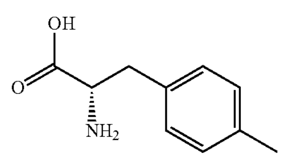 |
| (S)-para-methoxy-phenylalanine | Pmy | 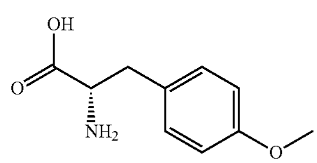 |
| (S)-3-(4-Pyridyl)-alanine | Ppa | 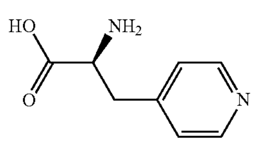 [SMILES: N[C@@H](Cc1ccncc1)C(=O)O] |
| (4-Amino-phenyl)-acetic acid | Ppe | 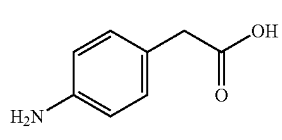 [SMILES: Nc1ccc(CC(=O)O)cc1] |

TABLE 2-continued

List of abbreviations of non-conventional amino acids and other chemical structures.

| Name | Abbr | Structure |
|---|---|---|
| (S)-2-amino-3-(phosphonooxy) propanoic acid | Pse | 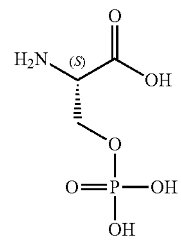 |
| (2S,3R)-2-Amino-3-(phosphonooxy) butanoic acid | Pth | 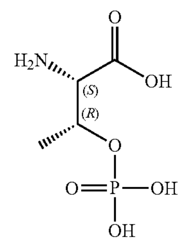 |
| Sarcosine | Sar | 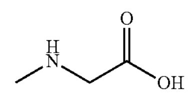 |
| 5-Butyl-thiazole | Sbt | 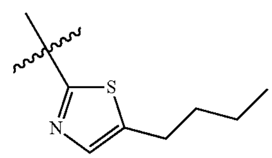 [SMILES: *c1ncc(CCCC)s1] |
| (S)-nipecotic acid | Sni | 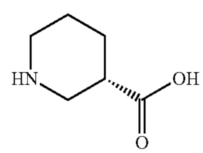 |
| (2S,4R)-4-aminopyrrolidine-2-carboxylic acid | Tap | 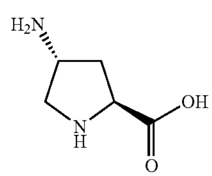 |
| (2S,4R)-4-(dimethylamino) pyrrolidine-2-carboxylic acid | Tap(2Me) | 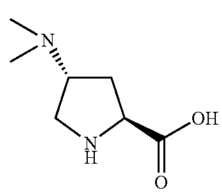 |
| (2S,4R)-4-acetamido-pyrrolidine-2-carboxylic acid | Tap(Ac) | 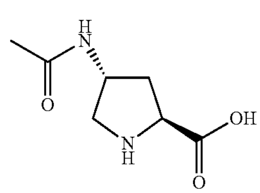 |

TABLE 2-continued

List of abbreviations of non-conventional amino acids and other chemical structures.

| Name | Abbr | Structure |
| --- | --- | --- |
| (2S,4R)-4-(2-aminoethylamino) pyrrolidine-2-carboxylic acid | Tap(Ae) | 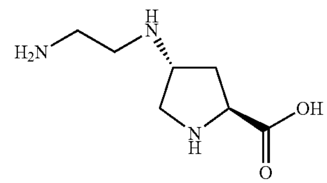 [SMILES: NCCN[C@H]1CN[C@H](C(=O)O)C1] |
| (2S,4R)-4-(S)-3-amino-3-carboxypropaneamido) pyrrolidine-2-carboxylic aicd | Tap(Asp (−)) | 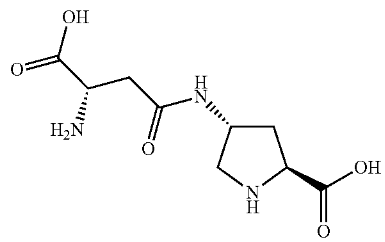 [SMILES: N[C@@H](CC(=O)N[C@H]1CN[C@H](C(=O)O)C1)C(=O)O] |
| 4-(3-Amino-propylamino)-pyrrolidine-2-carboxylic acid | Tap(Ap) | 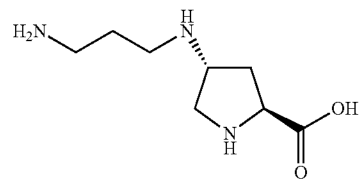 [SMILES: NCCCN[C@H]1CN[C@H](C(=O)O)C1] |
| (2S,4R)-4-(3-amino-propanamido)pyrrolidine-2-carboxylic acid | Tap(Bal) | 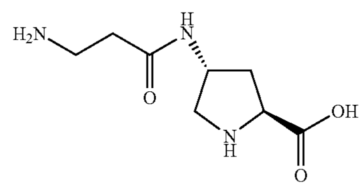 [SMILES: NCCC(=O)N[C@H]1CN[C@H](C(=O)O)C1] |
| (2S,4R)-4-(diethylamino)pyrrolidine-2-carboxylic acid | Tap(Et2) | 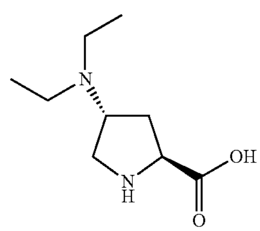 |
| (2S,4R)-4-(ethylamino) pyrrolidine-2-carboxylic acid | Tap(Et) | 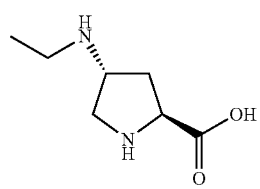 |
| (2S,4R)-4-(2-aminoacetamido) pyrrolidine-2-carboxylic acid | Tap(G) | 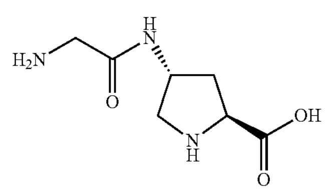 [SMILES: NCC(=O)N[C@H]1CN[C@H](C(=O)O)C1] |
| (S)-α-tert-butylglycine | Tbg | 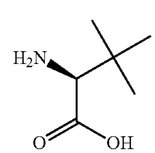 |

TABLE 2-continued

List of abbreviations of non-conventional amino acids and other chemical structures.

| Name | Abbr | Structure |
|---|---|---|
| (R)-α-tert-butylglycine | tbg | 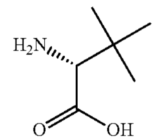 |
| (2S,4R)-4-fluoropyrrolidine-2-carboxylic acid | Tfp | 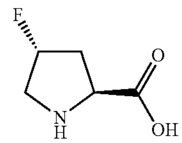 |
| (S)-2-thienyl-alanine | Thi | 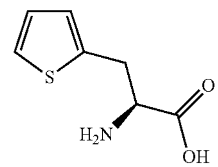 [SMILES: N[C@@H](Cc1cccs1)C(=O)O] |
| (S)-3-thienyl-alanine | Thk | 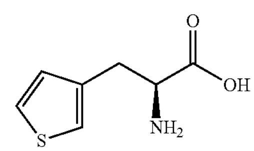 [SMILES: N[C@@H](Cc1ccsc1)C(=O)O] |
| (S)-thiazolidine-4-carboxylic acid | Thz | 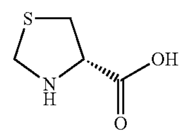 |
| (S)-1,2,3,4-tetrahydroiso-quinoline-3-carboxylic acid | Tic | 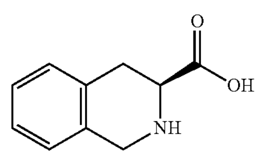 [SMILES: O=C(O)[C@@H]1Cc2ccccc2CN1] |
| 4-Amino-thiazol-2-carboxylic acid | Tnc | 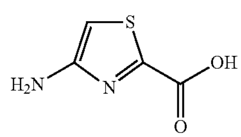 |
| (S)-2,3-Diamino-propionic acid (side chain prolongation) | Udp | 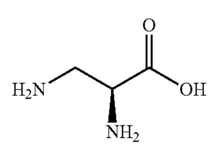 |

The novel NPR-B agonists of the invention comprise the general amino acid sequence of Formula I:

B-Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Z  (I)

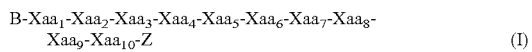

wherein

B is selected from the group consisting of H, R$^{b1}$—, R$^{b2}$—C(O)—, R$^{b2}$—S(O$_2$)—, R$^{b3}$-Baa-;

Baa is a conventional α-amino acid, a non-conventional α-amino acid or a β-amino acid;

R$^{b1}$ is selected from C$_1$-C$_{12}$ alkyl optionally substituted by NR$^{b4}$R$^{b5}$, OH, OR$^{b6}$, C$_3$-C$_8$ cyclic alkyl, aryl, heteroaryl, or heterocyclyl; C$_1$-C$_{12}$ alkenyl optionally substituted by NR$^{b4}$R$^{b5}$, OH, OR$^{b6}$, C$_3$-C$_8$ cyclic alkyl, aryl, heteroaryl, or heterocyclyl; C$_1$-C$_{12}$ alkyl aryl optionally substituted by NR$^{4b}$R$^{b5}$, OH, or OR$^{b6}$; C$_1$-C$_{12}$ alkynyl optionally substituted by NR$^{b4}$R$^{b5}$, OH, OR$^{b6}$, C$_3$-C$_8$ cyclic alkyl, aryl, heteroaryl, or heterocyclyl; aryl C$_1$-C$_{12}$ alkyl optionally substituted by NR$^{b4}$R$^{b5}$, OH, OR$^{b6}$, C$_3$-C$_8$ cyclic alkyl, aryl, heteroaryl, or heterocyclyl; C$_1$-C$_{12}$ alkyl C$_3$-C$_8$ cyclic alkyl optionally substituted by NR$^{b4}$R$^{b5}$, OH, OR$^{b6}$, aryl, heteroaryl, or heterocyclyl; C$_3$-C$_6$ cyclic alkyl C$_1$-C$_{12}$ alkyl optionally substituted by NR$^{b4}$R$^{b5}$, OH, OR$^{b6}$, aryl, heteroaryl, or heterocyclyl; C$_1$-C$_9$ alkylthio C$_2$-C$_{10}$ alkyl optionally substituted by $NR^{b4}R^{b5}$, OH, $OR^{b6}$, $C_3$-$C_8$ cyclic alkyl, aryl, heteroaryl, or heterocyclyl; $C_1$-$C_9$ alkylsulfonyl $C_1$-$C_4$ alkyl optionally substituted by $NR^{b4}R^{b5}$, OH, $OR^{b6}$, $C_3$-$C_8$ cyclic alkyl, aryl, heteroaryl, or heterocyclyl; $C_1$-$C_9$ alkylsulfoxyl $C_1$-$C_{10}$ alkyl optionally substituted by $NR^{b4}R^{b5}$, OH, $OR^{b6}$, $C_3$-$C_8$ cyclic alkyl, aryl, heteroaryl, or heterocyclyl; $CH_3$—$(CH_2)_{qb}$—O—[—$CH_2$—$(CH_2)_{nb}O]_{mb}$—$CH_2$—$(CH_2)_{pb}$—, 2-thiazolo optionally substituted by $C_{1-8}$ alkyl;

qb=0-3
nb=1-3
mb=1-3
pb=1-3

$R^{b2}$ is selected from $C_1$-$C_{12}$ alkyl optionally substituted by $NR^{b4}R^{b5}$, OH, $OR^{b6}$, $C_3$-$C_8$ cyclic alkyl, aryl, heteroaryl, or heterocyclyl; $C_1$-$C_{12}$ alkenyl optionally substituted by $NR^{b4}R^{b5}$, OH, $OR^{b6}$ $C_3$-$C_8$ cyclic alkyl, aryl, heteroaryl, or heterocyclyl; aryl $C_1$-$C_{12}$ alkyl optionally substituted by $NR^{b4}R^{b5}$, OH, $OR^{b6}$, $C_3$-$C_8$ cyclic alkyl, aryl, heteroaryl, or heterocyclyl; $C_1$-$C_{12}$ alkynyl optionally substituted by $NR^{b4}R^{b5}$, OH, $OR^{b6}$ $C_3$-$C_8$ cyclic alkyl, aryl, heteroaryl, or heterocyclyl; $C_1$-$C_{12}$ alkyl aryl optionally substituted by $NR^{b4}R^{b5}$, OH, or $OR^{b6}$; $C_1$-$C_{12}$ alkyl $C_3$-$C_8$ cyclic alkyl optionally substituted by $NR^{b4}R^{b5}$, OH, $OR^{b6}$, $C_3$-$C_8$ cyclic alkyl, aryl, heteroaryl, or heterocyclyl; $C_3$-$C_6$ cyclic alkyl $C_1$-$C_{12}$ alkyl optionally substituted by $NR^{b4}R^{b5}$, OH, $OR^{b6}$ $C_3$-$C_8$ cyclic alkyl, aryl, heteroaryl, or heterocyclyl; $C_1$-$C_9$ alkylthio $C_1$-$C_{10}$ alkyl optionally substituted by $NR^{b4}R^{b5}$, OH, $OR^{b6}$, $C_3$-$C_8$ cyclic alkyl, aryl, heteroaryl, or heterocyclyl; $C_1$-$C_9$ alkylsulfonyl $C_1$-$C_{10}$ alkyl optionally substituted by $NR^{b4}R^{b5}$, OH, $OR^{b6}$, $C_3$-$C_8$ cyclic alkyl, aryl, heteroaryl, or heterocyclyl; $C_1$-$C_9$ alkylsulfoxyl $C_1$-$C_4$ alkyl optionally substituted by $NR^{b4}R^{b5}$, OH, $OR^{b6}$, $C_3$-$C_8$ cyclic alkyl, aryl, heteroaryl, or heterocyclyl, $CH_3$—$(CH_2)_{qb}$—O—[—$CH_2$—$(CH_2)_{nb}O]_{mb}$—$CH_2$—$(CH_2)_{pb}$—;

qb=0-3
nb=1-3
mb=1-3
pb=0-3

$R^{b3}$ is selected from H, $R^{b1}$—, $R^{b2}$—C(O)—, or $R^{b2}$—S($O_2$)—;

$R^{b4}$, $R^{b5}$ and $R^{b6}$ are, independently, selected from a group consisting of H, or $C_1$-$C_4$ alkyl, and $Xaa_1$ is selected from the group consisting of a direct bond, a conventional α-amino acid; a non-conventional α-amino acid; a β-amino acid; a γ-amino acid; or a residue of Formula IIa-y:

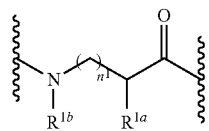

(IIa)

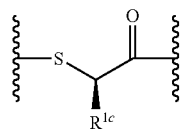

(IIb)

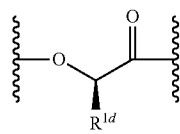

(IIc)

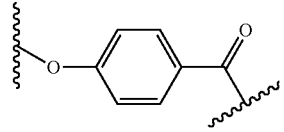

(IId)

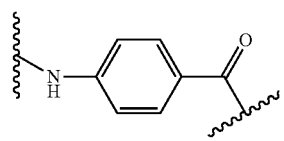

(IIe)

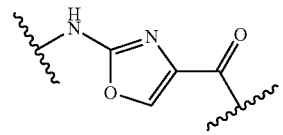

(IIf)

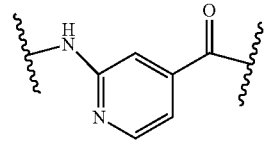

(IIg)

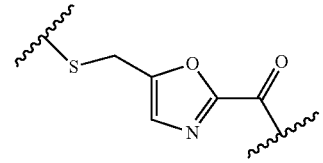

(IIh)

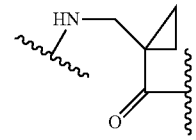

(IIi)

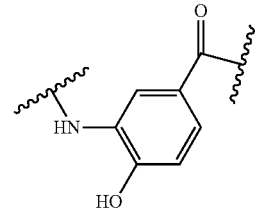

(IIj)

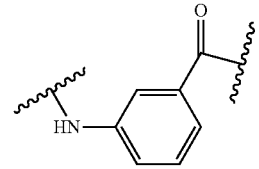

(IIk)

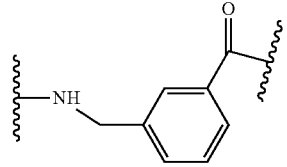

(IIl)

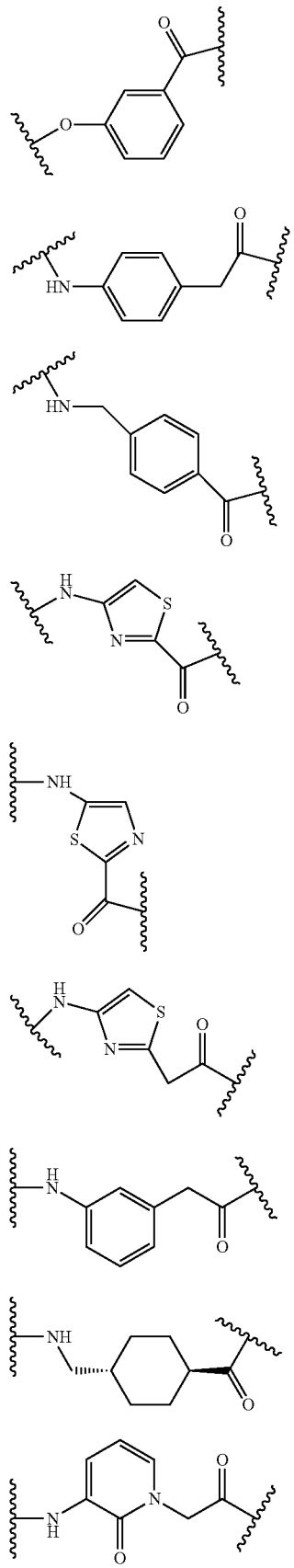
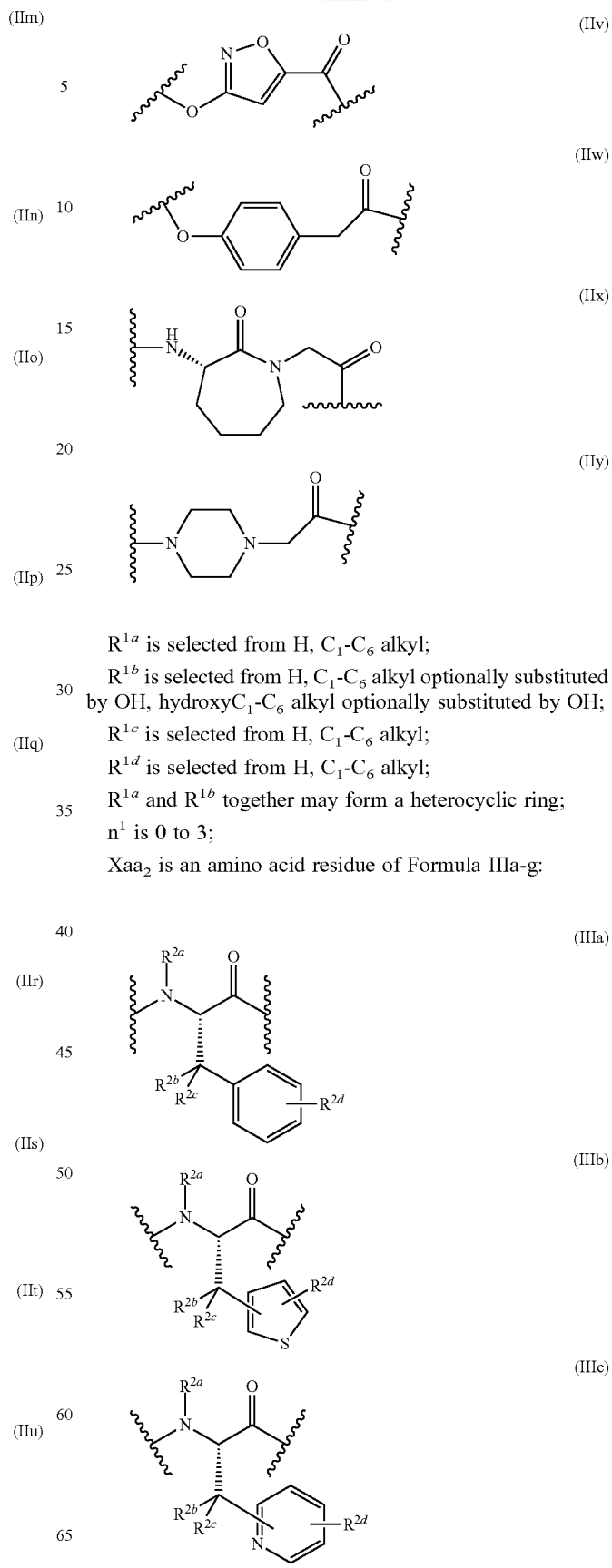
$R^{1a}$ is selected from H, $C_1$-$C_6$ alkyl;
$R^{1b}$ is selected from H, $C_1$-$C_6$ alkyl optionally substituted by OH, hydroxy$C_1$-$C_6$ alkyl optionally substituted by OH;
$R^{1c}$ is selected from H, $C_1$-$C_6$ alkyl;
$R^{1d}$ is selected from H, $C_1$-$C_6$ alkyl;
$R^{1a}$ and $R^{1b}$ together may form a heterocyclic ring;
$n^1$ is 0 to 3;
Xaa$_2$ is an amino acid residue of Formula IIIa-g:

-continued (IIId)
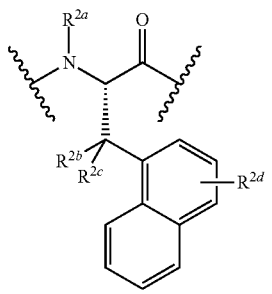

(IIIe)
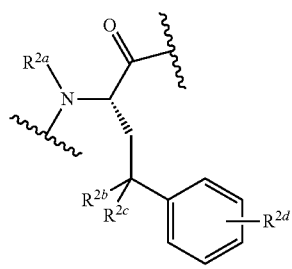

(IIIf)
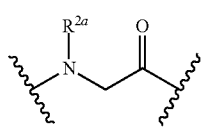

(IIIg)
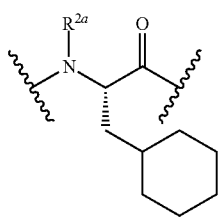

wherein
$R^{2a}$ is selected from the group consisting of H, methyl, ethyl, propyl, isopropyl, $C_1$-$C_2$ alkyl $C_3$-$C_7$ cycloalkyl and aryl $C_1$-$C_2$ alkyl;

$R^{2b}$ and $R^{2c}$ are, independently, selected from the group consisting of H, methyl, ethyl, propyl; and isopropyl, with the proviso that at least one of $R^{2b}$ and $R^{2c}$ is H;

$R^{2d}$ represents from 0 to 3 substituents, each such substituent being, independently, selected from the group consisting of H, Cl, F, Br, $NO_2$, $NH_2$, CN, $CF_3$, OH, $OR^{2e}$ and $C_1$-$C_4$ alkyl;

$R^{2a}$ and $R^{2b}$ or $R^{2a}$ and $R^{2c}$ together may form a heterocyclic ring;

$R^{2e}$ is selected from the group consisting of methyl, ethyl, propyl, and isopropyl; or Xaa$_1$ and Xaa$_2$ together may be selected from an amino acid residue of Formula IVa-b (IVa)
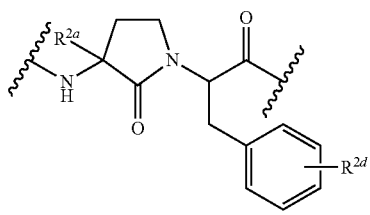

-continued (IVb)
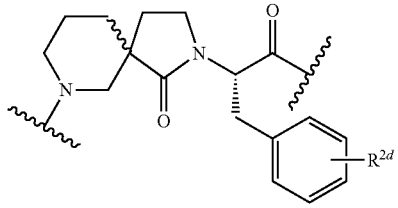

Xaa$_3$ is selected from the group consisting of Gly, Ala, a conventional D-α-amino acid, a non-conventional D-α-amino acid, and an amino acid residue of Formula Va:

(Va)
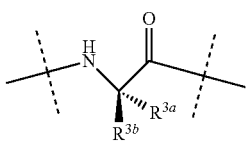

wherein $R^{3a}$ is selected from the group consisting of H or $C_1$-$C_4$ alkyl;

$R^{3b}$ is selected from the group consisting of H, —$(CH_2)_{n3a}$—$X^{3a}$;

n3a is 1 to 5;

$X^{3a}$ is selected from the group consisting of H, $NR^{3c}R^{3d}$;

$R^{3c}$ and $R^{3d}$ are independently selected from a group consisting of H, $C_1$-$C_8$ alkyl, —(C=N)—$NH_2$ and —$(CH_2)_{n3b}X^{3b}$;

n3b is 1 to 4;

$X^{3b}$ is selected from the group consisting of $NR^{3e}R^{3f}$, $C_5$-$C_6$ heteroaryl, $C_4$-$C_7$ heterocyclyl, —NHC(=N)$NH_2$;

$R^{3e}$ and $R^{3f}$ are independently selected from a group consisting of H, $C_1$-$C_8$ alkyl, wherein $R^{3e}$ and $R^{3f}$ can form a cyclic structure;

$R^{3a}$ and $R^{3b}$ can be linked to form a cyclic structure;

or $R^{3a}$ and $R^{3b}$ can be linked with a heteroatom selected from the group consisting of N, O, and S, to form a heterocyclic structure;

or

Xaa$_2$ and Xaa$_3$ together may be selected from an amino acid residue of Formula Vb:

(Vb)

wherein $R^{3g}$ represents from 0 to 3 substituents, each such substituent being, independently, selected from the group consisting of H, Cl, F, Br, $NO_2$, $NH_2$, CN; $CF_3$, OH, $OR^{3h}$ and $C_1$-$C_4$ alkyl;

$R^{3h}$ is selected from the group consisting of $C_1$-$C_4$ alkyl

Xaa₄ is an amino acid residue of Formula VIa-h:

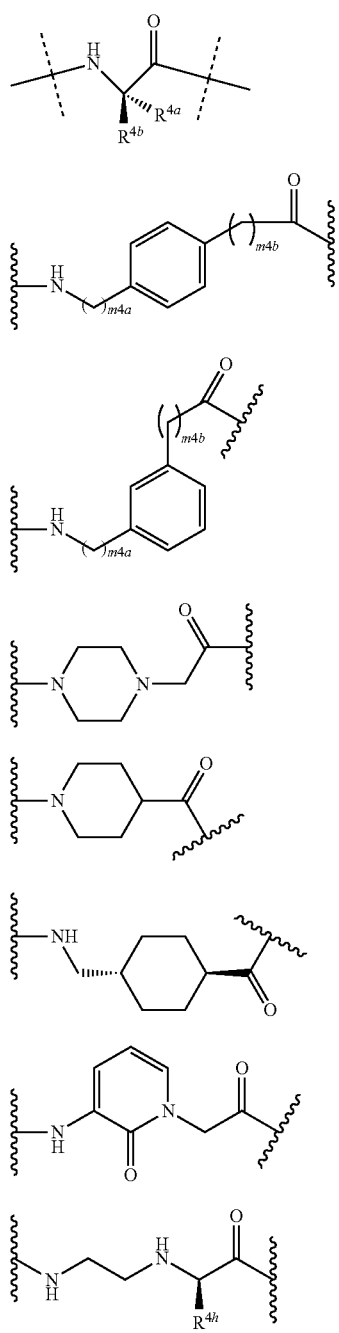

wherein $R^{4a}$ is selected from the group consisting of H, $C_1$-$C_8$ alkyl which may be substituted with a moiety selected from the group consisting of OH, $CO_2R^{4c}$, $C(=O)$—$NH_2$, a 5-6 membered heteroaryl, $C_1$-$C_{10}$ alkyl, $C_5$-$C_8$ cycloalkyl$C_1$-$C_{10}$ alkyl, and $C_5$-$C_8$ cycloalkyl, —$(CH_2)_{n4a}$—$X^{4a}$;

$n^{4a}$ is 1 or 2;

$R^{4b}$ is selected from the group consisting of H and methyl;

$R^{4c}$ is selected from the group consisting of H, and $C_1$-$C_3$alkyl; and $X^{4a}$ is OH, $CO_2R^{4d}$, $NR^{4e}R^{4f}$, $SR^{4g}$, 4-imidazoyl, 4-hydroxyphenyl;

$R^{4d}$, $R^{4e}$ and $R^{4f}$ independently are selected from the group consisting of H, and $C_1$-$C_3$ alkyl;

$R^{4g}$ is selected from the group consisting of $C_1$-$C_3$ alkyl;

m4a, and m4b are independently selected from 0 or 1;

$R^{4h}$ is $C_2$-$C_6$ alkyl;

or

Xaa₃ and Xaa₄ together may be selected from an amino acid residue of Formula VIb-h;

Xaa₅ is an amino acid residue of Formula VII:

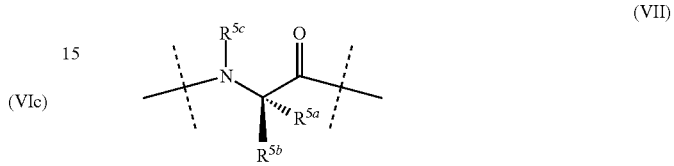

wherein $R^{5a}$ is $(CH_2)_{n5a}$—$X^{5a}$;

n5a is 1 to 6;

$X^{5a}$ is selected from the group consisting of H, $NH_2$, and a $C_{4-7}$ amine-containing aliphatic heterocyclic ring;

$R^{5b}$ is selected from the group consisting of H and methyl;

$R^{5c}$ is selected from the group consisting of H and methyl;

and wherein $R^{5c}$ and $R^{5a}$ can combine to form a four to six membered heterocyclic ring or can be linked with a heteroatom selected from the group consisting of N, O, and S to form a monocyclic or bicyclic heterocyclic structure; wherein said heterocyclic ring may have from 0 to 3 substituents, each such substituent being, independently, selected from the group consisting of OH, $OR^{5d}$, F, $C_1$-$C_4$ alkyl, —$NHC(=NH)NH_2$, aryl and $NR^{5e}R^{5f}$;

$R^{5d}$ is selected from $C_1$-$C_4$ alkyl, $C_1$-$C_4$ alkylaryl;

$R^{5e}$ is selected from the group consisting of H, $C_1$-$C_4$ alkyl, —$C(=O)(CH_2)_{n5b}$—$X^{5b}$, —$CH_2(CH_2)_{n5c}$—$X^{5b}$;

$R^{5f}$ is selected from the group consisting of H, $C_1$-$C_4$ alkyl, —$CH_2(CH_2)_{n5d}$—$X^{5c}$;

n5b is selected from the group consisting of 1, 2, 3, and 4;

n5c and n5d are independently selected from the group consisting of 2, 3, and 4;

$X^{5b}$ and $X^{5c}$ are independently selected from the group consisting of H, $NR^{5g}R^{5h}$;

$R^{5g}$ and $R^{5h}$ are independently selected from a group consisting of H, $C_1$-$C_4$ alkyl;

Xaa₆ is an amino acid residue of Formula VIIIa-d:

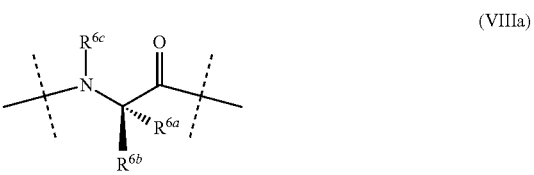

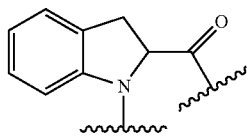

-continued (VIIIc)

(VIIId)

wherein $R^{6a}$ is selected from the group consisting of $C_1$-$C_8$ alkyl, aryl $C_1$-$C_4$ alkyl, $C_4$-$C_7$ cycloalkyl $C_1$-$C_4$ alkyl, $C_1$-$C_4$ alkyl S($C_1$-$C_4$alkyl), and $C_4$-$C_7$ cycloalkyl, wherein said $C_1$-$C_8$ alkyl and $C_4$-$C_7$ cycloalkyl may be substituted with a moiety selected from the group consisting of OH, O($C_1$-$C_4$ alkyl), S($C_1$-$C_4$ alkyl), and $NR^{6d}R^{6e}$;

$R^{6b}$ is H;

$R^{6c}$ is selected from the group consisting of H, and $C_1$-$C_4$alkyl;

$R^{6d}$, and $R^{6e}$ are, independently, selected from the group consisting of H, and $C_1$-$C_4$ alkyl;

wherein $R^{6a}$ and $R^{6c}$ can form a cyclic structure, which may be substituted with a moiety selected from the group consisting of OH, $C_1$-$C_4$ alkyl, $NH_2$ and F;

or $R^{6a}$ and $R^{6c}$ can be linked with a heteroatom selected from the group consisting of N, O, and S, to form a heterocyclic structure;

or $Xaa_5$ and $Xaa_6$ together may be an amino acid residue of Formula VIIIe:

(VIIIe)

$Xaa_7$ is an amino acid residue of Formula IXa-b:

(IXa)

(IXb)

wherein $R^{7a}$ is selected from the group consisting of $C_1$-$C_4$ alkyl, $C_3$-$C_7$ cycloalkyl, 2-thienyl, $(CH_2)_{n7a}$—$X^{7a}$, and $C_1$-$C_4$ alkyl substituted with OH;

$R^{7b}$ is H, and 2-thienyl;

$R^{7c}$ is selected from a group consisting of H, and methyl;

$R^{7d}$ is $C_1$-$C_4$ alkyl;

$n^{7d}$ is selected from the group consisting of 1 and 2;

$X^{7a}$ is selected from the group consisting of 2-thienyl, $C(=O)OR^{7e}$, $C(=O)NH_2$, $S(=O)_2OH$, $OS(=O)_2OH$, $B(OH)_2$, $P(=O)(OH)_2$, and $OP(=O)(OH)_2$;

wherein $R^{7e}$ is selected from the group consisting of H, and $C_1$-$C_4$ alkyl;

$Xaa_8$ is an amino acid residue of Formula Xa-g:

(Xa)

(Xb)

(Xc)

(Xd)

(Xe)

(Xf)

(Xg)

wherein $R^{8a}$ is selected from the group consisting of $(CH_2)_{m8a}$—$X^{8a}$, and a $C_4$-$C_7$ nitrogen-containing aliphatic heterocyclic ring;

$m^{8a}$=1-5;

$X^{8a}$ is selected from the group consisting of H, $NH_2$, and —$NHC(=NH)NH_2$;

$R^{8b}$ is selected from the group consisting of H and methyl;

$R^{8c}$ is selected from the group consisting of H, $NH_2$, and OH;

$Y^{8a}$ is selected from the group consisting of $CH(R^{8d})$, and S;

$R^{8d}$ is selected from the group consisting H, aryl, and OH;
$Y^{8b}$ is selected from the group consisting of CH($R^{8e}$), and NH;
$R^{8e}$ is selected from the group consisting H, NH$_2$ and OH;
$Y^{8c}$ is selected from the group CH$_2$, and NR$^{8f}$;
$R^{8f}$ is selected from the group H, —C(=NH)NH$_2$, and —C(=O)CH$_2$NH$_2$;
or Xaa$_7$ and Xaa$_8$ together may be an amino acid residue of Formula Xh:

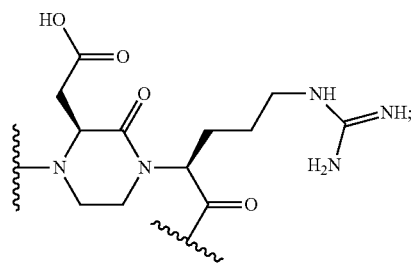

(Xh)

Xaa$_9$ is selected from the group consisting of a direct bond, and an amino acid residue of Formula XIa-c,

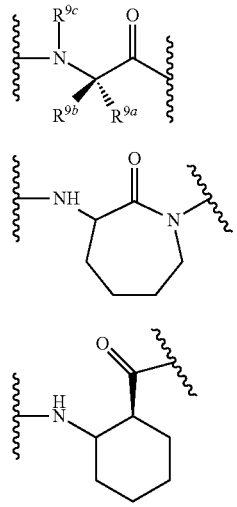

(XIa)

(XIb)

(XIc)

wherein $R^{9a}$ is selected from the group consisting of C$_1$-C$_5$ alkyl, and C$_4$-C$_7$ cycloalkyl;
$R^{9b}$ is selected from the group consisting of H, C$_1$-C$_5$ alkyl;
and wherein $R^{9a}$ and $R^{9b}$ can form a 5-7 membered cycloalkyl ring;
$R^{9c}$ is selected from the group consisting of H, methyl;
or Xaa$_8$ and Xaa$_9$ together may be a residue of Formula XId:

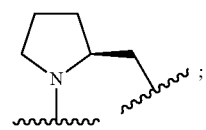

(XId)

and
Z is selected from the group consisting of H, OR$^{11a}$, NHR$^{11b}$ a conventional α-amino acid, a non-conventional α-amino acid, a α-amino acid; and a peptide consisting of from 2 to 30 amino acids selected from the group consisting of conventional α-amino acids, non-conventional α-amino acids, and α-amino acids;
wherein $R^{11a}$ and $R^{11b}$ are independently selected from the group consisting of H, C$_1$-C$_8$ alkyl, C$_4$-C$_8$ cycloalkyl, C$_7$-C$_{12}$ bicycloalkyl, C$_7$-C$_{12}$ cycloalkylaryl, C$_1$-C$_4$ alkyl C$_4$-C$_8$ cycloalkyl, or a residue of formula XIIa-c:

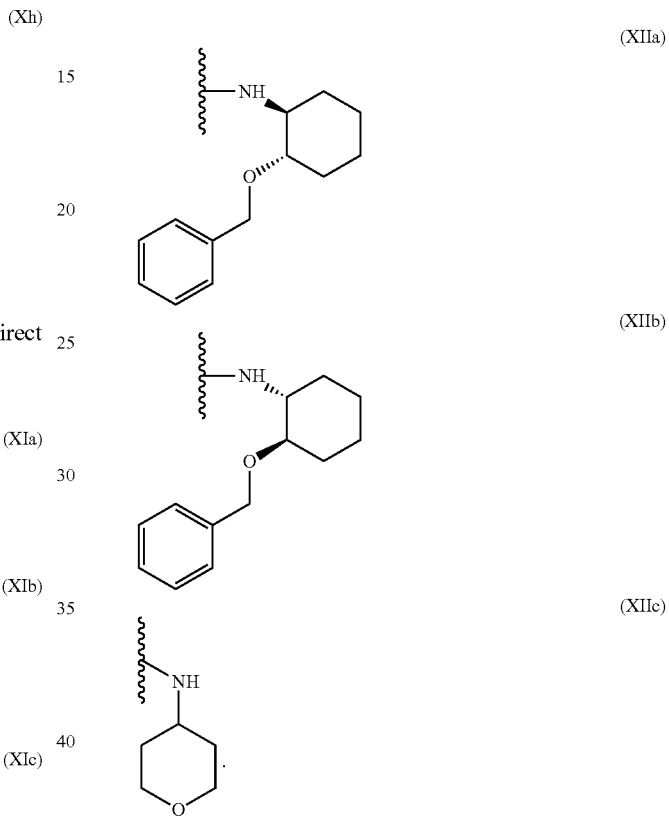

(XIIa)

(XIIb)

(XIIc)

As used herein, the phrase "optionally substituted" shall be understood by the skilled artisan to mean that the moiety to which the phrase refers may be unsubstituted, or it may be substituted with certain specified additional moieties. For example, the phrase "C$_1$-C$_{12}$ alkyl optionally substituted by NR$^{b4}$R$^{b5}$, OH, OR$^{b6}$, C$_3$-C$_8$ cyclic alkyl, aryl, heteroaryl, or heterocyclyl" refers to a C$_1$-C$_{12}$ alkyl compound that is either non-substituted or is substituted by a moiety selected from the group consisting of NR$^{b4}$R$^{b5}$, OH, OR$^{b6}$, C$_3$-C$_8$ cyclic alkyl, aryl, heteroaryl, and heterocyclyl. The compound, hexane, would be considered a C$_6$ alkyl compound that is not substituted, while the compound 3-hexanol is a C$_6$ alkyl compound that is substituted on the third carbon atom with an OH moiety.

In certain preferred NPR-B agonists of the invention:
B is selected from the group consisting of $R^{b1}$—, $R^{b2}$—C(O)—;
$R^{b1}$ is selected from C$_1$-C$_{12}$ alkyl optionally substituted by NR$^{b4}$R$^{b5}$;
$R^{b2}$ is selected from C$_1$-C$_{12}$ alkyl optionally substituted by NR$^{b4}$R$^{b5}$;
$R^{b4}$, and $R^{b5}$ are, independently, selected from a group consisting of H, and C$_1$-C$_4$ alkyl, and Xaa$_1$ is selected from the group consisting of a direct bond, a conventional α-amino acid; a non-conventional α-amino acid; β-amino acid; or a residue selected from the group consisting of Formula IIa, IIs, IIt, IIu, and IIv:

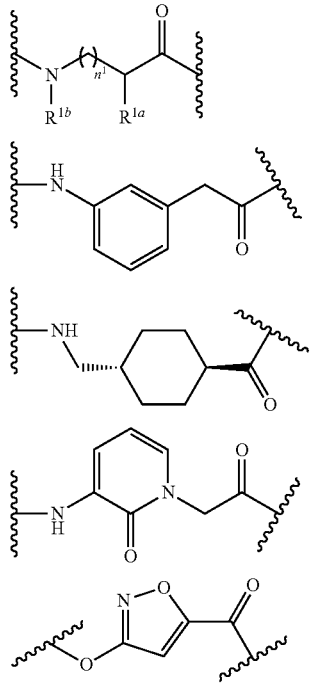

(IIa)

(IIs)

(IIt)

(IIu)

(IIv)

$R^{1a}$ is selected from H, $C_1$-$C_6$ alkyl;
$R^{1b}$ is selected from H, $C_1$-$C_6$ alkyl optionally substituted by OH, hydroxy$C_1$-$C_6$ alkyl optionally substituted by OH;
$R^{1c}$ is selected from H, $C_1$-$C_6$ alkyl;
$R^{1a}$ and $R^{1b}$ together may form a heterocyclic ring;
$n^1$ is 0 to 3; and
Xaa$_2$ is an amino acid residue of Formula IIIa or Formula IIIb:

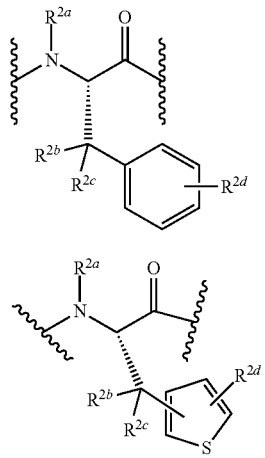

(IIIa)

(IIIb)

wherein
$R^{2a}$ is selected from the group consisting of H, methyl, ethyl, propyl, isopropyl, $C_1$-$C_2$ alkyl $C_3$-$C_7$ cycloalkyl and aryl $C_1$-$C_2$ alkyl;
$R^{2b}$ and $R^{2c}$ are, independently, selected from the group consisting of H, methyl, ethyl, propyl; and isopropyl; with the proviso that at least one of $R^{2b}$ and $R^{2c}$ is H;

$R^{2d}$ represents from 0 to 3 substituents, each such substituent being, independently, selected from the group consisting of H, Cl, F, Br, $NO_2$, $NH_2$, CN, $CF_3$, OH, $OR^{2e}$ and $C_1$-$C_4$ alkyl;
$R^{2a}$ and $R^{2b}$ or $R^{2a}$ and $R^{2c}$ together may form a heterocyclic ring;
$R^{2e}$ is selected from the group consisting of methyl, ethyl, propyl, and isopropyl; and
Xaa$_3$ is an amino acid residue of Formula Va:

(Va)

wherein $R^{3a}$ is selected from the group consisting of H or $C_1$-$C_4$ alkyl;
$R^{3b}$ is selected from the group consisting of H, —(CH$_2$)$_{n3a}$—X$^{3a}$;
n3a is 1 to 5;
$X^{3a}$ is selected from the group consisting of H, $NR^{3c}R^{3d}$;
$R^{3c}$ and $R^{3d}$ are independently selected from a group consisting of H, $C_1$-$C_8$ alkyl, —(C=N)—NH$_2$ and —(CH$_2$)$_{n3b}$X$^{3b}$;
n3b is 1 to 4;
$X^{3b}$ is selected from the group consisting of $NR^{3e}R^{3f}$, $C_5$-$C_6$ heteroaryl, $C_4$-$C_7$ heterocyclyl, —NHC(=N)NH$_2$;
$R^{3e}$ and $R^{3f}$ are independently selected from a group consisting of H, $C_1$-$C_8$ alkyl,
wherein $R^{3e}$ and $R^{3f}$ can form a cyclic structure;
$R^{3a}$ and $R^{3b}$ can be linked to form a cyclic structure;
or $R^{3a}$ and $R^{3b}$ can be linked with a heteroatom selected from the group consisting of N, O, and S, to form a heterocyclic structure;
and
Xaa$_4$ is an amino acid residue of Formula VIa:

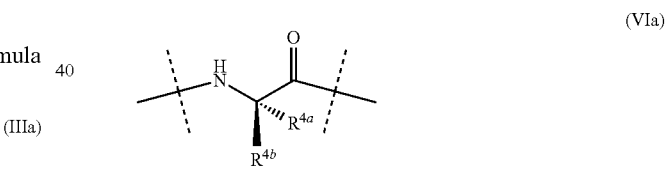

(VIa)

wherein $R^{4a}$ is selected from the group consisting of H, $C_1$-$C_8$ alkyl which may be substituted with a moiety selected from the group consisting of OH, $CO_2R^{4c}$, C(=O)—NH$_2$, a 5-6 membered heteroaryl, $C_1$-$C_{10}$ alkyl, $C_5$-$C_8$ cycloalkyl $C_1$-$C_{10}$ alkyl, and $C_5$-$C_8$ cycloalkyl;
n4a is 1 or 2;
$R^{4b}$ is selected from the group consisting of H and methyl;
$R^{4c}$ is selected from the group consisting of H, and $C_{1-3}$alkyl; and
and
Xaa$_5$ is an amino acid residue of Formula VII:

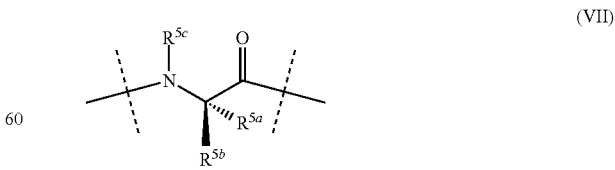

(VII)

wherein $R^{5a}$ is (CH$_2$)$_{n5a}$—X$^{5a}$;
n5a is 1 to 6;
$X^{5a}$ is selected from the group consisting of H, NH$_2$, and a $C_{4-7}$ amine-containing aliphatic heterocyclic ring;
$R^{5b}$ is selected from the group consisting of H and methyl;

$R^{5c}$ is selected from the group consisting of H and methyl;
and wherein $R^{5c}$ and $R^{5a}$ can combine to form a four to six membered heterocyclic ring wherein said heterocyclic ring may have from 0 to 2 substituents, each such substituent being, independently, selected from the group consisting of OH, $OR^{5d}$, F, $C_1$-$C_4$ alkyl, —NHC(=NH)NH$_2$, aryl and $NR^{5e}R^{5f}$;

$R^{5d}$ is selected from $C_1$-$C_4$ alkyl, $C_1$-$C_4$ alkylaryl;

$R^{5e}$ is selected from the group consisting of H, $C_1$-$C_4$ alkyl, —C(=O)(CH$_2$)$_{n5b}$—X$^{5b}$, —CH$_2$(CH$_2$)$_{n5c}$—X$^{5b}$;

$R^{5f}$ is selected from the group consisting of H, $C_1$-$C_4$ alkyl, —CH$_2$(CH$_2$)$_{n5d}$—X$^{5c}$;

n5b is selected from the group consisting of 1, 2, 3, and 4;

n5c and n5d are independently selected from the group consisting of 2, 3, and 4;

$X^{5b}$ and $X^{5c}$ are independently selected from the group consisting of H, $NR^{5g}R^{5h}$;

$R^{5g}$ and $R^{5h}$ are independently selected from a group consisting of H, $C_1$-$C_4$ alkyl and Xaa$_6$ is an amino acid residue of Formula VIIIa:

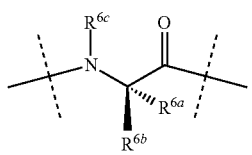

(VIIIa)

wherein $R^{6a}$ is selected from the group consisting of $C_1$-$C_8$ alkyl, aryl $C_1$-$C_4$ alkyl, $C_4$-$C_7$ cycloalkyl $C_1$-$C_4$ alkyl, $C_1$-$C_4$ alkyl S($C_1$-$C_4$ alkyl), and $C_4$-$C_7$ cycloalkyl, wherein said $C_1$-$C_8$ alkyl and $C_4$-$C_7$ cycloalkyl may be substituted with a moiety selected from the group consisting of OH, O($C_1$-$C_4$ alkyl), and S($C_1$-$C_4$ alkyl);

$R^{6b}$ is H;

$R^{6c}$ is selected from the group consisting of H, and $C_1$-$C_4$ alkyl; and

Xaa$_7$ is an amino acid residue of Formula IXa:

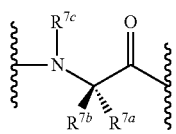

(IXa)

wherein $R^{7a}$ is selected from the group consisting of $C_1$-$C_4$ alkyl, $C_3$-$C_7$ cycloalkyl, 2-thienyl, and $C_1$-$C_4$ alkyl substituted with OH;

$R^{7b}$ is H, and 2-thienyl;

$R^{7c}$ is selected from a group consisting of H, and methyl; and

Xaa$_8$ is an amino acid residue of Formula X(a)-(g):

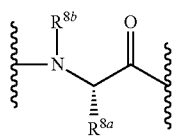

(Xa)

wherein $R^{8a}$ is (CH$_2$)$_{m8a}$—X$^{8a}$;
$m^{8a}$=1-5;

$X^{8a}$ is selected from the group consisting of H, NH$_2$, and —NHC(=NH)NH$_2$;

$R^{8b}$ is selected from the group consisting of H and methyl; and

Xaa$_9$ is selected from the group consisting of a direct bond, and an amino acid residue of Formula XIa-c,

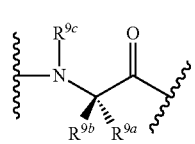

(XIa)

wherein $R^{9a}$ is selected from the group consisting of $C_1$-$C_5$ alkyl, and $C_4$-$C_7$ cycloalkyl;

$R^{9b}$ is selected from the group consisting of H, and $C_1$-$C_5$ alkyl;

or $R^{9a}$ and $R^{9b}$ can form a 5-7 membered cycloalkyl ring;

$R^{9c}$ is selected from the group consisting of H, and methyl;

and

Z is NHR$^{11b}$;

wherein $R^{11b}$ is selected from the group consisting of H, $C_1$-$C_8$ alkyl, $C_4$-$C_8$ cycloalkyl, $C_7$-$C_{12}$ bicycloalkyl, $C_7$-$C_{12}$ cycloalkylaryl, $C_1$-$C_4$ alkyl $C_4$-$C_8$ cycloalkyl, or a residue of formula XIIa-c

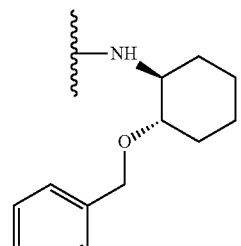

(XIIa)

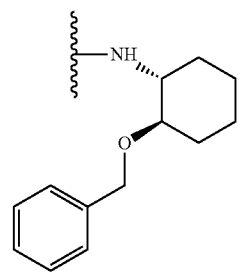

(XIIb)

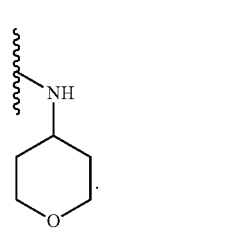

(XIIc)

In more preferred embodiments of the present invention, B is selected from the group consisting of $R^{b1}$—, and $R^{b2}$—C(O)—;

$R^{b1}$ is selected from the group consisting of $C_6$-$C_{10}$ alkyl and $C_6$-$C_{10}$ alkyl substituted by $NR^{b4}R^{b5}$;

$R^{b2}$ is selected from the group consisting of $C_6$-$C_{10}$ alkyl and $C_6$-$C_{10}$ alkyl substituted by $NR^{b4}R^{b5}$;

$R^{b4}$, and $R^{b5}$ are, independently, selected from a group consisting of H, and $C_1$-$C_4$ alkyl, and $Xaa_1$ is selected from the group consisting of a direct bond, a conventional α-amino acid; a non-conventional α-amino acid; a β-amino acid; a residue of Formula IIa, a residue of Formula IIs, a residue of Formula IIt, a residue of Formula IIu, and a residue of Formula IIv

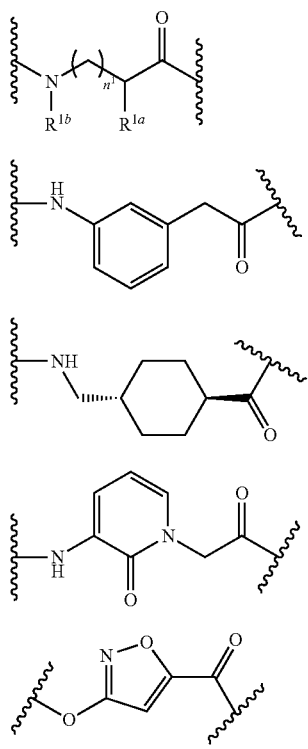

(IIa)

(IIs)

(IIt)

(IIu)

(IIv)

wherein $R^{1a}$ is selected from H, and $C_1$-$C_4$ alkyl;

$R^{1b}$ is selected from H, $C_1$-$C_4$ alkyl optionally substituted by OH, and hydroxy $C_1$-$C_4$ alkyl optionally substituted by OH;

$R^{1c}$ is selected from H, $C_1$-$C_6$ alkyl;

$R^{1a}$ and $R^{1b}$ together may form a heterocyclic ring;

$n^1$ is 0, 1; and $Xaa_2$ is an amino acid residue of Formula III:

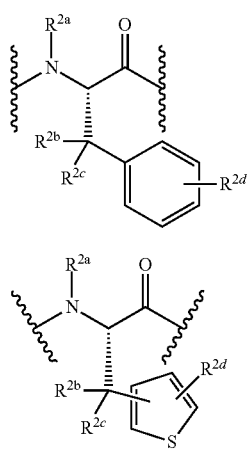

(IIIa)

(IIIb)

wherein $R^{2a}$ is selected from the group consisting of H, methyl, ethyl, propyl, isopropyl, $C_1$-$C_2$ alkyl $C_3$-$C_7$ cycloalkyl and aryl $C_1$-$C_2$ alkyl;

$R^{2b}$ and $R^{2c}$ are, independently, selected from the group consisting of H, methyl, ethyl, propyl; and isopropyl, with the proviso that at least one of $R^{2b}$ and $R^{2c}$ is H;

$R^{2d}$ represents from 0 to 3 substituents, each such substituent being, independently, selected from the group consisting of H, Cl, F, Br, CN, $CF_3$, OH, $OR^{2e}$ and $C_1$-$C_4$ alkyl;

$R^{2e}$ is selected from the group consisting of methyl, ethyl, propyl, and isopropyl; and $Xaa_3$ is an amino acid residue of Formula Va:

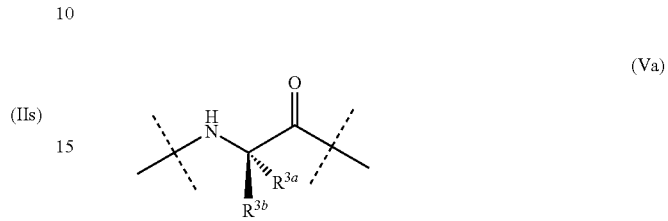

(Va)

wherein $R^{3a}$ is selected from the group consisting of H and $C_1$-$C_4$ alkyl;

$R^{3b}$ is selected from the group consisting of H, and —$(CH_2)_{n3a}$—$X^{3a}$;

n3a is 1 to 5;

$X^{3a}$ is selected from the group consisting of H, and $NR^{3c}R^{3d}$;

$R^{3c}$ and $R^{3d}$ are independently selected from a group consisting of H, $C_1$-$C_8$ alkyl, and —(C=N)—$NH_2$;

$R^{3a}$ and $R^{3b}$ can be linked to form a cyclic structure;

or $R^{3a}$ and $R^{3b}$ can be linked with a heteroatom selected from the group consisting of N, O, and S, to form a heterocyclic structure;

and $Xaa_4$ is an amino acid residue of Formula VIa:

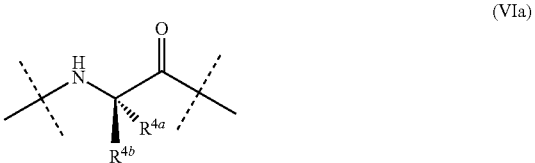

(VIa)

wherein $R^{4a}$ is selected from the group consisting of H, $C_1$-$C_8$ alkyl which may be substituted with a moiety selected from the group consisting of OH, and $CO_2R^{4c}$;

$R^{4b}$ is selected from the group consisting of H and methyl;

$R^{4c}$ is selected from the group consisting of H, and $C_1$-$C_3$alkyl; and and $Xaa_5$ is an amino acid residue of Formula VII:

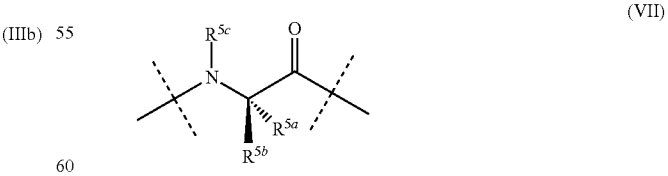

(VII)

wherein $R^{5a}$ is $(CH_2)_{n5a}$—$X^{5a}$;

n5a is 1 to 6;

$X^{5a}$ is selected from the group consisting of H, $NH_2$, and a $C_{4-7}$ amine-containing aliphatic heterocyclic ring;

$R^{5b}$ is selected from the group consisting of H and methyl;

$R^{5c}$ is selected from the group consisting of H and methyl;

and wherein $R^{5c}$ and $R^{5a}$ can combine to form a four to six membered heterocyclic ring wherein said heterocyclic ring may have from 0 to 2 substituents, each such substituent being independently selected from the group consisting of OH, F, $C_1$-$C_4$ alkyl, —NHC(=NH)NH$_2$, aryl and $NR^{5e}R^{5f}$;

$R^{5e}$ is selected from the group consisting of H, $C_1$-$C_4$ alkyl, —C(=O)(CH$_2$)$_{n5b}$—$X^{5b}$, and —CH$_2$(CH$_2$)$_{n5c}$—$X^{5b}$;

$R^{5f}$ is selected from the group consisting of H, $C_1$-$C_4$ alkyl, and —CH$_2$(CH$_2$)$_{n5d}$—$X^{5c}$;

n5b is selected from the group consisting of 1, 2, 3, and 4;

n5c and n5d are independently selected from the group consisting of 2, 3, and 4;

$X^{5b}$ and $X^{5c}$ are independently selected from the group consisting of H, and $NR^{5g}R^{5h}$;

$R^{5g}$ and $R^{5h}$ are independently selected from a group consisting of H, and $C_1$-$C_4$ alkyl and Xaa$_6$ is an amino acid residue of Formula VIIIa:

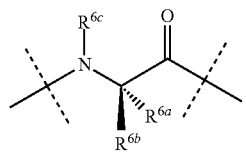

(VIIIa)

wherein $R^{6a}$ is selected from the group consisting of $C_1$-$C_8$ alkyl, aryl $C_1$-$C_4$ alkyl, $C_4$-$C_7$ cycloalkyl $C_1$-$C_4$ alkyl, and $C_4$-$C_7$ cycloalkyl, wherein said $C_1$-$C_8$ alkyl and $C_4$-$C_7$ cycloalkyl may be substituted with a moiety selected from the group consisting of OH, and O($C_1$-$C_4$ alkyl);

$R^{6b}$ is H;

$R^{6c}$ is selected from the group consisting of H, and $C_1$-$C_4$alkyl; and

Xaa$_7$ is an amino acid residue of Formula IX:

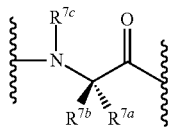

(IXa)

wherein $R^{7a}$ is selected from the group consisting of $C_1$-$C_4$ alkyl, $C_3$-$C_7$ cycloalkyl, 2-thienyl, and $C_1$-$C_4$ alkyl substituted with OH;

$R^{7b}$ is H, and 2-thienyl;

$R^{7c}$ is selected from a group consisting of H, and methyl; and

Xaa$_8$ is an amino acid residue of Formula Xa:

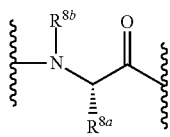

(Xa)

wherein $R^{8a}$ is (CH$_2$)$_{m8a}$—$X^{8a}$;

$m^{8a}$=1-5;

$X^{8a}$ is selected from the group consisting of H, NH$_2$, and —NHC(=NH)NH$_2$;

$R^{8b}$ is selected from the group consisting of H and methyl; and

Xaa$_9$ is selected from the group consisting of a direct bond, and an amino acid residue of Formula XIa,

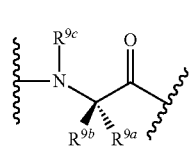

(XIa)

wherein $R^{9a}$ is selected from the group consisting of $C_1$-$C_5$ alkyl, and $C_4$-$C_7$ cycloalkyl;

$R^{9b}$ is selected from the group consisting of H, and $C_1$-$C_5$alkyl;

and wherein $R^{9a}$ and $R^{9b}$ can form a 5-7 membered cycloalkyl ring;

$R^{9c}$ is selected from the group consisting of H, and methyl;

and

Z is $NHR^{11b}$;

wherein $R^{11b}$ is selected from the group consisting of H, $C_1$-$C_8$ alkyl, $C_4$-$C_8$ cycloalkyl, $C_7$-$C_{12}$ bicycloalkyl, $C_7$-$C_{12}$ cycloalkylaryl, and $C_1$-$C_4$ alkyl $C_4$-$C_8$ cycloakyl.

The sequences of the preferred novel NPR-B agonists of the invention are provided herein in typical peptide sequence format, as would be understood by the ordinary skilled artisan. For example, the three-letter code of a conventional amino acid, or the abbreviation for a non-conventional amino acid, indicates the presence of a particular amino acid in a specified position in the sequence of the molecule, each amino acid being connected to the next and/or previous amino acid by a hyphen. The hyphen, which represents a chemical bond, typically an amide bond, removes OH from the 1-carboxyl group of the amino acid when it is placed right of the abbreviation, and removes H from the 2-amino group (or the only present amino group in case of amino acids lacking a 2-amino group, e.g., Bal) of the amino acid when it is placed on the left of the abbreviation. It is understood that both modifications can apply to one amino acid.

In the case of additional functional groups in the side chains of conventional or non-conventional amino acids, only the 2-amino and/or the 1-carboxy group is used for the formation of peptide bonds.

The C-termini of the novel NPR-B agonists described herein are shown in explicit form by adding either OH, NH2 or an abbreviation for a specific terminating amine separated by a hyphen on the right of the abbreviation of the C-terminal amino acid.

These specific terminating amines are provided in Table 2 as full formulas and similar conventions with regard to hyphens and its structure in a peptide context apply to them, e.g.,

3791=NH$_2$—CH(CH$_2$—CH$_3$)—CH$_2$—CH$_3$

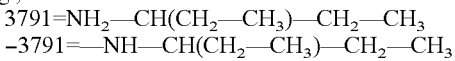

The N-termini of the novel peptides described herein are shown in explicit form by adding either H (for a free N-terminus), or an abbreviation for a specific terminating carboxylic acid, sulfonic acid or another terminating group in front of the symbol of the N-terminal amino acid.

These specific terminating carboxylic acids, sulfonic acids or other terminating groups like alkyl are provided in Table 2 as full formulas and similar conventions with regard to hyphens and its structure in a peptide context apply to them, e.g., Hex=Hexanoic acid
Hex-=Hexanoyl-.

For conventional amino acids and some non-conventional amino acids, a 3-letter code was used where the first letter indicates the stereochemistry of the C-alpha-atom. For example, a capital first letter indicates that the L-form of the amino acid is present in the peptide sequence, while a lower case first letter indicates that the D-form of the correspondent amino acid is present in the peptide sequence.

In preferred embodiments of the present invention, the novel NPR-B agonist is an 8-13 amino acid peptide having a sequence as set forth in Table 3. The agonistic activity of the preferred compounds is also provided in Table 3 and was categorized based upon the following conventions:

| NPR-B activation (assayed with GTM-3 Cells) | | |
| --- | --- | --- |
| $EC_{50}$ | Emax (CNP = 100%) | Group |
| ≤1 µM | >50% | A |
| ≤5 µM | >20% | B |
| ≤15 µM | >10% | C |

The agonistic activity data of each compound was checked first to determine whether it fulfills the criteria for the activity group A. If it did not fulfill the criteria for activity group A, it was checked for group B criteria. If it did not fulfill the criteria for activity group A or activity group B, it was finally checked for group C criteria. If it did not fulfill the criteria for activity group C, it was not included in Table 3.

All examples in Table 3 are linear peptides written in three letter code where applicable. For non-conventional amino acids and other chemical moieties the abbreviations which are listed in Table 2 were used. In vitro activities reported in Table 3 resulted from experiments performed according to the methods described in Example 4.

In certain embodiments of the NPR-B agonists of the invention, in the compound of Formula I:

B will be selected from a bond, Occ, Oct, Sbt, 1319, 1320, and 5587;

$Xaa_1$ will be selected from Gly, AR-201-49, AR-201-68, ala, abu, his, aze, pro, pip, thz, thi, asn, ser, His, Ala, Ser, Bal, Sni, Az3, and Gab;

$Xaa_2$ will be selected from Phe, Pcf, Nmf, Pbf, Pff, Pmf, Eaa. Mcf, Thk, and Mtf;

$Xaa_3$ will be selected from Gly, Aib, Ebc, a conventional D-α-amino acid, and a non-conventional D-α-amino acid, and will preferably be selected from Gly, Fhy, Apc, Egz, Aib, Ebc, ala, lys, lys(Me2), arg, leu, nle, ctb, abu, AR-385-12, Egg, ser, orn, orn(Me2), and dap($Me_2$);

$Xaa_4$ will be selected from Leu, Nva, Nie, Hle, Npg, Cha, and Ala;

$Xaa_5$ will be selected from Lys, Orn, Hly, Hpa, Dab, Arg, N(alkyl) derivatives of any of the preceding amino acids, Nmk, Hpr, Pro, Tfp, Apr, Eaz, Hyp, Tap, Tap(G), Tap(Bal), Tap(Et), Tap(Ae), Tap(Ap), Amp, Pip, and Chy;

$Xaa_6$ will be selected from a bond, Leu, Ile, Nml, Tap, Npg, SH-158, Dap(Me2), Cpg, Val, Tbg, Chg, Hle, Nle, and N(alkyl) derivatives of any of the preceding amino acids;

$Xaa_7$ will be selected from Asp, Val, BB725, BB727, Ser, Thr, and Cya;

$Xaa_8$ will be selected from Arg, Nmr, Pro, Eaz, Pca, Orn, Fhz, Har, Nar, Cyr, Mmr, Dmr, Bmr, Opy, and N(alkyl) derivatives of any of the preceding amino acids;

$Xaa_9$ will be selected from Ile, Tbg, Deg, Egz, Aml, 1860, Che, Nmi, Leu, Val, Ecb, and Eca; and $Xaa_{10}$ will be selected from a bond, Ser and a N(alkyl) derivative thereof.

TABLE 3

Preferred compounds according to the present invention and their agonistic activity in in vitro assays.

| Structure | JAL | SEQ ID NO: | (M + H)⁺ in MS [amu] | Activity (group) |
| --- | --- | --- | --- | --- |
| Hex-Ebe-pro-Phe-Gly-Leu-Pro-Ile-Asp-Arg-Ile-Ser-Ebe-$NH_2$; | JAL-0533 | 19 | 1446 | C |
| Hex-Ebe-pro-Phe-Gly-Leu-Lys-Ile-Asp-Arg-Ile-Ser-Ebe-$NH_2$; | JAL-0534 | 20 | 1477 | C |
| Hex-Ser-ala-Phe-Gly-Leu-Lys-Leu-Asp-Arg-Ile-Ser-Ser-$NH_2$; | JAL-0535 | 21 | 1391 | C |
| Hex-Ala-ala-Phe-Gly-Leu-Lys-Leu-Asp-Arg-Ile-Ser-Ala-$NH_2$; | JAL-0536 | 22 | 1359 | B |
| Hex-Ala-ala-Phe-Gly-Leu-Lys-Leu-Asp-Arg-Ile-Ser-Gly-$NH_2$; | JAL-0537 | 23 | 1345 | C |
| Hex-Gly-ala-Phe-Gly-Leu-Lys-Leu-Asp-Arg-Ile-Ser-Ala-$NH_2$; | JAL-0538 | 24 | 1345 | B |
| Hex-Gly-ala-Phe-Gly-Leu-Lys-Leu-Asp-Arg-Ile-Ser-Gly-$NH_2$; | JAL-0539 | 25 | 1331 | B |
| Hex-Ebe-ala-Phe-Gly-Leu-Lys-Leu-Asp-Arg-Ile-Ser-$NH_2$; | JAL-0540 | 26 | 1334 | C |
| Hex-Ebe-ala-Phe-Gly-Leu-Lys-Leu-Asp-Arg-Ile-$NH_2$; | JAL-0541 | 27 | 1247 | C |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Hex-Gab-Phe-Gly-Leu-Lys-Leu-Asp-Arg-Ile-Ser-Ebe-NH$_2$; | JAL-0542 | 28 | 1348 | C |
| Hex-Mam-Phe-Gly-Leu-Lys-Leu-Asp-Arg-Ile-Ser-Ebe-NH$_2$; | JAL-0543 | 29 | 1396 | C |
| Hex-Gly-ala-Phe-Gly-Leu-Lys-Leu-Asp-Arg-Ile-NH$_2$; | JAL-0631 | 30 | 1188 | C |
| Hex-Ala-ala-Phe-Gly-Leu-Lys-Leu-Asp-Arg-Ile-NH$_2$; | JAL-0632 | 31 | 1202 | C |
| Hex-Ser-ala-Phe-Gly-Leu-Lys-Leu-Asp-Arg-Ile-NH$_2$; | JAL-0633 | 32 | 1218 | C |
| Hex-Pro-ala-Phe-Gly-Leu-Lys-Leu-Asp-Arg-Ile-NH$_2$; | JAL-0634 | 33 | 1228 | C |
| Hex-ala-ala-Phe-Gly-Leu-Lys-Leu-Asp-Arg-Ile-NH$_2$; | JAL-0635 | 34 | 1201 | C |
| Hex-Gly-pro-Phe-Gly-Leu-Lys-Leu-Asp-Arg-Ile-NH$_2$; | JAL-0636 | 35 | 1213 | C |
| Hex-Ser-pro-Phe-Gly-Leu-Lys-Leu-Asp-Arg-Ile-NH$_2$; | JAL-0638 | 36 | 1241 | C |
| Hex-Mam-Phe-Gly-Leu-Lys-Leu-Asp-Arg-Ile-NH$_2$; | JAL-0647 | 37 | 1193 | C |
| Hex-Pam-Phe-Gly-Leu-Lys-Leu-Asp-Arg-Ile-NH$_2$; | JAL-0648 | 38 | 1193 | C |
| Hex-Mpe-Phe-Gly-Leu-Lys-Leu-Asp-Arg-Ile-NH$_2$; | JAL-0649 | 39 | 1193 | C |
| Hex-Ppe-Phe-Gly-Leu-Lys-Leu-Asp-Arg-Ile-NH$_2$; | JAL-0650 | 40 | 1193 | C |
| Hex-Inp-Phe-Gly-Leu-Lys-Leu-Asp-Arg-Ile-NH$_2$; | JAL-0651 | 41 | 1171 | C |
| Hex-Acp-Phe-Gly-Leu-Lys-Leu-Asp-Arg-Ile-NH$_2$; | JAL-0652 | 42 | 1210 | C |
| Hex-Fir-Phe-Gly-Leu-Lys-Leu-Asp-Arg-Ile-NH$_2$; | JAL-0653 | 43 | 1199 | C |
| Hex-Nip-Phe-Gly-Leu-Lys-Leu-Asp-Arg-Ile-NH$_2$; | JAL-0654 | 44 | 1171 | C |
| Hex-Eah-Phe-Gly-Leu-Lys-Leu-Asp-Arg-Ile-NH$_2$; | JAL-0656 | 45 | 1228 | C |
| Hex-Fio-Phe-Gly-Leu-Lys-Leu-Asp-Arg-Ile-NH$_2$; | JAL-0657 | 46 | 1185 | C |
| Hex-ala-ala-Phe-Gly-Leu-Lys-Leu-Asp-Arg-Eca-NH$_2$; | JAL-0692 | 47 | 1199 | C |
| 1339-ala-ala-Phe-Gly-Leu-Lys-Leu-Asp-Arg-Ile-NH$_2$; | JAL-0693 | 48 | 1255 | C |
| Occ-pro-Phe-Gly-Leu-Lys-Leu-Asp-Arg-Ile-NH$_2$; | JAL-0694 | 49 | 1184 | C |
| 1339-pro-Phe-Gly-Leu-Lys-Leu-Asp-Arg-Ile-NH$_2$; | JAL-0695 | 50 | 1210 | C |
| 1320-pro-Phe-Gly-Leu-Lys-Leu-Asp-Arg-Ile-NH$_2$; | JAL-0696 | 51 | 1218 | C |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Occ-Nip-Phe-Gly-Leu-Lys-Leu-Asp-Arg-Ile-NH$_2$; | JAL-0697 | 52 | 1198 | B |
| Occ-ala-ala-Phe-Gly-Leu-Lys-Leu-Asp-Arg-Ile-NH$_2$; | JAL-0701 | 53 | 1229 | B |
| 1340-ala-ala-Phe-Gly-Leu-Lys-Leu-Asp-Arg-Ile-NH$_2$; | JAL-0703 | 54 | 1241 | C |
| Hex-Tnc-Phe-Gly-Leu-Lys-Leu-Asp-Arg-Ile-NH$_2$; | JAL-0713 | 55 | 1186 | C |
| Hex-ala-ala-Phe-Gly-Leu-Lys-Leu-Asp-Arg-Chg-NH$_2$; | JAL-0718 | 56 | 1227 | C |
| Hex-ala-ala-Phe-Paa-Lys-Leu-Asp-Arg-Ile-NH$_2$; | JAL-0731 | 57 | 1157 | C |
| Occ-ala-Phe-Gly-Leu-Lys-Leu-Asp-Arg-Ile-NH$_2$; | JAL-0738 | 58 | 1158 | C |
| Occ-thz-Phe-Gly-Leu-Lys-Leu-Asp-Arg-Ile-NH$_2$; | JAL-0739 | 59 | 1202 | C |
| Occ-aze-Phe-Gly-Leu-Lys-Leu-Asp-Arg-Ile-NH$_2$; | JAL-0740 | 60 | 1170 | C |
| Occ-Az3-Phe-Gly-Leu-Lys-Leu-Asp-Arg-Ile-NH$_2$; | JAL-0742 | 61 | 1170 | C |
| Occ-Sni-Phe-Gly-Leu-Lys-Leu-Asp-Arg-Ile-NH$_2$; | JAL-0743 | 62 | 1198 | B |
| Occ-Rni-Phe-Gly-Leu-Lys-Leu-Asp-Arg-Ile-NH$_2$; | JAL-0744 | 63 | 1198 | C |
| Occ-ala-ala-Phe-Gly-Leu-Lys-Leu-Asp-Arg-2137; | JAL-0748 | 64 | 1199 | C |
| Occ-ala-ala-Phe-Gly-Leu-Lys-Leu-Asp-Arg-3816; | JAL-0749 | 65 | 1201 | C |
| Occ-ala-ala-Phe-Gly-Leu-Lys-Leu-Asp-Arg-3806; | JAL-0751 | 66 | 1187 | C |
| Occ-ala-ala-Phe-Gly-Leu-Lys-Leu-Asp-Arg-565; | JAL-0752 | 67 | 1200 | B |
| Occ-ala-ala-Phe-Gly-Leu-Lys-Leu-Asp-Arg-2797; | JAL-0754 | 68 | 1252 | B |
| Occ-val-Phe-Gly-Leu-Lys-Leu-Asp-Arg-Ile-NH$_2$; | JAL-0756 | 69 | 1186 | C |
| Occ-tbg-Phe-Gly-Leu-Lys-Leu-Asp-Arg-Ile-NH$_2$; | JAL-0758 | 70 | 1200 | C |
| Occ-Amcp-Phe-Gly-Leu-Lys-Leu-Asp-Arg-Ile-NH$_2$; | JAL-0760 | 71 | 1184 | C |
| Occ-Ebc-Phe-Gly-Leu-Lys-Leu-Asp-Arg-Ile-NH$_2$; | JAL-0761 | 72 | 1170 | C |
| Occ-abu-Phe-Gly-Leu-Lys-Leu-Asp-Arg-Ile-NH$_2$; | JAL-0762 | 73 | 1171 | C |
| Occ-ser-Phe-Gly-Leu-Lys-Leu-Asp-Arg-Ile-NH$_2$; | JAL-0763 | 74 | 1174 | C |
| Occ-ala-ala-Phe-Gly-Leu-Lys-leu-Asp-Arg-Ile-NH$_2$; | JAL-0769 | 75 | 1229 | C |
| Occ-ala-ala-Phe-Gly-Leu-Lys-Ile-Asp-Arg-Ile-NH$_2$; | JAL-0770 | 76 | 1229 | C |

TABLE 3-continued

Preferred compounds according to the present invention and their agonistic activity in in vitro assays.

| Structure | JAL | SEQ ID NO: | (M + H)$^+$ in MS [amu] | Activity (group) |
|---|---|---|---|---|
| Occ-ala-ala-Phe-Gly-Leu-Lys-Val-Asp-Arg-Ile-NH$_2$; | JAL-0771 | 77 | 1215 | C |
| Occ-ala-ala-Phe-Gly-Leu-Lys-Chg-Asp-Arg-Ile-NH$_2$; | JAL-0772 | 78 | 1255 | C |
| Occ-ala-ala-Phe-Gly-Leu-Lys-Nle-Asp-Arg-Ile-NH$_2$; | JAL-0775 | 79 | 1229 | C |
| Occ-ala-ala-Phe-Gly-Leu-Lys-Nml-Asp-Arg-Ile-NH$_2$; | JAL-0776 | 80 | 1243 | C |
| Occ-ala-ala-Phe-Gly-Leu-Pro-Leu-Asp-Arg-Ile-NH$_2$; | JAL-0781_01 | 81 | 1214 | B |
| Occ-ala-ala-Phe-Gly-Leu-Nmk-Leu-Asp-Arg-Ile-NH$_2$; | JAL-0782 | 82 | 1243 | C |
| 933-ala-Phe-Gly-Leu-Lys-Leu-Asp-Arg-Ile-NH$_2$; | JAL-0786 | 83 | 1208 | C |
| 1270-ala-Phe-Gly-Leu-Lys-Leu-Asp-Arg-Ile-NH$_2$; | JAL-0787 | 84 | 1160 | C |
| 4956-ala-Phe-Gly-Leu-Lys-Leu-Asp-Arg-Ile-NH$_2$; | JAL-0788 | 85 | 1144 | C |
| Occ-ala-ala-Phe-Gly-Leu-Lys-Leu-Asp-Arg-1860; | JAL-0789 | 86 | 1213 | B |
| Occ-ala-ala-Phe-Gly-Leu-Lys-Leu-Asp-Arg-504; | JAL-0790 | 87 | 1251 | C |
| Occ-ala-ala-Phe-Gly-Leu-Lys-Leu-Asp-Arg-559; | JAL-0791 | 88 | 1185 | C |
| Occ-ala-ala-Phe-Gly-Leu-Lys-Leu-Asp-Arg-3791; | JAL-0792 | 89 | 1187 | C |
| Occ-ala-ala-Phe-Gly-Leu-Lys-Leu-Asp-Arg-Che; | JAL-0797 | 90 | 1212 | B |
| Occ-ala-ala-Phe-Gly-Leu-Lys-Leu-Asp-Arg-1859; | JAL-0798 | 91 | 1211 | C |
| Occ-ala-ala-Phe-Gly-Leu-Lys-Leu-Asp-Arg-1934; | JAL-0799 | 92 | 1304 | B |
| Occ-ala-ala-Phe-Gly-Leu-Lys-Leu-Asp-Arg-1906; | JAL-0801 | 93 | 1209 | B |
| Occ-ala-ala-Phe-Gly-Leu-Lys-Leu-Asp-Arg-873; | JAL-0824 | 94 | 1192 | C |
| Occ-ala-ala-Phe-Gly-Leu-Lys-Leu-Asp-Arg-5116; | JAL-0825 | 95 | 1241 | C |
| Occ-ala-ala-Phe-Gly-Leu-Lys-Leu-Asp-Arg-5119; | JAL-0826 | 96 | 1270 | B |
| Occ-ala-ala-Phe-Gly-Leu-Lys-Leu-Asp-Arg-5118; | JAL-0831 | 97 | 1270 | C |
| Occ-ala-ala-Phe-Gly-Leu-Lys-Leu-Asp-Arg-5163; | JAL-0833 | 98 | 1227 | C |
| Occ-ala-ala-Phe-Gly-Leu-Lys-Leu-Asp-Arg-5164; | JAL-0834 | 99 | 1255 | C |
| Occ-ala-Phe-Gly-Leu-Pro-Leu-Asp-Arg-Ile-NH$_2$; | JAL-0835 | 100 | 1127 | C |

TABLE 3-continued

Preferred compounds according to the present invention and their agonistic activity in in vitro assays.

| Structure | JAL | SEQ ID NO: | (M + H)$^+$ in MS [amu] | Activity (group) |
|---|---|---|---|---|
| Occ-pro-Phe-Gly-Leu-Pro-Leu-Asp-Arg-Ile-NH$_2$; | JAL-0836 | 101 | 1153 | C |
| Occ-Sni-Phe-Gly-Leu-Pro-Leu-Asp-Arg-Ile-NH$_2$; | JAL-0837 | 102 | 1167 | C |
| Occ-ala-Phe-Gly-Leu-Lys-Leu-Asp-Arg-1860; | JAL-0839 | 103 | 1141 | B |
| Occ-ala-Phe-Gly-Leu-Lys-Leu-Asp-Arg-Che; | JAL-0840 | 104 | 1141 | C |
| Occ-ala-Phe-Gly-Leu-Lys-Leu-Asp-Arg-5121; | JAL-0841 | 105 | 1143 | C |
| Occ-ala-Phe-Gly-Leu-Pro-Ile-Asp-Arg-Ile-NH$_2$; | JAL-0894 | 106 | 1127 | C |
| Occ-ala-Phe-Gly-Leu-Pro-Nml-Asp-Arg-Ile-NH$_2$; | JAL-0895 | 107 | 1141 | B |
| Occ-ala-Phe-Gly-Leu-Pro-Npg-Asp-Arg-Ile-NH$_2$; | JAL-0896 | 108 | 1141 | C |
| Occ-ala-Phe-Gly-Leu-Hyp-Leu-Asp-Arg-Ile-NH$_2$; | JAL-0898 | 109 | 1143 | B |
| Occ-ala-Phe-Gly-Npg-Pro-Leu-Asp-Arg-Ile-NH$_2$; | JAL-0903 | 110 | 1141 | C |
| Occ-ala-Nmf-Gly-Leu-Pro-Leu-Asp-Arg-Ile-NH$_2$; | JAL-0906 | 111 | 1141 | C |
| Occ-ala-Phe-Gly-Leu-Pro-Leu-Asp-Nmr-Ile-NH$_2$; | JAL-0921 | 112 | 1141 | C |
| Occ-ala-Phe-Gly-Leu-Pro-Leu-Asn-Arg-Ile-NH$_2$; | JAL-0924 | 113 | 1127 | C |
| Occ-ala-Phe-Gly-Leu-Pro-Leu-Nva-Arg-Ile-NH$_2$; | JAL-0926 | 114 | 1111 | C |
| Occ-ala-Phe-Gly-Leu-Pro-Leu-Val-Arg-Ile-NH$_2$; | JAL-0927 | 115 | 1111 | C |
| Occ-ala-Phe-Gly-Leu-Pro-Leu-Thr-Arg-Ile-NH$_2$; | JAL-0929 | 116 | 1113 | C |
| Occ-ala-Phe-Gly-Cha-Pro-Leu-Asp-Arg-Ile-NH$_2$; | JAL-0940 | 117 | 1167 | C |
| Occ-ala-Phe-Gly-Nle-Pro-Leu-Asp-Arg-Ile-NH$_2$; | JAL-0942 | 118 | 1127 | C |
| Occ-ala-Phe-Aib-Leu-Pro-Leu-Asp-Arg-Ile-NH$_2$; | JAL-0943 | 119 | 1155 | C |
| Occ-ala-Phe-ala-Leu-Pro-Leu-Asp-Arg-Ile-NH$_2$; | JAL-0944 | 120 | 1141 | C |
| Occ-ala-Phe-Ebc-Leu-Pro-Leu-Asp-Arg-Ile-NH$_2$; | JAL-0945 | 121 | 1153 | C |
| Occ-ala-Mcf-Gly-Leu-Pro-Leu-Asp-Arg-Ile-NH$_2$; | JAL-0946 | 122 | 1161 | C |
| Occ-Sar-Phe-Gly-Leu-Pro-Leu-Asp-Arg-Ile-NH$_2$; | JAL-0950 | 123 | 1127 | C |
| Occ-Gly-Phe-Gly-Leu-Pro-Leu-Asp-Arg-Ile-NH$_2$; | JAL-0951 | 124 | 1113 | C |
| Occ-aze-Phe-Gly-Leu-Pro-Leu-Asp-Arg-Ile-NH$_2$; | JAL-0953 | 125 | 1139 | B |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-ala-Nmf-Gly-Leu-Pro-Nml-Asp-Arg-Ile-NH$_2$; | JAL-0954 | 126 | 1155 | B |
| Occ-pro-Phe-Gly-Leu-Pro-Nml-Asp-Arg-Ile-NH$_2$; | JAL-0955_01 | 127 | 1167 | B |
| Occ-Sni-Phe-Gly-Leu-Pro-Nml-Asp-Arg-Ile-NH$_2$; | JAL-0956 | 128 | 1181 | B |
| Occ-pro-Nmf-Gly-Leu-Pro-Nml-Asp-Arg-Ile-NH$_2$; | JAL-0957 | 129 | 1181 | C |
| Occ-Sni-Nmf-Gly-Leu-Pro-Nml-Asp-Arg-Ile-NH$_2$; | JAL-0958_01 | 130 | 1195 | B |
| Occ-ala-Phe-Gly-Leu-Pro-Hle-Asp-Arg-Ile-NH$_2$; | JAL-0959 | 131 | 1141 | C |
| Occ-ala-Phe-Gly-Leu-Amp-Leu-Asp-Arg-Ile-NH$_2$; | JAL-0962 | 132 | 1141 | C |
| Occ-ala-Phe-Gly-Leu-Chy-Leu-Asp-Arg-Ile-NH$_2$; | JAL-0964 | 133 | 1143 | C |
| Occ-pro-Nmf-Gly-Leu-Pro-Leu-Asp-Arg-Ile-NH$_2$; | JAL-0966 | 134 | 1167 | C |
| Occ-Sni-Nmf-Gly-Leu-Pro-Leu-Asp-Arg-Ile-NH$_2$; | JAL-0967_01 | 135 | 1181 | C |
| Occ-ala-Phe-Gly-Leu-Apr-Leu-Asp-Arg-Ile-NH$_2$; | JAL-0974 | 136 | 1142 | B |
| Occ-ala-Phe-Gly-Leu-Eay-Leu-Asp-Arg-Ile-NH$_2$; | JAL-0975 | 137 | 1204 | C |
| Occ-ala-Phe-Gly-Leu-Fpr-Leu-Asp-Arg-Ile-NH$_2$; | JAL-0978 | 138 | 1145 | C |
| Occ-ala-Phe-Gly-Leu-Dtp-Leu-Asp-Arg-Ile-NH$_2$; | JAL-0979 | 139 | 1174 | C |
| Occ-ala-Phe-Gly-Leu-Eaz-Leu-Asp-Arg-Ile-NH$_2$; | JAL-0980 | 140 | 1146 | C |
| Occ-Az3-Phe-Gly-Leu-Pro-Leu-Asp-Arg-Ile-NH$_2$; | JAL-0985 | 141 | 1139 | C |
| Occ-ala-Phe-Gly-Leu-Pro-Leu-Asp-Arg-Tbg-NH$_2$; | JAL-0989 | 142 | 1127 | C |
| Occ-ala-Phe-Gly-Leu-Pro-Leu-Ser-Arg-Ile-NH$_2$; | JAL-0992 | 143 | 1099 | C |
| Occ-ala-Phe-Gly-Leu-Pro-Leu-Hse-Arg-Ile-NH$_2$; | JAL-0993 | 144 | 1113 | C |
| Occ-ala-Phe-Gly-Ile-Pro-Leu-Asp-Arg-Ile-NH$_2$; | JAL-0995 | 145 | 1127 | C |
| Occ-ala-Phe-Gly-Nva-Pro-Leu-Asp-Arg-Ile-NH$_2$; | JAL-0996 | 146 | 1113 | C |
| Occ-ala-Phe-Gly-Hle-Pro-Leu-Asp-Arg-Ile-NH$_2$; | JAL-0998 | 147 | 1141 | C |
| Occ-ala-Thi-Gly-Leu-Pro-Leu-Asp-Arg-Ile-NH$_2$; | JAL-1000 | 148 | 1133 | C |
| Occ-ala-Pcf-Gly-Leu-Pro-Leu-Asp-Arg-Ile-NH$_2$; | JAL-1002 | 149 | 1161 | C |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-ala-Thk-Gly-Leu-Pro-Leu-Asp-Arg-Ile-NH$_2$; | JAL-1003 | 150 | 1133 | C |
| Occ-ala-Mtf-Gly-Leu-Pro-Leu-Asp-Arg-Ile-NH$_2$; | JAL-1005 | 151 | 1195 | C |
| Occ-ala-Mmf-Gly-Leu-Pro-Leu-Asp-Arg-Ile-NH$_2$; | JAL-1006 | 152 | 1141 | C |
| Occ-ala-Phe-ser-Leu-Pro-Leu-Asp-Arg-Ile-NH$_2$; | JAL-1010 | 153 | 1157 | B |
| Occ-ala-Phe-thr-Leu-Pro-Leu-Asp-Arg-Ile-NH$_2$; | JAL-1011 | 154 | 1171 | B |
| Occ-ala-Phe-val-Leu-Pro-Leu-Asp-Arg-Ile-NH$_2$; | JAL-1012 | 155 | 1169 | C |
| Occ-ala-Phe-leu-Leu-Pro-Leu-Asp-Arg-Ile-NH$_2$; | JAL-1013 | 156 | 1183 | B |
| Occ-ala-Phe-nle-Leu-Pro-Leu-Asp-Arg-Ile-NH$_2$; | JAL-1014 | 157 | 1183 | B |
| Occ-Sni-Phe-Gly-Leu-Hyp-Nml-Asp-Arg-Ile-NH$_2$; | JAL-1015 | 158 | 1197 | B |
| Occ-ala-Phe-Gly-Leu-Hyp-Nml-Asp-Arg-Ile-NH$_2$; | JAL-1016 | 159 | 1157 | B |
| Occ-ala-Phe-asn-Leu-Pro-Leu-Asp-Arg-Ile-NH$_2$; | JAL-1017 | 160 | 1184 | B |
| Occ-ala-Phe-met-Leu-Pro-Leu-Asp-Arg-Ile-NH$_2$; | JAL-1018 | 161 | 1201 | B |
| Occ-ala-Phe-abu-Leu-Pro-Leu-Asp-Arg-Ile-NH$_2$; | JAL-1019 | 162 | 1155 | B |
| Occ-ala-Phe-dap-Leu-Pro-Leu-Asp-Arg-Ile-NH$_2$; | JAL-1020 | 163 | 1156 | B |
| Occ-Sni-Phe-nle-Leu-Pro-Leu-Asp-Arg-Ile-NH$_2$; | JAL-1021 | 164 | 1223 | B |
| Occ-Sni-Nmf-nle-Leu-Pro-Leu-Asp-Arg-Ile-NH$_2$; | JAL-1022 | 165 | 1237 | B |
| Occ-Sni-Phe-nle-Leu-Hyp-Leu-Asp-Arg-Ile-NH$_2$; | JAL-1024 | 166 | 1239 | A |
| Occ-ala-Phe-nle-Leu-Hyp-Leu-Asp-Arg-Ile-NH$_2$; | JAL-1025 | 167 | 1199 | B |
| Occ-ala-Phe-leu-Leu-Hyp-Leu-Asp-Arg-Ile-NH$_2$; | JAL-1026 | 168 | 1199 | B |
| Occ-ala-Phe-nva-Leu-Hyp-Leu-Asp-Arg-Ile-NH$_2$; | JAL-1027 | 169 | 1185 | B |
| Occ-ala-Phe-phe-Leu-Hyp-Leu-Asp-Arg-Ile-NH$_2$; | JAL-1028 | 170 | 1029 | B |
| Occ-ala-Phe-ctb-Leu-Hyp-Leu-Asp-Arg-Ile-NH$_2$; | JAL-1029 | 171 | 1244 | B |
| Occ-ala-Phe-lys-Leu-Pro-Leu-Asp-Arg-Ile-NH$_2$; | JAL-1030 | 172 | 1198 | B |
| Occ-ala-Phe-arg-Leu-Pro-Leu-Asp-Arg-Ile-NH$_2$; | JAL-1031 | 173 | 1226 | B |
| Occ-ala-Phe-his-Leu-Pro-Leu-Asp-Arg-Ile-NH$_2$; | JAL-1032 | 174 | 1207 | B |

TABLE 3-continued

Preferred compounds according to the present invention and their agonistic activity in in vitro assays.

| Structure | JAL | SEQ ID NO: | (M + H)$^+$ in MS [amu] | Activity (group) |
|---|---|---|---|---|
| Ac-Hgl-ala-ala-Phe-Gly-Leu-Pro-Leu-Asp-Arg-Ile-NH$_2$; | JAL-1033 | 175 | 1255 | B |
| Ac-hgl-ala-ala-Phe-Gly-Leu-Pro-Leu-Asp-Arg-Ile-NH$_2$; | JAL-1034 | 176 | 1255 | B |
| Occ-pip-Phe-Gly-Leu-Pro-Leu-Asp-Arg-Ile-NH$_2$; | JAL-1035 | 177 | 1167 | C |
| Occ-ala-Phe-Gly-Leu-Pro-Leu-cDR-Ile-NH$_2$; | JAL-1037 | 178 | 1153 | C |
| Occ-ala-Phe-Gly-Leu-Bhp-Leu-Asp-Arg-Ile-NH$_2$; | JAL-1038 | 179 | 1234 | C |
| Occ-ala-Phe-leu-Leu-Pro-Nml-Asp-Arg-Ile-NH$_2$; | JAL-1039 | 180 | 1196 | A |
| Occ-Sni-Phe-leu-Leu-Pro-Nml-Asp-Arg-Ile-NH$_2$; | JAL-1040 | 181 | 1236 | A |
| Occ-Sni-Phe-leu-Leu-Hyp-Nml-Asp-Arg-Ile-NH$_2$; | JAL-1041 | 182 | 1253 | A |
| Occ-ala-Phe-leu-Leu-Hyp-Nml-Asp-Arg-Ile-NH$_2$; | JAL-1042 | 183 | 1213 | A |
| Occ-ala-Pcf-leu-Leu-Hyp-Nml-Asp-Arg-Ile-NH$_2$; | JAL-1043 | 184 | 1247 | A |
| Occ-ala-Phe-nle-Leu-Hyp-Nml-Asp-Arg-Ile-NH$_2$; | JAL-1044 | 185 | 1213 | A |
| Occ-ala-Phe-Gly-Leu-Pro-Npl-Asp-Arg-Ile-NH$_2$; | JAL-1045 | 186 | 1169 | C |
| Occ-ala-Phe-arg-Leu-Hyp-Leu-Asp-Arg-Ile-NH$_2$; | JAL-1047 | 187 | 1242 | A |
| Occ-ala-Phe-asp-Leu-Hyp-Leu-Asp-Arg-Ile-NH$_2$; | JAL-1048 | 188 | 1201 | C |
| Occ-ala-Phe-glu-Leu-Hyp-Leu-Asp-Arg-Ile-NH$_2$; | JAL-1049 | 189 | 1215 | C |
| Occ-ala-Pcf-leu-Leu-Hyp-Leu-Asp-Arg-Ile-NH$_2$; | JAL-1050 | 190 | 1233 | A |
| Occ-ala-Pmf-leu-Leu-Hyp-Leu-Asp-Arg-Ile-NH$_2$; | JAL-1051 | 191 | 1213 | B |
| Occ-ala-Nmf-leu-Leu-Hyp-Leu-Asp-Arg-Ile-NH$_2$; | JAL-1052 | 192 | 1213 | A |
| Occ-pro-Phe-leu-Leu-Hyp-Leu-Asp-Arg-Ile-NH$_2$; | JAL-1053 | 193 | 1225 | A |
| Occ-pip-Phe-leu-Leu-Hyp-Leu-Asp-Arg-Ile-NH$_2$; | JAL-1054 | 194 | 1239 | A |
| Occ-ala-Phe-lys-Leu-Hyp-Nml-Asp-Arg-Ile-NH$_2$; | JAL-1060 | 195 | 1228 | A |
| Occ-ala-Phe-orn-Leu-Hyp-Nml-Asp-Arg-Ile-NH$_2$; | JAL-1061 | 196 | 1214 | A |
| Occ-ala-Phe-lys-Leu-Pro-Nml-Asp-Arg-Ile-NH$_2$; | JAL-1065 | 197 | 1212 | B |
| Occ-ala-Phe-lys-Leu-Pro-Nml-Ala-Arg-Ile-NH$_2$; | JAL-1068 | 198 | 1168 | C |
| Occ-ala-Phe-arg-Leu-Pro-Nml-Asp-Arg-Ile-NH$_2$; | JAL-1075 | 199 | 1240 | B |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-ala-Nmf-arg-Leu-Pro-Nml-Asp-Arg-Ile-NH$_2$; | JAL-1076 | 200 | 1254 | B |
| Occ-pip-Nmf-arg-Leu-Pro-Nml-Asp-Arg-Ile-NH$_2$; | JAL-1077 | 201 | 1294 | A |
| Occ-pip-Phe-arg-Leu-Pro-Nml-Asp-Arg-Ile-NH$_2$; | JAL-1078 | 202 | 1280 | A |
| Occ-ala-Nmf-arg-Leu-Hyp-Nml-Asp-Arg-Ile-NH$_2$; | JAL-1085 | 203 | 1270 | A |
| Occ-ala-Phe-arg-Leu-Hyp-Nml-Asp-Arg-Ile-NH$_2$; | JAL-1086 | 204 | 1256 | A |
| Occ-pip-Phe-arg-Leu-Hyp-Nml-Asp-Arg-Ile-NH$_2$; | JAL-1087 | 205 | 1296 | A |
| Occ-ala-Phe-arg-Leu-Tfp-Leu-Asp-Arg-Ile-NH$_2$; | JAL-1114 | 206 | 1244 | B |
| Occ-ala-Phe-Gly-Leu-Tfp-Leu-Asp-Arg-Ile-NH$_2$; | JAL-1115 | 207 | 1145 | B |
| Occ-ala-Pbf-arg-Leu-Hyp-Leu-Asp-Arg-Ile-NH$_2$; | JAL-1116 | 208 | 1321 | A |
| Occ-ala-Phe-dab-Leu-Pro-Leu-Asp-Arg-Ile-NH$_2$; | JAL-1120 | 209 | 1169 | B |
| Occ-ala-Phe-nar-Leu-Pro-Leu-Asp-Arg-Ile-NH$_2$; | JAL-1121 | 210 | 1212 | B |
| Occ-ala-Phe-gdp-Leu-Pro-Leu-Asp-Arg-Ile-NH$_2$; | JAL-1122 | 211 | 1198 | B |
| Oct-ala-Phe-arg-Leu-Hyp-Leu-Asp-Arg-Ile-NH$_2$; | JAL-1156_02 | 212 | 1227 | B |
| Oct-pip-Phe-arg-Leu-Hyp-Leu-Asp-Arg-Ile-NH$_2$; | JAL-1157_02 | 213 | 1267 | C |
| Occ-ala-Phe-arg-(KM-116-167)-Nml-Asp-Arg-Ile-NH$_2$; | JAL-1159 | 214 | 1226 | C |
| 832-Phe-arg-Leu-Hyp-Nml-Asp-Arg-Ile-NH$_2$; | JAL-1214 | 215 | 1241 | B |
| Occ-ala-Phe-arg-Leu-Hyp-Ile-Asp-Arg-Ile-NH$_2$; | JAL-1224 | 216 | 1242 | B |
| Occ-ala-Phe-arg-Leu-Hyp-Npg-Asp-Arg-Ile-NH$_2$; | JAL-1225 | 217 | 1256 | A |
| Occ-ala-Phe-arg-Leu-Hyp-Tbg-Asp-Arg-Ile-NH$_2$; | JAL-1226 | 218 | 1242 | C |
| Occ-ala-Phe-arg-Leu-Hyp-Ebe-Asp-Arg-Ile-NH$_2$; | JAL-1227 | 219 | 1246 | B |
| Occ-ala-Phe-arg-Leu-Lys-Nml-Asp-Arg-Ile-NH$_2$; | JAL-1228 | 220 | 1271 | B |
| Occ-ala-Phe-arg-Leu-Nmk-Nml-Asp-Arg-Ile-NH$_2$; | JAL-1229 | 221 | 1285 | B |
| Occ-ala-Phe-arg-Leu-Nma-Nml-Asp-Arg-Ile-NH$_2$; | JAL-1230 | 222 | 1228 | C |
| Occ-ala-Phe-arg-Leu-Sar-Nml-Asp-Arg-Ile-NH$_2$; | JAL-1231 | 223 | 1214 | B |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-ala-Phe-arg-Nva-Hyp-Nml-Asp-Arg-Ile-NH$_2$; | JAL-1232 | 224 | 1242 | B |
| Occ-ala-Phe-arg-Ebe-Hyp-Nml-Asp-Arg-Ile-NH$_2$; | JAL-1233 | 225 | 1260 | B |
| 6014-Phe-arg-Leu-Hyp-Nml-Asp-Arg-IleNH$_2$; | JAL-1237 | 226 | 1239 | B |
| 6015-Phe-arg-Leu-Hyp-Nml-Asp-Arg-Ile-NH$_2$; | JAL-1238 | 227 | 1239 | B |
| 6054-Phe-arg-Leu-Hyp-Nml-Asp-Arg-Ile-NH$_2$; | JAL-1239 | 228 | 1241 | B |
| 6056-Phe-arg-Leu-Hyp-Nml-Asp-Arg-Ile-NH$_2$; | JAL-1240 | 229 | 1239 | B |
| 6057-Phe-arg-Leu-Hyp-Nml-Asp-Arg-Ile-NH$_2$; | JAL-1241 | 230 | 1259 | B |
| 6058-Phe-arg-Leu-Hyp-Nml-Asp-Arg-Ile-NH$_2$; | JAL-1242 | 231 | 1259 | B |
| 6059-Phe-arg-Leu-Hyp-Nml-Asp-Arg-Ile-NH$_2$; | JAL-1243 | 232 | 1274 | B |
| 832-Nmf-arg-Leu-Hyp-Nml-Asp-Arg-Ile-NH$_2$; | JAL-1244 | 233 | 1255 | C |
| 832-Phe-leu-Leu-Hyp-Nml-Asp-Arg-Ile-NH$_2$; | JAL-1245 | 234 | 1196 | B |
| 832-Phe-arg-Leu-Hyp-Leu-Asp-Arg-Ile-NH$_2$; | JAL-1246 | 235 | 1225 | C |
| Oct-Sni-FrL-Hyp-Leu-Asp-Arg-Ile-NH$_2$; | JAL-1248 | 236 | 1268 | B |
| Occ-ala-Phe-Gly-Leu-Tap-Leu-Asp-Arg-Ile-NH$_2$; | JAL-1249 | 237 | 1142 | A |
| Occ-ala-Phe-arg-Leu-Tap-Leu-Asp-Arg-Ile-NH$_2$; | JAL-1250 | 238 | 1241 | A |
| Occ-ala-Phe-leu-Leu-Tap-Asp-Arg-Ile-NH$_2$; | JAL-1251 | 239 | 1198 | A |
| Occ-ala-Phe-ser-Leu-Hyp-Nml-Asp-Arg-Ile-NH$_2$; | JAL-1252 | 240 | 1187 | A |
| Occ-Sni-Phe-ser-Leu-Hyp-Nml-Asp-Arg-Ile-NH$_2$; | JAL-1253 | 241 | 1227 | B |
| Occ-Sni-Phe-lys-Leu-Hyp-Nml-Asp-Arg-Ile-NH$_2$; | JAL-1254 | 242 | 1268 | A |
| Occ-Sni-Phe-arg-Leu-Hyp-Nml-Asp-Arg-Ile-NH$_2$; | JAL-1255 | 243 | 1296 | A |
| Occ-Sni-Mpa-leu-Leu-Hyp-Nml-Asp-Arg-Ile-NH$_2$; | JAL-1256 | 244 | 1254 | C |
| Occ-Sni-Ppa-leu-Leu-Hyp-Nml-Asp-Arg-Ile-NH$_2$; | JAL-1257 | 245 | 1254 | C |
| (6071-OH)-Phe-arg-Leu-Hyp-Nml-Asp-Arg-Ile-NH$_2$; | JAL-1259 | 246 | 1230 | C |
| (6072-OH)-Phe-arg-Leu-Hyp-Nml-Asp-Arg-Ile-NH$_2$; | JAL-1260 | 247 | 1258 | B |
| 5587-Phe-arg-Leu-Hyp-Nml-Asp-Arg-Ile-NH$_2$; | JAL-1261 | 248 | 1214 | C |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-ala-Phe-Gly-Leu-Tap(2Me)-Leu-Asp-Arg-Ile-NH$_2$; | JAL-1262 | 249 | 1170 | B |
| Occ-ala-Phe-arg-Leu-Tap(2Me)-Leu-Asp-Arg-Ile-NH$_2$; | JAL-1263 | 250 | 1269 | B |
| Occ-ala-Phe-leu-Leu-Tap(2Me)-Leu-Asp-Arg-Ile-NH$_2$; | JAL-1264 | 251 | 1226 | B |
| Occ-Sni-Phe-orn-Leu-Hyp-Nml-Asp-Arg-Ile-NH$_2$; | JAL-1265 | 252 | 1254 | A |
| Occ-Sni-Opa-leu-Leu-Hyp-Nml-Asp-Arg-Ile-NH$_2$; | JAL-1266 | 253 | 1254 | B |
| Occ-ala-Nmf-leu-Leu-Hyp-Nml-Asp-Arg-Ile-NH$_2$; | JAL-1267 | 254 | 1227 | A |
| Occ-ala-Nmf-lys-Leu-Hyp-Nml-Asp-Arg-Ile-NH$_2$; | JAL-1268 | 255 | 1242 | B |
| Occ-ala-Nmf-orn-Leu-Hyp-Nml-Asp-Arg-Ile-NH$_2$; | JAL-1269 | 256 | 1228 | B |
| Occ-ala-Phe-Gly-Leu-Gup-Leu-Asp-Arg-Ile-NH$_2$; | JAL-1270 | 257 | 1184 | B |
| Occ-ala-Phe-arg-Leu-Gup-Leu-Asp-Arg-Ile-NH$_2$; | JAL-1271 | 258 | 1283 | B |
| Occ-ala-Phe-leu-Leu-Gup-Leu-Asp-Arg-Ile-NH$_2$; | JAL-1272 | 259 | 1240 | B |
| Oct-Sar-Phe-arg-Leu-Hyp-Nml-Asp-Arg-Ile-NH$_2$; | JAL-1273 | 260 | 1242 | B |
| Oct-aze-Phe-arg-Leu-Hyp-Nml-Asp-Arg-Ile-NH$_2$; | JAL-1274 | 261 | 1254 | B |
| Oct-Az3-Phe-arg-Leu-Hyp-Nml-Asp-Arg-Ile-NH$_2$; | JAL-1275 | 262 | 1254 | B |
| Occ-ala-Phe-leu-Leu-Eal-Nml-Asp-Arg-Ile-NH$_2$; | JAL-1281_01 | 263 | 1198 | B |
| Occ-ala-Phe-Gly-Leu-Eal-Nml-Asp-Arg-Ile-NH$_2$; | JAL-1282 | 264 | 1144 | C |
| Occ-ala-Phe-leu-Leu-Hyp-(SH-158)-Asp-Arg-Ile-NH$_2$; | JAL-1283 | 265 | 1227 | A |
| Occ-ala-Phe-arg-Leu-Hyp-(SH-158)-Asp-Arg-Ile-NH$_2$; | JAL-1284 | 266 | 1271 | A |
| Occ-Sni-Phe-dap(Me2)-Leu-Hyp-Nml-Asp-Arg-Ile-NH$_2$; | JAL-1287 | 267 | 1254 | A |
| Occ-ala-Phe-orn(Me2)-Leu-Hyp-Nml-Asp-Arg-Ile-NH$_2$; | JAL-1288 | 268 | 1242 | A |
| Occ-Sni-Phe-orn(Me2)-Leu-Hyp-Nml-Asp-Arg-Ile-NH$_2$; | JAL-1289 | 269 | 1282 | A |
| (AR-201-48)-arg-Leu-Hyp-Nml-Asp-Arg-Ile-NH$_2$; | JAL-1291 | 270 | 1242 | C |
| (AR-201-49)-Phe-arg-Leu-Hyp-Nml-Asp-Arg-Ile-NH$_2$; | JAL-1292 | 271 | 1257 | B |
| (AR-201-48)-leu-Leu-Hyp-Nml-Asp-Arg-Ile-NH$_2$; | JAL-1293 | 272 | 1199 | C |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| (AR-201-49)-Phe-leu-Leu-Hyp-Nml-Asp-Arg-Ile-NH$_2$; | JAL-1294 | 273 | 1214 | A |
| Occ-Sni-Phe-leu-Leu-Tap-Nml-Asp-Arg-Ile-NH$_2$; | JAL-1295 | 274 | 1252 | A |
| Occ-ala-Phe-leu-Leu-Tap-Nml-Asp-Arg-Ile-NH$_2$; | JAL-1296 | 275 | 1212 | A |
| Oct-Sni-Phe-arg-Leu-Hyp-Nml-Asp-Arg-Ile-NH$_2$; | JAL-1297 | 276 | 1282 | A |
| 6182-ala-Phe-arg-Leu-Hyp-Nml-Asp-Arg-Ile-NH$_2$; | JAL-1298 | 277 | 1280 | B |
| Oct-Sni-Phe-leu-Leu-Hyp-Nml-Asp-Arg-Ile-NH$_2$; | JAL-1302 | 278 | 1239 | A |
| Occ-ala-Phe-arg-Leu-Hyp-Nml-Asp-Arg-Tbg-NH$_2$; | JAL-1305 | 279 | 1256 | A |
| Occ-ala-Phe-arg-Leu-Hyp-Nml-Asp-Arg-Eca-NH$_2$; | JAL-1306 | 280 | 1254 | B |
| Occ-ala-Phe-arg-Leu-Hyp-Dap(Me2)-Asp-Arg-Ile-NH$_2$; | JAL-1314 | 281 | 1242 | B |
| Occ-ala-Phe-arg-Dap(Me2)-Hyp-Nml-Asp-Arg-Ile-NH$_2$; | JAL-1315 | 282 | 1257 | C |
| (AR-201-54)-Phe-arg-Leu-Hyp-Nml-Asp-Arg-Ile-NH$_2$; | JAL-1316 | 283 | 1277 | B |
| Occ-Sni-Phe-arg-Leu-Tap-Nml-Asp-Arg-Ile-NH$_2$; | JAL-1317 | 284 | 1295 | A |
| Occ-Sni-Phe-orn-Leu-Tap-Nml-Asp-Arg-Ile-NH$_2$; | JAL-1318 | 285 | 1253 | A |
| Occ-Sni-Phe-nle-Leu-Tap-Nml-Asp-Arg-Ile-NH$_2$; | JAL-1319 | 286 | 1252 | B |
| Occ-Sni-Phe-Gly-Leu-Tap-Nml-Asp-Arg-Ile-NH$_2$; | JAL-1320 | 287 | 1196 | A |
| Occ-Sni-Phe-leu-Leu-Tap(Ac)-Nml-Asp-Arg-Ile-NH$_2$; | JAL-1321 | 288 | 1294 | B |
| Occ-Sni-Phe-leu-Leu-Tap(G)-Nml-Asp-Arg-Ile-NH$_2$; | JAL-1322 | 289 | 1309 | A |
| Occ-Sni-Phe-leu-Leu-Tap(Bal)-Nml-Asp-Arg-Ile-NH$_2$; | JAL-1323 | 290 | 1323 | A |
| 6059(O)-Phe-arg-Leu-Hyp-Nml-Asp-Arg-Ile-NH$_2$; | JAL-1324 | 291 | 1291 | B |
| Occ-Sni-Phe-dap(Me2)-Leu-Tap-Nml-Asp-Arg-Ile-NH$_2$; | JAL-1325 | 292 | 1253 | A |
| Oct-Sni-Phe-leu-Leu-Tap-Nml-Asp-Arg-Ile-NH$_2$; | JAL-1326 | 293 | 1238 | A |
| Occ-ala-Phe-arg-Leu-Hyp-Nml-Asp-Orn-Ile-NH$_2$; | JAL-1327 | 294 | 1214 | B |
| Occ-ala-Phe-leu-Leu-Hyp-Nml-Asp-Orn-Ile-NH$_2$; | JAL-1328 | 295 | 1171 | B |
| Occ-ala-Phe-arg-Leu-Hyp-Nml-Glu-Arg-Ile-NH$_2$; | JAL-1329 | 296 | 1270 | C |
| Occ-ala-Phe-leu-Leu-Hyp-Nml-Glu-Arg-Ile-NH$_2$; | JAL-1330 | 297 | 1227 | B |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-ala-Phe-arg-Leu-Hyp-Nml-Val-Arg-Ile-NH$_2$; | JAL-1331 | 298 | 1240 | B |
| Occ-ala-Phe-leu-Leu-Hyp-Nml-Val-Arg-Ile-NH$_2$; | JAL-1332 | 299 | 1197 | A |
| Occ-ala-Phe-leu-Leu-Hyp-Nml-Val-Arg-Ile-NH$_2$; | JAL-1332_02 | 300 | 1197 | B |
| Occ-ala-Phe-arg-Leu-Hyp-Nml-Thr-Arg-Ile-NH$_2$; | JAL-1333 | 301 | 1242 | B |
| Occ-ala-Phe-leu-Leu-Hyp-Nml-Thr-Arg-Ile-NH$_2$; | JAL-1334 | 302 | 1199 | B |
| Occ-ala-Phe-leu-Leu-Hyp-Nml-Asp-Arg-Eca-NH$_2$; | JAL-1335 | 303 | 1211 | B |
| Occ-ala-Phe-Fhy-Leu-Hyp-Nml-Asp-Arg-Ile-NH$_2$; | JAL-1336 | 304 | 1240 | A |
| Occ-ala-Phe-Egg-Leu-Hyp-Nml-Asp-Arg-Ile-NH$_2$; | JAL-1337 | 305 | 1254 | B |
| Occ-ala-Phe-Apc-Leu-Hyp-Nml-Asp-Arg-Ile-NH$_2$; | JAL-1338 | 306 | 1226 | A |
| (AR-201-58)-Phe-arg-Leu-Hyp-Nml-Asp-Arg-Ile-NH$_2$; | JAL-1339 | 307 | 1254 | C |
| (AR-201-59)-Phe-arg-Leu-Hyp-Nml-Asp-Arg-Ile-NH$_2$; | JAL-1340 | 308 | 1267 | C |
| (AR-201-62)-Phe-arg-Leu-Hyp-Nml-Asp-Arg-Ile-NH$_2$; | JAL-1341 | 309 | 1253 | B |
| (AR-201-69)-Phe-arg-Leu-Hyp-Nml-Asp-Arg-Ile-NH$_2$; | JAL-1342 | 310 | 1317 | B |
| Sbt-Sni-Phe-arg-Leu-Hyp-Nml-Asp-Arg-Ile-NH$_2$; | JAL-1343 | 311 | 1309 | A |
| Nbt-Sni-Phe-arg-Leu-Hyp-Nml-Asp-Arg-Ile-NH$_2$; | JAL-1344 | 312 | 1309 | B |
| Sbt-ala-Phe-arg-Leu-Hyp-Nml-Asp-Arg-Ile-NH$_2$; | JAL-1345 | 313 | 1269 | C |
| Nbt-ala-Phe-arg-Leu-Hyp-Nml-Asp-Arg-Ile-NH$_2$; | JAL-1346 | 314 | 1269 | C |
| Occ-ala-Phe-dap(Me2)-Leu-Tap-Nml-Asp-Arg-Ile-NH$_2$; | JAL-1347 | 315 | 1213 | B |
| Occ-Sni-Phe-leu-Leu-Tap(Et2)-Nml-Asp-Arg-Ile-NH$_2$; | JAL-1348 | 316 | 1308 | B |
| Occ-Sni-Phe-leu-Leu-Tap(Et)-Nml-Asp-Arg-Ile-NH$_2$; | JAL-1349 | 317 | 1280 | A |
| Occ-ala-Phe-Apc-Leu-Tap-Nml-Asp-Arg-Ile-NH$_2$; | JAL-1350 | 318 | 1265 | A |
| Occ-Sni-Phe-Apc-Leu-Tap-Nml-Asp-Arg-Ile-NH$_2$; | JAL-1351 | 319 | 1265 | A |
| Occ-ala-Phe-leu-Leu-Hyp-Nml-Asp-Arg-Tbg-NH$_2$; | JAL-1352 | 320 | 1213 | A |
| Occ-ala-Phe-leu-Leu-Hyp-Nml-Asp-Arg-Egz-NH$_2$; | JAL-1358 | 321 | 1225 | A |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Occ-ala-Phe-arg-Leu-Hyp-Nml-Asp-Arg-Egz-NH$_2$; | JAL-1359 | 322 | 1268 | B |
| Occ-ala-Phe-leu-Leu-Hyp-Nml-Asp-Nle-Ile-NH$_2$; | JAL-1360 | 323 | 1170 | C |
| Occ-ala-Phe-arg-Leu-Hyp-Nml-Asp-Nle-Ile-NH$_2$; | JAL-1361 | 324 | 1213 | C |
| Occ-ala-Phe-arg-Leu-Hyp-Nml-Ile-Arg-Ile-NH$_2$; | JAL-1362 | 325 | 1254 | C |
| Occ-ala-Phe-leu-Leu-Hyp-Nml-Ile-Arg-Ile-NH$_2$; | JAL-1363 | 326 | 1211 | B |
| Occ-ala-Phe-arg-Leu-Hyp-Oic-Asp-Arg-Ile-NH$_2$; | JAL-1364 | 327 | 1280 | B |
| Occ-ala-Phe-arg-Leu-Hyp-Pip-Asp-Arg-Ile-NH$_2$; | JAL-1365 | 328 | 1240 | C |
| Occ-ala-Phe-leu-Leu-Hyp-Pip-Asp-Arg-Ile-NH$_2$; | JAL-1366 | 329 | 1197 | B |
| Occ-ala-Phe-leu-Leu-Hyp-Dap(Me2)-Asp-Arg-Ile-NH$_2$; | JAL-1367 | 330 | 1200 | A |
| Occ-ala-Phe-leu-Dap(Me2)-Hyp-Nml-Asp-Arg-Ile-NH$_2$; | JAL-1368 | 331 | 1214 | B |
| Oct-Sni-Phe-dap(Me2)-Leu-Tap-Nml-Asp-Arg-Ile-NH$_2$; | JAL-1369 | 332 | 1239 | A |
| Occ-Sni-Phe-dap(6263)2-Leu-Tap-Nml-Asp-Arg-Ile-NH$_2$; | JAL-1370 | 333 | 1311 | B |
| Occ-Sni-Phe-leu-Leu-Tap(Ae)-Nml-Asp-Arg-Ile-NH$_2$; | JAL-1371 | 334 | 1295 | A |
| Occ-Sni-Phe-leu-Leu-Tap(Ap)-Nml-Asp-Arg-Ile-NH$_2$; | JAL-1372 | 335 | 1309 | A |
| (AR-201-58)-Phe-leu-Leu-Hyp-Nml-Asp-Arg-Ile-NH$_2$; | JAL-1373 | 336 | 1211 | B |
| (AR-201-62)-Phe-leu-Leu-Hyp-Nml-Asp-Arg-Ile-NH$_2$; | JAL-1374 | 337 | 1210 | B |
| (AR-201-69)-Phe-leu-Leu-Hyp-Nml-Asp-Arg-Ile-NH$_2$; | JAL-1375 | 338 | 1274 | B |
| (AR-201-72)-Phe-leu-Leu-Hyp-Nml-Asp-Arg-Ile-NH$_2$; | JAL-1376 | 339 | 1227 | C |
| (AR-201-72)-Phe-arg-Leu-Hyp-Nml-Asp-Arg-Ile-NH$_2$; | JAL-1377 | 340 | 1270 | C |
| (AR-201-73)-Phe-leu-Leu-Hyp-Nml-Asp-Arg-Ile-NH$_2$; | JAL-1378 | 341 | 1216 | B |
| (AR-201-73)-Phe-arg-Leu-Hyp-Nml-Asp-Arg-Ile-NH$_2$; | JAL-1379 | 342 | 1259 | B |
| (AR-201-68)-Phe-leu-Leu-Hyp-Nml-Asp-Arg-Ile-NH$_2$; | JAL-1380 | 343 | 1274 | A |
| (AR-201-68)-Phe-arg-Leu-Hyp-Nml-Asp-Arg-Ile-NH$_2$; | JAL-1381 | 344 | 1317 | B |
| Sbt-Sni-Phe-leu-Leu-Hyp-Nml-Asp-Arg-Ile-NH$_2$; | JAL-1382 | 345 | 1266 | A |
| Nbt-Sni-Phe-leu-Leu-Hyp-Nml-Asp-Arg-Ile-NH$_2$; | JAL-1383 | 346 | 1266 | B |

TABLE 3-continued

Preferred compounds according to the present invention and their agonistic activity in in vitro assays.

| Structure | JAL | SEQ ID NO: | (M + H)⁺ in MS [amu] | Activity (group) |
|---|---|---|---|---|
| Occ-ala-Phe-leu-Leu-Hyp-Oic-Asp-Arg-Ile-NH$_2$; | JAL-1386 | 347 | 1237 | B |
| Occ-ala-Phe-arg-Leu-Hyp-Pro-Asp-Arg-Ile-NH$_2$; | JAL-1387 | 348 | 1226 | C |
| Occ-ala-Phe-arg-Leu-Hyp-Aze-Asp-Arg-Ile-NH$_2$; | JAL-1393 | 349 | 1212 | C |
| Occ-ala-Phe-arg-Leu-Hyp-Eat-Asp-Arg-Ile-NH$_2$; | JAL-1394 | 350 | 1244 | C |
| Occ-ala-Phe-arg-Leu-Hyp-Eaz-Asp-Arg-Ile-NH$_2$; | JAL-1395 | 351 | 1244 | C |
| Occ-ala-Phe-arg-Leu-Hyp-Tic-Asp-Arg-Ile-NH$_2$; | JAL-1396 | 352 | 1288 | B |
| Occ-Sni-Phe-leu-Leu-Hyp-Nml-Val-Arg-Ile-NH$_2$; | JAL-1398 | 353 | 1237 | A |
| Oct-Sni-Phe-leu-Leu-Hyp-Nml-Val-Arg-Ile-NH$_2$; | JAL-1399 | 354 | 1223 | B |
| Occ-Sni-Phe-dap(Me2)-Leu-Hyp-Nml-Val-Arg-Ile-NH$_2$; | JAL-1400 | 355 | 1238 | C |
| Occ-Sni-Phe-leu-Leu-Tap-Nml-Val-Arg-Ile-NH$_2$; | JAL-1401 | 356 | 1236 | A |
| Oct-Sni-Phe-dap(Me2)-Leu-Hyp-Nml-Val-Arg-Ile-NH$_2$; | JAL-1402 | 357 | 1224 | B |
| Occ-Sni-Phe-dap(Me2)-Leu-Tap-Nml-Val-Arg-Ile-NH$_2$; | JAL-1403 | 358 | 1237 | A |
| Oct-Sni-Phe-leu-Leu-Tap-Nml-Val-Arg-Ile-NH$_2$; | JAL-1404 | 359 | 1222 | B |
| Oct-Sni-Phe-dap(Me2)-Leu-Tap-Nml-Val-Arg-Ile-NH$_2$; | JAL-1405 | 360 | 1223 | A |
| Occ-ala-Phe-Apc(Me)-Met-glu--Leu-Hyp-Nml-Asp-Arg-Ile-NH$_2$; | JAL-1406 | 361 | 1240 | A |
| Occ-ala-Phe-Apc(Et)-Glu-thr--Leu-Hyp-Nml-Asp-Arg-Ile-NH$_2$; | JAL-1407 | 362 | 1254 | A |
| Occ-ala-Phe-Apc(Ae)-Ala-glu--Leu-Hyp-Nml-Asp-Arg-Ile-NH$_2$; | JAL-1408 | 363 | 1269 | B |
| Occ-ala-Phe-leu-Leu-Hyp-Nml-Asp-Arg-Aib-NH$_2$; | JAL-1413 | 364 | 1185 | B |
| Occ-ala-Phe-leu-Leu-Hyp-Nml-Asp-Arg-Aml-NH$_2$; | JAL-1414 | 365 | 1227 | A |
| Occ-ala-Phe-leu-Leu-Hyp-Nml-Asp-Arg-Deg-NH$_2$; | JAL-1416 | 366 | 1213 | A |
| Occ-ala-Phe-leu-Leu-Hyp-Nml-Asp-Nmr-Ile-NH$_2$; | JAL-1417 | 367 | 1227 | A |
| Occ-ala-Phe-leu-Leu-Hyp-Nml-Asp-Pro-Ile-NH$_2$; | JAL-1418 | 368 | 1254 | B |
| Occ-ala-Phe-leu-Leu-Hyp-Nml-Tbg-Arg-Ile-NH$_2$; | JAL-1420 | 369 | 1211 | C |
| Occ-ala-Phe-leu-Leu-Hyp-Nml-Chg-Arg-Ile-NH$_2$; | JAL-1421 | 370 | 1237 | C |
| Occ-ala-Phe-leu-Leu-Hyp-Nml-Cpa-Arg-Ile-NH$_2$; | JAL-1424 | 371 | 1195 | C |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Oct-Sni-Phe-dap(Me2)-Leu-Hyp-Nml-Asp-Arg-Ile-NH$_2$; | JAL-1429 | 372 | 1240 | A |
| Miy-Hgl-ala-Phe-arg-Leu-Hyp-Nml-Asp-Arg-Ile-NH$_2$; | JAL-1430 | 373 | 1561 | A |
| Miy-Gab-Hgl-ala-Phe-arg-Leu-Hyp-Nml-Asp-Arg-Ile-NH$_2$; | JAL-1431 | 374 | 1647 | C |
| Ac-Miy-Gab-Hgl-ala-Phe-arg-Leu-Hyp-Nml-Asp-Arg-Ile-NH$_2$; | JAL-1432 | 375 | 1730 | C |
| Occ-ala-Phe-arg-Leu-Hyp-Nml-Asp-Pro-Ile-NH$_2$; | JAL-1434 | 376 | 1198 | B |
| Occ-ala-Phe-Apc-Leu-Hyp-Nml-Asp-Pro-Ile-NH$_2$; | JAL-1435 | 377 | 1167 | B |
| Occ-Sni-Phe-leu-Leu-Hyp-Nml-Asp-Pro-Ile-NH$_2$; | JAL-1436 | 378 | 1194 | B |
| Occ-ala-Phe-leu-Leu-Hyp-Nml-Asp-Aze-Ile-NH$_2$; | JAL-1437 | 379 | 1140 | B |
| Occ-ala-Phe-leu-Leu-Hyp-Nml-Asp-Pip-Ile-NH$_2$; | JAL-1438 | 380 | 1168 | B |
| Occ-ala-Phe-leu-Leu-Hyp-Nml-Asp-Hyp-Ile-NH$_2$; | JAL-1441 | 381 | 1170 | C |
| Occ-ala-Phe-leu-Leu-Hyp-Nml-Asp-Eaz-Ile-NH$_2$; | JAL-1442 | 382 | 1173 | B |
| Occ-ala-Phe-leu-Leu-Hyp-Nml-Asp-Cpp-Ile-NH$_2$; | JAL-1443 | 383 | 1167 | B |
| Occ-ala-Phe-leu-Leu-Tap-Nml-Asp-Pro-Ile-NH$_2$; | JAL-1450 | 384 | 1153 | B |
| Occ-ala-Phe-Apc-Leu-Hyp-Nml-Asp-Pro-Ile-NH$_2$; | JAL-1451 | 385 | 1207 | B |
| Occ-ala-Phe-Apc-Leu-Tap-Nml-Asp-Pro-Ile-NH$_2$; | JAL-1452 | 386 | 1166 | A |
| Occ-ala-Phe-dap(Me2)-Leu-Tap-Nml-Asp-Pro-Ile-NH$_2$; | JAL-1453 | 387 | 1154 | A |
| Occ-ala-Phe-Egz-Leu-Tap-Nml-Asp-Arg-Ile-NH$_2$; | JAL-1454 | 388 | 1224 | A |
| Occ-ala-Phe-leu-Leu-Hyp-Nml-Asp-Eay-Ile-NH$_2$; | JAL-1456 | 389 | 1230 | C |
| Occ-ala-Phe-leu-Leu-Hyp-Nml-Asp-Egz-Ile-NH$_2$; | JAL-1457 | 390 | 1182 | C |
| Occ-ala-Phe-leu-Leu-Hyp-Nml-Asp-Apc-Ile-NH$_2$; | JAL-1458 | 391 | 1183 | B |
| Occ-ala-Phe-leu-Leu-Hyp-Nml-Asp-Tap-Ile-NH$_2$; | JAL-1459 | 392 | 1169 | C |
| Occ-ala-Phe-dap(6238)2-Leu-Tap-Nml-Asp-Arg-Ile-NH$_2$; | JAL-1460 | 393 | 1380 | B |
| Occ-ala-Phe-dap(6238)-Leu-Tap-Nml-Asp-Arg-Ile-NH$_2$; | JAL-1461 | 394 | 1282 | B |
| Occ-ala-Phe-dap(3846)2-Leu-Tap-Nml-Asp-Arg-Ile-NH$_2$; | JAL-1462 | 395 | 1345 | B |
| Occ-ala-Phe-dap(1464)-Leu-Tap-Nml-Asp-Arg-Ile-NH$_2$; | JAL-1463 | 396 | 1255 | A |

TABLE 3-continued

Preferred compounds according to the present invention and their agonistic activity in in vitro assays.

| Structure | JAL | SEQ ID NO: | (M + H)$^+$ in MS [amu] | Activity (group) |
|---|---|---|---|---|
| Occ-Sni-Phe-leu-Leu-Hyp-Nml-Asp-Pro-558; | JAL-1464 | 397 | 1162 | B |
| Occ-Sni-Phe-leu-Leu-Hyp-Nml-Asp-Pro-Ile-OH; | JAL-1474 | 398 | 1194 | C |
| Occ-Sni-Phe-leu-Leu-Hyp-Nml-Asp-Pro-Ile-(NH-CH$_3$; | JAL-1475 | 399 | 1207 | B |
| Occ-ala-Phe-leu-Leu-Hyp-Nml-Asp-Chy-Ile-NH$_2$; | JAL-1476 | 400 | 1170 | B |
| Occ-ala-Phe-leu-Leu-Hyp-Nml-Asp-H3p-Ile-NH$_2$; | JAL-1477 | 401 | 1170 | B |
| Occ-ala-Phe-leu-Leu-Hyp-Nml-Asp-Dhp-Ile-NH$_2$; | JAL-1479 | 402 | 1152 | B |
| Occ-ala-Phe-leu-Leu-Hyp-Nml-Asp-Udp-Ile-NH$_2$; | JAL-1482 | 403 | 1143 | B |
| Occ-ala-Phe-leu-Leu-Hyp-Nml-Asp-Bhk-Ile-NH$_2$; | JAL-1483 | 404 | 1199 | B |
| Occ-Sni-Nif-leu-Leu-Hyp-Nml-Asp-Arg-Ile-NH$_2$; | JAL-1486 | 405 | 1298 | B |
| Occ-Sni-Pff-leu-Leu-Hyp-Nml-Asp-Arg-Ile-NH$_2$; | JAL-1487 | 406 | 1271 | A |
| Occ-Sni-Pmy-leu-Leu-Hyp-Nml-Asp-Arg-Ile-NH$_2$; | JAL-1488 | 407 | 1283 | B |
| Occ-Sni-Tyr-leu-Leu-Hyp-Nml-Asp-Arg-Ile-NH$_2$; | JAL-1489 | 408 | 1269 | C |
| Occ-Sni-Bmf-leu-Leu-Hyp-Nml-Asp-Arg-Ile-NH$_2$; | JAL-1490 | 409 | 1267 | C |
| Occ-Sni-Eay-leu-Leu-Hyp-Nml-Asp-Arg-Ile-NH$_2$; | JAL-1491 | 410 | 1279 | B |
| Occ-Sni-Paf-leu-Leu-Hyp-Nml-Asp-Arg-Ile-NH$_2$; | JAL-1492 | 411 | 1268 | B |
| Occ-Sni-Pcf-leu-Leu-Hyp-Nml-Asp-Arg-Ile-NH$_2$; | JAL-1493 | 412 | 1287 | A |
| Occ-Sni-Pmf-leu-Leu-Hyp-Nml-Asp-Arg-Ile-NH$_2$; | JAL-1494 | 413 | 1267 | A |
| Occ-Sni-Eaa-leu-Leu-Hyp-Nml-Asp-Arg-Ile-NH$_2$; | JAL-1496 | 414 | 1322 | A |
| Occ-Sni-Phe-leu-Leu-Hyp-Nml-Asp-Pro-2118; | JAL-1506 | 415 | 1210 | B |
| Occ-Sni-Phe-leu-Leu-Hyp-Nml-Asp-Pro-2906; | JAL-1508 | 416 | 1134 | C |
| Occ-Sni-Phe-leu-Leu-Hyp-Nml-Asp-Pro-1381; | JAL-1509 | 417 | 1164 | B |
| Occ-Sni-Phe-leu-Leu-Hyp-Nml-Asp-Pro-1381; | JAL-1509_02 | 418 | 1164 | B |
| Occ-Sni-Phe-leu-Leu-Hyp-Nml-Asp-Pro-1860; | JAL-1510 | 419 | 1176 | A |
| Occ-Sni-Phe-leu-Leu-Hyp-Nml-Asp-Pro-1906 | JAL-1511 | 420 | 1174 | B |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-leu-Leu-Hyp-Nml-Asp-Pro-Che; | JAL-1512_02 | 421 | 1176 | A |
| Occ-Sni-Phe-leu-Leu-Hyp-Nml-Asp-Pro-5121 | JAL-1513 | 422 | 1178 | C |
| Occ-Sni-Phe-Ala-Leu-Hyp-Nml-Asp-Arg-Ile-NH$_2$; | JAL-1553 | 423 | 1211 | C |
| Occ-Sni-Phe-Leu-Leu-Hyp-Nml-Asp-Arg-Ile-NH$_2$; | JAL-1554 | 424 | 1253 | B |
| Occ-Sni-Phe-Apc-Leu-Hyp-Nml-Asp-Arg-Ile-NH$_2$; | JAL-1555 | 425 | 1266 | A |
| Occ-ala-Phe-leu-Leu-Hyp-Nml-(BB725)-Arg-Ile-NH$_2$; | JAL-1556 | 426 | 1224 | A |
| Occ-ala-Phe-leu-Leu-Hyp-Nml-(BB726)-Arg-Ile-NH$_2$; | JAL-1557 | 427 | 1238 | C |
| Occ-ala-Phe-leu-Leu-Hyp-Nml-(BB727)-Arg-Ile-NH$_2$; | JAL-1558 | 428 | 1238 | A |
| Occ-Sni-Phe-leu-Leu-Tap-Nml-Asp-Pro-Ile-NH$_2$; | JAL-1559 | 429 | 1194 | A |
| Occ-Sni-Phe-Gly-Leu-Tap-Nml-Asp-Pro-Ile-NH$_2$; | JAL-1560 | 430 | 1138 | B |
| Occ-Sni-Phe-Apc-Leu-Tap-Nml-Asp-Pro-Ile-NH$_2$; | JAL-1561 | 431 | 1207 | A |
| Occ-Sni-Phe-leu-Leu-Tap-Nml-Asp-Pro-Che; | JAL-1568 | 432 | 1176 | A |
| Occ-Sni-Phe-leu-Leu-Hyp-Nml-Asp-Arg-Nmi-NH$_2$; | JAL-1569 | 433 | 1267 | A |
| Occ-Sni-Phe-leu-Leu-Hyp-Nml-Asp-Nmr-Ile-NH$_2$; | JAL-1570 | 434 | 1267 | B |
| Occ-Sni-Phe-leu-Nml-Hyp-Nml-Asp-Arg-Ile-NH$_2$; | JAL-1572 | 435 | 1267 | C |
| Occ-Sni-Nmf-leu-Leu-Hyp-Nml-Asp-Arg-Ile-NH$_2$; | JAL-1573 | 436 | 1267 | A |
| Occ-Sni-Phe-nml-Leu-Hyp-Nml-Asp-Arg-Ile-NH$_2$; | JAL-1574 | 437 | 1267 | C |
| Occ-Sni-Phe-dap(Me2)-Leu-Hyp-Nml-Asp-Arg-Nmi-NH$_2$; | JAL-1575 | 438 | 1268 | C |
| Occ-Sni-Phe-dap(Me2)-Leu-Hyp-Nml-Asp-Nmr-Ile-NH$_2$; | JAL-1576 | 439 | 1268 | A |
| Occ-Sni-Phe-dap(Me2)-Leu-Hyp-Nml-Nmd-Arg-Ile-NH$_2$; | JAL-1577 | 440 | 1268 | C |
| Occ-Sni-Phe-dap(Me2)-Nml-Hyp-Nml-Asp-Arg-Ile-NH$_2$; | JAL-1578 | 441 | 1268 | B |
| Occ-Sni-Nmf-dap(Me2)-Leu-Hyp-Nml-Asp-Arg-Ile-NH$_2$; | JAL-1579 | 442 | 1268 | A |
| Occ-Sni-Phe-dap(Me2)-Leu-Hyp-Nml-Asp-Pro-Ile-NH$_2$; | JAL-1580 | 443 | 1195 | A |
| Occ-Sni-Phe-leu-Leu-Hyp-Nml-Val-Pro-Che; | JAL-1594 | 444 | 1160 | B |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-leu-Leu-Hyp-Npg-Asp-Pro-Che; | JAL-1595 | 445 | 1177 | A |
| Occ-Sni-Phe-leu-Leu-Hyp-Ile-Asp-Pro-Che; | JAL-1596 | 446 | 1162 | B |
| Occ-Sni-Nmf-leu-Leu-Hyp-Nml-Asp-Pro-Che; | JAL-1597 | 447 | 1191 | A |
| Occ-Sni-Phe-leu-Nml-Hyp-Nml-Asp-Pro-Che; | JAL-1598 | 448 | 1190 | C |
| Occ-Sni-Eaa-leu-Leu-Hyp-Nml-Asp-Pro-Che; | JAL-1599 | 449 | 1245 | A |
| Occ-Sni-Phe-Gly-Leu-Hyp-Nml-Asp-Pro-Che; | JAL-1600 | 450 | 1120 | B |
| Occ-Sni-Phe-Apc-Leu-Hyp-Nml-Asp-Pro-Che | JAL-1601 | 451 | 1190 | B |
| Occ-Sni-Phe-Apc-Leu-Tap-Nml-Asp-Pro-Che; | JAL-1602 | 452 | 1190 | A |
| Occ-Sni-Phe-dap(Me2)-Leu-Tap-Nml-Asp-Pro-Che; | JAL-1603 | 453 | 1177 | A |
| Occ-Sni-Phe-dap(Me2)-Leu-Hyp-Nml-Asp-Pro-Che; | JAL-1604 | 454 | 1177 | A |
| 1319-Sni-Phe-leu-Leu-Hyp-Nml-Asp-Arg-Ile-NH$_2$; | JAL-1605 | 455 | 1272 | A |
| 1320-Sni-Phe-leu-Leu-Hyp-Nml-Asp-Arg-Ile-NH$_2$; | JAL-1606 | 456 | 1286 | A |
| 2553-Sni-Phe-leu-Leu-Hyp-Nml-Asp-Arg-Ile-NH$_2$; | JAL-1607 | 457 | 1302 | C |
| 4734-Sni-Phe-leu-Leu-Hyp-Nml-Asp-Arg-Ile-NH$_2$; | JAL-1609 | 458 | 1316 | B |
| 4703-Sni-Phe-leu-Leu-Hyp-Nml-Asp-Arg-Ile-NH$_2$; | JAL-1612 | 459 | 1339 | B |
| 6988-Sni-Phe-leu-Leu-Hyp-Nml-Asp-Arg-Ile-NH$_2$; | JAL-1615 | 460 | 1342 | C |
| Hex-(3421)-Sni-Phe-leu-Leu-Hyp-Nml-Asp-Arg-Ile-NH$_2$; | JAL-1616 | 461 | 1360 | B |
| 1695-Sni-Phe-leu-Leu-Hyp-Nml-Asp-Arg-Ile-NH$_2$; | JAL-1617 | 462 | 1372 | C |
| Occ-Sni-Mcf-leu-Leu-Hyp-Nml-Asp-Arg-Ile-NH$_2$; | JAL-1618 | 463 | 1287 | A |
| Occ-Sni-Pbf-leu-Leu-Hyp-Nml-Asp-Arg-Ile-NH$_2$; | JAL-1619 | 464 | 1332 | A |
| Occ-Sni-Thk-leu-Leu-Hyp-Nml-Asp-Arg-Ile-NH$_2$; | JAL-1620 | 465 | 1259 | A |
| Occ-Sni-Mtf-leu-Leu-Hyp-Nml-Asp-Arg-Ile-NH$_2$; | JAL-1621 | 466 | 1321 | A |
| Occ-Sni-Otf-leu-Leu-Hyp-Nml-Asp-Arg-Ile-NH$_2$; | JAL-1622 | 467 | 1321 | C |
| Occ-Sni-Phe-ctb-Leu-Hyp-Nml-Asp-Arg-Ile-NH$_2$; | JAL-1623 | 468 | 1299 | A |
| Occ-Sni-Phe-leu-Nle-Hyp-Nml-Asp-Arg-Ile-NH$_2$; | JAL-1624 | 469 | 1253 | A |

TABLE 3-continued

Preferred compounds according to the present invention and their agonistic activity in in vitro assays.

| Structure | JAL | SEQ ID NO: | (M + H)$^+$ in MS [amu] | Activity (group) |
|---|---|---|---|---|
| Occ-Sni-Phe-leu-Leu-Hyp-Ile-Asp-Arg-Ile-NH$_2$; | JAL-1625 | 470 | 1239 | A |
| Occ-Sni-Phe-leu-Leu-Hyp-Cpg-Asp-Arg-Ile-NH$_2$; | JAL-1626 | 471 | 1251 | A |
| Occ-Sni-Phe-leu-Leu-Hyp-Chg-Asp-Arg-Ile-NH$_2$; | JAL-1627 | 472 | 1265 | B |
| Occ-Sni-NPhe-leu-Leu-Hyp-Nml-Asp-Arg-Ile-NH$_2$; | JAL-1634 | 473 | 1253 | C |
| Occ-Sni-NHfe-leu-Leu-Hyp-Nml-Asp-Arg-Ile-NH$_2$; | JAL-1635 | 474 | 1267 | C |
| Occ-(aFL)-leu-Leu-Hyp-Nml-Asp-Arg-Ile-NH$_2$; | JAL-1636 | 475 | 1225 | B |
| Occ-(afL)-leu-Leu-Hyp-Nml-Asp-Arg-Ile-NH$_2$; | JAL-1637 | 476 | 1225 | B |
| Occ-Sni-Phe-leu-Leu-Hyp-Nml-Asp-Eaz-Che; | JAL-1638 | 477 | 1195 | A |
| Occ-Sni-Phe-leu-Leu-Hyp-Nml-Asp-Eal-Che; | JAL-1639 | 478 | 1177 | B |
| Occ-Sni-Phe-leu-Leu-Hyp-Nml-Asp-(ES-283-049); | JAL-1646 | 479 | 1163 | B |
| Occ-Sni-Phe-leu-Leu-Hyp-Nml-Glu-Pro-Che; | JAL-1652 | 480 | 1191 | B |
| Occ-Sni-Phe-leu-Leu-Tap-Nml-Val-Pro-Che; | JAL-1654 | 481 | 1160 | A |
| Occ-Sni-Phe-leu-Nle-Hyp-Nml-Asp-Pro-Che; | JAL-1657 | 482 | 1177 | A |
| 779-Sni-Phe-leu-Leu-Hyp-Nml-Asp-Arg-Ile-NH$_2$; | JAL-1659 | 483 | 1263 | B |
| 785-Sni-Phe-leu-Leu-Hyp-Nml-Asp-Arg-Ile-NH$_2$; | JAL-1660 | 484 | 1335 | C |
| 1281-Sni-Phe-leu-Leu-Hyp-Nml-Asp-Arg-Ile-NH$_2$; | JAL-1661 | 485 | 1259 | B |
| 3218-Sni-Phe-leu-Leu-Hyp-Nml-Asp-Arg-Ile-NH$_2$; | JAL-1664 | 486 | 1293 | C |
| 6013-Sni-Phe-leu-Leu-Hyp-Nml-Asp-Arg-Ile-NH$_2$; | JAL-1665 | 487 | 1285 | B |
| 5587-Sni-Phe-leu-Leu-Hyp-Nml-Asp-Arg-Ile-NH$_2$; | JAL-1666 | 488 | 1281 | A |
| 1281-G-Sni-Phe-leu-Leu-Hyp-Nml-Asp-Arg-Ile-NH$_2$; | JAL-1668 | 489 | 1316 | C |
| 1281-Bal-Sni-Phe-leu-Leu-Hyp-Nml-Asp-Arg-Ile-NH$_2$; | JAL-1669 | 490 | 1330 | C |
| Occ-(AFL)-leu-Leu-Hyp-Nml-Asp-Arg-Ile-NH$_2$; | JAL-1671 | 491 | 1225 | A |
| Occ-Sni-Phe-leu-Leu-Hyp-Nml-Asp-Apc-Che; | JAL-1672 | 492 | 1204 | C |
| Occ-Sni-Phe-leu-Leu-Hyp-Nml-NP-Che; | JAL-1673 | 493 | 1176 | C |
| Occ-Sni-Phe-leu-Leu-Tap-Nml-(BB726)-Pro-Che; | JAL-1676 | 494 | 1200 | B |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-leu-Leu-Hyp-Nml-Asp-Pca-Che; | JAL-1679 | 495 | 1192 | A |
| Occ-Sni-Phe-leu-Leu-Hyp-Nml-Asp-Arg-Che; | JAL-1680 | 496 | 1236 | A |
| Occ-Sni-Phe-leu-Leu-Tap(Ae)-Nml-Asp-Arg-Che; | JAL-1681 | 497 | 1278 | A |
| Occ-Sni-Phe-leu-Leu-Tap-Nml-Asp-Arg-Che; | JAL-1682 | 498 | 1235 | A |
| Occ-Sni-Phe-leu-Leu-Tap(Ae)-Nml-Val-Arg-Che; | JAL-1683 | 499 | 1262 | C |
| Occ-Sni-Phe-leu-Leu-Hyp-Nml-Asp-Apc(Gua)-Che; | JAL-1685 | 500 | 1248 | C |
| Occ-Sni-Phe-leu-Leu-Hyp-Nml-Asp-Apc(Gly)-Che; | JAL-1687 | 501 | 1263 | B |
| Occ-Sni-Phe-leu-Leu-Hyp-Nml-Asp-(BB394)-Che; | JAL-1694 | 502 | 1166 | C |
| Occ-Sni-Phe-leu-Leu-Hyp-Nml-Asp-(BB785)-Che; | JAL-1697 | 503 | 1192 | B |
| Occ-Sni-Hfe-leu-Leu-Hyp-Nml-Asp-Arg-Ile-NH$_2$; | JAL-1701 | 504 | 1267 | C |
| Occ-ala-Nmf-leu-Leu-Hyp-Nml-Asp-Arg-Ile-NH$_2$; | JAL-1702 | 505 | 1227 | C |
| Occ-Sni-Phe-leu-Leu-Tap-Nml-Val-Arg-Che; | JAL-1729 | 506 | 1218 | A |
| Occ-Sni-Phe-leu-Leu-Hyp-Nml-Val-Arg-Che; | JAL-1730 | 507 | 1219 | A |
| Occ-Sni-Phe-leu-Leu-Hyp-Nml-Ala-Arg-Che; | JAL-1750 | 508 | 1193 | C |
| Occ-Sni-Phe-leu-Leu-Hyp-Nml-Asn-Arg-Che; | JAL-1751 | 509 | 1236 | C |
| Occ-Sni-Phe-leu-Leu-Hyp-Nml-Ser-Arg-Che; | JAL-1752 | 510 | 1209 | A |
| Occ-Sni-Phe-leu-Leu-Hyp-Nml-Thr-Arg-Che; | JAL-1753 | 511 | 1223 | A |
| Occ-Sni-Phe-leu-Leu-Hyp-Nml-Nle-Arg-Che; | JAL-1755 | 512 | 1235 | C |
| Occ-Sni-Phe-leu-Leu-Hyp-Nml-Ble-Arg-Che; | JAL-1756 | 513 | 1235 | B |
| Occ-Sni-Phe-leu-Leu-Hyp-Nml-Thi-Arg-Che; | JAL-1758 | 514 | 1275 | C |
| Occ-Sni-Phe-leu-Leu-Hyp-Nml-Chg-Arg-Che; | JAL-1763 | 515 | 1261 | C |
| (AR-314-87)-leu-Leu-Hyp-Nml-Asp-Arg-Ile-NH$_2$; | JAL-1765-2 | 516 | 1279 | A |
| (AR-314-102)-leu-Leu-Hyp-Nml-Asp-Arg-Ile-NH$_2$; | JAL-1774 | 517 | 1239 | A |
| Occ-Sni-Phe-orn(Me2)-Leu-Hyp-Nml-Asp-Arg-Che; | JAL-1776 | 518 | 1265 | A |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-lys(Me2)-Leu-Hyp-Nml-Asp-Arg-Che; | JAL-1777 | 519 | 1279 | A |
| Occ-Sni-Phe-orn(Me2)-Leu-Hyp-Nml-Val-Arg-Che; | JAL-1778 | 520 | 1249 | B |
| Occ-Sni-Phe-lys(Me2)-Leu-Hyp-Nml-Val-Arg-Che; | JAL-1779 | 521 | 1263 | A |
| Occ-Sni-Phe-lys(Me2)-Leu-Hyp-Nml-Asp-Arg-Ile-NH$_2$; | JAL-1781 | 522 | 1296 | B |
| Occ-Sni-Phe-orn(Me2)-Leu-Hyp-Nml-Val-Arg-Ile-NH$_2$; | JAL-1782 | 523 | 1266 | A |
| Occ-Sni-Phe-lys(Me2)-Leu-Hyp-Nml-Val-Arg-Ile-NH$_2$; | JAL-1783 | 524 | 1280 | C |
| Occ-Sni-Phe-dab(Me2)-Leu-Hyp-Nml-Val-Arg-Che; | JAL-1784 | 525 | 1235 | A |
| Occ-Sni-Phe-dab(Me2)-Leu-Hyp-Nml-Asp-Arg-Ile-NH$_2$; | JAL-1785 | 526 | 1268 | A |
| Occ-Sni-Phe-dab(Me2)-Leu-Hyp-Nml-Val-Arg-Ile-NH$_2$; | JAL-1786 | 527 | 1252 | B |
| Occ-Nhpr-Phe-leu-Leu-Hyp-Nml-Asp-Arg-Ile-NH$_2$; | JAL-1798 | 528 | 1257 | B |
| Occ-Nbhp-Phe-leu-Leu-Hyp-Nml-Asp-Arg-Ile-NH$_2$; | JAL-1799 | 529 | 1273 | B |
| Occ-ser-Phe-leu-Leu-Hyp-Nml-Asp-Arg-Ile-NH$_2$; | JAL-1800 | 530 | 1229 | B |
| Occ-hse-Phe-leu-Leu-Hyp-Nml-Asp-Arg-Ile-NH$_2$; | JAL-1801 | 531 | 1243 | B |
| Gluc-Aoa-Hgl-Sni-Phe-leu-Leu-Hyp-Nml-Asp-Arg-Ile-NH$_2$; | JAL-1802 | 532 | 1503 | B |
| Gluc-Aoa-hgl-Sni-Phe-leu-Leu-Hyp-Nml-Asp-Arg-Ile-NH$_2$; | JAL-1803 | 533 | 1503 | A |
| (1913)-Hgl-Sni-Phe-leu-Leu-Hyp-Nml-Asp-Arg-Ile-NH$_2$; | JAL-1804 | 534 | 1384 | B |
| (1270)-Hgl-Sni-Phe-leu-Leu-Hyp-Nml-Asp-Arg-Ile-NH$_2$; | JAL-1805 | 535 | 1396 | C |
| (1888)-Hgl-Sni-Phe-leu-Leu-Hyp-Nml-Asp-Arg-Ile-NH$_2$; | JAL-1806 | 536 | 1428 | B |
| Occ-Hgl-Sni-Phe-leu-Leu-Hyp-Nml-Asp-Arg-Ile-NH$_2$; | JAL-1807 | 537 | 1394 | C |
| H-Adx-Hgl-Sni-Phe-leu-Leu-Hyp-Nml-Asp-Arg-Ile-NH$_2$; | JAL-1808 | 538 | 1413 | A |
| 1888-hgl-Sni-Phe-leu-Leu-Hyp-Nml-Asp-Arg-Ile-NH$_2$; | JAL-1837 | 539 | 1428 | B |
| H-Adx-hgl-Sni-Phe-leu-Leu-Hyp-Nml-Asp-Arg-Ile-NH$_2$; | JAL-1838 | 540 | 1413 | B |
| Oct-Sni-Phe-leu-Leu-Tap-Nml-Asp-Arg-Che; | JAL-1843 | 541 | 1221 | A |
| Oct-Sni-Phe-leu-Leu-Tap-Nml-Val-Pro-Che; | JAL-1844 | 542 | 1146 | B |
| Occ-Sni-Phe-orn(Me2)-Leu-Hyp-Nml-Val-Pro-Che; | JAL-1845 | 543 | 1190 | B |

TABLE 3-continued

Preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-Sni-Phe-orn(Me2)-Leu-Tap-Nml-Val-Pro-Che; | JAL-1846 | 544 | 1189 | B |
| Oct-Sni-Phe-orn(Me2)-Leu-Hyp-Nml-Val-Pro-Che; | JAL-1847 | 545 | 1176 | C |
| Oct-Sni-Phe-leu-Leu-Hyp-Nml-Val-Arg-Che; | JAL-1848 | 546 | 1206 | B |
| Oct-Sni-Phe-leu-Leu-Tap-Nml-Val-Arg-Che; | JAL-1849 | 547 | 1205 | B |
| Occ-Sni-Phe-orn(Me2)-Leu-Tap-Nml-Val-Arg-Che; | JAL-1850 | 548 | 1248 | A |
| Oct-Sni-Phe-orn(Me2)-Leu-Hyp-Nml-Val-Arg-Che; | JAL-1851 | 549 | 1235 | B |
| Occ-Sni-Phe-leu-Leu-Hyp-Nml-Bmf-Arg-Ile-NH$_2$; | JAL-1857 | 550 | 1299 | C |
| Occ-Sni-Phe-leu-Leu-Hyp-Nml-Phg-Arg-Ile-NH$_2$; | JAL-1858 | 551 | 1859 | C |
| Occ-Sni-Phe-leu-Leu-Hyp-Nml-Cpg-Arg-Ile-NH$_2$; | JAL-1859 | 552 | 1263 | B |
| Occ-Sni-Phe-leu-Leu-Hyp-Nml-(AR-314-145)-Arg-Ile-NH$_2$; | JAL-1864 | 553 | 1277 | C |
| (AR-314-169)-Phe-leu-Leu-Hyp-Nml-Asp-Arg-Ile-NH$_2$; | JAL-1868-2 | 554 | 1281 | B |
| (AR-314-170)-Phe-leu-Leu-Hyp-Nml-Asp-Arg-Ile-NH$_2$; | JAL-1869-2 | 555 | 1253 | C |
| (AR-314-171)-Phe-leu-Leu-Hyp-Nml-Asp-Arg-Ile-NH$_2$; | JAL-1870-2 | 556 | 1281 | C |
| (AR-385-008)-leu-Leu-Hyp-Nml-Asp-Arg-Ile-NH$_2$; | JAL-1873 | 557 | 1273 | C |
| (AR-314-172)-leu-Leu-Hyp-Nml-Asp-Arg-Ile-NH$_2$; | JAL-1874 | 558 | 1287 | B |
| Occ-Sni-Phe-(AR-385-12)-Leu-Hyp-Nml-Asp-Arg-Ile-NH$_2$; | JAL-1877 | 559 | 1294 | A |
| Occ-Sni-Phe-hse-Leu-Hyp-Nml-Asp-Arg-Ile-NH$_2$; | JAL-1878 | 560 | 1241 | B |
| Occ-Sni-Phe-abu(pip)-Leu-Hyp-Nml-Asp-Arg-Ile-NH$_2$; | JAL-1879 | 561 | 1308 | B |
| (AR-385-042)-leu-Leu-Hyp-Nml-Asp-Arg-Ile-NH$_2$; | JAL-1880 | 562 | 1287 | B |
| Occ-Sni-Phe-Fhz-Leu-Hyp-Nml-Asp-Arg-Ile-NH$_2$; | JAL-1881 | 563 | 1280 | B |
| Occ-Sni-Phe-Fhy-Leu-Hyp-Nml-Asp-Arg-Ile-NH$_2$; | JAL-1882 | 564 | 1280 | B |
| Occ-Sni-Phe-thr-Leu-Hyp-Nml-Asp-Arg-Ile-NH$_2$; | JAL-1883 | 565 | 1241 | C |
| Occ-Sni-Phe-his-Leu-Hyp-Nml-Asp-Arg-Ile-NH$_2$; | JAL-1884 | 566 | 1277 | B |
| Occ-Sni-Phe-metO2-Leu-Hyp-Nml-Asp-Arg-Ile-NH$_2$; | JAL-1885 | 567 | 1303 | B |

TABLE 3-continued

Preferred compounds according to the present invention and their agonistic activity in in vitro assays.

| Structure | JAL | SEQ ID NO: | (M + H)$^+$ in MS [amu] | Activity (group) |
|---|---|---|---|---|
| Occ-Sni-Phe-(AR-385-017)-Leu-Hyp-Nml-Asp-Arg-Ile-NH$_2$; | JAL-1886 | 568 | 1310 | B |
| Occ-Sni-Phe-opa-Leu-Hyp-Nml-Asp-Arg-Ile-NH$_2$; | JAL-1887 | 569 | 1288 | B |
| Occ-Sni-Phe-mpa-Leu-Hyp-Nml-Asp-Arg-Ile-NH$_2$; | JAL-1888 | 570 | 1288 | B |
| Occ-Sni-Phe-ppa-Leu-Hyp-Nml-Asp-Arg-Ile-NH$_2$; | JAL-1889 | 571 | 1288 | B |
| Occ-Sni-Phe-Egg-Leu-Hyp-Nml-Asp-Arg-Ile-NH$_2$; | JAL-1890 | 572 | 1294 | A |
| Occ-Sni-Phe-Eao-Leu-Hyp-Nml-Asp-Arg-Ile-NH$_2$; | JAL-1892 | 573 | 1299 | B |
| Occ-Sni-Phe-Aic-Leu-Hyp-Nml-Asp-Arg-Ile-NH$_2$; | JAL-1893 | 574 | 1299 | B |
| Occ-Sni-Phe-orn(Me2)-Leu-Hyp-Nml-Ser-Arg-Che; | JAL-1894 | 575 | 1237 | B |
| Occ-Sni-Phe-orn(Me2)-Leu-Hyp-Nml-Thr-Arg-Che; | JAL-1895 | 576 | 1251 | A |
| H-Hgl-Sni-Phe-leu-Leu-Hyp-Nml-Asp-Arg-Ile-NH$_2$; | JAL-1896 | 577 | 1268 | B |
| H-hgl-Sni-Phe-leu-Leu-Hyp-Nml-Asp-Arg-Ile-NH$_2$; | JAL-1897 | 578 | 1268 | B |
| H-Lys-Hgl-Sni-Phe-leu-Leu-Hyp-Nml-Asp-Arg-Ile-NH$_2$; | JAL-1898 | 579 | 1396 | B |
| H-Lys-hgl-Sni-Phe-leu-Leu-Hyp-Nml-Asp-Arg-Ile-NH$_2$; | JAL-1899 | 580 | 1396 | B |
| H-Lys-Pro-Hgl-Sni-Phe-leu-Leu-Hyp-Nml-Asp-Arg-Ile-NH$_2$; | JAL-1900 | 581 | 1493 | A |
| (2857-Ac)-Hgl-Sni-Phe-leu-Leu-Hyp-Nml-Asp-Arg-Ile-NH$_2$; | JAL-1901 | 582 | 1489 | B |
| (1625-Ac)-Sni-Phe-leu-Leu-Hyp-Nml-Asp-Arg-Ile-NH$_2$; | JAL-1907 | 583 | 1268 | B |
| Occ-Sni-Phe-orn(Me2)-Leu-Hyp-Nml-Dim-Arg-Ile-NH$_2$; | JAL-1910 | 584 | 1264 | B |
| Occ-Sni-Phe-leu-Leu-Hyp-Nml-Pse-Arg-Ile-NH$_2$; | JAL-1912 | 585 | 1305 | C |
| Occ-Sni-Phe-orn(Me2)-Leu-Hyp-Nml-Pth-Arg-Ile-NH$_2$; | JAL-1913 | 586 | 1348 | C |
| Occ-Sni-Phe-Dha-Leu-Hyp-Nml-Asp-Arg-Ile-NH$_2$; | JAL-1915-2 | 587 | 1209 | B |
| Occ-Sni-Phe-orn(Me2)-Leu-Hyp-Nml-Pse-Arg-Che; | JAL-1916 | 588 | 1316 | C |
| Occ-Sni-Phe-leu-Leu-Hyp-Nml-Pse-Arg-Che; | JAL-1917 | 589 | 1288 | C |
| Occ-Sni-Phe-orn(Me2)-Leu-Hyp-Nml-Pth-Arg-Che; | JAL-1918 | 590 | 1330 | B |
| Occ-Sni-Phe-leu-Leu-Hyp-Nml-Pth-Arg-Che; | JAL-1919 | 591 | 1302 | B |

TABLE 3-continued

Preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-leu-Leu-Hyp-Nml-Ser-Arg-Ile-NH$_2$; | JAL-1920 | 592 | 1225 | B |
| Occ-Sni-Phe-orn(Me2)-Leu-Hyp-Nml-Ser-Arg-Ile-NH$_2$; | JAL-1921 | 593 | 1254 | C |
| Occ-Sni-Phe-leu-Leu-Hyp-Nml-Cya-Arg-Ile-NH$_2$; | JAL-1922 | 594 | 1289 | B |
| Occ-Sni-Phe-orn(Me2)-Leu-Hyp-Nml-Cya-Arg-Ile-NH$_2$; | JAL-1923 | 595 | 1318 | B |
| Occ-Sni-Phe-orn(Me2)-Leu-Hyp-Nml-Thr-Arg-Ile-NH$_2$; | JAL-1924 | 596 | 1268 | B |
| Occ-Sni-Phe-leu-Leu-Hyp(Asp(-))-Nml-Asp-Arg-Ile-NH$_2$; | JAL-1928 | 597 | 1368 | B |
| Occ-Sni-Phe-leu-Leu-Hyp(2581)-Nml-Asp-Arg-Ile-NH$_2$; | JAL-1929 | 598 | 1338 | B |
| Occ-Sni-Phe-leu-Leu-Hyp-Nml-Asp-Arg-Ile-OH; | JAL-1930 | 599 | 1254 | B |
| Occ-Sni-Phe-orn(Me2)-Leu-Hyp-Nml-Asp-Arg-Ile-OH; | JAL-1931 | 600 | 1283 | B |
| Occ-Sni-Phe-leu-Leu-Hyp-Nml-Thr-Arg-Ile-NH$_2$; | JAL-1932 | 601 | 1239 | A |
| Occ-Sni-Phe-leu-Leu-Tap(Asp(-))-Nml-Asp-Arg-Ile-NH$_2$; | JAL-1935 | 602 | 1367 | B |
| Occ-Sni-Phe-orn(Me2)-Leu-Tap-Nml-Asp-Arg-Ile-NH$_2$; | JAL-1936 | 603 | 1281 | A |

Preferred NPR-B agonists of the present invention are those peptides within activity group B, as presented in Table 3, above. Most preferred NPR-B agonists of the present invention are those peptides within activity group A, as presented in Table 4, below.

TABLE 4

Most preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-nle-Leu-Hyp-Leu-Asp-Arg-Ile-NH$_2$ | JAL-1024 | 166 | 1239 | A |
| Occ-ala-Phe-leu-Leu-Pro-Nml-Asp-Arg-Ile-NH$_2$ | JAL-1039 | 180 | 1196 | A |
| Occ-Sni-Phe-leu-Leu-Pro-Nml-Asp-Arg-Ile-NH$_2$ | JAL-1040 | 181 | 1236 | A |
| Occ-Sni-Phe-leu-Leu-Hyp-Nml-Asp-Arg-Ile-NH$_2$ | JAL-1041 | 182 | 1253 | A |
| Occ-ala-Phe-leu-Leu-Hyp-Nml-Asp-Arg-Ile-NH$_2$ | JAL-1042 | 183 | 1213 | A |
| Occ-ala-Pcf-leu-Leu-Hyp-Nml-Asp-Arg-Ile-NH$_2$ | JAL-1043 | 184 | 1247 | A |
| Occ-ala-Phe-nle-Leu-Hyp-Nml-Asp-Arg-Ile-NH$_2$ | JAL-1044 | 185 | 1213 | A |

TABLE 4-continued

Most preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-ala-Phe-arg-Leu-Hyp-Leu-Asp-Arg-Ile-NH$_2$ | JAL-1047 | 187 | 1242 | A |
| Occ-ala-Pcf-leu-Leu-Hyp-Leu-Asp-Arg-Ile-NH$_2$ | JAL-1050 | 190 | 1233 | A |
| Occ-ala-Nmf-leu-Leu-Hyp-Leu-Asp-Arg-Ile-NH$_2$ | JAL-1052 | 192 | 1213 | A |
| Occ-pro-Phe-leu-Leu-Hyp-Leu-Asp-Arg-Ile-NH$_2$ | JAL-1053 | 193 | 1225 | A |
| Occ-pip-Phe-leu-Leu-Hyp-Leu-Asp-Arg-Ile-NH$_2$ | JAL-1054 | 194 | 1239 | A |
| Occ-ala-Phe-lys-Leu-Hyp-Nml-Asp-Arg-Ile-NH$_2$ | JAL-1060 | 195 | 1228 | A |
| Occ-ala-Phe-orn-Leu-Hyp-Nml-Asp-Arg-Ile-NH$_2$ | JAL-1061 | 196 | 1214 | A |
| Occ-pip-Nmf-arg-Leu-Pro-Nml-Asp-Arg-Ile-NH$_2$ | JAL-1077 | 201 | 1294 | A |
| Occ-pip-Phe-arg-Leu-Pro-Nml-Asp-Arg-Ile-NH$_2$ | JAL-1078 | 202 | 1280 | A |
| Occ-ala-Nmf-arg-Leu-Hyp-Nml-Asp-Arg-Ile-NH$_2$ | JAL-1085 | 203 | 1270 | A |
| Occ-ala-Phe-arg-Leu-Hyp-Nml-Asp-Arg-Ile-NH$_2$ | JAL-1086 | 204 | 1256 | A |
| Occ-pip-Phe-arg-Leu-Hyp-Nml-Asp-Arg-Ile-NH$_2$ | JAL-1087 | 205 | 1296 | A |
| Occ-ala-Pbf-arg-Leu-Hyp-Leu-Asp-Arg-Ile-NH$_2$ | JAL-1116 | 208 | 1321 | A |
| Occ-ala-Phe-arg-Leu-Hyp-Npg-Asp-Arg-Ile-NH$_2$ | JAL-1225 | 217 | 1256 | A |
| Occ-ala-Phe-Gly-Leu-Tap-Leu-Asp-Arg-Ile-NH$_2$ | JAL-1249 | 237 | 1142 | A |
| Occ-ala-Phe-arg-Leu-Tap-Leu-Asp-Arg-Ile-NH$_2$ | JAL-1250 | 238 | 1241 | A |
| Occ-ala-Phe-leu-Leu-Tap-Asp-Arg-Ile-NH$_2$ | JAL-1251 | 239 | 1198 | A |
| Occ-ala-Phe-ser-Leu-Hyp-Nml-Asp-Arg-Ile-NH$_2$ | JAL-1252 | 240 | 1187 | A |
| Occ-Sni-Phe-lys-Leu-Hyp-Nml-Asp-Arg-Ile-NH$_2$ | JAL-1254 | 242 | 1268 | A |
| Occ-Sni-Phe-arg-Leu-Hyp-Nml-Asp-Arg-Ile-NH$_2$ | JAL-1255 | 243 | 1296 | A |
| Occ-Sni-Phe-orn-Leu-Hyp-Nml-Asp-Arg-Ile-NH$_2$ | JAL-1265 | 252 | 1254 | A |
| Occ-ala-Nmf-leu-Leu-Hyp-Nml-Asp-Arg-Ile-NH$_2$ | JAL-1267 | 254 | 1227 | A |
| Occ-ala-Phe-leu-Leu-Hyp-(SH-158)-Asp-Arg-Ile-NH$_2$ | JAL-1283 | 265 | 1227 | A |
| Occ-ala-Phe-arg-Leu-Hyp-(SH-158)-Asp-Arg-Ile-NH$_2$ | JAL-1284 | 266 | 1271 | A |
| Occ-Sni-Phe-dap(Me2)-Leu-Hyp-Nml-Asp-Arg-Ile-NH$_2$ | JAL-1287 | 267 | 1254 | A |

TABLE 4-continued

Most preferred compounds according to the present invention and their agonistic activity in in vitro assays.

| Structure | JAL | SEQ ID NO: | (M + H)+ in MS [amu] | Activity (group) |
|---|---|---|---|---|
| Occ-ala-Phe-orn(Me2)-Leu-Hyp-Nml-Asp-Arg-Ile-NH$_2$ | JAL-1288 | 268 | 1242 | A |
| Occ-Sni-Phe-orn(Me2)-Leu-Hyp-Nml-Asp-Arg-Ile-NH$_2$ | JAL-1289 | 269 | 1282 | A |
| (AR-201-49)-Phe-leu-Leu-Hyp-Nml-Asp-Arg-Ile-NH$_2$ | JAL-1294 | 273 | 1214 | A |
| Occ-Sni-Phe-leu-Leu-Tap-Nml-Asp-Arg-Ile-NH$_2$ | JAL-1295 | 274 | 1252 | A |
| Occ-ala-Phe-leu-Leu-Tap-Nml-Asp-Arg-Ile-NH$_2$ | JAL-1296 | 275 | 1212 | A |
| Oct-Sni-Phe-arg-Leu-Hyp-Nml-Asp-Arg-Ile-NH$_2$ | JAL-1297 | 276 | 1282 | A |
| Oct-Sni-Phe-leu-Leu-Hyp-Nml-Asp-Arg-Ile-NH$_2$ | JAL-1302 | 278 | 1239 | A |
| Occ-ala-Phe-arg-Leu-Hyp-Nml-Asp-Arg-Tbg-NH$_2$ | JAL-1305 | 279 | 1256 | A |
| Occ-Sni-Phe-arg-Leu-Tap-Nml-Asp-Arg-Ile-NH$_2$ | JAL-1317 | 284 | 1295 | A |
| Occ-Sni-Phe-orn-Leu-Tap-Nml-Asp-Arg-Ile-NH$_2$ | JAL-1318 | 285 | 1253 | A |
| Occ-Sni-Phe-Gly-Leu-Tap-Nml-Asp-Arg-Ile-NH$_2$ | JAL-1320 | 287 | 1196 | A |
| Occ-Sni-Phe-leu-Leu-Tap(G)-Nml-Asp-Arg-Ile-NH2 | JAL-1322 | 289 | 1309 | A |
| Occ-Sni-Phe-leu-Leu-Tap(Bal)-Nml-Asp-Arg-Ile-NH$_2$ | JAL-1323 | 290 | 1323 | A |
| Occ-Sni-Phe-dap(Me2)-Leu-Tap-Nml-Asp-Arg-Ile-NH$_2$ | JAL-1325 | 292 | 1253 | A |
| Oct-Sni-Phe-leu-Leu-Tap-Nml-Asp-Arg-Ile-NH$_2$ | JAL-1326 | 293 | 1238 | A |
| Occ-ala-Phe-leu-Leu-Hyp-Nml-Val-Arg-Ile-NH$_2$ | JAL-1332 | 299 | 1197 | A |
| Occ-ala-Phe-Fhy-Leu-Hyp-Nml-Asp-Arg-Ile-NH$_2$ | JAL-1336 | 304 | 1240 | A |
| Occ-ala-Phe-Apc-Leu-Hyp-Nml-Asp-Arg-Ile-NH$_2$ | JAL-1338 | 306 | 1226 | A |
| Occ-Sni-Phe-leu-Leu-Tap (Et)-Nml-Asp-Arg-Ile-NH$_2$ | JAL-1349 | 317 | 1280 | A |
| Occ-ala-Phe-Apc-Leu-Tap-Nml-Asp-Arg-Ile-NH$_2$ | JAL-1350 | 318 | 1265 | A |
| Occ-Sni-Phe-Apc-Leu-Tap-Nml-Asp-Arg-Ile-NH$_2$ | JAL-1351 | 319 | 1265 | A |
| Occ-ala-Phe-leu-Leu-Hyp-Nml-Asp-Arg-Tbg-NH$_2$ | JAL-1352 | 320 | 1213 | A |
| Occ-ala-Phe-leu-Leu-Hyp-Nml-Asp-Arg-Egz-NH$_2$ | JAL-1358 | 321 | 1225 | A |
| Occ-ala-Phe-leu-Leu-Hyp-Dap(Me2)-Asp-Arg-Ile-NH$_2$ | JAL-1367 | 330 | 1200 | A |
| Oct-Sni-Phe-dap(Me2)-Leu-Tap-Nml-Asp-Arg-Ile-NH$_2$ | JAL-1369 | 332 | 1239 | A |

TABLE 4-continued

Most preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-Sni-Phe-leu-Leu-Tap(Ae)-Nml-Asp-Arg-Ile-NH$_2$ | JAL-1371 | 334 | 1295 | A |
| Occ-Sni-Phe-leu-Leu-Tap(Ap)-Nml-Asp-Arg-Ile-NH$_2$ | JAL-1372 | 335 | 1309 | A |
| (AR-201-68)-Phe-leu-Leu-Hyp-Nml-Asp-Arg-Ile-NH$_2$ | JAL-1380 | 343 | 1274 | A |
| Sbt-Sni-Phe-leu-Leu-Hyp-Nml-Asp-Arg-Ile-NH$_2$ | JAL-1382 | 345 | 1266 | A |
| Occ-Sni-Phe-leu-Leu-Hyp-Nml-Val-Arg-Ile-NH$_2$ | JAL-1398 | 353 | 1237 | A |
| Occ-Sni-Phe-leu-Leu-Tap-Nml-Val-Arg-Ile-NH$_2$ | JAL-1401 | 356 | 1236 | A |
| Occ-Sni-Phe-dap(Me2)-Leu-Tap-Nml-Val-Arg-Ile-NH$_2$ | JAL-1403 | 358 | 1237 | A |
| Oct-Sni-Phe-dap(Me2)-Leu-Tap-Nml-Val-Arg-Ile-NH$_2$ | JAL-1405 | 360 | 1223 | A |
| Occ-ala-Phe-Apc(Me)-Met-glu--Leu-Hyp-Nml-Asp-Arg-Ile-NH$_2$ | JAL-1406 | 361 | 1240 | A |
| Occ-ala-Phe-Apc(E0-Glu-thr--Leu-Hyp-Nml-Asp-Arg-Ile-NH$_2$ | JAL-1407 | 362 | 1254 | A |
| Occ-ala-Phe-leu-Leu-Hyp-Nml-Asp-Arg-Ami-NH$_2$ | JAL-1414 | 365 | 1227 | A |
| Occ-ala-Phe-leu-Leu-Hyp-Nml-Asp-Arg-Deg-NH$_2$ | JAL-1416 | 366 | 1213 | A |
| Occ-ala-Phe-leu-Leu-Hyp-Nml-Asp-Nmr-Ile-NH$_2$ | JAL-1417 | 367 | 1227 | A |
| Oct-Sni-Phe-dap(Me2)-Leu-Hyp-Nml-Asp-Arg-Ile-NH$_2$ | JAL-1429 | 372 | 1240 | A |
| Miy-Hgl-ala-Phe-arg-Leu-Hyp-Nml-Asp-Arg-Ile-NH$_2$ | JAL-1430 | 373 | 1561 | A |
| Occ-ala-Phe-Apc-Leu-Tap-Nml-Asp-Pro-Ile-NH$_2$ | JAL-1452 | 386 | 1166 | A |
| Occ-ala-Phe-dap(Me2)-Leu-Tap-Nml-Asp-Pro-Ile-NH$_2$ | JAL-1453 | 387 | 1154 | A |
| Occ-ala-Phe-Egz-Leu-Tap-Nml-Asp-Arg-Ile-NH$_2$ | JAL-1454 | 388 | 1224 | A |
| Occ-ala-Phe-dap(1464)-Leu-Tap-Nml-Asp-Arg-Ile-NH$_2$ | JAL-1463 | 396 | 1255 | A |
| Occ-Sni-Pff-leu-Leu-Hyp-Nml-Asp-Arg-Ile-NH$_2$ | JAL-1487 | 406 | 1271 | A |
| Occ-Sni-Pcf-leu-Leu-Hyp-Nml-Asp-Arg-Ile-NH$_2$ | JAL-1493 | 412 | 1287 | A |
| Occ-Sni-Pmf-leu-Leu-Hyp-Nml-Asp-Arg-Ile-NH$_2$ | JAL-1494 | 413 | 1267 | A |
| Occ-Sni-Eaa-leu-Leu-Hyp-Nml-Asp-Arg-Ile-NH$_2$ | JAL-1496 | 414 | 1322 | A |
| Occ-Sni-Phe-leu-Leu-Hyp-Nml-Asp-Pro-1860 | JAL-1510 | 419 | 1176 | A |

TABLE 4-continued

Most preferred compounds according to the present invention and their agonistic activity in in vitro assays.

| Structure | JAL | SEQ ID NO: | $(M + H)^+$ in MS [amu] | Activity (group) |
|---|---|---|---|---|
| Occ-Sni-Phe-leu-Leu-Hyp-Nml-Asp-Pro-Che | JAL-1512_02 | 421 | 1176 | A |
| Occ-Sni-Phe-Apc-Leu-Hyp-Nml-Asp-Arg-Ile-NH$_2$ | JAL-1555 | 425 | 1266 | A |
| Occ-ala-Phe-leu-Leu-Hyp-Nml-(BB725)-Arg-Ile-NH$_2$ | JAL-1556 | 426 | 1224 | A |
| Occ-ala-Phe-leu-Leu-Hyp-Nml-(BB727)-Arg-Ile-NH$_2$ | JAL-1558 | 428 | 1238 | A |
| Occ-Sni-Phe-leu-Leu-Tap-Nml-Asp-Pro-Ile-NH$_2$ | JAL-1559 | 429 | 1194 | A |
| Occ-Sni-Phe-Apc-Leu-Tap-Nml-Asp-Pro-Ile-NH$_2$ | JAL-1561 | 431 | 1207 | A |
| Occ-Sni-Phe-leu-Leu-Tap-Nml-Asp-Pro-Che | JAL-1568 | 432 | 1176 | A |
| Occ-Sni-Phe-leu-Leu-Hyp-Nml-Asp-Arg-Nmi-NH$_2$ | JAL-1569 | 433 | 1267 | A |
| Occ-Sni-Nmf-leu-Leu-Hyp-Nml-Asp-Arg-Ile-NH$_2$ | JAL-1573 | 436 | 1267 | A |
| Occ-Sni-Phe-dap(Me2)-Leu-Hyp-Nml-Asp-Nmr-Ile-NH$_2$ | JAL-1576 | 439 | 1268 | A |
| Occ-Sni-Nmf-dap(Me2)-Leu-Hyp-Nml-Asp-Arg-Ile-NH$_2$ | JAL-1579 | 442 | 1268 | A |
| Occ-Sni-Phe-dap(Me2)-Leu-Hyp-Nml-Asp-Pro-Ile-NH$_2$ | JAL-1580 | 443 | 1195 | A |
| Occ-Sni-Phe-leu-Leu-Hyp-Npg-Asp-Pro-Che | JAL-1595 | 445 | 1177 | A |
| Occ-Sni-Nmf-leu-Leu-Hyp-Nml-Asp-Pro-Che | JAL-1597 | 447 | 1191 | A |
| Occ-Sni-Eaa-leu-Leu-Hyp-Nml-Asp-Pro-Che | JAL-1599 | 449 | 1245 | A |
| Occ-Sni-Phe-Apc-Leu-Tap-Nml-Asp-Pro-Che | JAL-1602 | 452 | 1190 | A |
| Occ-Sni-Phe-dap(Me2)-Leu-Tap-Nml-Asp-Pro-Che | JAL-1603 | 453 | 1177 | A |
| Occ-Sni-Phe-dap(Me2)-Leu-Hyp-Nml-Asp-Pro-Che | JAL-1604 | 454 | 1177 | A |
| 1319-Sni-Phe-leu-Leu-Hyp-Nml-Asp-Arg-Ile-NH$_2$ | JAL-1605 | 455 | 1272 | A |
| 1320-Sni-Phe-leu-Leu-Hyp-Nml-Asp-Arg-Ile-NH$_2$ | JAL-1606 | 456 | 1286 | A |
| Occ-Sni-Mcf-leu-Leu-Hyp-Nml-Asp-Arg-Ile-NH$_2$ | JAL-1618 | 463 | 1287 | A |
| Occ-Sni-Pbf-leu-Leu-Hyp-Nml-Asp-Arg-Ile-NH$_2$ | JAL-1619 | 464 | 1332 | A |
| Occ-Sni-Thk-leu-Leu-Hyp-Nml-Asp-Arg-Ile-NH$_2$ | JAL-1620 | 465 | 1259 | A |
| Occ-Sni-Mtf-leu-Leu-Hyp-Nml-Asp-Arg-Ile-NH$_2$ | JAL-1621 | 466 | 1321 | A |

TABLE 4-continued

Most preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-ctb-Leu-Hyp-Nml-Asp-Arg-Ile-NH$_2$ | JAL-1623 | 468 | 1299 | A |
| Occ-Sni-Phe-leu-Nle-Hyp-Nml-Asp-Arg-Ile-NH$_2$ | JAL-1624 | 469 | 1253 | A |
| Occ-Sni-Phe-leu-Leu-Hyp-Ile-Asp-Arg-Ile-NH$_2$ | JAL-1625 | 470 | 1239 | A |
| Occ-Sni-Phe-leu-Leu-Hyp-Cpg-Asp-Arg-Ile-NH$_2$ | JAL-1626 | 471 | 1251 | A |
| Occ-Sni-Phe-leu-Leu-Hyp-Nml-Asp-Eaz-Che | JAL-1638 | 477 | 1195 | A |
| Occ-Sni-Phe-leu-Leu-Tap-Nml-Val-Pro-Che | JAL-1654 | 481 | 1160 | A |
| Occ-Sni-Phe-leu-Nle-Hyp-Nml-Asp-Pro-Che | JAL-1657 | 482 | 1177 | A |
| 5587-Sni-Phe-leu-Leu-Hyp-Nml-Asp-Arg-Ile-NH$_2$ | JAL-1666 | 488 | 1281 | A |
| Occ-(AFL)-leu-Leu-Hyp-Nml-Asp-Arg-Ile-NH$_2$ | JAL-1671 | 491 | 1225 | A |
| Occ-Sni-Phe-leu-Leu-Hyp-Nml-Asp-Pca-Che | JAL-1679 | 495 | 1192 | A |
| Occ-Sni-Phe-leu-Leu-Hyp-Nml-Asp-Arg-Che | JAL-1680 | 496 | 1236 | A |
| Occ-Sni-Phe-leu-Leu-Tap(Ae)-Nml-Asp-Arg-Che | JAL-1681 | 497 | 1278 | A |
| Occ-Sni-Phe-leu-Leu-Tap-Nml-Asp-Arg-Che | JAL-1682 | 498 | 1235 | A |
| Occ-Sni-Phe-leu-Leu-Tap-Nml-Val-Arg-Che | JAL-1729 | 506 | 1218 | A |
| Occ-Sni-Phe-leu-Leu-Hyp-Nml-Val-Arg-Che | JAL-1730 | 507 | 1219 | A |
| Occ-Sni-Phe-leu-Leu-Hyp-Nml-Ser-Arg-Che | JAL-1752 | 510 | 1209 | A |
| Occ-Sni-Phe-leu-Leu-Hyp-Nml-Thr-Arg-Che | JAL-1753 | 511 | 1223 | A |
| (AR-314-87)-leu-Leu-Hyp-Nml-Asp-Arg-Ile-NH$_2$ | JAL-1765-2 | 516 | 1279 | A |
| (AR-314-102)-leu-Leu-Hyp-Nml-Asp-Arg-Ile-NH$_2$ | JAL-1774 | 517 | 1239 | A |
| Occ-Sni-Phe-orn(Me2)-Leu-Hyp-Nml-Asp-Arg-Che | JAL-1776 | 518 | 1265 | A |
| Occ-Sni-Phe-lys(Me2)-Leu-Hyp-Nml-Asp-Arg-Che | JAL-1777 | 519 | 1279 | A |
| Occ-Sni-Phe-lys(Me2)-Leu-Hyp-Nml-Val-Arg-Che | JAL-1779 | 521 | 1263 | A |
| Occ-Sni-Phe-orn(Me2)-Leu-Hyp-Nml-Val-Arg-Ile-NH$_2$ | JAL-1782 | 523 | 1266 | A |
| Occ-Sni-Phe-dab(Me2)-Leu-Hyp-Nml-Val-Arg-Che | JAL-1784 | 525 | 1235 | A |

TABLE 4-continued

Most preferred compounds according to the present invention and their agonistic activity in in vitro assays.

| Structure | JAL | SEQ ID NO: | (M + H)+ in MS [amu] | Activity (group) |
|---|---|---|---|---|
| Occ-Sni-Phe-dab(Me2)-Leu-Hyp-Nml-Asp-Arg-Ile-NH$_2$ | JAL-1785 | 526 | 1268 | A |
| H-Adx-Hgl-Sni-Phe-leu-Leu-Hyp-Nml-Asp-Arg-Ile-NH$_2$ | JAL-1808 | 538 | 1413 | A |
| Oct-Sni-Phe-leu-Leu-Tap-Nml-Asp-Arg-Che | JAL-1843 | 541 | 1221 | A |
| Occ-Sni-Phe-orn(Me2)-Leu-Tap-Nml-Val-Arg-Che | JAL-1850 | 548 | 1248 | A |
| Occ-Sni-Phe-(AR-385-12)-Leu-Hyp-Nml-Asp-Arg-Ile-NH$_2$ | JAL-1877 | 559 | 1294 | A |
| Occ-Sni-Phe-Egg-Leu-Hyp-Nml-Asp-Arg-Ile-NH$_2$ | JAL-1890 | 572 | 1294 | A |
| Occ-Sni-Phe-orn(Me2)-Leu-Hyp-Nml-Thr-Arg-Che | JAL-1895 | 576 | 1251 | A |
| H-Lys-Pro-Hgl-Sni-Phe-leu-Leu-Hyp-Nml-Asp-Arg-Ile-NH$_2$ | JAL-1900 | 581 | 1493 | A |
| Occ-Sni-Phe-leu-Leu-Hyp-Nml-Thr-Arg-Ile-NH$_2$ | JAL-1932 | 601 | 1239 | A |
| Occ-Sni-Phe-orn(Me2)-Leu-Tap-Nml-Asp-Arg-Ile-NH$_2$ | JAL-1936 | 603 | 1281 | A |

B. Diseases to be Treated and/or Prevented

The present invention is also directed to methods of treating or preventing diseases in a subject that involve administering to the subject a therapeutically effective amount of a composition that includes one or more NPR-B agonists as described herein, wherein the disease is one of the following. The subject may be a mammal, such as a human, a primate, a cow, a horse, a dog, a cat, a mouse, or a rat. In particular embodiments, the subject is a human.

1. Definitions

"Treatment" and "treating" refer to administration or application of a drug to a subject or performance of a procedure or modality on a subject for the purpose of obtaining a therapeutic benefit of a disease or health-related condition. The term "therapeutic benefit" used throughout this application refers to anything that promotes or enhances the well-being of the subject with respect to the medical treatment of his condition. This includes, but is not limited to, a reduction in the frequency or severity of the signs or symptoms of a disease. Therapeutic benefit also includes reducing the signs or symptoms associated with glaucoma in a subject with glaucoma. For example, a therapeutic benefit in a patient with glaucoma is obtained where there is no further progression of visual field loss in the affected eye, or a slowing of the rate of progression of visual field loss in the affected eye, or an improvement in vision.

A "disease" or "health-related condition" can be any pathological condition of a body part, an organ, or a system resulting from any cause, such as infection, trauma, genetic defect, age-related deterioration of bodily functions, and/or environmental stress. The cause may or may not be known. Examples of diseases include glaucoma, retinopathies, ocular trauma, and optic neuropathies. Thus, one of skill in the art realizes that a treatment may improve the disease condition, but may not be a complete cure for the disease.

The terms "prevention" and "preventing" are used herein according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking or minimizing the onset of a disease or health-related condition. For example, an individual with an eye that is at risk of developing glaucoma (such as an individual with ocular hypertension) can be treated with a NPR-B agonist as set forth herein for the purpose of blocking or minimizing the onset of the signs or symptoms of glaucoma (i.e., prevention of glaucoma). In a specific embodiment, prevention pertains to lowering elevated intraocular pressure, blocking detectable optic nerve damage as a result of glaucoma in a subject, reducing the rate of vision loss in a subject, or halting loss of vision in a subject. The subject can be a subject who is known or suspected of being free of a particular disease or health-related condition at the time the relevant preventive agent is administered. The subject, for example, can be a subject with no known disease or health-related condition (i.e., a healthy subject). In some embodiments, the subject had a previous disease that has been treated in the past and is now known or suspected to be disease-free.

For those skilled in the art it is easy to understand, that different diseases are summarized under certain terms or generic terms. These summaries are no limitation and each disease can be viewed on its own and can be treated or

2. Glaucoma and Ocular Hypertension

Glaucoma is the second leading cause of blindness worldwide (Thylefors and Negrel 1994, Bull World Health Organ. 72:323-326). Open-angle glaucoma (OAG) and angle closure glaucoma combined represent the second leading cause of blindness worldwide (Quigley and Broman, 2006 Br J Ophthalmol. 90:262-267). Angle-closure glaucoma is more common in the Asian population (Foster et al. 2000, Arch Ophthalmol. 118:1105-11), while open-angle glaucoma is more commonly found in black patients (Leske et al. 2007, Ophthalmic Epidemiol. 14:166-172). Glaucoma is a progressive disease in which the risk of vision loss increases with disease duration. In light of an aging population worldwide, the impact of this blinding disorder can be expected to increase in the future.

The disease state referred to as glaucoma is a family of diseases characterized by a permanent loss of visual function due to irreversible damage to the optic nerve. More specifically, glaucoma results in optic neuropathy leading to the loss of retinal ganglion cell (RGC) function followed by apoptotic cell death and a progressive increase in vision loss. Morphologically or functionally distinct types of glaucoma are typically characterized by elevated intraocular pressure (TOP), which is considered to be an important risk factor of the pathological course of the disease. Disruption of normal aqueous outflow leading to elevated IOP is integral to glaucoma pathophysiology. Ocular hypertension is a condition wherein IOP is elevated but no apparent loss of visual function has occurred; such patients are considered to be at high risk for the eventual development of the visual loss associated with glaucoma. Some patients with glaucomatous field loss have relatively low IOPs. These so called normotension or low tension glaucoma patients can also benefit from agents that lower and control IOP.

Glaucoma is typically identified by changes in IOP, visual field deficits and/or fundus changes at the optic disk. Elevated IOP, found in most glaucoma patients, is a result of morphological and biochemical changes in the trabecular meshwork (TM), an aqueous humor filtering tissue located at the iris-cornea angle of the eye. As glaucoma progresses, there is a loss of TM cells and a buildup of extracellular products which inhibit the normal aqueous humor outflow resulting in IOP elevation. In addition to elevated IOP, other factors, such as genetic defects, may lead to mechanical distortion of the optic nerve head (ONH) ultimately resulting in ONH cupping and loss of RGC and their axons. The exact mechanism of this pathological process is currently unknown. It has been suggested that lowering the IOP of patients diagnosed with glaucoma by at least 20-30% will decrease the progressive worsening of the disease by 50-60% (Quigley 2005 Ophthalmology 112:1642-1643). Without proper diagnosis and treatment, glaucoma can progress to total irreversible blindness.

Initially, most open-angle glaucoma patients are managed with one or more of a wide variety of topical ocular or oral hypotensive medications that act to increase aqueous fluid outflow and/or decrease aqueous fluid production, or with surgical procedures such as laser trabeculoplasty and filtration surgery. Treatment regimens currently available for patients exhibiting elevated IOP, regardless of cause, typically include the topical application, from once daily to multiple times per day, of one or multiple eyedrops or pills containing a small molecule IOP-lowering compound. Also, pills that decrease the amount of aqueous humor created can be given between two and four times daily. Glaucoma medications typically prescribed include cholinergic agonists, adrenergic agonists, beta adrenergic blockers, carbonic anhydrase inhibitors and prostaglandin analogs. Although these classes of medications are effective in controlling IOP, each of them has certain limitations in efficacy and untoward effects. For example, beta adrenergic blockers do not lower IOP at night; many glaucoma patients do not respond to a particular drug class; and a majority of glaucoma patients require the use of a combination of drugs. In addition, many of the drugs cause local irritation of the eye, such as burning, stinging, itching, tearing, conjunctival hyperemia, foreign body sensation, blurred vision, and eye pain. Some occasionally induce systemic side effects. Hence, there is a genuine and continuous need for novel and improved glaucoma medications.

"Glaucoma" and "glaucomatous optic neuropathy" and "glaucomatous retinopathy," as used herein, are interchangeable. Glaucoma refers to a disease characterized by the permanent loss of visual function due to irreversible damage to the retinal ganglion cells in the retina and optic nerve. The major risk factor for glaucoma and the related loss of visual function is elevated intraocular pressure. There are different types of glaucoma, including primary open angle glaucoma (POAG), angle closure glaucoma, and congenital/developmental glaucoma.

As used herein, the term "intraocular pressure" or "IOP" refers to the pressure of the content inside the eye. In a normal human eye, IOP is typically in the range of 10 to 21 mm Hg. IOP varies among individuals, for example, it may become elevated due to anatomical problems, inflammation of the eye, as a side-effect from medication or due to genetic factors. "Elevated" intraocular pressure is currently considered to be ≥21 mm Hg, which is also considered to be a major risk factor for the development of glaucoma.

However, some individuals with an elevated IOP may not develop glaucoma and are considered to have ocular hypertension. "Ocular hypertension" as used herein refers to a condition in which the intraocular pressure in the eye of a subject is higher than normal but the optic nerve and visual fields are within normal limits. These individuals may be susceptible to developing the loss of visual function that is typically associated with glaucoma. As used herein, the terms "susceptible," or "susceptibility" refers to an individual or subject that is or at risk of developing optic nerve damage or retinal damage that is associated with elevated intraocular pressure.

Thus, the present invention is directed to methods of treating or preventing an ophthalmic disease in a subject that involve administering to the subject a therapeutically effective amount of a composition that includes one or more NPR-B agonists as described herein, wherein the ophthalmic disease is glaucoma, elevated intraocular pressure or ocular hypertension. The subject may be a mammal, such as a human, a primate, a cow, a horse, a dog, a cat, a mouse, or a rat. In particular embodiments, the subject is a human.

In preferred aspects, the NPR-B agonists of the invention will lower intraocular pressure associated with glaucoma. The glaucoma may be any type of glaucoma, such as primary open angle glaucoma, angle closure glaucoma, normal tension glaucoma, congenital glaucoma, neovascular glaucoma, steroid-induced glaucoma, or glaucoma related to ocular trauma (e.g., ghost cell glaucoma or glaucoma related to choroidal detachment).

The present invention is also directed to methods of lowering intraocular pressure in a subject, comprising administering to the subject a pharmaceutically effective amount of a composition comprising a NPR-B agonist described herein, wherein intraocular pressed is lowered. In particular embodiments, the subject is a human. For example, in specific embodiments, the human is a patient with ocular hypertension or elevated IOP.

3. CNP Deficiencies as in Diabetes

Diabetic nephropathy is a progressive kidney disease, resulting from longstanding diabetes mellitus. Experimental evidence shows that natriuretic peptides play a pathophysiological role in the glomerular abnormalities seen in diabetes mellitus. BNP overexpression prevented diabetic nephropathy in a streptozotocin-induced mouse model of diabetes (Makino et al. 2006, *Diabetologia*. 49:2514-2524). In another study with streptozotocin-induced diabetic rats, cardiac CNP mRNA concentrations were decreased 2.6-fold (Walther et al. 2000, *J Mol Endocrinol*. 24:391-395). In a genetic model of diabetes, the non-obese diabetic mouse, mesangial cells derived from diabetic mice showed constitutive overexpression of NPR-C; this was associated with a reduced response of cGMP production to ANP or CNP treatment (Ardaillou et al. 1999, *Kidney Int* 55:1293-1302).

4. Conditions with Hyperproliferation of Vascular Smooth Muscle Cells

The abnormal growth of vascular smooth muscle cells (VSMC) is a common cause of many vascular diseases. A disturbance of the balance between growth inhibitors and growth promoters results in the hyperproliferation of those cells, and vasoactive substances, including natriuretic peptides, seem to play a major role in this process. Early experimental findings indicate that the guanylyl-cyclase-linked natriuretic peptide receptors mediate anti-proliferative activity of the natriuretic peptides on vascular smooth muscle cell growth (Hutchinson et al. 1997, *Cardiovasc Res*. 35:158-167). Ex vivo experiments showed a direct inhibition of growth in rat VSMCs by CNP (Furuya et al. 1991, *Biochem Biophys Res Commun*. 177:927-931). Furthermore, migration of rat VSMCs could be inhibited by CNP (Ikeda et al. 1997, *Arterioscler Thromb Vasc Biol*. 17:731-736). CNP gene transfer resulted in a reduction of the VSMC proliferation in pig femoral arteries in vivo, and the effect was even superior over CNP peptide application (Pelisek et al. 2006, *J Gene Med*. 8:835-844). In another report, CNP gene transfer resulted in the suppression of vascular remodelling in porcine coronary arteries in vivo (Morishige et al. 2000, *J Am Coll Cardiol*. 35:1040-1047), thus further strengthening the rationale of using CNP to offset the hyperproliferation of VSMCs.

5. Cardiac Pathologies, Especially Heart Failure and Hypertrophy

Considerable evidence supports a central pathophysiological role for natriuretic peptides in cardiovascular diseases, and in particular heart failure. The advantage of focusing on CNP in this indication is the unchanged reactivity of NPR-B, while NPR-A activity was shown to be reduced in this condition (Dickey et al. 2007, *Endocrinology*. 148:3518-3522, Nakamura et al. 1994, *Circulation*. 90:1210-1214). The fact that plasma CNP is elevated in heart failure patients (Del Ry et al. 2005, *Eur J Heart Fail*. 7:1145-1148, Del Ry et al. 2007, *Peptides*. 28:1068-1073) is interpreted as part of a compensatory vasodilating response in the peripheral vasculature (Del Ry et al. 2005, *Eur J Heart Fail*. 7:1145-1148, Wright et al. 2004, *Hypertension*. 43:94-100). Traditional treatment of heart failure aims at the support of cardiac function by preventing cardiomyocyte loss and hypertrophy. CNP is able to support cardiac function via a positive effect on the vitality of cardiomyocytes (Rosenkranz et al. 2003, Cardiovasc Res. 57:515-522, Tokudome et al. 2004, *Endocrinology*. 145:2131-2140). Also, CNP reduced cardiac fibrosis (Horio et al. 2003, *Endocrinology*. 144:2279-2284), the effect being stronger than that by ANP or BNP. Results from studies on dogs showed a potential inotropic effect of CNP (Beaulieu et al. 1997, *Am J Physiol*. 273:H1933-1940), supporting the potential of CNP to treat heart failure.

Hypertrophy of the heart is an enlargement of the organ, due to an increase in the volume of its muscular fibres. Experimental evidence suggests that CNP exhibits important autocrine and paracrine functions within the heart and the coronary circulation (D'Souza et al. 2004, *Pharmacol Ther*. 101:113-129). In vivo administration of CNP has been shown to improve cardiac function and attenuate cardiac remodelling after myocardial infarction in rats (Soeki et al. 2005, *J Am Coll Cardiol* 45:608-616). Another recent study shows that CNP is able to reduce reactive hypertrophy of cardiomyocytes after an experimental myocardial infarction in transgenic mice over-expressing CNP in cardiomyocytes (Wang et al. 2007, *Eur J Heart Fail*. 9:548-557).

6. Cardiovascular Pathologies, Especially Atherosclerosis, Hypertension, Endothelial Dysfunction and Thrombotic Events Atherosclerosis is a chronic inflammatory response in the walls of arterial blood vessels. In vitro evidence suggests that CNP has an inhibitory role in vascular smooth muscle cell proliferation and migration (Furuya et al. 1991, *Biochem Biophys Res Commun*. 177:927-931, Shinomiya et al. 1994, *Biochem Biophys Res Commun*. 205:1051-1056). Type-C natriuretic peptide inhibited neointimal thickening in injured arteries of rabbits and rats in vivo (Furuya et al. 1995, *Ann N Y Acad Sci*. 748:517-523, Ueno et al. 1997, *Circulation*. 96:2272-2279). In an experimental model of atherosclerosis in rabbits, local infusion of CNP resulted in the preservation of endothelial function and the prevention of neointimal thickening, which normally results from endothelial injury (Gaspari et al. 2000, *Clin Exp Pharmacol Physiol*. 27:653-655).

Pulmonary hypertension is a progressive disease, characterized by an elevated pressure in the pulmonary arterial system. Common treatment is the use of vasodilatory substances. The ability of CNP to relax arteries, possibly via direct interaction with the VSMCs, has been show before in isolated pig coronary arteries (Marton et al. 2005, *Vascul Pharmacol*. 43:207-212). More specifically, CNP was able to ameliorate monocrotaline-induced pulmonary hypertension in rats and improved survival (Itoh et al. 2004, *Am J Respir Crit Care Med*. 170:1204-1211), even if treatment with CNP started 3 weeks after the onset of symptoms.

Endothelial dysfunction plays a fundamental role in the development of atherosclerosis and restenosis. In a rabbit model with features similar to those of the early stage of atherosclerosis or restenosis, chronic pen-arterial administration of ANP or CNP prevented endothelial dysfunction and development of neointima (Gaspari et al. 2000, Clin Exp Pharmacol Physiol. 27:653-655, Barber et al. 2005, *J Vasc Res*. 42:101-110).

Prevention of thrombotic events is critical to the management of cardiovascular diseases. The anti-thrombotic effect of CNP is well known (Ahluwalia et al. 2004, Basic Res Cardiol. 99:83-89). Thrombus formation was significantly suppressed in the presence of CNP in antilogous rabbit jugular vein grafts (Ohno et al. 2002, Circulation. 105:1623-1626). In a model of balloon-injured rabbit carotid arteries CNP was shown to exert anti-thrombotic activity, probably via an increase in the NO production by enhancing the expression of inducible NO synthase (Qian et al. 2002, Circ Res 91:1063-1069).

7. Stimulation of Arteriogenesis

Arteriogenesis refers to the growth of collateral arterioles into functional collateral arteries, and is linked to elevated blood pressure, and elevated flow, causing shear stress against the wall of the arterioles. The stimulation of this event presents a strategy to treat arterial occlusive diseases (van Royen et al. 2001, Cardiovasc Res. 49:543-553). A beneficial effect of ANP on coronary collateral blood flow has been shown earlier (Kyriakides et al. 1998, Clin Cardiol. 21:737-742).

8. Inflammation, Especially Reduction of Inflammatory Mediators, e.g. TNF-Alpha, Other Cytokines or any Kind of Inflammatory Mediator Several publications suggest a role of CNP in the modulation of inflammatory responses: in a model of balloon-injured rabbit carotid arteries, in vivo expression of CNP lowered the expression of the inflammatory marker ICAM-1, and reduced the infiltration of macrophages, supposedly via enhancement of NO generation (Qian et al. 2002, Circ Res 91:1063-1069). In another study, in rat aortic smooth muscle cells in vitro, CNP augmented the transcriptional activation of iNOS induced by inflammatory cytokines (interleukin-1 and tumour necrosis factor-α) and hence the production of NO (Marumo et al. 1995, Endocrinology. 136:2135-2142). CNP infusion in rats with an acute experimental myocarditis led to a reduction of CD68-positive inflammatory cell infiltration, and lowered myocardial and serum levels of monocyte chemoattractant protein-1 (Obata et al. 2007, Biochem Biophys Res Commun. 356:60-66). By selectively attenuating the expression of P-selectin, CNP suppressed leukocyte rolling induced by IL-113 or histamine in a rapid, reversible, and concentration-dependent manner in mice (Scotland et al. 2005, Proc Natl Acad Sci USA. 102:14452-14457). In a model of bleomycin-induced pulmonary fibrosis in mice, infusion of CNP markedly reduced bronchoalveolar lavage fluid IL-1β levels (Murakami et al. 2004, Am J Physiol Lung Cell Mol Physiol. 287:L1172-1177).

9. Pathological Leukocyte Adhesion to Endothelium and Diapedesis into Tissue In mouse mesenteric postcapillary venules in vivo in animals with high basal leukocyte activation (endothelial nitric oxide synthase knockout mice) or under acute inflammatory conditions (induced by IL-1β or histamine), CNP suppressed basal leukocyte rolling in a rapid, reversible, and concentration-dependent manner. CNP was also able to inhibit platelet-leukocyte interactions (Scotland et al. 2005, Proc Natl Acad Sci USA. 102:14452-14457). In a model of bleomycin-induced pulmonary fibrosis in mice, infusion of CNP for 14 days significantly inhibited infiltration of macrophages into the alveolar and interstitial regions (Murakami et al. 2004, Am J Physiol Lung Cell Mol Physiol. 287:L1172-1177). CNP is also known to lower the expression of cell adhesion molecules such as ICAM-1 (Qian et al. 2002, Circ Res 91:1063-1069), and P-Selectin (Scotland et al. 2005, Proc Natl Acad Sci USA. 102:14452-14457), further strengthening its role in adhesion molecule modulation.

10. Kidney Disease, Especially Renal Insufficiency, Renal Failure Due to Reduced Renal Perfusion, Glomerulonephritis and Kidney Fibrosis Local CNP production and CNP receptor expression have previously been demonstrated in glomeruli (Terada et al. 1994, Am J Physiol. 267:F215-222, Lohe et al. 1995, J Am Soc Nephrol. 6:1552-1558, Mattingly et al. 1994, Kidney Int. 46:744-747, Dean et al. 1994, Am J Physiol. 266:F491-496), in kidney cells (Zhao et al. 1994, Kidney Int. 46:717-725) and in mesangial cells (Suga et al. 1992, Hypertension. 19:762-765), suggesting a role in kidney physiology. In several conditions CNP levels in plasma or urine are altered. CNP in plasma and urine was increased in nephrotic syndrome (Cataliotti et al. 2002, Am J Physiol Renal Physiol 283:F464-472), CNP was increased in urine in cirrhosis with renal impairment (Gulberg et al. 2000, Gut. 47:852-857), renal and urine levels of CNP were increased in experimental diabetes (Shin et al. 1998, J Endocrinol. 158:35-42), and NP levels were elevated in chronic kidney disease, but decreased after hemodialysis or transplantation (Horl 2005, J Investig Med 53:366-370).

The benefit from using CNP in indications such as renal insufficiency, and renal failure, comes from its ability to relax smooth muscles in conduit arteries (Drewett et al. 1995, J Biol Chem. 270:4668-4674, Madhani et al. 2003, Br J Pharmacol. 139:1289-1296), venodilation (Chen and Burnett 1998, J Cardiovasc Pharmacol. 32 Suppl 3:S22-28, Wei et al. 1993, J Clin Invest. 92:2048-2052), and dilation of both, afferent and efferent arterioles in glomeruli, as shown in the hydronephrotic rat kidney (Endlich and Steinhausen 1997, Kidney Int. 52:202-207).

Glomerulopathies like glomerulonephritis are typically associated with mesangial cell proliferation, and leukocyte infiltration (Buschhausen et al. 2001, Cardiovasc Res. 51:463-469). The inhibitory effect of CNP on leukocyte infiltration via downregulation of ICAM-1 has been shown before (Qian et al. 2002, Circ Res 91:1063-1069, Buschhausen et al. 2001, Cardiovasc Res. 51:463-469). In addition, all NPs show anti-proliferative effects on mesangial cells in vitro on rat cells (Suganami et al. 2001, J Am Soc Nephrol 12:2652-2663). In vivo, CNP infusion improved immune mediated glomerulonephritis in a rat mesangioproliferative anti-Thy 1.1 model (Canaan-Kuhl et al. 1998, Kidney Int 53:1143-1151). In yet another study CNP inhibited glomerular mesangial cell proliferation, MCP-1 secretion, and reduced collagen IV production from mesangial cells (Osawa et al. 2000, Nephron. 86:467-472).

The inhibitory effect of CNP on the proliferation of glomerular mesangial cells (Suganami et al. 2001, J Am Soc Nephrol 12:2652-2663, Canaan-Kuhl et al. 1998, Kidney Int 53:1143-1151, Osawa et al. 2000, Nephron. 86:467-472) suggests its use in the treatment of kidney fibrosis.

11. Liver Diseases, Especially Portal Vein Hypertension, Liver Cirrhosis, Liver Ascites, Liver Fibrosis and Hepatorenal Syndrome Evidence for a local natriuretic peptide system in the human liver comes from mRNA analysis; specific transcripts for all three NPRs, namely NPR-A, NPR-B, and NPR-C, could be detected, along with mRNA for ANP and CNP, but not BNP (Vollmar et al. 1997, Gut. 40:145-150). During chronic liver diseases, hepatic stellate cells, believed to play a role in the pathogenesis of liver fibrosis and portal hypertension (Friedman 1993, N Engl J Med. 328:1828-1835), acquire a myofibroblastic phenotype, proliferate, and synthetize components associated with fibrosis. Activation of NPR-B by CNP in myofibroblastic hepatic stellate cells was shown to inhibit both growth and contraction (Tao et al. 1999, J Biol Chem. 274:23761-23769), suggesting that during chronic liver diseases, CNP may counteract both liver fibrogenesis and associated portal hypertension.

Liver cirrhosis is the result of a chronic liver disease characterized by replacement of liver tissue by fibrous scar tissue. The presence of CNP in the human kidney and urine (Mattingly et al. 1994, Kidney Int. 46:744-747) suggests a role for CNP in fluid and electrolyte homeostasis, and thus possibly a role in renal function disturbances in patients with cirrhosis of the liver. CNP in the urine of cirrhotic patients with impaired renal function was increased, while plasma levels were normal (Gulberg et al. 2000, Gut. 47:852-857). In cirrhotic patients, ANP infusion reduced the portal pressure and increased the hepatic blood flow, indicative of a lowering of intra-hepatic resistance to portal flow (Brenard et al. 1992, J Hepatol. 14:347-356). Administration of pharmacological doses of CNP to cirrhotic rats significantly decreased portal pressure and peripheral vascular resistance, and increased cardiac output (Komeichi et al. 1995, J Hepatol. 22:319-325).

Many disorders can cause ascites, but cirrhosis is the most common. Hence, treatment of disorders such as liver cirrhosis will eventually help in the avoidance of ascites.

According to the vasodilation theory, the hepatorenal syndrome is the result of the effect of vasoconstrictor systems acting on the renal circulation. Due to this increased activity of the vasoconstrictor systems, renal perfusion and glomerular filtration rate are markedly reduced, while tubular function is preserved. Any substance that increases renal perfusion and/or glomerular filtration rate is thus suited to be used against the hepatorenal syndrome.

12. Lung Diseases, Especially Pulmonary Hypertension, Asthma and Pulmonary Fibrosis CNP was shown to be locally synthesized in pulmonary tissues and therefore might have action on airway patency (Suga et al. 1992, Circ Res. 71:34-39). In vitro CNP was one order of magnitude more potent than ANP in cGMP production in cultured aortic smooth muscle cells.

Pulmonary hypertension is a progressive disease, characterized by an elevated pressure in the pulmonary arterial system. Common treatment is the use of vasodilatory substances. The ability to relax arteries, probably via direct interaction with the VSMCs, has been shown before in isolated pig coronary arteries (Marton et al. 2005, Vascul Pharmacol. 43:207-212). More specifically, CNP was able to ameliorate monocrotaline-induced pulmonary hypertension in rats and to improve survival (Itoh et al. 2004, Am J Respir Crit Care Med. 170:1204-1211), even if treatment with CNP started 3 weeks after the onset of symptoms.

In an ovalbumin-induced asthmatic guinea pig model CNP was able to significantly inhibit the bronchoconstriction and microvascular leakage in a dose-dependent manner (Ohbayashi et al. 1998, Eur J Pharmacol. 346:55-64). In vivo in asthmatics Fluge et al. could demonstrate dose-dependent bronchodilating properties of intravenous natriuretic peptide (Fluge et al. 1995, Regul Pept. 59:357-370).

In a model of bleomycin-induced pulmonary fibrosis in mice, infusion of CNP markedly attenuated the fibrosis, as indicated by significant decreases in Ashcroft score and lung hydroxyproline content (Murakami et al. 2004, Am J Physiol Lung Cell Mol Physiol. 287:L1172-1177). Immunohistochemistry on lung sections revealed a significantly reduced infiltration of macrophages into the alveolar and interstitial regions. The markedly decreased number of Ki-67-positive cells in fibrotic lesions of the lung further supports the notion of CNP's anti-proliferative effects on pulmonary fibrosis.

13. Male and Female Fertility Problems, Especially Erectile Dysfunction, Stimulation of Male Fertility and Stimulation of Female Fertility Penile erection depends on relaxation of the smooth muscle of the corpus cavernosum, one of the sponge-like regions of erectile tissue. The presence of NPR-B in rat and rabbit cavernosal membrane was shown by Kim et al. (Kim et al. 1998, J Urol. 159:1741-1746). They also showed that CNP could trigger the production of cGMP in this tissue, and that CNP was much more potent than BNP and ANP in doing so. NPR-B was also shown to be located in the human corpus cavernosum penis; in organ bath studies with corpus cavernosum muscle strips CNP at concentrations of 0.1 nM to 1 µM led to smooth muscle relaxation from 5% to 40% (Kuthe et al. 2003, J Urol. 169:1918-1922); further support for a role of CNP in erectile dysfunction comes from a recent study, showing that CNP levels are associated with the presence, severity, and duration of erectile dysfunction (Vlachopoulos et al. 2008, Eur Urol. in press).

The rationale for using CNP to stimulate male fertility is based on its potential function in testicular blood supply, the modulation of germ cell development and spermatozoan motility, and its role in penile erection (as described above). CNP has been found in seminal plasma of several species (Hosang and Scheit 1994, DNA Cell Biol. 13:409-417, Chrisman et al. 1993, J Biol Chem. 268:3698-3703); human Leydig cells, located adjacent to the seminiferous tubules in the testicle, contain both, CNP and the NPR-B receptor (Middendorff et al. 1996, J Clin Endocrinol Metab. 81:4324-4328). CNP was able to increase testosterone levels in vitro in purified mouse Leydig cells (Khurana and Pandey 1993, Endocrinology. 133:2141-2149), as well as in vivo in the spermatic vein in men (Foresta et al. 1991, J Clin Endocrinol Metab. 72:392-395). Because testosterone activates the initiation, processing and maintenance of spermatogenesis, CNP has thus an immediate influence on spermatogenesis. Local injection of natriuretic peptides in vivo in rats caused a dose-related increase in testicular blood flow (Collin et al. 1997, Int J Androl. 20:55-60).

A function of CNP in fertilization, pregnancy and embryonic development was first proposed after the detection of CNP in porcine seminal plasma (Chrisman et al. 1993, J Biol Chem. 268:3698-3703). Further studies showed expression of NPR-A and -B receptors in human placenta (Itoh et al. 1994, Biochem Biophys Res Commun. 203:602-607), and their modulation in rat ovary and uterus by the estrous cycle (Huang et al. 1996, Am J Physiol. 271:H1565-1575, Dos Reis et al. 1995, Endocrinology. 136:4247-4253, Noubani et al. 2000, Endocrinology. 141:551-559). In mice, uterine CNP mRNA concentrations increased during pregnancy, whereas in the ovaries these levels decreased compared to non-pregnant controls (Stepan et al. 2001, Regul Pept. 102:9-13). In human placenta and myometrium CNP is expressed with no dependency on gestational age in the third trimester. Pregnancies with intra-uterine growth retardation showed an opposite regulation of CNP in placenta and myometrium, indicating an organ-specific function of the peptide in human reproductive tissue (Stepan et al. 2002, *Fetal Diagn Ther.* 17:37-41). This could be substantiated by studying NPR-B knock-out mice; female mice were infertile due to the failure of the female reproductive tract to develop (Tamura et al. 2004, *Proc Natl Acad Sci USA.* 101:17300-17305).

14. Pre-Eclampsia and/or Preterm Labor

Pre-eclampsia, a hypertensive disorder of pregnancy, is usually associated with raised blood pressure, and affects about 2-8% of pregnancies. Inadequate blood supply to the placenta leads to endothelial dysfunction, eventually resulting in damage to the maternal endothelium and kidney and liver. In severe pre-eclampsia BNP levels are elevated, which might reflect ventricular stress and/or subclinical cardiac dysfunction associated with the condition (Resnik et al. 2005, *Am J Obstet Gynecol.* 193:450-454). Pregnancies with intra-uterine growth retardation or pre-eclampsia showed an opposite regulation of CNP, with a decrease in the placenta and an increase in the myometrium compared with normal pregnancies (Stepan et al. 2002, *Fetal Diagn Ther.* 17:37-41), while maternal CNP plasma levels remained constant; this could indicate a compensatory or causative organ-specific function of the peptide in human reproductive tissue under these pathophysiological conditions, suggesting that application of CNP may have benefits.

15. Skeletal Growth Disturbances, Especially Decreased Body Height (Dwarfism)

Dwarfism can be caused by over 200 separate medical conditions. C-type natriuretic peptide, acting through its receptor, NPR-B, plays a critical role in longitudinal bone growth (Olney 2006, *Growth Horm IGF Res.* 16 Suppl A:S6-14), as it stimulates endochondral ossification (Tamura et al. 2004, *Proc Natl Acad Sci USA.* 101:17300-17305, Miyazawa et al. 2002, *Endocrinology.* 143:3604-3610). A spontaneous autosomal recessive point mutation in the CNP gene, called long bone abnormality (lbab), causes severe dwarfism in mice (Yoder et al. 2008, *Peptides.* 29:1575-1581, Tsuji et al. 2008, *Biochem Biophys Res Commun.* 376:186-190). Complete absence of CNP in mice resulted in dwarfism and early death (Chusho et al. 2001, *Proc Natl Acad Sci USA.* 98:4016-4021).

16. Defects of FGF-R (Fibroblast Derived Growth Factor Receptor) Signalling, Especially Overactivity of FGF-R, or Deficiency of CNP or Osteocrin, or Reduced Level of CNP or Osteocrin in the Growth Plates of Long Bones In vitro and ex vivo studies showed that CNP acts within the growth plate. CNP, most likely synthetised by proliferating chondrocytes (Chusho et al. 2001, *Proc Natl Acad Sci US A.* 98:4016-4021), acts locally to stimulate further proliferation. As opposing element, the FGF/FGFR-3 pathway is known to negatively regulate endochondral ossification via activation of the Erk MAP kinase pathway, thus inhibiting chondrocyte proliferation and cartilage matrix production (Krejci et al. 2005, *J Cell Sci.* 118:5089-5100). The targeted overexpression of CNP in chondrocytes offset dwarfism in a mouse model of achondroplasia with activated fibroblast growth factor receptor 3 in the cartilage, suggesting a direct interaction of their signaling pathways (Yasoda et al. 2004, *Nat Med.* 10:80-86). Moreover, Ozasa et al. found that CNP was able to antagonize the activation of the MAPK cascade by FGFs, making the CNP/NPR-B pathway attractive as a novel therapeutic target in the treatment of achondroplasia (Ozasa et al. 2005, *Bone.* 36:1056-1064). CNP also partially antagonized the FGF2-induced expression, release and activation of several matrix-remodeling molecules including several matrix metalloproteinases. Independent of FGF signaling, CNP stimulated the upregulation of matrix production (Krejci et al. 2005, *J Cell Sci.* 118:5089-5100).

Osteocrin is a specific ligand of the natriuretic peptide clearance receptor NPR-C that modulates bone growth (Thomas et al. 2003, *J Biol Chem.* 278:50563-50571). By blocking the clearance function of NPR-C, it causes the local elevation of CNP levels, resulting in the proliferation of chondrocytes (Moffatt et al. 2007, *J Biol Chem.* 282:36454-36462).

In summary, there is a strong rationale to use CNP in order to compensate for overactive FGF receptors, and for deficiencies or reduced levels of CNP or osteocrin.

17. Arthritis, Especially Degenerative Diseases of Cartilage Tissue, Osteoarthritis and Cartilage Degeneration and Arthritis in Response to Traumatic Cartilage Injury The rationale for the use of natriuretic peptides for the treatment and/or prevention of arthritic diseases comes from the observation that CNP is involved in the skeletal growth, especially in the generation of cartilage extracellular matrix (Chusho et al. 2001, *Proc Natl Acad Sci USA.* 98:4016-4021, Yasoda et al. 2004, *Nat Med.* 10:80-86), which is able to stabilize damaged cartilage.

CNP depletion was shown to result in impaired bone growth, like that observed in achondroplastic bones, with a similar histological picture of decreased width in both the proliferative and hypertrophic chondrocyte layers of the growth plate (Chusho et al. 2001, *Proc Natl Acad Sci USA.* 98:4016-4021). The targeted overexpression of CNP in chondrocytes counteracted dwarfism in a mouse model of achondroplasia with activated fibroblast growth factor receptor 3 in the cartilage. CNP corrected the decreased extracellular matrix synthesis in the growth plate through inhibition of the MAPK pathway of FGF signaling, resulting in the stimulation of glucosaminoglycans and cartilage collagen (type II) synthesis (Yasoda et al. 2004, *Nat Med.* 10:80-86).

In rat chondrosarcoma chondrocytes, after FGF2-mediated growth arrest, CNP mediated the inhibition of MMP induction, and stimulated extracellular matrix synthesis (Krejci et al. 2005, *J Cell Sci.* 118:5089-5100, Ozasa et al. 2005, *Bone.* 36:1056-1064), both effects resulting in a net increase in cartilage extracellular matrix (Krejci et al. 2005, *J Cell Sci.* 118:5089-5100).

18. Tissue Engineering and Cartilage Regeneration, Especially for the Ex Vivo Expansion of Cartilage Cells to a Cell Number Sufficient to Transplant Cells Back into a Patient CNP has stimulatory activity on glucosaminoglycan and cartilage collagen (type II) synthesis in chondrocytes (Krejci et al. 2005, *J Cell Sci.* 118:5089-5100, Yasoda et al. 2004, *Nat Med.* 10:80-86), a feature that is beneficial for in vivo regeneration of cartilage. To produce ex vivo tissue from the limited number of cells that can be extracted from an individual for therapeutic purposes, it is also necessary to have a stimulation of cell proliferation. In a key publication, Waldman et al. reported, that in high-density 3D cultures low doses of CNP (10 to 100 pM) elicited chondrocyte proliferation of up to 43% increase in cellularity at the highest dose. Higher doses of CNP (10 nM) predominantly stimulated matrix deposition without affecting tissue cellularity (Waldman et al. 2008, Tissue Eng Part A. 14:441-448). CNP is thus suitable as a modulator of both chondrocyte proliferation and ECM deposition during in vitro cartilage growth.

19. Tissue Engineering and Bone Regeneration, Especially for the Acceleration of Bone Healing or for the Improvement of Regenerating Bone Tissue The role of the NPR-B/CNP system as an important regulator of bone growth has been established by several publications: NPR-B knock-out mice displayed reduced bone growth (Tamura et al. 2004, Proc Natl Acad Sci USA. 101:17300-17305, Pfeifer et al. 1996, Science. 274:2082-2086); mice with a deletion of the CNP gene also showed reduced bone growth, and this phenotype could be rescued by the overexpression of CNP in chondrocytes (Chusho et al. 2001, Proc Natl Acad Sci USA. 98:4016-4021); overexpression of BNP in mice resulted in skeletal overgrowth (Suda et al. 1998, Proc Natl Acad Sci USA. 95:2337-2342). More specifically, CNP was able to promote chondrocyte proliferation and matrix formation (Krejci et al. 2005, J Cell Sci. 118:5089-5100, Ozasa et al. 2005, Bone. 36:1056-1064). Using an organ culture of fetal mouse tibias, an in vitro model of endochondral ossification, longitudinal bone growth was stimulated by CNP (Yasoda et al. 1998, J Biol Chem. 273:11695-11700).

In summary, the experimental evidence strongly supports the use of CNP in bone regenerating applications.

20. Modulation of Neuronal Activity, Especially for Replacement of CNP in its "Central Nervous Function"

The extensive distribution of the NPR-C receptor in the brainstem suggests an involvement of NPR-C in the neuromodulatory effect of natriuretic peptides (Abdelalim et al. 2008, Neuroscience. 155:192-202), which were shown to evoke a variety of peripheral effects when applied to the brain (Puurunen and Ruskoaho 1987, Eur J Pharmacol. 141:493-495, Bianciotti et al. 2001, Regul Pept. 102:127-133). Intra-cerebroventricular administration of atrial natriuretic peptide in anaesthetized rats, for example, resulted in the stimulation of gastric acid secretion, that was totally abolished by vagotomy, suggesting vagus nerve involvement (Puurunen and Ruskoaho 1987, Eur J Pharmacol. 141:493-495). In two studies by Sabbatini et al., the cerebroventricular administration of CNP in rats dose-dependently enhanced the exocrine pancreatic fluid output through the activation of the NPR-C receptor and the vago-vagal reflex (Sabbatini et al. 2005, Eur J Pharmacol. 524:67-74, Sabbatini et al. 2007, Eur J Pharmacol. 577:192-202), thus mimicking the effect of endogenous CNP.

21. Cancer, Through Inhibition of Proliferation of Tumor Cells, Especially Glioma Cells, Neuroblastoma Cells, Adenocarcinoma Cells, Adenocarcinoma Cells in Breast Pancreas and Prostate, Melanoma Cells and Renal Carcinoma Cells Several publications have shown the presence of natriuretic peptide receptors on tumor cells, suggesting a potential to affect the proliferation of those cells via application of CNP, as has been shown in a range of other cell types.

Early in vitro data from cultered rat glioma cells demonstrated the presence of receptors on those cells, that showed strongest activation by CNP, i.e. cGMP production (Eguchi et al. 1992, Eur J Pharmacol. 225:79-82). In another cell line, a AtT-20 pituitary tumor cell line, the only natriuretic receptor present on the cell surface was the NPR-B receptor. cGMP production in these AtT-20 cells was stimulated up to 200-fold by CNP (Gilkes et al. 1994, Biochem J. 299 (Pt 2):481-487).

Western immunoblotting identified NPR-A and NPR-C receptors in human colon adenocarcinoma cells. Application of 1 mM ANP to these cells resulted in a decrease of up to 97% in cell number within 24 h, suggesting an anti-proliferative activity (Gower et al. 2005, Int J Gastrointest Cancer. 36:77-87).

CNP caused a 39% decrease in the number of small-cell lung cancer cells at 100 µM. The mechanism of growth inhibition supposedly is based on the inhibition of DNA synthesis, mediated in part by cGMP (Vesely et al. 2005, Eur J Clin Invest. 35:388-398).

In yet another cell type, in human renal carcinoma cells, CNP also decreased the cell number, at a concentration of 100 µM by 10%. This effect was sustained without any proliferation of the cells occurring for three days after treatment with CNP. All three types of natriuretic peptide receptors, NPR-A, NPR-B, and NPR-C, were identified on renal cancer cells (Vesely et al. 2006, Eur J Clin Invest. 36:810-819).

22. Fibrosis, Especially Pulmonary Fibrosis, Renal Fibrosis, Cardiac Fibrosis, Hepatic Fibrosis or Systemic Fibrosis/Sclerosis Several studies, investigating fibrotic events in different organ systems, have shown that the application of natriuretic peptides, in particular of CNP, has a beneficial effect on disease progression. A more general effect of CNP-mediated cGMP generation in fibroblasts is the block of the activation of the mitogen-activated protein kinase cascade (Chrisman and Garbers 1999, J Biol Chem. 274:4293-4299), which could be exploited to treat any kind of fibrosis, in particular the multiorgan systemic fibrosis/sclerosis; treatment of single organ fibrosis with CNP is supported by the following data:

In a model of bleomycin-induced pulmonary fibrosis in mice, infusion of CNP markedly reduced bronchoalveolar lavage fluid levels of inflammatory IL-10, inhibited infiltration of macrophages into the alveolar and interstitial regions, and markedly attenuated the fibrosis, as indicated by significant decreases in Ashcroft score and lung hydroxyproline content (Murakami et al. 2004, Am J Physiol Lung Cell Mol Physiol. 287:L1172-1177).

With regard to kidney fibrosis, it was described that CNP had an inhibitory effect on the proliferation of glomerular mesangial cells (Suganami et al. 2001, J Am Soc Nephrol 12:2652-2663, Canaan-Kuhl et al. 1998, Kidney Int 53:1143-1151, Osawa et al. 2000, Nephron. 86:467-472). In particular, CNP inhibited also MCP-1 secretion, and reduced collagen IV production from glomerular mesangial cells (Osawa et al. 2000, Nephron. 86:467-472).

Cardiac fibrosis, characterized by the proliferation of interstitial fibroblasts and the biosynthesis of extracellular matrix components in the ventricles of the heart, is a consequence of remodeling processes. Soeki et al. showed that the application of CNP improved cardiac function and protected against cardiac remodeling after myocardial infarct in rats (Soeki et al. 2005, J Am Coll Cardiol 45:608-616). In vitro, in cardiac fibroblasts, CNP had a suppressive effect on fibroblast proliferation and extracellular matrix production, the effect being stronger than by ANP or BNP (Horio et al. 2003, Endocrinology. 144:2279-2284).

During chronic liver diseases, hepatic stellate cells, believed to play a role in the pathogenesis of liver fibrosis and portal hypertension (Friedman 1993, N Engl J Med. 328:1828-1835), acquired a my ofibroblastic phenotype, proliferated, and synthesized components associated with fibrosis. The activation of NPR-B by CNP in myofibroblastic hepatic stellate cells was shown to inhibit both growth and contraction (Tao et al. 1999, *J Biol Chem.* 274:23761-23769), suggesting that during chronic liver diseases, CNP may counteract fibrogenesis.

C. Pharmaceutical Preparations

Other embodiments of the present invention are directed to pharmaceutical compositions, comprising at least one novel NPR-B agonist described herein, directed to the treatment or prevention of a disease in a subject that is associated with elevated IOP, glaucoma, ocular hypertension, and/or retinal ganglion cell loss.

1. Effective Amount

As used herein, the term "effective amount," or "therapeutically effective amount," refers to an amount of the agent that will activate the function and/or activity of a type B natriuretic peptide receptor. The novel NPR-B agonists described herein lower intraocular pressure or treat ocular hypertension in a patient having elevated IOP or ocular hypertension. Thus, an effective amount is an amount sufficient to detectably and repeatedly ameliorate, reduce, minimize or limit the extent of any disease associated with elevated intraocular pressure or ocular hypertension, such as any of those diseases discussed above.

Treatment and/or prevention methods will involve treating an individual with an effective amount of a composition containing a therapeutically effective amount of at least one NPR-B agonist of the invention. A therapeutically effective amount is described, generally, as that amount that is known to be or suspected to be of benefit in the reduction of the signs or symptoms of a disease. In some embodiments of the present invention, an effective amount is generally an amount that is known or suspected to be of benefit in reducing the signs or symptoms of glaucoma and associated optic nerve or retinal damage in a subject. It is envisioned that the treatment with the NPR-B agonists hereof will stabilize or improve visual function (as measured by visual acuity, visual field, or other method known to those of ordinary skill in the art).

In some embodiments, an effective amount of a NPR-B agonist that may be administered to a subject includes a dose from about 1 microgram/kg/body weight to about 500 microgram/kg/body weight or more per administration, and any range derivable therein.

2. Formulations

Regarding the methods set forth herein, a NPR-B agonist can be formulated in any manner known to those of ordinary skill in the art. In the compositions set forth herein, the concentration of a NPR-B agonist can be any concentration known or suspected by those of ordinary skill in the art to be of benefit in the treatment and/or prevention of ophthalmic disease associated with elevated intraocular pressure or ocular hypertension.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain non-limiting embodiments, the ophthalmic pharmaceutical compositions may comprise, for example, at least about 0.03%, by weight or volume, of an active ingredient. In other embodiments, the active ingredient may comprise between about 0.001% to about 75% of the weight or volume of the unit, or between about 0.01% to about 60%, and any range derivable therein. In more particular embodiments, the pharmaceutical composition may comprise between about 0.03% to about 2.0% by weight or volume, of an active ingredient. In more particular embodiments, the composition comprises between about 0.05% to about 1.5% by weight or volume of an active ingredient. In further embodiments, the composition comprises between about 0.05% to about 1.2% by weight or volume of an active ingredient.

A dose may be any amount of pharmaceutical composition that is known or suspected to be of therapeutic benefit. For example, a dose may be about 1 microgram/kg/body weight to about 500 microgram/kg/body weight or more per administration, and any range derivable therein. A dose may be repeated as necessary as determined by one of ordinary skill in the art to achieve a desired therapeutic effect. For example, a dose may be repeated once, twice, three times, and so forth. In some embodiments, a dose is administered twice a day, three times a day, four times a day, or more often. In further embodiments, a dose is administered every other day, twice a week, once a month, or at a longer interval.

In certain embodiments of the present invention, the compositions set forth herein can include more than one NPR-B agonist. One of ordinary skill in the art would be familiar with preparing and administering pharmaceutical compositions that include more than one therapeutic agent. In some embodiments, the composition includes one or more additional therapeutic agents that are not NPR-B agonists.

In addition to the NPR-B agonists, the compositions of the present invention optionally comprise one or more excipients. Excipients commonly used in pharmaceutical compositions include, but are not limited to, carriers, tonicity agents, preservatives, chelating agents, buffering agents, surfactants and antioxidants.

A person of ordinary skill will recognize that the compositions of the present invention can include any number of combinations of ingredients (e.g., active agent, polymers, excipients, etc.). It is also contemplated that that the concentrations of these ingredients can vary. In non-limiting aspects, the percentage of each ingredient in the composition can be calculated by weight or volume of the total composition. A person of ordinary skill in the art would understand that the concentrations can vary depending on the addition, substitution, and/or subtraction of ingredients in a given composition.

In some embodiments of the invention, a specific amount of a NPR-B agonist is administered via the compositions described herein.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient.

Any of a variety of carriers may be used in the formulations of the present invention including water, mixtures of water and water-miscible solvents, such as C1-7-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, mixtures of those polymers. The concentration of the carrier is, typically, from 1 to 100000 times the concentration of the active ingredient.

Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquatemium-1 and the like. Suitable chelating agents include sodium edetate and the like. Suitable buffering agents include phosphates, borates, citrates, acetates and the like. Suitable surfactants include ionic and nonionic surfactants, though nonionic surfactants are preferred, such as polysorbates, polyethoxylated castor oil derivatives and oxyethylated tertiary octylphenol formaldehyde polymer (tyloxapol). Suitable antioxidants include sulfites, ascorbates, BHA and BHT. The compositions of the present invention optionally comprise an additional active agent.

In particular embodiments, the compositions are suitable for application to mammalian eyes. For example, for ophthalmic administration, the formulation may be a solution, a suspension, a gel, or an ointment.

In preferred aspects, the compositions that include NPR-B agonists will be formulated for topical application to the eye in aqueous solution in the form of drops. The term "aqueous" typically denotes an aqueous composition wherein the carrier is to an extent of >50%, more preferably >75% and in particular >90% by weight water. These drops may be delivered from a single dose ampoule which may preferably be sterile and thus rendering bacteriostatic or bacteriocidal components of the formulation unnecessary. Alternatively, the drops may be delivered from a multi-dose bottle which may preferably comprise a device which extracts preservative from the formulation as it is delivered, such devices being known in the art.

In other aspects, components of the invention may be delivered to the eye as a concentrated gel or similar vehicle which forms dissolvable inserts that are placed beneath the eyelids.

The compositions of the present invention may also be formulated as solutions that undergo a phase transition to a gel upon administration to the eye.

In addition to the one or more NPR-B agonists, the compositions of the present invention may contain other ingredients as excipients. For example, the compositions may include one or more pharmaceutically acceptable buffering agents, preservatives (including preservative adjuncts), non-ionic tonicity-adjusting agents, surfactants, solubilizing agents, stabilizing agents, comfort-enhancing agents, polymers, emollients, pH-adjusting agents and/or lubricants.

For topical formulations to the eye, the formulations are preferably isotonic, or slightly hypotonic in order to combat any hypertonicity of tears caused by evaporation and/or disease. The compositions of the present invention generally have an osmolality in the range of 220-320 mOsm/kg, and preferably have an osmolality in the range of 235-260 mOsm/kg. The compositions of the invention have a pH in the range of 5-9, preferably 6.5-7.5, and most preferably 6.9-7.4.

The formulations set forth herein may comprise one or more preservatives. Examples of preservatives include quaternary ammonium compounds, such as benzalkonium chloride or benzoxonium chloride. Other examples of preservatives include alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, or sorbic acid.

In certain embodiments, the NPR-B agonists are formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. The formulation of the present invention may be used with contact lenses or other ophthalmic products.

In some embodiments, the compositions set forth herein have a viscosity of 0.5-10 cps, preferably 0.5-5 cps, and most preferably 1-2 cps. This relatively low viscosity insures that the product is comfortable, does not cause blurring, and is easily processed during manufacturing, transfer and filling operations.

3. Route of Administration

Administration of the compositions of the invention can be by any method known to those of ordinary skill in the art, however, local administration is preferred. It is contemplated that all local routes to the eye may be used including topical, subconjunctival, periocular, retrobulbar, subtenon, intracameral, intravitreal; intraocular, subretinal, juxtascleral and suprachoroidal administration. Systemic or parenteral administration may be feasible including but not limited to intravenous, subcutaneous, intramuscular and oral delivery. The most preferred method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel formulation.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

While a particular embodiment of the invention has been shown and described, numerous variations and alternate embodiments will occur to those skilled in the art. Accordingly, the invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

D. Secondary Forms of Therapy

In certain embodiments of the present invention, the subject is receiving one or more secondary forms of therapy directed to treatment or prevention of a particular eye disease.

A NPR-B agonist-containing ophthalmic composition of the present invention may be administered along with another agent or therapeutic method. For example, administration of the NPR-B agonist-containing composition of the present invention to a human subject may precede, follow, or be concurrent with other therapies for glaucoma, elevated intraocular pressure or ocular hypertension. In some embodiments, the NPR-B agonist is formulated in the same composition as the secondary form of therapy. In other embodiments, the NPR-B agonist is formulated separately from the secondary form of therapy. One of ordinary skill in the art would be familiar with protocols for administering more than one form of pharmacological therapy to a subject with a disease, and would be familiar with methods of formulating more than one pharmacological agent in the same composition.

Examples of secondary therapeutic agents include, but are not limited to: anti-glaucoma agents, such as beta-blockers including timolol, betaxolol, levobetaxolol, carteolol, miotics including pilocarpine, carbonic anhydrase inhibitors, prostaglandins, seretonergics, muscarinics, dopaminergic agonists, adrenergic agonists including apraclonidine and brimonidine; anti-angiogenesis agents; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as nerve growth factor (NGF), basic fibroblast growth factor (bFGF), brain-derived neurotrophic factor (BDNF), ciliary neutrophic factor (CNTF); immunosuppressant agents; and anti-allergic agents including olopatadine. Information pertaining to olopatadine formulations can be found in U.S. Pat. No. 6,995,186, U.S. Patent App. Pub. No. 2005/0158387, and U.S. Patent App. Pub. No. 2003/0055102, each of which is hereby specifically incorporated by reference. The ophthalmic drug may be present in the form of a pharmaceutically acceptable salt, such as timolol maleate, brimonidine tartrate or sodium diclofenac.

Other examples of a secondary therapeutic agent include a receptor tyrosine kinase (RTK) inhibitor. Exemplary RTK inhibitors are described in U.S. Patent App. Pub. No. 2006/0189608, and U.S. Pat. No. 7,297,709, both of which are hereby specifically incorporated by reference. In preferred embodiments, the receptor tyrosine kinase inhibitor is N-[4-[3-amino-1H-indazol-4-yl]phenyl]-N'-(2-fluoro-5-methylphenyl)urea.

In other particular embodiments, the secondary therapeutic agent is a prostaglandin or a prostaglandin analog. For example, the prostaglandin analog may be latanoprost, bimatoprost, unoprostone or travoprost.

In particular embodiments, the secondary therapeutic agent is a steroid. For example, the steroid may be a glucocorticoid, a progestin, a mineralocorticoid, or a corticosteroid. Exemplary corticosteroids include cortisone, hydrocortisone, prednisone, prednisolone, methylprednisone, triamcinolone, fluoromethalone, dexamethasone, medrysone, betamethasone, loteprednol, fluocinolone, flumethasone, or mometasone. Other examples of steroids include androgens, such as testosterone, methyltestosterone, or danazol. The secondary therapeutic agent may also be a glucocorticoid that is devoid of typical glucocorticoid side-effects, such as a cortisene. Preferred cortisenes for use in the methods of the invention include anecortave acetate and anecortave desacetate. Often steroids are administered as ester, acetal, or ketal prodrugs, many of which are water-insoluble. The secondary therapeutic agents may be directed to treatment or prevention of a single disease, or can be directed to treatment or prevention of two or more diseases.

In addition to pharmacological agents, surgical procedures can be performed in combination with the administration of the NPR-B agonists. One such surgical procedure can include laser trabeculoplasty or trabeculectomy. In laser trabeculoplasty, energy from a laser is applied to a number of noncontiguous spots in the trabecular meshwork. It is believed that the laser energy stimulates the metabolism of the trabecular cells, and changes the extracellular material in the trabecular meshwork.

Another surgical procedure may include filtering surgery. With filtering surgery, a hole is made in the sclera near the angle. This hole allows the aqueous fluid to leave the eye through an alternate route. The most commonly performed filtering procedure is a trabeculectomy. In a trabeculectomy, a conjunctiva incision is made, the conjunctiva being the transparent tissue that covers the sclera. The conjunctiva is moved aside, exposing the sclera at the limbus. A partial thickness scleral flap is made and dissected half-thickness into the cornea. The anterior chamber is entered beneath the scleral flap and a section of deep sclera and/or trabecular meshwork is excised. The scleral flap is loosely sewn back into place. The conjunctival incision is tightly closed. Postoperatively, the aqueous fluid passes through the hole, beneath the scleral flap which offers some resistance and collects in an elevated space beneath the conjunctiva called a bleb. The fluid then is either absorbed through blood vessels in the conjunctiva or traverses across the conjunctiva into the tear film.

E. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods

The materials and methods as well as general methods are further illustrated by the following examples:

Solvents:

Solvents were used in the specified quality without further purification.

Acetonitrile (Gradient grade, J.T. Baker); dichloromethane (for synthesis, VWR); diethylether (for synthesis, VWR); N,N-dimethylformamide (LAB, VWR); dioxane (for synthesis, Aldrich); methanol (for synthesis, VWR).

Water: Milli-Q Plus, Millipore, demineralized.

Reagents:

The used reagents were purchased from Advanced ChemTech (Bamberg, Germany), Sigma-Aldrich-Fluka (Deisenhofen, Germany), Bachem (Heidelberg, Germany), J.T. Baker (Phillipsburg, USA), Iris Biotech (Marktredwitz, Germany), Lancaster (Griesheim, Germany), VWR (Darmstadt, Germany), NeoMPS (Strasbourg, France), Novabiochem (Bad Soden, Germany, from 2003 on Merck Biosciences, Darmstadt, Germany) and Acros (Geel, Belgium, distributor Fisher Scientific GmbH, Schwerte, Germany), Peptech (Cambridge, Mass., USA), Synthetech (Albany, Oreg., USA), Pharmacore (High Point, N.C., USA), Anaspec (San Jose, Calif., USA) and used in the specified quality without further purification.

Non-commercially available non-conventional amino acids were prepared according to standard protocols either as building blocks for solid phase synthesis or by derivatization of commercially available amino acids during solid phase synthesis.

If not stated differently, concentrations are given as percent by volume.

Analysis of Peptides According to the Present Invention:

The analyses of peptides were performed with analytical HPLC methods followed by either ESI-MS or MALDI-MS detection. For analytic chromatography a Hewlett Packard 1100-system together with an ESI-MS (Finnigan LCQ ion trap mass spectrometer) was used. Helium was used as impact gas in the ion trap. For chromatographic separation a RP-18-column (Vydac (Merck) at 30° C. was used. A binary gradient was applied for all chromatograms (5-95% B, linear, A: 0.1% TFA in water and B: 0.1% TFA in CH3CN). UV detection was at λ=220 nm.

Analyses by means of HPLC/MS was performed using a linear gradient from 95:5 to 5:95 (A: 0.1% TFA in water and B: 0.1% TFA in acetonitrile), RP columns were from the companies Phenomenex or Waters (Typ Luna C-18, 3 μm, 2.00×50 mm, Symmetry C18 Column MV Kit, 5 μm, 4.6×250 mm, respectively); For ESI-MS measurements a mass spectrometer ThermoFinnigan Advantage and/or LCQ Classic (both iontrap) was used. For ESI ionization helium served as impact gas in the ion trap. In case of MALDI-MS analyses an Applied Biosystems Voyager RP MALDI mass spectrometer was used with α-Cyano-4-hydroxycinnamic acid as internal calibration matrix.

Purification of Peptides with Preparative HPLC:

Preparative HPLC separations were performed using Varian PLRP-S (10 μm, 100 Å) columns (150×25 mm or 150×50 mm) with the following gradient solvents: A: 0.05% TFA in H$_2$O and B: 0.05% TFA in CH$_3$CN

TABLE 4

| Abbreviations: | |
|---|---|
| AAV | general procedure |
| Ac | Acetyl |
| Acm | Acetamidomethyl |
| DCM | Dichloromethane |
| DIC | Diisopropylcarbodiimide |
| DIPEA | N,N-diisopropylethylamine |
| DMF | N,N-dimethylformamide |
| DMSO | Dimethylsulfoxide |
| eq. | Equivalent(s) |
| ESI | Electrospray ionisation |
| Fig. | Figure |
| Fmoc | 9-fluorenylmethyloxycarbonyl |
| H | hour(s) |
| HATU | O-(7-azabenzotriazol-1-yl)-1,1,3,3-tetramethyluronium-hexafluorophosphate |
| HBTU | O-(benzotriazol-1-yl)-1,1,3,3-tetramethyluronium-hexafluorophosphate |
| HOBt | 1-hydroxybenzotriazole |
| HPLC | high-pressure liquid chromatography |
| MALDI | Matrix Assisted Laser Desorption/Ionization |
| Me | Methyl |
| min | minute(s) |
| ml | Milliliter |
| MS | Mass spectrometry |
| MW | Molecular weight |
| NMP | N-methylpyrrolidone |
| Ph | Phenyl |
| RP | Reversed phase |
| $^t$Bu | tert-butyl |
| THF | Tetrahydrofuran |
| TIPS | Triisopropyl silane |
| TFA | trifluoroacetic acid |
| UV | Ultraviolet |

Example 2

Synthesis of Peptides

Linear peptides were synthesized using the Fmoc-tBu-strategy. The synthesis was done either manually in polypropylene syringes or via an automatic synthesizer (Syro from Multisyntech, Witten or Sophas from Zinsser-Analytic, Frankfurt).

For the preparation of peptides carrying a C-terminal carboxylic acid, the C-terminal amino acid was either attached to a tritylchloride resin (approx. 100 mg resin; loading of reactive groups approx. 1.5 mmol/g; coupling with 0.8 eq. Fmoc-amino acid and 3.0 eq. DIPEA in DCM for 2 h; loading of the first amino acid approx. 0.2-0.4 mmol/g) or to Wang resin (100-200 mg resin; loading of reactive groups approx. 0.6 mmol/g; coupling with 4 eq. Fmoc-amino acid, 4 eq. DIC and 3 eq. NMI in DMF for 3 h; loading of the first amino acid approx. 0.2-0.6 mmol/g).

For the preparation of peptides carrying a C-terminal carboxylic amide, the first amino acid was attached to the resin via Fmoc deprotection of the Fmoc-Rink amide resin (ca. 100 mg resin, ca. 0.5 mmol/g loading; Fmoc deprotection with 20% piperidine in DMF for 20 min) and subsequent coupling of the Fmoc amino acid (reaction with 5 eq. Fmoc amino acid; 5 eq. HBTU or 5 eq. HATU and 10 eq. DIPEA in NMP for 30-60 min and this step was optionally repeated).

After the coupling of the first amino acid, the synthesis of the peptide was done via a repeated sequence of steps, as necessary, consisting of Fmoc deprotection and coupling of the corresponding Fmoc amino acid or carboxylic acid. For the Fmoc deprotection the resin was treated with 20% piperidine in DMF for 20 min. The coupling of the amino acids was carried out via reaction with 5 eq. of the amino acid, 5 eq. HBTU or 5 eq. HATU and 10 eq. DIPEA in DMF for 30-60 min. Each coupling step was optionally repeated.

For the introduction of the N-terminal acetyl group, the N-terminal free peptide, bound to the resin, was incubated with a solution of 10% acetic acid anhydride and 20% DIPEA in DMF for 20 min. For the introduction of the N-terminal sulfonyl group, the N-terminal free peptide, bound to the resin, was incubated with a solution of 2 eq. of the corresponding sulfonyl chloride and 4 eq. DIPEA in DMF or DCM for 30 min and this treatment was repeated once.

For the cleavage of the peptide from the resin and its side chain protecting groups, a mixture of 95% TFA, 2.5% H2O, 2.5% TIPS or a similar solution was added. Finally the crude peptide was isolated either by evaporation of TFA using a rotary evaporator or by precipitation with the aid of methyl-$^t$butyl-ether at 0° C.

Example 3

NPR-A Induced Production of Cyclic GMP in Stably Transfected Cell

To assess the specificity of compounds for NPR activation, human 293-T cells transfected with NPR-A (Potter and Garbers 1992, J Biol Chem. 267:14531-14534) are used in stimulation experiments.

In this homogenous assay, the cells are stimulated in suspension with the test compound and the production of cyclic GMP (cGMP) is determined, from which EC50 values are calculated. ANP, the naturally occurring ligand of NPR-A is used as an internal control and to determine the maximal cGMP production of the cells, which allows the calculation of activation values of the tested compounds relative to ANP.

Preparation of Cells:

NPR-A transfected 293-T cells are washed once with phosphate buffered saline (PBS) and detached from a 75 cm$^2$ tissue culture flask by addition of 3 ml of non enzymatic cell dissociation solution (Sigma-Aldrich) and incubation for 10 min. at room temperature. Detached cells are harvested in 20 ml PBS and centrifuged for 10 min at 200×g at room temperature. The cells are resuspended in DMEM/Ham's F12 mix supplemented with 1 mM IBMX (Medium) and adjusted to a density of $1.25 \times 10^5$ cells/ml and incubated for 15 min. at room temperature.

Stimulation of Cells:

20 µl of cells ($2.5 \times 10^3$ cells) are added to each well of a 96 well white optical bottom tissue culture plate (Nunc, Germany). 10 µl of compound dilution is added and the cells are stimulated for 25 min. at room temperature. The stimulation is stopped by addition of 20 µl of Lysis buffer (reagent included in cGMP Assay Kit).

Determination of cGMP:

The amount of produced cGMP in the cells is determined using HitHunter™ cGMP Assay kit (DiscoveRX) according to manufacturer's instructions.

Dilution of Compounds:

For EC50 determinations, duplicate wells are stimulated with a serial dilution of a 10 mM DMSO compound stock solution. Dilutions are prepared in Medium supplemented with IBMX (1 mM). The final compound concentration in the assay is in the range from 45 µM to 20 nM. The internal standard compound ANP is used at concentrations ranging from 5 µM to 310 pM.

Example 4

NPR-B Induced Production of Cyclic GMP in Human Glaucoma Trabecular Meshwork Cells (GTM-3)

The potency of compounds to activate NPR-B was evaluated in a functional assay using endogenously NPR-B expressing GTM-3 cells (Pang, Shade et al. 1994). In this assay the dose dependent production of cyclic GMP (cGMP) is determined and $EC_{50}$ values are calculated. The natural occurring ligand for NPR-B, i.e. CNP is used as an internal control and to determine the maximal cGMP production of the cells, which allows the calculation of activation values of the tested compounds relative to CNP.

Preparation of Cells:

In a 96 well white optical bottom tissue culture plate (Nunc, Germany) $1.5 \times 10^5$ cells/well are seeded in Dulbecco's MEM (DMEM, Biochrom) supplemented with Gentamycin (0.056 mg/ml) and incubated for 18 h with 10% $CO_2$ in a humidified atmosphere.

Stimulation of Cells:

The cell culture medium is aspirated and each well is washed with 200 µl DMEM/Ham's F12=Medium (Gibco). Then, 200 µl Medium supplemented with 1.5 mM IBMX (3-Isobutyl-1-methyl-Xanthin, Sigma) is added to each well and incubated for 15 min. at room temperature. 25 µl of compound dilution is added and the cells are stimulated for 15 min. at room temperature. The stimulation is stopped by aspiration of the medium and addition of 20 µl of Lysis buffer (reagent included in cGMP Assay Kit).

Determination of cGMP:

The amount of produced cGMP in the cells is determined using HitHunter™ cGMP Assay kit (DiscoveRX) according to manufacturer's instructions.

Dilution of Compounds:

For $EC_{50}$ determinations, duplicate wells are stimulated with a serial dilution of a 10 mM DMSO compound stock solution. Dilutions are prepared in Medium supplemented with IBMX (1.5 mM). Final compound concentrations are in the range from 45 µM to 20 nM. Highly active compounds, e.g. CNP are used for stimulation at concentrations ranging from 5 µM to 6 nM.

Example 5

Efficacy in the Rabbit

A single 30 µL drop of a test item formulation was administered to rabbit eyes (n=8 to 10). Intraocular pressure (IOP) was assessed in each eye at 0 hr, just prior to dosing, and again hourly for up to 4 hr post dose. The efficacy of a given formulation was determined based on the difference between the pretreatment IOP readings at 0 hr and the post treatment readings. A maximum percent reduction in IOP greater than 15% was noted by the "+" symbol. A maximum IOP reduction of less than 15% was assigned the "−" symbol.

Results obtained with novel compounds of the invention in the above-described assays are provided in Table 5, below:

TABLE 5

In vivo results with novel compounds of the invention according to the methods described in Example 5.

| SEQ ID NO: | JAL | STRUCTURE | RIOP dose 300 ug - IOP reduction <15% + IOP reduction >15% |
|---|---|---|---|
| 3 | CNP | CNP | − |
| 81 | 781[+] | Occ-ala-ala-Phe-Gly-Leu-Pro-Leu-Asp-Arg-Lle-NH$_2$; | − |
| 127 | 955[++] | Occ-pro-Phe-Gly-Leu-Pro-Nml-Asp-Arg-Ile-NH$_2$; | − |
| 130 | 958[++] | Occ-Sni-Nmf-Gly-Leu-Pro-Nml-Asp-Arg-Ile-NH$_2$; | − |
| 135 | 967[+] | Occ-Sni-Nmf-Gly-Leu-Pro-Leu-Asp-Arg-Ile-NH$_2$; | − |
| 182 | 1041[+] | Occ-Sni-Phe-leu-Leu-Hyp-Nml-Asp-Arg-Ile-NH$_2$; | + |
| 203 | 1085[+] | Occ-ala-Nmf-arg-Leu-Hyp-Nml-Asp-Arg-Ile-NH$_2$; | + |
| 187 | 1047[++] | Occ-ala-Phe-arg-Leu-Hyp-Leu-Asp-Arg-Ile-NH$_2$; | + |
| 204 | 1086[++] | Occ-ala-Phe-arg-Leu-Hyp-Nml-Asp-Arg-Ile-NH$_2$; | + |
| 183 | 1042[+] | Occ-ala-Phe-leu-Leu-Hyp-Nml-Asp-Arg-Ile-NH$_2$; | − |
| 195 | 1060[++] | Occ-ala-Phe-lys-Leu-Hyp-Nml-Asp-Arg-Ile-NH$_2$; | + |
| 267 | 1287 | Occ-Sni-Phe-dap(Me2)-Leu-Hyp-Nml-Asp-Arg-Ile-NH$_2$; | + |
| 274 | 1295[+] | Occ-Sni-Phe-leu-Leu-Tap-Nml-Asp-Arg-Ile-NH$_2$; | + |
| 355 | 1400[+] | Occ-Sni-Phe-dap(Me2)-Leu-Hyp-Nml-Val-Arg-Ile-NH$_2$; | + |
| 292 | 1325[+] | Occ-Sni-Phe-dap(Me2)-Leu-Tap-Nml-Asp-Arg-Ile-NH$_2$; | + |
| 332 | 1369[+] | Oct-Sni-Phe-dap(Me2)-Leu-Tap-Nml-Asp-Arg-Ile-NH$_2$; | + |
| 372 | 1429[++] | Oct-Sni-Phe-dap(Me2)-Leu-Hyp-Nml-Asp-Arg-Ile-NH$_2$; | + |
| 414 | 1496[+] | Occ-Sni-Eaa-leu-Leu-Hyp-Nml-Asp-Arg-Ile-NH$_2$; | − |
| 421 | 1512[++] | Occ-Sni-Phe-leu-Leu-Hyp-Nml-Asp-Pro-Che; | + |
| 425 | 1555[++] | Occ-Sni-Phe-Apc-Leu-Hyp-Nml-Asp-Arg-Ile-NH$_2$; | + |
| 481 | 1654[+] | Occ-Sni-Phe-leu-Leu-Tap-Nml-Val-Pro-Che; | − |
| 506 | 1729[+] | Occ-Sni-Phe-leu-Leu-Tap-Nml-Val-Arg-Che; | + |

TABLE 5-continued

In vivo results with novel compounds of the invention according to the methods described in Example 5.

| SEQ ID NO: | JAL | STRUCTURE | RIOP dose 300 ug<br>- IOP reduction <15%<br>+ IOP reduction >15% |
|---|---|---|---|
| 507 | 1730+ | Occ-Sni-Phe-leu-Leu-Hyp-Nml-Val-Arg-Che; | + |
| 269 | 1289+ | Occ-Sni-Phe-orn(Me2)-Leu-Hyp-Nml-Asp-Arg-Ile-NH$_2$ | + |

HCl salt except *TFA;
Dose is 300 μg topical ocular unless (##);
DB rabbits unless NZA, scores 1-4 (4 = IOP could not be taken);
"" indicates hypertensive phase;
(n = #R) means # responders out of 10-12 animals tested;
1% is +susp ++sol All of the methods disclosed and claimed herein can be made and executed without undue experimentation in light of the present disclosure. While the methods of this invention have been described in terms of preferred embodiments, it will be apparent to those of skill in the art that variations may be applied to the methods described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All references cited herein, to the extent that they provide exemplary procedural or other details supplementary to those set forth herein, are specifically incorporated herein by reference.

What is claimed is:

1. A compound selected from:
6054-Phe-arg-Leu-Hyp-Nml-Asp-Arg-Ile-NH$_2$ (SEQ ID NO:228);
Occ-Sni-Mpa-leu-Leu-Hyp-Nml-Asp-Arg-Ile-NH$_2$ (SEQ ID NO:244);
Occ-Sni-Ppa-leu-Leu-Hyp-Nml-Asp-Arg-Ile-NH$_2$ (SEQ ID NO:245);
(6071-OH)-Phe-arg-Leu-Hyp-Nml-Asp-Arg-Ile-NH$_2$ (SEQ ID NO:246);
5587-Phe-arg-Leu-Hyp-Nml-Asp-Arg-Ile-NH$_2$ (SEQ ID NO:248);
(AR-201-48)-arg-Leu-Hyp-Nml-Asp-Arg-Ile-NH$_2$ (SEQ ID NO:270);
(AR-201-48)-leu-Leu-Hyp-Nml-Asp-Arg-Ile-NH$_2$ (SEQ ID NO:272);
(AR-201-58)-Phe-arg-Leu-Hyp-Nml-Asp-Arg-Ile-NH$_2$ (SEQ ID NO:307);
(AR-201-59)-Phe-arg-Leu-Hyp-Nml-Asp-Arg-Ile-NH$_2$ (SEQ ID NO:308);
Sbt-Sni-Phe-arg-Leu-Hyp-Nml-Asp-Arg-Ile-NH$_2$ (SEQ ID NO:311);
Sbt-ala-Phe-arg-Leu-Hyp-Nml-Asp-Arg-Ile-NH$_2$ (SEQ ID NO:313);
Nbt-ala-Phe-arg-Leu-Hyp-Nml-Asp-Arg-Ile-NH$_2$ (SEQ ID NO:314);
(AR-201-72)-Phe-leu-Leu-Hyp-Nml-Asp-Arg-Ile-NH$_2$ (SEQ ID NO:339);
(AR-201-72)-Phe-arg-Leu-Hyp-Nml-Asp-Arg-Ile-NH$_2$ (SEQ ID NO:340);
Miy-Gab-Hgl-ala-Phe-arg-Leu-Hyp-Nml-Asp-Arg-Ile-NH$_2$ (SEQ ID NO:374);
Ac-Miy-Gab-Hgl-ala-Phe-arg-Leu-Hyp-Nml-Asp-Arg-Ile-NH$_2$ (SEQ ID NO:375);
Occ-Sni-Tyr-leu-Leu-Hyp-Nml-Asp-Arg-Ile-NH$_2$ (SEQ ID NO:408);
Occ-Sni-Bmf-leu-Leu-Hyp-Nml-Asp-Arg-Ile-NH$_2$ (SEQ ID NO:409);
Occ-Sni-Phe-Ala-Leu-Hyp-Nml-Asp-Arg-Ile-NH$_2$ (SEQ ID NO:423);
Occ-Sni-Phe-nml-Leu-Hyp-Nml-Asp-Arg-Ile-NH$_2$ (SEQ ID NO:437);
2553-Sni-Phe-leu-Leu-Hyp-Nml-Asp-Arg-Ile-NH$_2$ (SEQ ID NO:457);
6988-Sni-Phe-leu-Leu-Hyp-Nml-Asp-Arg-Ile-NH$_2$ (SEQ ID NO:460);
1695-Sni-Phe-leu-Leu-Hyp-Nml-Asp-Arg-Ile-NH$_2$ (SEQ ID NO:462);
Occ-Sni-Otf-leu-Leu-Hyp-Nml-Asp-Arg-Ile-NH$_2$ (SEQ ID NO:467);
Occ-Sni-NHfe-leu-Leu-Hyp-Nml-Asp-Arg-Ile-NH$_2$ (SEQ ID NO:474);
785-Sni-Phe-leu-Leu-Hyp-Nml-Asp-Arg-Ile-NH$_2$ (SEQ ID NO:484);
3218-Sni-Phe-leu-Leu-Hyp-Nml-Asp-Arg-Ile-NH$_2$ (SEQ ID NO:486);
1281-G-Sni-Phe-leu-Leu-Hyp-Nml-Asp-Arg-Ile-NH$_2$ (SEQ ID NO:489);
1281-Bal-Sni-Phe-leu-Leu-Hyp-Nml-Asp-Arg-Ile-NH$_2$ (SEQ ID NO:490);
Occ-Sni-Hfe-leu-Leu-Hyp-Nml-Asp-Arg-Ile-NH$_2$ (SEQ ID NO:504);
Occ-ala-Nmf-leu-Leu-Hyp-Nml-Asp-Arg-Ile-NH$_2$ (SEQ ID NO:505);
Gluc-Aoa-hgl-Sni-Phe-leu-Leu-Hyp-Nml-Asp-Arg-Ile-NH$_2$ (SEQ ID NO:533);
(1270)-Hgl-Sni-Phe-leu-Leu-Hyp-Nml-Asp-Arg-Ile-NH$_2$ (SEQ ID NO:535);
Occ-Hgl-Sni-Phe-leu-Leu-Hyp-Nml-Asp-Arg-Ile-NH$_2$ (SEQ ID NO:537);
(AR-314-170)-Phe-leu-Leu-Hyp-Nml-Asp-Arg-Ile-NH$_2$ (SEQ ID NO:555);
(AR-314-171)-Phe-leu-Leu-Hyp-Nml-Asp-Arg-Ile-NH$_2$ (SEQ ID NO:556);
(AR-385-008)-leu-Leu-Hyp-Nml-Asp-Arg-Ile-NH$_2$ (SEQ ID NO:557); and
Occ-Sni-Phe-thr-Leu-Hyp-Nml-Asp-Arg-Ile-NH$_2$ (SEQ ID NO:565).

2. The compound of claim 1 selected from:
2553-Sni-Phe-leu-Leu-Hyp-Nml-Asp-Arg-Ile-NH$_2$ (SEQ ID NO:457);
6988-Sni-Phe-leu-Leu-Hyp-Nml-Asp-Arg-Ile-NH$_2$ (SEQ ID NO:460);
1695-Sni-Phe-leu-Leu-Hyp-Nml-Asp-Arg-Ile-NH$_2$ (SEQ ID NO:462);
785-Sni-Phe-leu-Leu-Hyp-Nml-Asp-Arg-Ile-NH$_2$ (SEQ ID NO:484);
3218-Sni-Phe-leu-Leu-Hyp-Nml-Asp-Arg-Ile-NH$_2$ (SEQ ID NO:486);
1281-G-Sni-Phe-leu-Leu-Hyp-Nml-Asp-Arg-Ile-NH$_2$ (SEQ ID NO:489);
1281-Bal-Sni-Phe-leu-Leu-Hyp-Nml-Asp-Arg-Ile-NH$_2$ (SEQ ID NO:490);
Gluc-Aoa-hgl-Sni-Phe-leu-Leu-Hyp-Nml-Asp-Arg-Ile-NH$_2$ (SEQ ID NO:533);
(1270)-Hgl-Sni-Phe-leu-Leu-Hyp-Nml-Asp-Arg-Ile-NH$_2$ (SEQ ID NO:535); and
Occ-Hgl-Sni-Phe-leu-Leu-Hyp-Nml-Asp-Arg-Ile-NH$_2$ (SEQ ID NO:537).

3. A compound of the formula:

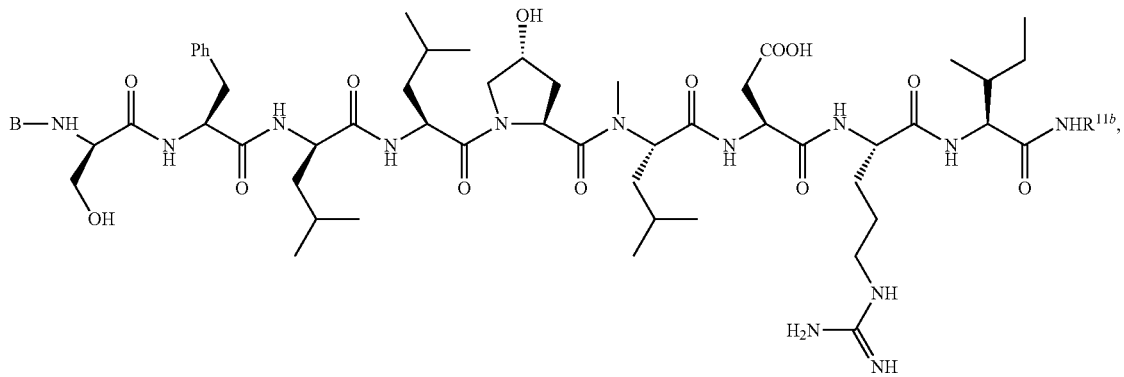

wherein
B is selected from the group consisting of $R^{b1}$— and $R^{b2}$—C(O)—, wherein:
  $R^{b1}$ is selected from the group consisting of $C_6$-$C_{10}$ alkyl and $C_6$-$C_{10}$ alkyl substituted by $NR^{b4}R^{b5}$;
  Rb2 is $C_6$-$C_{10}$ alkyl substituted by $NR^{b4}R^{b5}$; and
  $R^{b4}$ and $R^{b5}$ are, independently, selected from the group consisting of H and $C_1$-$C_4$ alkyl; and
$R^{11b}$ is selected from the group consisting of H, $C_1$-$C_8$ alkyl, $C_4$-$C_8$ cycloalkyl, $C_7$-$C_{12}$ bicycloalkyl, and $C_1$-$C_4$ alkyl-$C_4$-$C_8$ cycloalkyl.

4. The compound of claim 3, wherein:
$R^{11b}$ is selected from the group consisting of H and $C_1$-$C_8$ alkyl.

5. A compound of the formula:

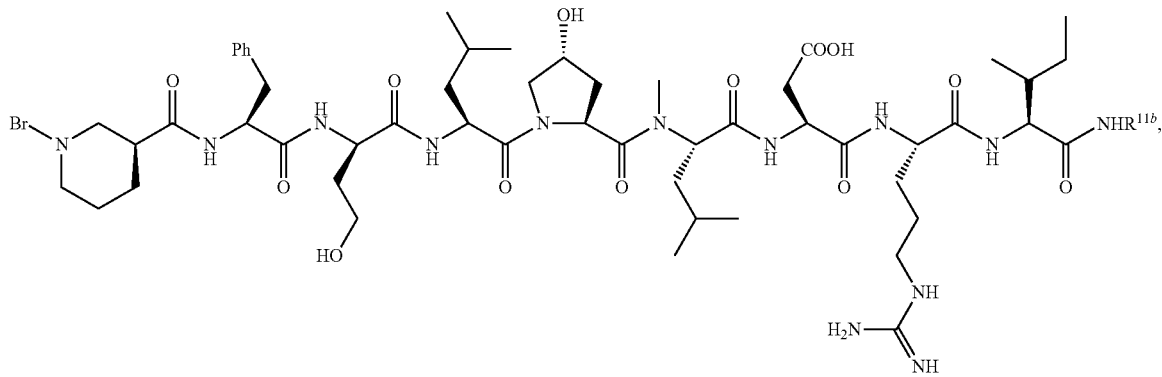

wherein
B is selected from the group consisting of $R^{b1}$— and $R^{b2}$—C(O)—, wherein:
  $R^{b1}$ is selected from the group consisting of $C_6$-$C_{10}$ alkyl and $C_6$-$C_{10}$ alkyl substituted by $NR^{b4}R^{b5}$;
  $R^{b2}$ is $C_6$-$C_{10}$ alkyl substituted by $NR^{b4}R^{b5}$; and
  $R^{b4}$ and $R^{b5}$ are, independently, selected from the group consisting of H and $C_1$-$C_4$ alkyl; and
$R^{11b}$ is selected from the group consisting of H, $C_1$-$C_8$ alkyl, $C_4$-$C_8$ cycloalkyl, $C_7$-$C_{12}$ bicycloalkyl, and $C_1$-$C_4$ alkyl-$C_4$-$C_8$ cycloalkyl.

6. The compound of claim 5, wherein:
$R^{11b}$ is selected from the group consisting of H and $C_1$-$C_8$ alkyl.

7. The compound of claim 1, wherein said compound is selected from:
  Occ-Sni-Mpa-leu-Leu-Hyp-Nml-Asp-Arg-Ile-NH$_2$ (SEQ ID NO:244);
  Occ-Sni-Ppa-leu-Leu-Hyp-Nml-Asp-Arg-Ile-NH$_2$ (SEQ ID NO:245);
  (AR-201-48)-leu-Leu-Hyp-Nml-Asp-Arg-Ile-NH$_2$ (SEQ ID NO:272);
  (AR-201-72)-Phe-leu-Leu-Hyp-Nml-Asp-Arg-Ile-NH$_2$ (SEQ ID NO:339);
  Occ-Sni-Tyr-leu-Leu-Hyp-Nml-Asp-Arg-Ile-NH$_2$ (SEQ ID NO:408);
  Occ-Sni-Bmf-leu-Leu-Hyp-Nml-Asp-Arg-Ile-NH$_2$ (SEQ ID NO:409);
  2553-Sni-Phe-leu-Leu-Hyp-Nml-Asp-Arg-Ile-NH$_2$ (SEQ ID NO:457);
  6988-Sni-Phe-leu-Leu-Hyp-Nml-Asp-Arg-Ile-NH$_2$ (SEQ ID NO:460);
  1695-Sni-Phe-leu-Leu-Hyp-Nml-Asp-Arg-Ile-NH$_2$ (SEQ ID NO:462);
  Occ-Sni-Otf-leu-Leu-Hyp-Nml-Asp-Arg-Ile-NH$_2$ (SEQ ID NO:467);
  Occ-Sni-NHfe-leu-Leu-Hyp-Nml-Asp-Arg-Ile-NH$_2$ (SEQ ID NO:474);
  785-Sni-Phe-leu-Leu-Hyp-Nml-Asp-Arg-Ile-NH$_2$ (SEQ ID NO:484);
  3218-Sni-Phe-leu-Leu-Hyp-Nml-Asp-Arg-Ile-NH$_2$ (SEQ ID NO:486);

1281-G-Sni-Phe-leu-Leu-Hyp-Nml-Asp-Arg-Ile-NH$_2$ (SEQ ID NO:489);
1281-Bal-Sni-Phe-leu-Leu-Hyp-Nml-Asp-Arg-Ile-NH$_2$ (SEQ ID NO:490);
Occ-Sni-Hfe-leu-Leu-Hyp-Nml-Asp-Arg-Ile-NH$_2$ (SEQ ID NO:504);
Occ-ala-Nmf-leu-Leu-Hyp-Nml-Asp-Arg-Ile-NH$_2$ (SEQ ID NO:505);
Gluc-Aoa-hgl-Sni-Phe-leu-Leu-Hyp-Nml-Asp-Arg-Ile-NH$_2$ (SEQ ID NO:533);
(1270)-Hgl-Sni-Phe-leu-Leu-Hyp-Nml-Asp-Arg-Ile-NH$_2$ (SEQ ID NO:535);
Occ-Hgl-Sni-Phe-leu-Leu-Hyp-Nml-Asp-Arg-Ile-NH$_2$ (SEQ ID NO:537);
(AR-314-170)-Phe-leu-Leu-Hyp-Nml-Asp-Arg-Ile-NH$_2$ (SEQ ID NO:555);
(AR-314-171)-Phe-leu-Leu-Hyp-Nml-Asp-Arg-Ile-NH$_2$ (SEQ ID NO:556); and
(AR-385-008)-leu-Leu-Hyp-Nml-Asp-Arg-Ile-NH$_2$ (SEQ ID NO:557).

8. The compound of claim 7, wherein said compound selected from:
(AR-201-72)-Phe-leu-Leu-Hyp-Nml-Asp-Arg-Ile-NH$_2$ (SEQ ID NO:339);
2553-Sni-Phe-leu-Leu-Hyp-Nml-Asp-Arg-Ile-NH$_2$ (SEQ ID NO:457);
6988-Sni-Phe-leu-Leu-Hyp-Nml-Asp-Arg-Ile-NH$_2$ (SEQ ID NO:460);
1695-Sni-Phe-leu-Leu-Hyp-Nml-Asp-Arg-Ile-NH$_2$ (SEQ ID NO:462);
785-Sni-Phe-leu-Leu-Hyp-Nml-Asp-Arg-Ile-NH$_2$ (SEQ ID NO:484);
3218-Sni-Phe-leu-Leu-Hyp-Nml-Asp-Arg-Ile-NH$_2$ (SEQ ID NO:486);
1281-G-Sni-Phe-leu-Leu-Hyp-Nml-Asp-Arg-Ile-NH$_2$ (SEQ ID NO:489);
1281-Bal-Sni-Phe-leu-Leu-Hyp-Nml-Asp-Arg-Ile-NH$_2$ (SEQ ID NO:490);
Gluc-Aoa-hgl-Sni-Phe-leu-Leu-Hyp-Nml-Asp-Arg-Ile-NH$_2$ (SEQ ID NO:533);
(1270)-Hgl-Sni-Phe-leu-Leu-Hyp-Nml-Asp-Arg-Ile-NH$_2$ (SEQ ID NO:535);
Occ-Hgl-Sni-Phe-leu-Leu-Hyp-Nml-Asp-Arg-Ile-NH$_2$ (SEQ ID NO:537);
(AR-314-170)-Phe-leu-Leu-Hyp-Nml-Asp-Arg-Ile-NH$_2$ (SEQ ID NO:555); and
(AR-314-171)-Phe-leu-Leu-Hyp-Nml-Asp-Arg-Ile-NH$_2$ (SEQ ID NO:556).

\* \* \* \* \*

UNITED STATES PATENT AND TRADEMARK OFFICE
CERTIFICATE OF CORRECTION

PATENT NO. : 9,745,344 B2
APPLICATION NO. : 14/824353
DATED : August 29, 2017
INVENTOR(S) : Osterkamp et al.

Page 1 of 1

It is certified that error appears in the above-identified patent and that said Letters Patent is hereby corrected as shown below:

In the Claims

In Column 679, in the formula under Claim 5, Delete:

"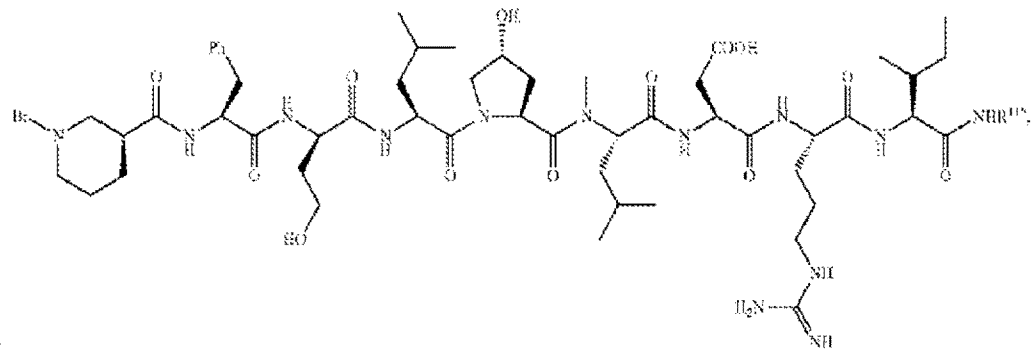"

And replace with:

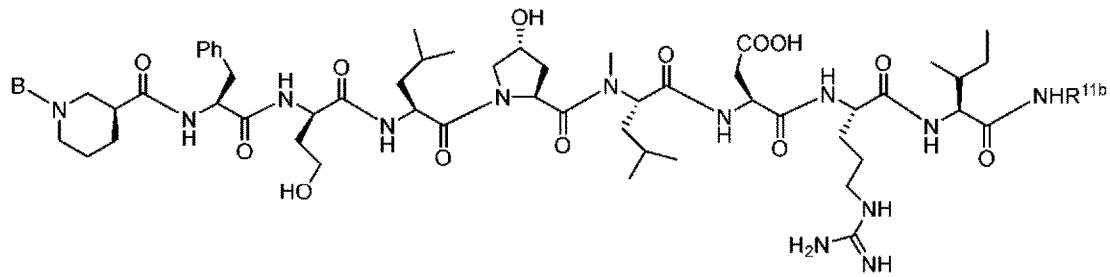

Signed and Sealed this
Twenty-fourth Day of July, 2018

Andrei Iancu
*Director of the United States Patent and Trademark Office*

SEQUENCE LISTING

```
<160> NUMBER OF SEQ ID NOS: 603

<210> SEQ ID NO 1
<211> LENGTH: 28
<212> TYPE: PRT
<213> ORGANISM: Homo sapiens
<220> FEATURE:
<221> NAME/KEY: DISULFID
<222> LOCATION: (7)..(23)

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 32
<212> TYPE: PRT
<213> ORGANISM: Homo sapiens
<220> FEATURE:
<221> NAME/KEY: DISULFID
<222> LOCATION: (10)..(26)

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 3
<211> LENGTH: 22
<212> TYPE: PRT
<213> ORGANISM: Homo sapiens
<220> FEATURE:
<221> NAME/KEY: DISULFID
```

<222> LOCATION: (6)..(22)

<400> SEQUENCE: 3

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 4
<211> LENGTH: 32
<212> TYPE: PRT
<213> ORGANISM: Homo sapiens

<400> SEQUENCE: 4

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 5
<211> LENGTH: 151
<212> TYPE: PRT
<213> ORGANISM: Homo sapiens

<400> SEQUENCE: 5

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150

<210> SEQ ID NO 6
<211> LENGTH: 126
<212> TYPE: PRT
<213> ORGANISM: Homo sapiens

<400> SEQUENCE: 6

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

```
Leu Ser Pro Leu Pro Glu Val Pro Pro Trp Thr Gly Glu Val Ser Pro
 50                  55                  60
Ala Gln Arg Asp Gly Gly Ala Leu Gly Arg Gly Pro Trp Asp Ser Ser
 65                  70                  75                  80
Asp Arg Ser Ala Leu Leu Lys Ser Lys Leu Arg Ala Leu Leu Thr Ala
                 85                  90                  95
Pro Arg Ser Leu Arg Arg Ser Ser Cys Phe Gly Gly Arg Met Asp Arg
            100                 105                 110
Ile Gly Ala Gln Ser Gly Leu Gly Cys Asn Ser Phe Arg Tyr
            115                 120                 125
```

<210> SEQ ID NO 7
<211> LENGTH: 30
<212> TYPE: PRT
<213> ORGANISM: Homo sapiens

<400> SEQUENCE: 7

```
Asn Pro Met Tyr Asn Ala Val Ser Asn Ala Asp Leu Met Asp Phe Lys
 1               5                  10                  15
Asn Leu Leu Asp His Leu Glu Glu Lys Met Pro Leu Glu Asp
            20                  25                  30
```

<210> SEQ ID NO 8
<211> LENGTH: 37
<212> TYPE: PRT
<213> ORGANISM: Homo sapiens

<400> SEQUENCE: 8

```
Glu Val Val Pro Pro Gln Val Leu Ser Glu Pro Asn Glu Glu Ala Gly
 1               5                  10                  15
Ala Ala Leu Ser Pro Leu Pro Glu Val Pro Pro Trp Thr Gly Glu Val
            20                  25                  30
Ser Pro Ala Gln Arg
        35
```

<210> SEQ ID NO 9
<211> LENGTH: 20
<212> TYPE: PRT
<213> ORGANISM: Homo sapiens

<400> SEQUENCE: 9

```
Ser Ser Asp Arg Ser Ala Leu Leu Lys Ser Lys Leu Arg Ala Leu Leu
 1               5                  10                  15
Thr Ala Pro Arg
        20
```

<210> SEQ ID NO 10
<211> LENGTH: 134
<212> TYPE: PRT
<213> ORGANISM: Homo sapiens

<400> SEQUENCE: 10

```
Met Asp Pro Gln Thr Ala Pro Ser Arg Ala Leu Leu Leu Leu Leu Phe
 1               5                  10                  15
Leu His Leu Ala Phe Leu Gly Gly Arg Ser His Pro Leu Gly Ser Pro
            20                  25                  30
Gly Ser Ala Ser Asp Leu Glu Thr Ser Gly Leu Gln Glu Gln Arg Asn
        35                  40                  45
His Leu Gln Gly Lys Leu Ser Glu Leu Gln Val Glu Gln Thr Ser Leu
    50                  55                  60
```

```
Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                 85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Gly Leu Gly Cys
        115                 120                 125

Lys Val Leu Arg Arg His
    130
```

<210> SEQ ID NO 11
<211> LENGTH: 108
<212> TYPE: PRT
<213> ORGANISM: Homo sapiens

<400> SEQUENCE: 11

```
His Pro Leu Gly Ser Pro Gly Ser Ala Ser Asp Leu Glu Thr Ser Gly
 1               5                  10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
 65                  70                  75                  80

Val Gln Gly Ser Gly Cys Phe Gly Arg Lys Met Asp Arg Ile Ser Ser
                 85                  90                  95

Ser Ser Gly Leu Gly Cys Lys Val Leu Arg Arg His
            100                 105
```

<210> SEQ ID NO 12
<211> LENGTH: 76
<212> TYPE: PRT
<213> ORGANISM: Homo sapiens

<400> SEQUENCE: 12

```
His Pro Leu Gly Ser Pro Gly Ser Ala Ser Asp Leu Glu Thr Ser Gly
 1               5                  10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
 65                  70                  75
```

<210> SEQ ID NO 13
<211> LENGTH: 126
<212> TYPE: PRT
<213> ORGANISM: Homo sapiens

<400> SEQUENCE: 13

```
Met His Leu Ser Gln Leu Leu Ala Cys Ala Leu Leu Leu Thr Leu Leu
 1               5                  10                  15
```

Ser Leu Arg Pro Ser Glu Ala Lys Pro Gly Ala Pro Pro Lys Val Pro
          20                  25                  30

Arg Thr Pro Pro Ala Glu Glu Leu Ala Glu Pro Gln Ala Ala Gly Gly
         35                  40                  45

Gly Gln Lys Lys Gly Asp Lys Ala Pro Gly Gly Gly Ala Asn Leu
     50                  55                  60

Lys Gly Asp Arg Ser Arg Leu Leu Arg Asp Leu Arg Val Asp Thr Lys
65                  70                  75                  80

Ser Arg Ala Ala Trp Ala Arg Leu Leu Gln Glu His Pro Asn Ala Arg
                85                  90                  95

Lys Tyr Lys Gly Ala Asn Lys Lys Gly Leu Ser Lys Gly Cys Phe Gly
            100                 105                 110

Leu Lys Leu Asp Arg Ile Gly Ser Met Ser Gly Leu Gly Cys
        115                 120                 125

<210> SEQ ID NO 14
<211> LENGTH: 53
<212> TYPE: PRT
<213> ORGANISM: Homo sapiens

<400> SEQUENCE: 14

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 15
<211> LENGTH: 541
<212> TYPE: PRT
<213> ORGANISM: Homo sapiens

<400> SEQUENCE: 15

Met Pro Ser Leu Leu Val Leu Thr Phe Ser Pro Cys Val Leu Leu Gly
1               5                   10                  15

Trp Ala Leu Leu Ala Gly Gly Thr Gly Gly Gly Val Gly Gly Gly
            20                  25                  30

Gly Gly Gly Ala Gly Ile Gly Gly Arg Gln Glu Arg Glu Ala Leu
        35                  40                  45

Pro Pro Gln Lys Ile Glu Val Leu Val Leu Leu Pro Gln Asp Asp Ser
    50                  55                  60

Tyr Leu Phe Ser Leu Thr Arg Val Arg Pro Ala Ile Glu Tyr Ala Leu
65                  70                  75                  80

Arg Ser Val Glu Gly Asn Gly Thr Gly Arg Arg Leu Leu Pro Pro Gly
                85                  90                  95

Thr Arg Phe Gln Val Ala Tyr Glu Asp Ser Asp Cys Gly Asn Arg Ala
            100                 105                 110

Leu Phe Ser Leu Val Asp Arg Val Ala Ala Arg Gly Ala Lys Pro
        115                 120                 125

Asp Leu Ile Leu Gly Pro Val Cys Glu Tyr Ala Ala Ala Pro Val Ala
        130                 135                 140

Arg Leu Ala Ser His Trp Asp Leu Pro Met Leu Ser Ala Gly Ala Leu
145                 150                 155                 160

```
Ala Ala Gly Phe Gln His Lys Asp Ser Glu Tyr Ser His Leu Thr Arg
                165                 170                 175

Val Ala Pro Ala Tyr Ala Lys Met Gly Glu Met Met Leu Ala Leu Phe
            180                 185                 190

Arg His His His Trp Ser Arg Ala Ala Leu Val Tyr Ser Asp Asp Lys
        195                 200                 205

Leu Glu Arg Asn Cys Tyr Phe Thr Leu Glu Gly Val His Glu Val Phe
    210                 215                 220

Gln Glu Glu Gly Leu His Thr Ser Ile Tyr Ser Phe Asp Glu Thr Lys
225                 230                 235                 240

Asp Leu Asp Leu Glu Asp Ile Val Arg Asn Ile Gln Ala Ser Glu Arg
                245                 250                 255

Val Val Ile Met Cys Ala Ser Ser Asp Thr Ile Arg Ser Ile Met Leu
            260                 265                 270

Val Ala His Arg His Gly Met Thr Ser Gly Asp Tyr Ala Phe Phe Asn
        275                 280                 285

Ile Glu Leu Phe Asn Ser Ser Tyr Gly Asp Gly Ser Trp Lys Arg
    290                 295                 300

Gly Asp Lys His Asp Phe Glu Ala Lys Gln Ala Tyr Ser Ser Leu Gln
305                 310                 315                 320

Thr Val Thr Leu Leu Arg Thr Val Lys Pro Glu Phe Glu Lys Phe Ser
                325                 330                 335

Met Glu Val Lys Ser Ser Val Glu Lys Gln Gly Leu Asn Met Glu Asp
            340                 345                 350

Tyr Val Asn Met Phe Val Glu Gly Phe His Asp Ala Ile Leu Leu Tyr
        355                 360                 365

Val Leu Ala Leu His Glu Val Leu Arg Ala Gly Tyr Ser Lys Lys Asp
    370                 375                 380

Gly Gly Lys Ile Ile Gln Gln Thr Trp Asn Arg Thr Phe Glu Gly Ile
385                 390                 395                 400

Ala Gly Gln Val Ser Ile Asp Ala Asn Gly Asp Arg Tyr Gly Asp Phe
                405                 410                 415

Ser Val Ile Ala Met Thr Asp Val Glu Ala Gly Thr Gln Glu Val Ile
            420                 425                 430

Gly Asp Tyr Phe Gly Lys Glu Gly Arg Phe Glu Met Arg Pro Asn Val
        435                 440                 445

Lys Tyr Pro Trp Gly Pro Leu Lys Leu Arg Ile Asp Glu Asn Arg Ile
    450                 455                 460

Val Glu His Thr Asn Ser Ser Pro Cys Lys Ser Ser Gly Gly Leu Glu
465                 470                 475                 480

Glu Ser Ala Val Thr Gly Ile Val Val Gly Ala Leu Leu Gly Ala Gly
                485                 490                 495

Leu Leu Met Ala Phe Tyr Phe Phe Arg Lys Lys Tyr Arg Ile Thr Ile
            500                 505                 510

Glu Arg Arg Thr Gln Gln Glu Glu Ser Asn Leu Gly Lys His Arg Glu
        515                 520                 525

Leu Arg Glu Asp Ser Ile Arg Ser His Phe Ser Val Ala
    530                 535                 540

<210> SEQ ID NO 16
<211> LENGTH: 1061
<212> TYPE: PRT
<213> ORGANISM: Homo sapiens

<400> SEQUENCE: 16
```

```
Met Pro Gly Pro Arg Pro Ala Gly Ser Arg Leu Arg Leu Leu Leu
1               5                   10                  15
Leu Leu Leu Leu Pro Pro Leu Leu Leu Leu Arg Gly Ser His Ala
            20                  25                  30
Gly Asn Leu Thr Val Ala Val Val Leu Pro Leu Ala Asn Thr Ser Tyr
            35                  40                  45
Pro Trp Ser Trp Ala Arg Val Gly Pro Ala Val Glu Leu Ala Leu Ala
50                      55                  60
Gln Val Lys Ala Arg Pro Asp Leu Leu Pro Gly Trp Thr Val Arg Thr
65                  70                  75                  80
Val Leu Gly Ser Ser Glu Asn Ala Leu Gly Val Cys Ser Asp Thr Ala
                85                  90                  95
Ala Pro Leu Ala Ala Val Asp Leu Lys Trp Glu His Asn Pro Ala Val
                100                 105                 110
Phe Leu Gly Pro Gly Cys Val Tyr Ala Ala Pro Val Gly Arg Phe
                115                 120                 125
Thr Ala His Trp Arg Val Pro Leu Leu Thr Ala Gly Ala Pro Ala Leu
            130                 135                 140
Gly Phe Gly Val Lys Asp Glu Tyr Ala Leu Thr Thr Arg Ala Gly Pro
145                 150                 155                 160
Ser Tyr Ala Lys Leu Gly Asp Phe Val Ala Ala Leu His Arg Arg Leu
                165                 170                 175
Gly Trp Glu Arg Gln Ala Leu Met Leu Tyr Ala Tyr Arg Pro Gly Asp
            180                 185                 190
Glu Glu His Cys Phe Phe Leu Val Gly Leu Phe Met Arg Val Arg
                195                 200                 205
Asp Arg Leu Asn Ile Thr Val Asp His Leu Glu Phe Ala Glu Asp Asp
            210                 215                 220
Leu Ser His Tyr Thr Arg Leu Leu Arg Thr Met Pro Arg Lys Gly Arg
225                 230                 235                 240
Val Ile Tyr Ile Cys Ser Ser Pro Asp Ala Phe Arg Thr Leu Met Leu
                245                 250                 255
Leu Ala Leu Glu Ala Gly Leu Cys Gly Glu Asp Tyr Val Phe Phe His
            260                 265                 270
Leu Asp Ile Phe Gly Gln Ser Leu Gln Gly Gly Gln Gly Pro Ala Pro
            275                 280                 285
Arg Arg Pro Trp Glu Arg Gly Asp Gly Gln Asp Val Ser Ala Arg Gln
            290                 295                 300
Ala Phe Gln Ala Ala Lys Ile Ile Thr Tyr Lys Asp Pro Asp Asn Pro
305                 310                 315                 320
Glu Tyr Leu Glu Phe Leu Lys Gln Leu Lys His Leu Ala Tyr Glu Gln
                325                 330                 335
Phe Asn Phe Thr Met Glu Asp Gly Leu Val Asn Thr Ile Pro Ala Ser
                340                 345                 350
Phe His Asp Gly Leu Leu Tyr Ile Gln Ala Val Thr Glu Thr Leu
            355                 360                 365
Ala His Gly Gly Thr Val Thr Asp Gly Glu Asn Ile Thr Gln Arg Met
            370                 375                 380
Trp Asn Arg Ser Phe Gln Gly Val Thr Gly Tyr Leu Lys Ile Asp Ser
385                 390                 395                 400
Ser Gly Asp Arg Glu Thr Asp Phe Ser Leu Trp Asp Met Asp Pro Glu
                405                 410                 415
```

```
Asn Gly Ala Phe Arg Val Val Leu Asn Tyr Asn Gly Thr Ser Gln Glu
            420                 425                 430

Leu Val Ala Val Ser Gly Arg Lys Leu Asn Trp Pro Leu Gly Tyr Pro
        435                 440                 445

Pro Pro Asp Ile Pro Lys Cys Gly Phe Asp Asn Glu Asp Pro Ala Cys
    450                 455                 460

Asn Gln Asp His Leu Ser Thr Leu Glu Val Leu Ala Leu Val Gly Ser
465                 470                 475                 480

Leu Ser Leu Leu Gly Ile Leu Ile Val Ser Phe Phe Ile Tyr Arg Lys
                485                 490                 495

Met Gln Leu Glu Lys Glu Leu Ala Ser Glu Leu Trp Arg Val Arg Trp
            500                 505                 510

Glu Asp Val Glu Pro Ser Ser Leu Glu Arg His Leu Arg Ser Ala Gly
        515                 520                 525

Ser Arg Leu Thr Leu Ser Gly Arg Gly Ser Asn Tyr Gly Ser Leu Leu
    530                 535                 540

Thr Thr Glu Gly Gln Phe Gln Val Phe Ala Lys Thr Ala Tyr Tyr Lys
545                 550                 555                 560

Gly Asn Leu Val Ala Val Lys Arg Val Asn Arg Lys Arg Ile Glu Leu
                565                 570                 575

Thr Arg Lys Val Leu Phe Glu Leu Lys His Met Arg Asp Val Gln Asn
            580                 585                 590

Glu His Leu Thr Arg Phe Val Gly Ala Cys Thr Asp Pro Asn Ile
        595                 600                 605

Cys Ile Leu Thr Glu Tyr Cys Pro Arg Gly Ser Leu Gln Asp Ile Leu
    610                 615                 620

Glu Asn Glu Ser Ile Thr Leu Asp Trp Met Phe Arg Tyr Ser Leu Thr
625                 630                 635                 640

Asn Asp Ile Val Lys Gly Met Leu Phe Leu His Asn Gly Ala Ile Cys
                645                 650                 655

Ser His Gly Asn Leu Lys Ser Ser Asn Cys Val Val Asp Gly Arg Phe
            660                 665                 670

Val Leu Lys Ile Thr Asp Tyr Gly Leu Glu Ser Phe Arg Asp Leu Asp
        675                 680                 685

Pro Glu Gln Gly His Thr Val Tyr Ala Lys Lys Leu Trp Thr Ala Pro
    690                 695                 700

Glu Leu Leu Arg Met Ala Ser Pro Pro Val Arg Gly Ser Gln Ala Gly
705                 710                 715                 720

Asp Val Tyr Ser Phe Gly Ile Ile Leu Gln Glu Ile Ala Leu Arg Ser
                725                 730                 735

Gly Val Phe His Val Glu Gly Leu Asp Leu Ser Pro Lys Glu Ile Ile
            740                 745                 750

Glu Arg Val Thr Arg Gly Glu Gln Pro Pro Phe Arg Pro Ser Leu Ala
        755                 760                 765

Leu Gln Ser His Leu Glu Glu Leu Gly Leu Leu Met Gln Arg Cys Trp
    770                 775                 780

Ala Glu Asp Pro Gln Glu Arg Pro Pro Phe Gln Gln Ile Arg Leu Thr
785                 790                 795                 800

Leu Arg Lys Phe Asn Arg Glu Asn Ser Ser Asn Ile Leu Asp Asn Leu
                805                 810                 815

Leu Ser Arg Met Glu Gln Tyr Ala Asn Asn Leu Glu Glu Leu Val Glu
            820                 825                 830

Glu Arg Thr Gln Ala Tyr Leu Glu Glu Lys Arg Lys Ala Glu Ala Leu
```

```
                    835                 840                 845
Leu Tyr Gln Ile Leu Pro His Ser Val Ala Glu Gln Leu Lys Arg Gly
    850                 855                 860

Glu Thr Val Gln Ala Glu Ala Phe Asp Ser Val Thr Ile Tyr Phe Ser
865                 870                 875                 880

Asp Ile Val Gly Phe Thr Ala Leu Ser Ala Glu Ser Thr Pro Met Gln
                885                 890                 895

Val Val Thr Leu Leu Asn Asp Leu Tyr Thr Cys Phe Asp Ala Val Ile
            900                 905                 910

Asp Asn Phe Asp Val Tyr Lys Val Glu Thr Ile Gly Asp Ala Tyr Met
        915                 920                 925

Val Val Ser Gly Leu Pro Val Arg Asn Gly Arg Leu His Ala Cys Glu
930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
                965                 970                 975

Thr Gly Pro Val Cys Ala Gly Val Val Gly Leu Lys Met Pro Arg Tyr
            980                 985                 990

Cys Leu Phe Gly Asp Thr Val Asn Thr Ala Ser Arg Met Glu Ser Asn
        995                1000                1005

Gly Glu Ala Leu Lys Ile His Leu Ser Ser Glu Thr Lys Ala Val
    1010                1015                1020

Leu Glu Glu Phe Gly Gly Phe Glu Leu Glu Leu Arg Gly Asp Val
    1025                1030                1035

Glu Met Lys Gly Lys Gly Lys Val Arg Thr Tyr Trp Leu Leu Gly
    1040                1045                1050

Glu Arg Gly Ser Ser Thr Arg Gly
    1055                1060

<210> SEQ ID NO 17
<211> LENGTH: 1047
<212> TYPE: PRT
<213> ORGANISM: Homo sapiens

<400> SEQUENCE: 17

Met Ala Leu Pro Ser Leu Leu Leu Val Ala Ala Leu Ala Gly Gly
1               5                   10                  15

Val Arg Pro Pro Gly Ala Arg Asn Leu Thr Leu Ala Val Val Leu Pro
                20                  25                  30

Glu His Asn Leu Ser Tyr Ala Trp Ala Trp Pro Arg Val Gly Pro Ala
            35                  40                  45

Val Ala Leu Ala Val Glu Ala Leu Gly Arg Ala Leu Pro Val Asp Leu
        50                  55                  60

Arg Phe Val Ser Ser Glu Leu Glu Gly Ala Cys Ser Glu Tyr Leu Ala
65                  70                  75                  80

Pro Leu Ser Ala Val Asp Leu Lys Leu Tyr His Asp Pro Asp Leu Leu
                85                  90                  95

Leu Gly Pro Gly Cys Val Tyr Pro Ala Ala Ser Val Ala Arg Phe Ala
            100                 105                 110

Ser His Trp Arg Leu Pro Leu Leu Thr Ala Gly Ala Val Ala Ser Gly
        115                 120                 125

Phe Ser Ala Lys Asn Asp His Tyr Arg Thr Leu Val Arg Thr Gly Pro
    130                 135                 140
```

```
Ser Ala Pro Lys Leu Gly Glu Phe Val Val Thr Leu His Gly His Phe
145                 150                 155                 160

Asn Trp Thr Ala Arg Ala Ala Leu Leu Tyr Leu Asp Ala Arg Thr Asp
                165                 170                 175

Asp Arg Pro His Tyr Phe Thr Ile Glu Gly Val Phe Glu Ala Leu Gln
            180                 185                 190

Gly Ser Asn Leu Ser Val Gln His Gln Val Tyr Ala Arg Glu Pro Gly
        195                 200                 205

Gly Pro Glu Gln Ala Thr His Phe Ile Arg Ala Asn Gly Arg Ile Val
    210                 215                 220

Tyr Ile Cys Gly Pro Leu Glu Met Leu His Glu Ile Leu Leu Gln Ala
225                 230                 235                 240

Gln Arg Glu Asn Leu Thr Asn Gly Asp Tyr Val Phe Phe Tyr Leu Asp
                245                 250                 255

Val Phe Gly Glu Ser Leu Arg Ala Gly Pro Thr Arg Ala Thr Gly Arg
            260                 265                 270

Pro Trp Gln Asp Asn Arg Thr Arg Glu Gln Ala Gln Ala Leu Arg Glu
        275                 280                 285

Ala Phe Gln Thr Val Leu Val Ile Thr Tyr Arg Glu Pro Pro Asn Pro
    290                 295                 300

Glu Tyr Gln Glu Phe Gln Asn Arg Leu Leu Ile Arg Ala Arg Glu Asp
305                 310                 315                 320

Phe Gly Val Glu Leu Gly Pro Ser Leu Met Asn Leu Ile Ala Gly Cys
                325                 330                 335

Phe Tyr Asp Gly Ile Leu Leu Tyr Ala Glu Val Leu Asn Glu Thr Ile
            340                 345                 350

Gln Glu Gly Gly Thr Arg Glu Asp Gly Leu Arg Ile Val Glu Lys Met
        355                 360                 365

Gln Gly Arg Arg Tyr His Gly Val Thr Gly Leu Val Val Met Asp Lys
    370                 375                 380

Asn Asn Asp Arg Glu Thr Asp Phe Val Leu Trp Ala Met Gly Asp Leu
385                 390                 395                 400

Asp Ser Gly Asp Phe Gln Pro Ala Ala His Tyr Ser Gly Ala Glu Lys
                405                 410                 415

Gln Ile Trp Trp Thr Gly Arg Pro Ile Pro Trp Val Lys Gly Ala Pro
            420                 425                 430

Pro Ser Asp Asn Pro Pro Cys Ala Phe Asp Leu Asp Asp Pro Ser Cys
        435                 440                 445

Asp Lys Thr Pro Leu Ser Thr Leu Ala Ile Val Ala Leu Gly Thr Gly
    450                 455                 460

Ile Thr Phe Ile Met Phe Gly Val Ser Ser Phe Leu Ile Phe Arg Lys
465                 470                 475                 480

Leu Met Leu Glu Lys Glu Leu Ala Ser Met Leu Trp Arg Ile Arg Trp
                485                 490                 495

Glu Glu Leu Gln Phe Gly Asn Ser Glu Arg Tyr His Lys Gly Ala Gly
            500                 505                 510

Ser Arg Leu Thr Leu Ser Leu Arg Gly Ser Ser Tyr Gly Ser Leu Met
        515                 520                 525

Thr Ala His Gly Lys Tyr Gln Ile Phe Ala Asn Thr Gly His Phe Lys
    530                 535                 540

Gly Asn Val Val Ala Ile Lys His Val Asn Lys Lys Arg Ile Glu Leu
545                 550                 555                 560

Thr Arg Gln Val Leu Phe Glu Leu Lys His Met Arg Asp Val Gln Phe
```

-continued

```
                565                 570                 575
Asn His Leu Thr Arg Phe Ile Gly Ala Cys Ile Asp Pro Asn Ile
                580                 585                 590

Cys Ile Val Thr Glu Tyr Cys Pro Arg Gly Ser Leu Gln Asp Ile Leu
                595                 600                 605

Glu Asn Asp Ser Ile Asn Leu Asp Trp Met Phe Arg Tyr Ser Leu Ile
                610                 615                 620

Asn Asp Leu Val Lys Gly Met Ala Phe Leu His Asn Ser Ile Ile Ser
625                 630                 635                 640

Ser His Gly Ser Leu Lys Ser Ser Asn Cys Val Val Asp Ser Arg Phe
                645                 650                 655

Val Leu Lys Ile Thr Asp Tyr Gly Leu Ala Ser Phe Arg Ser Thr Ala
                660                 665                 670

Glu Pro Asp Asp Ser His Ala Leu Tyr Ala Lys Lys Leu Trp Thr Ala
                675                 680                 685

Pro Glu Leu Leu Ser Gly Asn Pro Leu Pro Thr Thr Gly Met Gln Lys
                690                 695                 700

Ala Asp Val Tyr Ser Phe Gly Ile Ile Leu Gln Glu Ile Ala Leu Arg
705                 710                 715                 720

Ser Gly Pro Phe Tyr Leu Glu Gly Leu Asp Leu Ser Pro Lys Glu Ile
                725                 730                 735

Val Gln Lys Val Arg Asn Gly Gln Arg Pro Tyr Phe Arg Pro Ser Ile
                740                 745                 750

Asp Arg Thr Gln Leu Asn Glu Glu Leu Val Leu Leu Met Glu Arg Cys
                755                 760                 765

Trp Ala Gln Asp Pro Ala Glu Arg Pro Asp Phe Gly Gln Ile Lys Gly
                770                 775                 780

Phe Ile Arg Arg Phe Asn Lys Glu Gly Gly Thr Ser Ile Leu Asp Asn
785                 790                 795                 800

Leu Leu Leu Arg Met Glu Gln Tyr Ala Asn Asn Leu Glu Lys Leu Val
                805                 810                 815

Glu Glu Arg Thr Gln Ala Tyr Leu Glu Glu Lys Arg Lys Ala Glu Ala
                820                 825                 830

Leu Leu Tyr Gln Ile Leu Pro His Ser Val Ala Glu Gln Leu Lys Arg
                835                 840                 845

Gly Glu Thr Val Gln Ala Glu Ala Phe Asp Ser Val Thr Ile Tyr Phe
                850                 855                 860

Ser Asp Ile Val Gly Phe Thr Ala Leu Ser Ala Glu Ser Thr Pro Met
865                 870                 875                 880

Gln Val Val Thr Leu Leu Asn Asp Leu Tyr Thr Cys Phe Asp Ala Ile
                885                 890                 895

Ile Asp Asn Phe Asp Val Tyr Lys Val Glu Thr Ile Gly Asp Ala Tyr
                900                 905                 910

Met Val Val Ser Gly Leu Pro Gly Arg Asn Gly Gln Arg His Ala Pro
                915                 920                 925

Glu Ile Ala Arg Met Ala Leu Ala Leu Leu Asp Ala Val Ser Ser Phe
                930                 935                 940

Arg Ile Arg His Arg Pro His Asp Gln Leu Arg Leu Arg Ile Gly Val
945                 950                 955                 960

His Thr Gly Pro Val Cys Ala Gly Val Val Gly Leu Lys Met Pro Arg
                965                 970                 975

Tyr Cys Leu Phe Gly Asp Thr Val Asn Thr Ala Ser Arg Met Glu Ser
                980                 985                 990
```

```
Asn Gly Gln Ala Leu Lys Ile His  Val Ser Ser Thr Thr  Lys Asp Ala
        995                 1000                 1005

Leu Asp  Glu Leu Gly Cys Phe  Gln Leu Glu Leu Arg  Gly Asp Val
    1010                1015                 1020

Glu Met  Lys Gly Lys Gly Lys  Met Arg Thr Tyr Trp  Leu Leu Gly
    1025                1030                 1035

Glu Arg  Lys Gly Pro Pro Gly  Leu Leu
    1040                1045

<210> SEQ ID NO 18
<211> LENGTH: 15
<212> TYPE: PRT
<213> ORGANISM: Homo sapiens
<220> FEATURE:
<221> NAME/KEY: DISULFID
<222> LOCATION: (2)..(13)

<400> SEQUENCE: 18

Met Cys His Phe Gly Gly Arg Met Asp Arg Ile Ser Cys Tyr Arg
1               5                   10                  15

<210> SEQ ID NO 19
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (R)-2-amino-3-(methylsulfanyl) propanoic
      acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (13)..(13)
<223> OTHER INFORMATION: Xaa = Ebe

<400> SEQUENCE: 19

Xaa Xaa Pro Phe Gly Leu Pro Ile Asp Arg Ile Ser Xaa
1               5                   10

<210> SEQ ID NO 20
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hex
<220> FEATURE:
<221> NAME/KEY: MISC_FEATURE
<222> LOCATION: (2)..(2)
<223> OTHER INFORMATION: Xaa = (R)-2-amino-3-(methylsulfanyl) propanoic
      acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
```

```
<222> LOCATION: (13)..(13)
<223> OTHER INFORMATION: Xaa = (R)-2-amino-3-(methylsulfanyl) propanoic
      acid

<400> SEQUENCE: 20

Xaa Xaa Pro Phe Gly Leu Lys Ile Asp Arg Ile Ser Xaa
1               5                   10

<210> SEQ ID NO 21
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 21

Xaa Ser Ala Phe Gly Leu Lys Leu Asp Arg Ile Ser Ser
1               5                   10

<210> SEQ ID NO 22
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 22

Xaa Ala Ala Phe Gly Leu Lys Leu Asp Arg Ile Ser Ala
1               5                   10

<210> SEQ ID NO 23
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 23

Xaa Ala Ala Phe Gly Leu Lys Leu Asp Arg Ile Ser Gly
1               5                   10

<210> SEQ ID NO 24
<211> LENGTH: 13
<212> TYPE: PRT
<213> ORGANISM: Artificial
<220> FEATURE:
<223> OTHER INFORMATION: synthetic
```

```
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 24

Xaa Gly Ala Phe Gly Leu Lys Leu Asp Arg Ile Ser Ala
1               5                   10

<210> SEQ ID NO 25
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 25

Xaa Gly Ala Phe Gly Leu Lys Leu Asp Arg Ile Ser Gly
1               5                   10

<210> SEQ ID NO 26
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (R)-2-amino-3-(methylsulfanyl) propanoic
      acid
<220> FEATURE:
<221> NAME/KEY: MISC_FEATURE
<222> LOCATION: (3)..(3)
<223> OTHER INFORMATION: D form of amino acid at this position

<400> SEQUENCE: 26

Xaa Xaa Ala Phe Gly Leu Lys Leu Asp Arg Ile Ser
1               5                   10

<210> SEQ ID NO 27
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (R)-2-amino-3-(methylsulfanyl) propanoic
      acid
<220> FEATURE:
<221> NAME/KEY: MISC_FEATURE
```

```
<222> LOCATION: (3)..(3)
<223> OTHER INFORMATION: D form of amino acid at this position

<400> SEQUENCE: 27

Xaa Xaa Ala Phe Gly Leu Lys Leu Asp Arg Ile
1               5                   10

<210> SEQ ID NO 28
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = 4-aminobutyric acid
<220> FEATURE:
<221> NAME/KEY: MISC_FEATURE
<222> LOCATION: (12)..(12)
<223> OTHER INFORMATION: Xaa = Ebe

<400> SEQUENCE: 28

Xaa Xaa Phe Gly Leu Lys Leu Asp Arg Ile Ser Xaa
1               5                   10

<210> SEQ ID NO 29
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = 3-aminomethyl-benzoic acid
<220> FEATURE:
<221> NAME/KEY: MISC_FEATURE
<222> LOCATION: (12)..(12)
<223> OTHER INFORMATION: Xaa = (R)-2-amino-3-(methylsulfanyl) propanoic
      acid

<400> SEQUENCE: 29

Xaa Xaa Phe Gly Leu Lys Leu Asp Arg Ile Ser Xaa
1               5                   10

<210> SEQ ID NO 30
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 30

Xaa Gly Ala Phe Gly Leu Lys Leu Asp Arg Ile
1               5                   10
```

<210> SEQ ID NO 31
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 31

Xaa Ala Ala Phe Gly Leu Lys Leu Asp Arg Ile
1               5                   10

<210> SEQ ID NO 32
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 32

Xaa Ser Ala Phe Gly Leu Lys Leu Asp Arg Ile
1               5                   10

<210> SEQ ID NO 33
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 33

Xaa Pro Ala Phe Gly Leu Lys Leu Asp Arg Ile
1               5                   10

<210> SEQ ID NO 34
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: D form of amino acid at this position

```
<220> FEATURE:
<221> NAME/KEY: MISC_FEATURE
<222> LOCATION: (3)..(3)
<223> OTHER INFORMATION: D form of amino acid at this position

<400> SEQUENCE: 34

Xaa Ala Ala Phe Gly Leu Lys Leu Asp Arg Ile
1               5                   10

<210> SEQ ID NO 35
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 35

Xaa Gly Pro Phe Gly Leu Lys Leu Asp Arg Ile
1               5                   10

<210> SEQ ID NO 36
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (3)..(3)
<223> OTHER INFORMATION: D form of amino acid at this position

<400> SEQUENCE: 36

Xaa Ser Pro Phe Gly Leu Lys Leu Asp Arg Ile
1               5                   10

<210> SEQ ID NO 37
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = 3-aminomethyl-benzoic acid

<400> SEQUENCE: 37

Xaa Xaa Phe Gly Leu Lys Leu Asp Arg Ile
1               5                   10

<210> SEQ ID NO 38
<211> LENGTH: 10
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (4-aminomethyl)-benzoic acid

<400> SEQUENCE: 38

Xaa Xaa Phe Gly Leu Lys Leu Asp Arg Ile
1               5                   10

<210> SEQ ID NO 39
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (3-amino-phenyl)-acetic acid

<400> SEQUENCE: 39

Xaa Xaa Phe Gly Leu Lys Leu Asp Arg Ile
1               5                   10

<210> SEQ ID NO 40
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (4-amino-phenyl) acetic acid

<400> SEQUENCE: 40

Xaa Xaa Phe Gly Leu Lys Leu Asp Arg Ile
1               5                   10

<210> SEQ ID NO 41
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = piperidine-4-carboxylic acid

<400> SEQUENCE: 41

Xaa Xaa Phe Gly Leu Lys Leu Asp Arg Ile
1               5                   10
```

```
<210> SEQ ID NO 42
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = 3-amino-1-carboxymethyl-pyridin-2-one

<400> SEQUENCE: 42

Xaa Xaa Phe Gly Leu Lys Leu Asp Arg Ile
1               5                   10

<210> SEQ ID NO 43
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = trans-4-(aminomethyl)
      cyclohexanecarboxylic acid

<400> SEQUENCE: 43

Xaa Xaa Phe Gly Leu Lys Leu Asp Arg Ile
1               5                   10

<210> SEQ ID NO 44
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = rac-nipecotic acid

<400> SEQUENCE: 44

Xaa Xaa Phe Gly Leu Lys Leu Asp Arg Ile
1               5                   10

<210> SEQ ID NO 45
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (S)-2-(3-amino-2-oxoazepan-1-yl) acetic
      acid
```

<400> SEQUENCE: 45

Xaa Xaa Phe Gly Leu Lys Leu Asp Arg Ile
1               5                   10

<210> SEQ ID NO 46
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = (1S,3R)-3-aminocyclohexane carboxylic
      acid

<400> SEQUENCE: 46

Xaa Xaa Phe Gly Leu Lys Leu Asp Arg Ile
1               5                   10

<210> SEQ ID NO 47
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = 1-amino-cyclopentanecarboxylic acid

<400> SEQUENCE: 47

Xaa Ala Ala Phe Gly Leu Lys Leu Asp Arg Xaa
1               5                   10

<210> SEQ ID NO 48
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-cyclohexyl-butyric acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 48

```
Xaa Ala Ala Phe Gly Leu Lys Leu Asp Arg Ile
1               5                   10

<210> SEQ ID NO 49
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 49

Xaa Pro Phe Gly Leu Lys Leu Asp Arg Ile
1               5                   10

<210> SEQ ID NO 50
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-cyclohexyl-butyric acid
<220> FEATURE:
<221> NAME/KEY: MISC_FEATURE
<222> LOCATION: (2)..(2)
<223> OTHER INFORMATION: D form of amino acid at this position

<400> SEQUENCE: 50

Xaa Pro Phe Gly Leu Lys Leu Asp Arg Ile
1               5                   10

<210> SEQ ID NO 51
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5-phenyl-pentanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 51

Xaa Pro Phe Gly Leu Lys Leu Asp Arg Ile
1               5                   10

<210> SEQ ID NO 52
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
```

```
<222> LOCATION: (2)..(2)
<223> OTHER INFORMATION: Xaa = rac-nipecotic acid

<400> SEQUENCE: 52

Xaa Xaa Phe Gly Leu Lys Leu Asp Arg Ile
1               5                   10

<210> SEQ ID NO 53
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 53

Xaa Ala Ala Phe Gly Leu Lys Leu Asp Arg Ile
1               5                   10

<210> SEQ ID NO 54
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-cyclohexyl-propionic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 54

Xaa Ala Ala Phe Gly Leu Lys Leu Asp Arg Ile
1               5                   10

<210> SEQ ID NO 55
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = 4-amino-thiazol-2-carboxylic acid

<400> SEQUENCE: 55

Xaa Xaa Phe Gly Leu Lys Leu Asp Arg Ile
1               5                   10
```

```
<210> SEQ ID NO 56
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (S)-cyclohexylglycine

<400> SEQUENCE: 56

Xaa Ala Ala Phe Gly Leu Lys Leu Asp Arg Xaa
1               5                   10

<210> SEQ ID NO 57
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = piperazine-1-yl-acetic acid

<400> SEQUENCE: 57

Xaa Ala Ala Phe Xaa Lys Leu Asp Arg Ile
1               5                   10

<210> SEQ ID NO 58
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 58

Xaa Ala Phe Gly Leu Lys Leu Asp Arg Ile
1               5                   10
```

```
<210> SEQ ID NO 59
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-thiazolidine-4-carboxylic acid
<220> FEATURE:
<221> NAME/KEY: MISC_FEATURE
<222> LOCATION: (2)..(2)
<223> OTHER INFORMATION: D form of amino acid at this position

<400> SEQUENCE: 59

Xaa Xaa Phe Gly Leu Lys Leu Asp Arg Ile
1               5                   10

<210> SEQ ID NO 60
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-azetidin-2-carboxylic acid
<220> FEATURE:
<221> NAME/KEY: MISC_FEATURE
<222> LOCATION: (2)..(2)
<223> OTHER INFORMATION: D form of amino acid at this position

<400> SEQUENCE: 60

Xaa Xaa Phe Gly Leu Lys Leu Asp Arg Ile
1               5                   10

<210> SEQ ID NO 61
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = Azetidine-3-carboxylic acid

<400> SEQUENCE: 61

Xaa Xaa Phe Gly Leu Lys Leu Asp Arg Ile
1               5                   10

<210> SEQ ID NO 62
<211> LENGTH: 10
<212> TYPE: PRT
<213> ORGANISM: Artificial
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid

<400> SEQUENCE: 62

Xaa Xaa Phe Gly Leu Lys Leu Asp Arg Ile
1               5                   10

<210> SEQ ID NO 63
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-nipecotic acid

<400> SEQUENCE: 63

Xaa Xaa Phe Gly Leu Lys Leu Asp Arg Ile
1               5                   10

<210> SEQ ID NO 64
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (S)-3-methylpiperidine

<400> SEQUENCE: 64

Xaa Ala Ala Phe Gly Leu Lys Leu Asp Arg Xaa
1               5                   10

<210> SEQ ID NO 65
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
```

```
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = 2-ethyl-butyl-amine

<400> SEQUENCE: 65

Xaa Ala Ala Phe Gly Leu Lys Leu Asp Arg Xaa
1               5                   10

<210> SEQ ID NO 66
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (R)-2-methylbutan-1-amine

<400> SEQUENCE: 66

Xaa Ala Ala Phe Gly Leu Lys Leu Asp Arg Xaa
1               5                   10

<210> SEQ ID NO 67
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = cyclohexylamine

<400> SEQUENCE: 67

Xaa Ala Ala Phe Gly Leu Lys Leu Asp Arg Xaa
1               5                   10

<210> SEQ ID NO 68
<211> LENGTH: 11
<212> TYPE: PRT
<213> ORGANISM: Artificial
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (1R,2R,4R)-1,7,7-
      trimethylbicyclo[2.2.1]heptan-2-amine

<400> SEQUENCE: 68

Xaa Ala Ala Phe Gly Leu Lys Leu Asp Arg Xaa
1               5                   10

<210> SEQ ID NO 69
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 69

Xaa Val Phe Gly Leu Lys Leu Asp Arg Ile
1               5                   10

<210> SEQ ID NO 70
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-alpha-tert-butylglycine
<220> FEATURE:
<221> NAME/KEY: MISC_FEATURE
<222> LOCATION: (2)..(2)
<223> OTHER INFORMATION: D form of amino acid at this position

<400> SEQUENCE: 70

Xaa Xaa Phe Gly Leu Lys Leu Asp Arg Ile
1               5                   10

<210> SEQ ID NO 71
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: Xaa = 1-aminomethyl-cyclopropanecarboxylic acid

<400> SEQUENCE: 71

Xaa Xaa Phe Gly Leu Lys Leu Asp Arg Ile
1               5                   10

<210> SEQ ID NO 72
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = 1-aminocyclopropanecarboxylic acid

<400> SEQUENCE: 72

Xaa Xaa Phe Gly Leu Lys Leu Asp Arg Ile
1               5                   10

<210> SEQ ID NO 73
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-2-aminobutanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 73

Xaa Xaa Phe Gly Leu Lys Leu Asp Arg Ile
1               5                   10

<210> SEQ ID NO 74
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 74

Xaa Ser Phe Gly Leu Lys Leu Asp Arg Ile
1               5                   10

<210> SEQ ID NO 75
```

```
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (8)..(8)
<223> OTHER INFORMATION: D form of amino acid at this position

<400> SEQUENCE: 75

Xaa Ala Ala Phe Gly Leu Lys Leu Asp Arg Ile
1               5                   10

<210> SEQ ID NO 76
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 76

Xaa Ala Ala Phe Gly Leu Lys Ile Asp Arg Ile
1               5                   10

<210> SEQ ID NO 77
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 77

Xaa Ala Ala Phe Gly Leu Lys Val Asp Arg Ile
1               5                   10

<210> SEQ ID NO 78
```

```
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (S)-cyclohexylglycine

<400> SEQUENCE: 78

Xaa Ala Ala Phe Gly Leu Lys Xaa Asp Arg Ile
1               5                   10

<210> SEQ ID NO 79
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (S)-norleucine

<400> SEQUENCE: 79

Xaa Ala Ala Phe Gly Leu Lys Xaa Asp Arg Ile
1               5                   10

<210> SEQ ID NO 80
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (S)-N-methyl-leucine
```

```
<400> SEQUENCE: 80

Xaa Ala Ala Phe Gly Leu Lys Xaa Asp Arg Ile
1               5                   10

<210> SEQ ID NO 81
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 81

Xaa Ala Ala Phe Gly Leu Pro Leu Asp Arg Ile
1               5                   10

<210> SEQ ID NO 82
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-lysine

<400> SEQUENCE: 82

Xaa Ala Ala Phe Gly Leu Xaa Leu Asp Arg Ile
1               5                   10

<210> SEQ ID NO 83
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanesulfonyl chloride
<220> FEATURE:
<221> NAME/KEY: MISC_FEATURE
<222> LOCATION: (2)..(2)
<223> OTHER INFORMATION: D form of amino acid at this position

<400> SEQUENCE: 83

Xaa Ala Phe Gly Leu Lys Leu Asp Arg Ile
```

```
1               5                    10
```

<210> SEQ ID NO 84
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = hexyl chloroformate
<220> FEATURE:
<221> NAME/KEY: MISC_FEATURE
<222> LOCATION: (2)..(2)
<223> OTHER INFORMATION: D form of amino acid at this position

<400> SEQUENCE: 84

```
Xaa Ala Phe Gly Leu Lys Leu Asp Arg Ile
1               5                    10
```

<210> SEQ ID NO 85
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4956
<220> FEATURE:
<221> NAME/KEY: MISC_FEATURE
<222> LOCATION: (2)..(2)
<223> OTHER INFORMATION: D form of amino acid at this position

<400> SEQUENCE: 85

```
Xaa Ala Phe Gly Leu Lys Leu Asp Arg Ile
1               5                    10
```

<210> SEQ ID NO 86
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (1R,2R)-2-methylcyclohexanamine

<400> SEQUENCE: 86

```
Xaa Ala Ala Phe Gly Leu Lys Leu Asp Arg Xaa
1               5                    10
```

<210> SEQ ID NO 87
<211> LENGTH: 11
<212> TYPE: PRT
<213> ORGANISM: Artificial
<220> FEATURE:

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = Adamantan-2-yl-amine

<400> SEQUENCE: 87

Xaa Ala Ala Phe Gly Leu Lys Leu Asp Arg Xaa
1               5                   10

<210> SEQ ID NO 88
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = cyclopentylamine

<400> SEQUENCE: 88

Xaa Ala Ala Phe Gly Leu Lys Leu Asp Arg Xaa
1               5                   10

<210> SEQ ID NO 89
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = 1-ethyl-propyl-amine

<400> SEQUENCE: 89

Xaa Ala Ala Phe Gly Leu Lys Leu Asp Arg Xaa
```

<210> SEQ ID NO 90
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = cycloheptyl-amine

<400> SEQUENCE: 90

Xaa Ala Ala Phe Gly Leu Lys Leu Asp Arg Xaa
1               5                   10

<210> SEQ ID NO 91
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = 4-methyl-cyclohexyl-amine

<400> SEQUENCE: 91

Xaa Ala Ala Phe Gly Leu Lys Leu Asp Arg Xaa
1               5                   10

<210> SEQ ID NO 92
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

```
<220> FEATURE:
<221> NAME/KEY: MISC_FEATURE
<222> LOCATION: (11)..(11)
<223> OTHER INFORMATION: Xaa = (1R,2R)-2-(benzyloxy)cyclohexanamine

<400> SEQUENCE: 92

Xaa Ala Ala Phe Gly Leu Lys Leu Asp Arg Xaa
1               5                   10

<210> SEQ ID NO 93
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (1R,2R,4R)-bicyclo[2.2.1]heptan-2-amine

<400> SEQUENCE: 93

Xaa Ala Ala Phe Gly Leu Lys Leu Asp Arg Xaa
1               5                   10

<210> SEQ ID NO 94
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = aniline

<400> SEQUENCE: 94

Xaa Ala Ala Phe Gly Leu Lys Leu Asp Arg Xaa
1               5                   10

<210> SEQ ID NO 95
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (1S,2R)-2-aminocyclohexanecarboxamide

<400> SEQUENCE: 95

Xaa Ala Ala Phe Gly Leu Lys Leu Asp Arg Xaa
1               5                   10

<210> SEQ ID NO 96
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (1R,2R)-ethyl-2-
      aminocyclohexanecaroxylate

<400> SEQUENCE: 96

Xaa Ala Ala Phe Gly Leu Lys Leu Asp Arg Xaa
1               5                   10

<210> SEQ ID NO 97
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (1R,2S)-ethyl-2-
      aminocyclohexanecarboxylate

<400> SEQUENCE: 97

Xaa Ala Ala Phe Gly Leu Lys Leu Asp Arg Xaa
1               5                   10
```

```
<210> SEQ ID NO 98
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (R)-3-amino-azepan-2-one

<400> SEQUENCE: 98

Xaa Ala Ala Phe Gly Leu Lys Leu Asp Arg Xaa
 1               5                  10

<210> SEQ ID NO 99
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (11)..(11)
<223> OTHER INFORMATION: Xaa = (S)-3-amino-1-ethylazepan-2-one

<400> SEQUENCE: 99

Xaa Ala Ala Phe Gly Leu Lys Leu Asp Arg Xaa
 1               5                  10

<210> SEQ ID NO 100
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 100

Xaa Ala Phe Gly Leu Pro Leu Asp Arg Ile
 1               5                  10
```

```
<210> SEQ ID NO 101
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 101

Xaa Pro Phe Gly Leu Pro Leu Asp Arg Ile
1               5                   10

<210> SEQ ID NO 102
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid

<400> SEQUENCE: 102

Xaa Xaa Phe Gly Leu Pro Leu Asp Arg Ile
1               5                   10

<210> SEQ ID NO 103
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = (1R,2R)-2-methylcyclohexanamine

<400> SEQUENCE: 103

Xaa Ala Phe Gly Leu Lys Leu Asp Arg Xaa
1               5                   10

<210> SEQ ID NO 104
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
```

<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 104

Xaa Ala Phe Gly Leu Lys Leu Asp Arg Xaa
1               5                   10

<210> SEQ ID NO 105
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = 1-propyl-butyl-amine

<400> SEQUENCE: 105

Xaa Ala Phe Gly Leu Lys Leu Asp Arg Xaa
1               5                   10

<210> SEQ ID NO 106
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 106

Xaa Ala Phe Gly Leu Pro Ile Asp Arg Ile
1               5                   10

<210> SEQ ID NO 107
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 107

-continued

```
Xaa Ala Phe Gly Leu Pro Xaa Asp Arg Ile
1               5                   10

<210> SEQ ID NO 108
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-2-amino-4,4-dimethylpentanoic acid

<400> SEQUENCE: 108

Xaa Ala Phe Gly Leu Pro Xaa Asp Arg Ile
1               5                   10

<210> SEQ ID NO 109
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 109

Xaa Ala Phe Gly Leu Xaa Leu Asp Arg Ile
1               5                   10

<210> SEQ ID NO 110
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-2-amino-4,4-dimethylpentanoic acid

<400> SEQUENCE: 110

Xaa Ala Phe Gly Xaa Pro Leu Asp Arg Ile
1               5                   10
```

```
<210> SEQ ID NO 111
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine

<400> SEQUENCE: 111

Xaa Ala Xaa Gly Leu Pro Leu Asp Arg Ile
1               5                   10

<210> SEQ ID NO 112
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (9)..(9)
<223> OTHER INFORMATION: Xaa = (S)-N-methyl-arginine

<400> SEQUENCE: 112

Xaa Ala Phe Gly Leu Pro Leu Asp Xaa Ile
1               5                   10

<210> SEQ ID NO 113
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 113

Xaa Ala Phe Gly Leu Pro Leu Asn Arg Ile
1               5                   10

<210> SEQ ID NO 114
<211> LENGTH: 10
<212> TYPE: PRT
<213> ORGANISM: Artificial
<220> FEATURE:
<223> OTHER INFORMATION: synthetic
```

```
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (S)-norvaline

<400> SEQUENCE: 114

Xaa Ala Phe Gly Leu Pro Leu Xaa Arg Ile
1               5                   10

<210> SEQ ID NO 115
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 115

Xaa Ala Phe Gly Leu Pro Leu Val Arg Ile
1               5                   10

<210> SEQ ID NO 116
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 116

Xaa Ala Phe Gly Leu Pro Leu Thr Arg Ile
1               5                   10

<210> SEQ ID NO 117
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-beta-cyclohexylalanine
```

```
<400> SEQUENCE: 117

Xaa Ala Phe Gly Xaa Pro Leu Asp Arg Ile
1               5                   10

<210> SEQ ID NO 118
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-norleucine

<400> SEQUENCE: 118

Xaa Ala Phe Gly Xaa Pro Leu Asp Arg Ile
1               5                   10

<210> SEQ ID NO 119
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 2-aminoisobutyric acid

<400> SEQUENCE: 119

Xaa Ala Phe Xaa Leu Pro Leu Asp Arg Ile
1               5                   10

<210> SEQ ID NO 120
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 120

Xaa Ala Phe Ala Leu Pro Leu Asp Arg Ile
```

<210> SEQ ID NO 121
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 1-aminocyclopropanecarboxylic acid

<400> SEQUENCE: 121

Xaa Ala Phe Xaa Leu Pro Leu Asp Arg Ile
1               5                   10

<210> SEQ ID NO 122
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-chloro-phenylalanine

<400> SEQUENCE: 122

Xaa Ala Xaa Gly Leu Pro Leu Asp Arg Ile
1               5                   10

<210> SEQ ID NO 123
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = Sarcosine

<400> SEQUENCE: 123

Xaa Xaa Phe Gly Leu Pro Leu Asp Arg Ile
1               5                   10

<210> SEQ ID NO 124
<211> LENGTH: 10
<212> TYPE: PRT
<213> ORGANISM: Artificial
<220> FEATURE:

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid

<400> SEQUENCE: 124

Xaa Gly Phe Gly Leu Pro Leu Asp Arg Ile
1               5                   10

<210> SEQ ID NO 125
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-azetidin-2-carboxylic acid
<220> FEATURE:
<221> NAME/KEY: MISC_FEATURE
<222> LOCATION: (2)..(2)
<223> OTHER INFORMATION: D form of amino acid at this position

<400> SEQUENCE: 125

Xaa Xaa Phe Gly Leu Pro Leu Asp Arg Ile
1               5                   10

<210> SEQ ID NO 126
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 126

Xaa Ala Xaa Gly Leu Pro Xaa Asp Arg Ile
1               5                   10

<210> SEQ ID NO 127
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
```

```
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 127

Xaa Pro Phe Gly Leu Pro Xaa Asp Arg Ile
1               5                   10

<210> SEQ ID NO 128
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 128

Xaa Xaa Phe Gly Leu Pro Xaa Asp Arg Ile
1               5                   10

<210> SEQ ID NO 129
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 129

Xaa Pro Xaa Gly Leu Pro Xaa Asp Arg Ile
1               5                   10

<210> SEQ ID NO 130
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
```

```
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 130

Xaa Xaa Xaa Gly Leu Pro Xaa Asp Arg Ile
1               5                   10

<210> SEQ ID NO 131
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-2-amino-5-methylhexanoic acid

<400> SEQUENCE: 131

Xaa Ala Phe Gly Leu Pro Xaa Asp Arg Ile
1               5                   10

<210> SEQ ID NO 132
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (R)-alpha-methyl-proline

<400> SEQUENCE: 132

Xaa Ala Phe Gly Leu Xaa Leu Asp Arg Ile
1               5                   10

<210> SEQ ID NO 133
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
```

```
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4S)-4-hydroxypyrrolidine-2-carboxylic
      acid

<400> SEQUENCE: 133

Xaa Ala Phe Gly Leu Xaa Leu Asp Arg Ile
1               5                   10

<210> SEQ ID NO 134
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine

<400> SEQUENCE: 134

Xaa Pro Xaa Gly Leu Pro Leu Asp Arg Ile
1               5                   10

<210> SEQ ID NO 135
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-N-methyl-phenylalanine

<400> SEQUENCE: 135

Xaa Xaa Xaa Gly Leu Pro Leu Asp Arg Ile
1               5                   10

<210> SEQ ID NO 136
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
```

```
<222> LOCATION: (6)..(6)
<223> OTHER INFORMATION: Xaa = (2S,4S)-4-aminopyrrolidine-2-carboxylic
      acid

<400> SEQUENCE: 136

Xaa Ala Phe Gly Leu Xaa Leu Asp Arg Ile
1               5                   10

<210> SEQ ID NO 137
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4S)-4-phenylpyrrolidine-2-carboxylic
      acid

<400> SEQUENCE: 137

Xaa Ala Phe Gly Leu Xaa Leu Asp Arg Ile
1               5                   10

<210> SEQ ID NO 138
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4S)-4-fluoropyrrolidine-2-carboxylic
      acid

<400> SEQUENCE: 138

Xaa Ala Phe Gly Leu Xaa Leu Asp Arg Ile
1               5                   10

<210> SEQ ID NO 139
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
```

<223> OTHER INFORMATION: Xaa = (R)-2,2-dimethylthiazolidine-4-carboxylic
    acid

<400> SEQUENCE: 139

Xaa Ala Phe Gly Leu Xaa Leu Asp Arg Ile
1               5                   10

<210> SEQ ID NO 140
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (R)-thiazolidine-4-carboxylic acid

<400> SEQUENCE: 140

Xaa Ala Phe Gly Leu Xaa Leu Asp Arg Ile
1               5                   10

<210> SEQ ID NO 141
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = Azetidine-3-carboxylic acid

<400> SEQUENCE: 141

Xaa Xaa Phe Gly Leu Pro Leu Asp Arg Ile
1               5                   10

<210> SEQ ID NO 142
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (10)..(10)
<223> OTHER INFORMATION: Xaa = (S)-tert-butylglycine

<400> SEQUENCE: 142

Xaa Ala Phe Gly Leu Pro Leu Asp Arg Xaa
1               5                   10

```
<210> SEQ ID NO 143
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 143

Xaa Ala Phe Gly Leu Pro Leu Ser Arg Ile
1               5                   10

<210> SEQ ID NO 144
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (S)-homoserine

<400> SEQUENCE: 144

Xaa Ala Phe Gly Leu Pro Leu Xaa Arg Ile
1               5                   10

<210> SEQ ID NO 145
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position

<400> SEQUENCE: 145

Xaa Ala Phe Gly Ile Pro Leu Asp Arg Ile
1               5                   10

<210> SEQ ID NO 146
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
```

```
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-norvaline

<400> SEQUENCE: 146

Xaa Ala Phe Gly Xaa Pro Leu Asp Arg Ile
1               5                   10

<210> SEQ ID NO 147
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-2-amino-5-methylhexanoic acid

<400> SEQUENCE: 147

Xaa Ala Phe Gly Xaa Pro Leu Asp Arg Ile
1               5                   10

<210> SEQ ID NO 148
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-2-thienyl-alanine

<400> SEQUENCE: 148

Xaa Ala Xaa Gly Leu Pro Leu Asp Arg Ile
1               5                   10

<210> SEQ ID NO 149
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
```

```
<221> NAME/KEY: MISC_FEATURE
<222> LOCATION: (3)..(3)
<223> OTHER INFORMATION: Xaa = (S)-para-chloro-phenylalanine

<400> SEQUENCE: 149

Xaa Ala Xaa Gly Leu Pro Leu Asp Arg Ile
1               5                   10

<210> SEQ ID NO 150
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-3-thienyl-alanine

<400> SEQUENCE: 150

Xaa Ala Xaa Gly Leu Pro Leu Asp Arg Ile
1               5                   10

<210> SEQ ID NO 151
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-trifluromethyl-phenylalanine

<400> SEQUENCE: 151

Xaa Ala Xaa Gly Leu Pro Leu Asp Arg Ile
1               5                   10

<210> SEQ ID NO 152
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-meta-methyl-phenylalanine
```

```
<400> SEQUENCE: 152

Xaa Ala Xaa Gly Leu Pro Leu Asp Arg Ile
1               5                   10

<210> SEQ ID NO 153
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 153

Xaa Ala Phe Ser Leu Pro Leu Asp Arg Ile
1               5                   10

<210> SEQ ID NO 154
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 154

Xaa Ala Phe Thr Leu Pro Leu Asp Arg Ile
1               5                   10

<210> SEQ ID NO 155
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 155

Xaa Ala Phe Val Leu Pro Leu Asp Arg Ile
1               5                   10
```

<210> SEQ ID NO 156
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 156

Xaa Ala Phe Leu Leu Pro Leu Asp Arg Ile
1               5                   10

<210> SEQ ID NO 157
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-norleucine
<220> FEATURE:
<221> NAME/KEY: MISC_FEATURE
<222> LOCATION: (4)..(4)
<223> OTHER INFORMATION: D form of amino acid at this position

<400> SEQUENCE: 157

Xaa Ala Phe Xaa Leu Pro Leu Asp Arg Ile
1               5                   10

<210> SEQ ID NO 158
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-N-methyl-leucine

```
<400> SEQUENCE: 158

Xaa Xaa Phe Gly Leu Xaa Xaa Asp Arg Ile
1               5                   10

<210> SEQ ID NO 159
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 159

Xaa Ala Phe Gly Leu Xaa Xaa Asp Arg Ile
1               5                   10

<210> SEQ ID NO 160
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 160

Xaa Ala Phe Asn Leu Pro Leu Asp Arg Ile
1               5                   10

<210> SEQ ID NO 161
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
```

<223> OTHER INFORMATION: D form of amino acid at this position

<400> SEQUENCE: 161

Xaa Ala Phe Met Leu Pro Leu Asp Arg Ile
1               5                   10

<210> SEQ ID NO 162
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-aminobutanoic acid
<220> FEATURE:
<221> NAME/KEY: MISC_FEATURE
<222> LOCATION: (4)..(4)
<223> OTHER INFORMATION: D form of amino acid at this position

<400> SEQUENCE: 162

Xaa Ala Phe Xaa Leu Pro Leu Asp Arg Ile
1               5                   10

<210> SEQ ID NO 163
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2,3-diaminopropanoic acid
<220> FEATURE:
<221> NAME/KEY: MISC_FEATURE
<222> LOCATION: (4)..(4)
<223> OTHER INFORMATION: D form of amino acid at this position

<400> SEQUENCE: 163

Xaa Ala Phe Xaa Leu Pro Leu Asp Arg Ile
1               5                   10

<210> SEQ ID NO 164
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)

```
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-norleucine
<220> FEATURE:
<221> NAME/KEY: MISC_FEATURE
<222> LOCATION: (4)..(4)
<223> OTHER INFORMATION: D form of amino acid at this position

<400> SEQUENCE: 164

Xaa Xaa Phe Xaa Leu Pro Leu Asp Arg Ile
1               5                   10

<210> SEQ ID NO 165
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: Xaa = (R)-norleucine
<220> FEATURE:
<221> NAME/KEY: MISC_FEATURE
<222> LOCATION: (4)..(4)
<223> OTHER INFORMATION: D form of amino acid at this position

<400> SEQUENCE: 165

Xaa Xaa Xaa Xaa Leu Pro Leu Asp Arg Ile
1               5                   10

<210> SEQ ID NO 166
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-norleucine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 166
```

```
Xaa Xaa Phe Xaa Leu Xaa Leu Asp Arg Ile
1               5                   10
```

<210> SEQ ID NO 167
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-norleucine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 167

```
Xaa Ala Phe Xaa Leu Xaa Leu Asp Arg Ile
1               5                   10
```

<210> SEQ ID NO 168
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 168

```
Xaa Ala Phe Leu Leu Xaa Leu Asp Arg Ile
1               5                   10
```

<210> SEQ ID NO 169
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:

```
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-norvaline
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 169

Xaa Ala Phe Xaa Leu Xaa Leu Asp Arg Ile
1               5                   10

<210> SEQ ID NO 170
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 170

Xaa Ala Phe Phe Leu Xaa Leu Asp Arg Ile
1               5                   10

<210> SEQ ID NO 171
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (S)--2-amino-3-(tert-butylthio) propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
```

-continued

```
<223> OTHER INFORMATION: Xaa = (2S,4R)-4-hydroxypyrrolidine-2-carboxylic
      acid

<400> SEQUENCE: 171

Xaa Ala Phe Xaa Leu Xaa Leu Asp Arg Ile
1               5                   10

<210> SEQ ID NO 172
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 172

Xaa Ala Phe Lys Leu Pro Leu Asp Arg Ile
1               5                   10

<210> SEQ ID NO 173
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa - Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 173

Xaa Ala Phe Arg Leu Pro Leu Asp Arg Ile
1               5                   10

<210> SEQ ID NO 174
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position

<400> SEQUENCE: 174
```

```
Xaa Ala Phe His Leu Pro Leu Asp Arg Ile
1               5                   10

<210> SEQ ID NO 175
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Ac-(S)-2-aminooctanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 175

Xaa Ala Ala Phe Gly Leu Pro Leu Asp Arg Ile
1               5                   10

<210> SEQ ID NO 176
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Ac-(r)-2-aminooctanoic acid
<220> FEATURE:
<221> NAME/KEY: MISC_FEATURE
<222> LOCATION: (1)..(1)
<223> OTHER INFORMATION: D form of amino acid at this position
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: D form of amino acid at this position

<400> SEQUENCE: 176

Xaa Ala Ala Phe Gly Leu Pro Leu Asp Arg Ile
1               5                   10

<210> SEQ ID NO 177
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-pipecolinic acid
<220> FEATURE:
<221> NAME/KEY: MISC_FEATURE
<222> LOCATION: (2)..(2)
<223> OTHER INFORMATION: D form of amino acid at this position

<400> SEQUENCE: 177
```

```
Xaa Xaa Phe Gly Leu Pro Leu Asp Arg Ile
1               5                   10

<210> SEQ ID NO 178
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa =
      (S)-2-((S)-3-(Carboxymethyl)-2-oxopiperazine-1-yl)-5-guanidinopen
      tanoic acid

<400> SEQUENCE: 178

Xaa Ala Phe Gly Leu Pro Leu Xaa Ile
1               5

<210> SEQ ID NO 179
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(benzyloxy)pyrrolidine-2-
      carboxylic acid

<400> SEQUENCE: 179

Xaa Ala Phe Gly Leu Xaa Leu Asp Arg Ile
1               5                   10

<210> SEQ ID NO 180
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa= Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa= (S)-N-methyl-leucine

<400> SEQUENCE: 180
```

Xaa Ala Phe Leu Leu Pro Xaa Asp Arg Ile
1               5                   10

<210> SEQ ID NO 181
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 181

Xaa Xaa Phe Leu Leu Pro Xaa Asp Arg Ile
1               5                   10

<210> SEQ ID NO 182
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 182

Xaa Xaa Phe Leu Leu Xaa Xaa Asp Arg Ile
1               5                   10

<210> SEQ ID NO 183
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 183

Xaa Ala Phe Leu Leu Xaa Xaa Asp Arg Ile
1               5                   10

<210> SEQ ID NO 184
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (s)-para-chloro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 184

Xaa Ala Xaa Leu Leu Xaa Xaa Asp Arg Ile
1               5                   10

<210> SEQ ID NO 185
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-norleucine
<220> FEATURE:

```
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 185

Xaa Ala Phe Xaa Leu Xaa Xaa Asp Arg Ile
1               5                   10

<210> SEQ ID NO 186
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-4-methyl-2-(propylamino) pentanoic
      acid

<400> SEQUENCE: 186

Xaa Ala Phe Gly Leu Pro Xaa Asp Arg Ile
1               5                   10

<210> SEQ ID NO 187
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 187

Xaa Ala Phe Arg Leu Xaa Leu Asp Arg Ile
1               5                   10

<210> SEQ ID NO 188
<211> LENGTH: 10
<212> TYPE: PRT
<213> ORGANISM: Artificial
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 188

Xaa Ala Phe Asp Leu Xaa Leu Asp Arg Ile
1               5                   10

<210> SEQ ID NO 189
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 189

Xaa Ala Phe Gln Leu Xaa Leu Asp Arg Ile
1               5                   10

<210> SEQ ID NO 190
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-para-chloro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
```

```
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 190

Xaa Ala Xaa Leu Leu Xaa Leu Asp Arg Ile
1               5                   10

<210> SEQ ID NO 191
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-para-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 191

Xaa Ala Xaa Leu Leu Xaa Leu Asp Arg Ile
1               5                   10

<210> SEQ ID NO 192
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 192

Xaa Ala Xaa Leu Leu Xaa Leu Asp Arg Ile
1               5                   10
```

```
<210> SEQ ID NO 193
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 193

Xaa Pro Phe Leu Leu Xaa Leu Asp Arg Ile
1               5                   10

<210> SEQ ID NO 194
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-pipecolinic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 194

Xaa Xaa Phe Leu Leu Xaa Leu Asp Arg Ile
1               5                   10

<210> SEQ ID NO 195
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
```

```
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 195

Xaa Ala Phe Lys Leu Xaa Xaa Asp Arg Ile
1               5                   10

<210> SEQ ID NO 196
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-ornithine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 196

Xaa Ala Phe Xaa Leu Xaa Xaa Asp Arg Ile
1               5                   10

<210> SEQ ID NO 197
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 197

Xaa Ala Phe Lys Leu Pro Xaa Asp Arg Ile
```

<210> SEQ ID NO 198
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 198

Xaa Ala Phe Lys Leu Pro Xaa Ala Arg Ile
1               5                   10

<210> SEQ ID NO 199
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 199

Xaa Ala Phe Arg Leu Pro Xaa Asp Arg Ile
1               5                   10

<210> SEQ ID NO 200
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine -continued

```
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 200

Xaa Ala Xaa Arg Leu Pro Xaa Asp Arg Ile
1               5                   10

<210> SEQ ID NO 201
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-pipecolinic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 201

Xaa Xaa Xaa Arg Leu Pro Xaa Asp Arg Ile
1               5                   10

<210> SEQ ID NO 202
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-pipecolinic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine
```

```
<400> SEQUENCE: 202

Xaa Xaa Phe Arg Leu Pro Xaa Asp Arg Ile
1               5                   10

<210> SEQ ID NO 203
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 203

Xaa Ala Xaa Arg Leu Xaa Xaa Asp Arg Ile
1               5                   10

<210> SEQ ID NO 204
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 204

Xaa Ala Phe Arg Leu Xaa Xaa Asp Arg Ile
1               5                   10

<210> SEQ ID NO 205
```

```
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-pipecolinic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 205

Xaa Xaa Phe Arg Leu Xaa Xaa Asp Arg Ile
1               5                   10

<210> SEQ ID NO 206
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-fluoropyrrolidine-2-carboxylic
      acid

<400> SEQUENCE: 206

Xaa Ala Phe Arg Leu Xaa Leu Asp Arg Ile
1               5                   10

<210> SEQ ID NO 207
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
```

```
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-fluoropyrrolidine-2-carboxylic
      acid

<400> SEQUENCE: 207

Xaa Ala Phe Gly Leu Xaa Leu Asp Arg Ile
1               5                   10

<210> SEQ ID NO 208
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-para-bromo-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 208

Xaa Ala Xaa Arg Leu Xaa Leu Asp Arg Ile
1               5                   10

<210> SEQ ID NO 209
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)--2,4-diaminobutanoic acid
<220> FEATURE:
<221> NAME/KEY: MISC_FEATURE
<222> LOCATION: (4)..(4)
<223> OTHER INFORMATION: D form of amino acid at this position

<400> SEQUENCE: 209

Xaa Ala Phe Xaa Leu Pro Leu Asp Arg Ile
1               5                   10

<210> SEQ ID NO 210
<211> LENGTH: 10
```

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-4-guanidinobutanoic acid
<220> FEATURE:
<221> NAME/KEY: MISC_FEATURE
<222> LOCATION: (4)..(4)
<223> OTHER INFORMATION: D form of amino acid at this position

<400> SEQUENCE: 210

Xaa Ala Phe Xaa Leu Pro Leu Asp Arg Ile
1               5                   10

<210> SEQ ID NO 211
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-3-guanidinopropanoic acid
<220> FEATURE:
<221> NAME/KEY: MISC_FEATURE
<222> LOCATION: (4)..(4)
<223> OTHER INFORMATION: D form of amino acid at this position

<400> SEQUENCE: 211

Xaa Ala Phe Xaa Leu Pro Leu Asp Arg Ile
1               5                   10

<210> SEQ ID NO 212
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
```

<400> SEQUENCE: 212

Xaa Ala Phe Arg Leu Xaa Leu Asp Arg Ile
1               5                   10

<210> SEQ ID NO 213
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (R)-pipecolinic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 213

Xaa Xaa Phe Arg Leu Xaa Leu Asp Arg Ile
1               5                   10

<210> SEQ ID NO 214
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa =
      (S)-1-((S)-2-amino-4-methyl-pentyl)-pyrrolidine-2-carboxylic acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 214

Xaa Ala Phe Arg Xaa Xaa Asp Arg Ile
1               5

<210> SEQ ID NO 215
<211> LENGTH: 9
<212> TYPE: PRT
<213> ORGANISM: Artificial

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = dodecanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 215

Xaa Phe Arg Leu Xaa Xaa Asp Arg Ile
1               5

<210> SEQ ID NO 216
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 216

Xaa Ala Phe Arg Leu Xaa Ile Asp Arg Ile
1               5                   10

<210> SEQ ID NO 217
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
```

```
<220> FEATURE:
<221> NAME/KEY: MISC_FEATURE
<222> LOCATION: (7)..(7)
<223> OTHER INFORMATION: Xaa = (S)-2-amino-4,4-dimethylpentanoic acid

<400> SEQUENCE: 217

Xaa Ala Phe Arg Leu Xaa Xaa Asp Arg Ile
1               5                   10

<210> SEQ ID NO 218
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-alpha-tert-butylglycine

<400> SEQUENCE: 218

Xaa Ala Phe Arg Leu Xaa Xaa Asp Arg Ile
1               5                   10

<210> SEQ ID NO 219
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (R)-2-amino-3-(methylsulfanyl)propanoic
      acid

<400> SEQUENCE: 219

Xaa Ala Phe Arg Leu Xaa Xaa Asp Arg Ile
1               5                   10
```

```
<210> SEQ ID NO 220
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 220

Xaa Ala Phe Arg Leu Lys Xaa Asp Arg Ile
1               5                   10

<210> SEQ ID NO 221
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (S)-N-methyl-lysine
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 221

Xaa Ala Phe Arg Leu Xaa Xaa Asp Arg Ile
1               5                   10

<210> SEQ ID NO 222
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
```

<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (S)-N-methyl-alanine
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 222

Xaa Ala Phe Arg Leu Xaa Xaa Asp Arg Ile
1               5                   10

<210> SEQ ID NO 223
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = Sarcosine
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 223

Xaa Ala Phe Arg Leu Xaa Xaa Asp Arg Ile
1               5                   10

<210> SEQ ID NO 224
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Occtanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-norvaline
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE

```
<222> LOCATION: (7)..(7)
<223> OTHER INFORMATION: Xaa = (S)-N-methyl-leucine

<400> SEQUENCE: 224

Xaa Ala Phe Arg Xaa Xaa Xaa Asp Arg Ile
1               5                   10

<210> SEQ ID NO 225
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (R)-2-amino-3-(methylsulfanyl)propanoic
      acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 225

Xaa Ala Phe Arg Xaa Xaa Xaa Asp Arg Ile
1               5                   10

<210> SEQ ID NO 226
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (E)-dodec-2-enoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 226

Xaa Phe Arg Leu Xaa Xaa Asp Arg Ile
1               5

<210> SEQ ID NO 227
```

```
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (Z)-dodec-5-enoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 227

Xaa Phe Arg Leu Xaa Xaa Asp Arg Ile
1               5

<210> SEQ ID NO 228
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (S)-2-methyl-undecanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 228

Xaa Phe Arg Leu Xaa Xaa Asp Arg Ile
1               5

<210> SEQ ID NO 229
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (2S)-2-octylcyclopropanecarboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
```

```
<221> NAME/KEY: MISC_FEATURE
<222> LOCATION: (6)..(6)
<223> OTHER INFORMATION: Xaa = (S)-N-methyl-leucine

<400> SEQUENCE: 229

Xaa Phe Arg Leu Xaa Xaa Asp Arg Ile
1               5

<210> SEQ ID NO 230
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-octylsulfanyl-propionic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyo-leucine

<400> SEQUENCE: 230

Xaa Phe Arg Leu Xaa Xaa Asp Arg Ile
1               5

<210> SEQ ID NO 231
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 7-butylsulfanyl-heptanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 231

Xaa Phe Arg Leu Xaa Xaa Asp Arg Ile
1               5

<210> SEQ ID NO 232
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: Xaa = 3-(octane-1-sulfinyl)-propionic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 232

Xaa Phe Arg Leu Xaa Xaa Asp Arg Ile
1               5

<210> SEQ ID NO 233
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = dodecanoic acid
<220> FEATURE:
<221> NAME/KEY: MISC_FEATURE
<222> LOCATION: (2)..(2)
<223> OTHER INFORMATION: Xaa = (S)-N-methyl-phenylalanine
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 233

Xaa Xaa Arg Leu Xaa Xaa Asp Arg Ile
1               5

<210> SEQ ID NO 234
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = dodecanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine
```

```
<400> SEQUENCE: 234

Xaa Phe Leu Leu Xaa Xaa Asp Arg Ile
1               5

<210> SEQ ID NO 235
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = dodecanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid

<400> SEQUENCE: 235

Xaa Phe Arg Leu Xaa Leu Asp Arg Ile
1               5

<210> SEQ ID NO 236
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = FrL
<220> FEATURE:
<221> NAME/KEY: MISC_FEATURE
<222> LOCATION: (4)..(4)
<223> OTHER INFORMATION: Xaa = (2S,4R)-4-hydroxypyrrolidine-2-carboxylic
      acid

<400> SEQUENCE: 236

Xaa Xaa Xaa Xaa Leu Asp Arg Ile
1               5

<210> SEQ ID NO 237
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
```

<223> OTHER INFORMATION: Xaa = (2S,4R)-4-aminopyrrolidine-2-carboxylic
      acid

<400> SEQUENCE: 237

Xaa Ala Phe Gly Leu Xaa Leu Asp Arg Ile
1               5                   10

<210> SEQ ID NO 238
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid

<400> SEQUENCE: 238

Xaa Ala Phe Arg Leu Xaa Leu Asp Arg Ile
1               5                   10

<210> SEQ ID NO 239
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid

<400> SEQUENCE: 239

Xaa Ala Phe Leu Leu Xaa Asp Arg Ile
1               5

<210> SEQ ID NO 240
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid

```
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 240

Xaa Ala Phe Ser Leu Xaa Xaa Asp Arg Ile
1               5                   10

<210> SEQ ID NO 241
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 241

Xaa Xaa Phe Ser Leu Xaa Xaa Asp Arg Ile
1               5                   10

<210> SEQ ID NO 242
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
```

```
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 242

Xaa Xaa Phe Lys Leu Xaa Xaa Asp Arg Ile
1               5                   10

<210> SEQ ID NO 243
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 243

Xaa Xaa Phe Arg Leu Xaa Xaa Asp Arg Ile
1               5                   10

<210> SEQ ID NO 244
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-3-(3-pyridyl)-alanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
```

-continued

```
<400> SEQUENCE: 244

Xaa Xaa Xaa Leu Leu Xaa Xaa Asp Arg Ile
1               5                   10

<210> SEQ ID NO 245
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-3-(4-pyridyl)-alanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 245

Xaa Xaa Xaa Leu Leu Xaa Xaa Asp Arg Ile
1               5                   10

<210> SEQ ID NO 246
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = rac-6-hydroxy-decanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 246

Xaa Phe Arg Leu Xaa Xaa Asp Arg Ile
1               5

<210> SEQ ID NO 247
<211> LENGTH: 9
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: Xaa = rac-7-hydroxy-dodecanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 247

Xaa Phe Arg Leu Xaa Xaa Asp Arg Ile
1               5

<210> SEQ ID NO 248
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = decanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 248

Xaa Phe Arg Leu Xaa Xaa Asp Arg Ile
1               5

<210> SEQ ID NO 249
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(dimethylamino)-pyrrolidine-2-
      carboxylic acid

<400> SEQUENCE: 249

Xaa Ala Phe Gly Leu Xaa Leu Asp Arg Ile
1               5                   10
```

```
<210> SEQ ID NO 250
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(dimethylamino)pyrrolidine-2-
      carboxylic acid

<400> SEQUENCE: 250

Xaa Ala Phe Arg Leu Xaa Leu Asp Arg Ile
1               5                   10

<210> SEQ ID NO 251
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(dimethylamino)pyrrolidine-2-
      carboxylic acid

<400> SEQUENCE: 251

Xaa Ala Phe Leu Leu Xaa Leu Asp Arg Ile
1               5                   10

<210> SEQ ID NO 252
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
```

```
<223> OTHER INFORMATION: Xaa = (R)-ornithine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 252

Xaa Xaa Phe Xaa Leu Xaa Xaa Asp Arg Ile
1               5                   10

<210> SEQ ID NO 253
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-3-(2-pyridyl)-alanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 253

Xaa Xaa Xaa Leu Leu Xaa Xaa Asp Arg Ile
1               5                   10

<210> SEQ ID NO 254
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
```

```
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 254

Xaa Ala Xaa Leu Leu Xaa Xaa Asp Arg Ile
1               5                   10

<210> SEQ ID NO 255
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 255

Xaa Ala Xaa Lys Leu Xaa Xaa Asp Arg Ile
1               5                   10

<210> SEQ ID NO 256
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: Xaa = (R)-ornithine
<220> FEATURE:
```

```
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 256

Xaa Ala Xaa Xaa Leu Xaa Xaa Asp Arg Ile
1               5                   10

<210> SEQ ID NO 257
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-guanidinopyrrolidine-2-
      carboxylic acid

<400> SEQUENCE: 257

Xaa Ala Phe Gly Leu Xaa Leu Asp Arg Ile
1               5                   10

<210> SEQ ID NO 258
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-guanidinopyrrolidine-2-
      carboxylic acid

<400> SEQUENCE: 258

Xaa Ala Phe Arg Leu Xaa Leu Asp Arg Ile
1               5                   10

<210> SEQ ID NO 259
<211> LENGTH: 10
<212> TYPE: PRT
<213> ORGANISM: Artificial
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-guanidinopyrrolidine-2-
      carboxylic acid

<400> SEQUENCE: 259

Xaa Ala Phe Leu Leu Xaa Leu Asp Arg Ile
1               5                   10

<210> SEQ ID NO 260
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = Sarcosine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 260

Xaa Xaa Phe Arg Leu Xaa Xaa Asp Arg Ile
1               5                   10

<210> SEQ ID NO 261
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (R)-azetidin-2-carboxylic acid
<220> FEATURE:
<221> NAME/KEY: MISC_FEATURE
<222> LOCATION: (2)..(2)
<223> OTHER INFORMATION: D form of amino acid at this position
<220> FEATURE:
```

<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 261

Xaa Xaa Phe Arg Leu Xaa Xaa Asp Arg Ile
1               5                   10

<210> SEQ ID NO 262
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = azetidine-3-carboxylic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 262

Xaa Xaa Phe Arg Leu Xaa Xaa Asp Arg Ile
1               5                   10

<210> SEQ ID NO 263
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = rac-imidazolidine-2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine

```
<400> SEQUENCE: 263

Xaa Ala Phe Leu Leu Xaa Xaa Asp Arg Ile
1               5                   10

<210> SEQ ID NO 264
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = rac-imidazolidine-2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 264

Xaa Ala Phe Gly Leu Xaa Xaa Asp Arg Ile
1               5                   10

<210> SEQ ID NO 265
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = 4,4-dimethyl-2-methylamino-pentanoic acid

<400> SEQUENCE: 265

Xaa Ala Phe Leu Leu Xaa Xaa Asp Arg Ile
1               5                   10

<210> SEQ ID NO 266
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = 4,4-dimethyl-2-methylamino-pentanoic acid

<400> SEQUENCE: 266

Xaa Ala Phe Arg Leu Xaa Xaa Asp Arg Ile
1               5                   10

<210> SEQ ID NO 267
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino-propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 267

Xaa Xaa Phe Xaa Leu Xaa Xaa Asp Arg Ile
1               5                   10

<210> SEQ ID NO 268
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
```

```
<221> NAME/KEY: MISC_FEATURE
<222> LOCATION: (4)..(4)
<223> OTHER INFORMATION: Xaa = (R)-2-amino-5-(dimethylamino)-pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 268

Xaa Ala Phe Xaa Leu Xaa Xaa Asp Arg Ile
1               5                   10

<210> SEQ ID NO 269
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)-pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 269

Xaa Xaa Phe Xaa Leu Xaa Xaa Asp Arg Ile
1               5                   10

<210> SEQ ID NO 270
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = dodecanoic acid 1-carboxy-2-phenyl-ethyl
      ester
<220> FEATURE:
<221> NAME/KEY: MISC_FEATURE
<222> LOCATION: (2)..(2)
<223> OTHER INFORMATION: D form of amino acid at this position
<220> FEATURE:
```

```
<221> NAME/KEY: MISC_FEATURE
<222> LOCATION: (4)..(4)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (5)..(5)
<223> OTHER INFORMATION: Xaa = (S)-N-methyl-leucine

<400> SEQUENCE: 270

Xaa Arg Leu Xaa Xaa Asp Arg Ile
1               5

<210> SEQ ID NO 271
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = octanoic acid 1-carboxy-ethyl ester
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 271

Xaa Phe Arg Leu Xaa Xaa Asp Arg Ile
1               5

<210> SEQ ID NO 272
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = dodecanoic acid 1-carboxy-2-phenyl-ethyl
      ester
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (5)..(5)
<223> OTHER INFORMATION: Xaa = (S)-N-methyl-leucine

<400> SEQUENCE: 272

Xaa Leu Leu Xaa Xaa Asp Arg Ile
1               5

<210> SEQ ID NO 273
<211> LENGTH: 9
<212> TYPE: PRT
```

```
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = octanoic acid 1-carboxy-ethyl ester
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 273

Xaa Phe Leu Leu Xaa Xaa Asp Arg Ile
1               5

<210> SEQ ID NO 274
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 274

Xaa Xaa Phe Leu Leu Xaa Xaa Asp Arg Ile
1               5                   10

<210> SEQ ID NO 275
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
```

```
<220> FEATURE:
<221> NAME/KEY: MISC_FEATURE
<222> LOCATION: (6)..(6)
<223> OTHER INFORMATION: Xaa = (2S,4R)-4-aminopyrrolideine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 275

Xaa Ala Phe Leu Leu Xaa Xaa Asp Arg Ile
1               5                   10

<210> SEQ ID NO 276
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 276

Xaa Xaa Phe Arg Leu Xaa Xaa Asp Arg Ile
1               5                   10

<210> SEQ ID NO 277
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5-butyl-2H-pyrrazole-3-carboxylic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 277
```

```
Xaa Ala Phe Arg Leu Xaa Xaa Asp Arg Ile
1               5                   10

<210> SEQ ID NO 278
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 278

Xaa Xaa Phe Leu Leu Xaa Xaa Asp Arg Ile
1               5                   10

<210> SEQ ID NO 279
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (S)-alpha-tert-butylglycine

<400> SEQUENCE: 279

Xaa Ala Phe Arg Leu Xaa Xaa Asp Arg Xaa
1               5                   10

<210> SEQ ID NO 280
<211> LENGTH: 10
```

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = 1-amino-cyclopentanecarboxylic acid

<400> SEQUENCE: 280

Xaa Ala Phe Arg Leu Xaa Xaa Asp Arg Xaa
1               5                   10

<210> SEQ ID NO 281
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-2-amino-3-(dimethylamino) propanoic
      acid

<400> SEQUENCE: 281

Xaa Ala Phe Arg Leu Xaa Xaa Asp Arg Ile
1               5                   10

<210> SEQ ID NO 282
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
```

```
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-2-amino-3-(dimethylamino)propanoic
      acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 282

Xaa Ala Phe Arg Xaa Xaa Xaa Asp Arg Ile
1               5                   10

<210> SEQ ID NO 283
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-hexanoylamino-isonicotinic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 283

Xaa Phe Arg Leu Xaa Xaa Asp Arg Ile
1               5

<210> SEQ ID NO 284
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
```

```
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 284

Xaa Xaa Phe Arg Leu Xaa Xaa Asp Arg Ile
1               5                   10

<210> SEQ ID NO 285
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-ornithine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 285

Xaa Xaa Phe Xaa Leu Xaa Xaa Asp Arg Ile
1               5                   10

<210> SEQ ID NO 286
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-norleucine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
```

```
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 286

Xaa Xaa Phe Xaa Leu Xaa Xaa Asp Arg Ile
1               5                   10

<210> SEQ ID NO 287
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 287

Xaa Xaa Phe Gly Leu Xaa Xaa Asp Arg Ile
1               5                   10

<210> SEQ ID NO 288
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-acetamidopyrrolidine-2-
      carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 288

Xaa Xaa Phe Leu Leu Xaa Xaa Asp Arg Ile
1               5                   10

<210> SEQ ID NO 289
<211> LENGTH: 10
```

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(2-aminoacetamido)pyrrolidine-
     2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 289

Xaa Xaa Phe Leu Leu Xaa Xaa Asp Arg Ile
1               5                   10

<210> SEQ ID NO 290
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(3-
     aminopropanamido)pyrrolidine-2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 290

Xaa Xaa Phe Leu Leu Xaa Xaa Asp Arg Ile
1               5                   10

<210> SEQ ID NO 291
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-(octane-1-sulfonyl-propionic acid
<220> FEATURE:
<221> NAME/KEY: MISC_FEATURE
<222> LOCATION: (3)..(3)
```

```
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 291

Xaa Phe Arg Leu Xaa Xaa Asp Arg Ile
1               5

<210> SEQ ID NO 292
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 292

Xaa Xaa Phe Xaa Leu Xaa Xaa Asp Arg Ile
1               5                   10

<210> SEQ ID NO 293
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
```

```
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 293

Xaa Xaa Phe Leu Leu Xaa Xaa Asp Arg Ile
1               5                   10

<210> SEQ ID NO 294
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-ornithine

<400> SEQUENCE: 294

Xaa Ala Phe Arg Leu Xaa Xaa Asp Xaa Ile
1               5                   10

<210> SEQ ID NO 295
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
```

<223> OTHER INFORMATION: Xaa = (S)-ornithine

<400> SEQUENCE: 295

Xaa Ala Phe Leu Leu Xaa Xaa Asp Xaa Ile
1               5                   10

<210> SEQ ID NO 296
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 296

Xaa Ala Phe Arg Leu Xaa Xaa Gln Arg Ile
1               5                   10

<210> SEQ ID NO 297
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 297

Xaa Ala Phe Leu Leu Xaa Xaa Gln Arg Ile
1               5                   10

<210> SEQ ID NO 298
<211> LENGTH: 10
<212> TYPE: PRT

```
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 298

Xaa Ala Phe Arg Leu Xaa Xaa Val Arg Ile
1               5                   10

<210> SEQ ID NO 299
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 299

Xaa Ala Phe Leu Leu Xaa Xaa Val Arg Ile
1               5                   10

<210> SEQ ID NO 300
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
```

```
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 300

Xaa Ala Phe Leu Leu Xaa Xaa Val Arg Ile
1               5                   10

<210> SEQ ID NO 301
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 301

Xaa Ala Phe Arg Leu Xaa Xaa Thr Arg Ile
1               5                   10

<210> SEQ ID NO 302
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
```

```
<222> LOCATION: (7)..(7)
<223> OTHER INFORMATION: Xaa = (S)-N-methyl-leucine

<400> SEQUENCE: 302

Xaa Ala Phe Leu Leu Xaa Xaa Thr Arg Ile
1               5                   10

<210> SEQ ID NO 303
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = 1-amino-cyclopentanecarboxylic acid

<400> SEQUENCE: 303

Xaa Ala Phe Leu Leu Xaa Xaa Asp Arg Xaa
1               5                   10

<210> SEQ ID NO 304
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = amino-peperidein-3-yl-acetic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 304

Xaa Ala Phe Xaa Leu Xaa Xaa Asp Arg Ile
1               5                   10
```

<210> SEQ ID NO 305
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 2-amino-3-piperidin-4-yl-propionic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 305

Xaa Ala Phe Xaa Leu Xaa Xaa Asp Arg Ile
1               5                   10

<210> SEQ ID NO 306
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 306

Xaa Ala Phe Xaa Leu Xaa Xaa Asp Arg Ile
1               5                   10

<210> SEQ ID NO 307
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)

```
<223> OTHER INFORMATION: Xaa = 3-hexyloxy-isoxazole-5-carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 307

Xaa Phe Arg Leu Xaa Xaa Asp Arg Ile
1               5

<210> SEQ ID NO 308
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-hexanoylamino-oxazole-4-carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 308

Xaa Phe Arg Leu Xaa Xaa Asp Arg Ile
1               5

<210> SEQ ID NO 309
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-hexylamino-oxazole-4-carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 309

Xaa Phe Arg Leu Xaa Xaa Asp Arg Ile
1               5
```

```
<210> SEQ ID NO 310
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-(4-butyl-thizol-2-ylamino)-benzoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 310

Xaa Phe Arg Leu Xaa Xaa Asp Arg Ile
1               5

<210> SEQ ID NO 311
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5 butyl-thiazole
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 311

Xaa Xaa Phe Arg Leu Xaa Xaa Asp Arg Ile
1               5                   10

<210> SEQ ID NO 312
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-butyl-thiazole
<220> FEATURE:
<221> NAME/KEY: MISC_FEATURE
<222> LOCATION: (2)..(2)
```

```
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 312

Xaa Xaa Phe Arg Leu Xaa Xaa Asp Arg Ile
1               5                   10

<210> SEQ ID NO 313
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5-butyl-thiazole
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 313

Xaa Ala Phe Arg Leu Xaa Xaa Asp Arg Ile
1               5                   10

<210> SEQ ID NO 314
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-butyl-thiazole
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
```

<221> NAME/KEY: MISC_FEATURE
<222> LOCATION: (7)..(7)
<223> OTHER INFORMATION: Xaa = (S)-N-methyl-leucine

<400> SEQUENCE: 314

Xaa Ala Phe Arg Leu Xaa Xaa Asp Arg Ile
1               5                   10

<210> SEQ ID NO 315
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 315

Xaa Ala Phe Xaa Leu Xaa Xaa Asp Arg Ile
1               5                   10

<210> SEQ ID NO 316
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(diethylamino)pyrrolidine-2-
      carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 316

Xaa Xaa Phe Leu Leu Xaa Xaa Asp Arg Ile
1               5                   10

<210> SEQ ID NO 317
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(ethylamino)pyrrolidine-2-
      carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 317

Xaa Xaa Phe Leu Leu Xaa Xaa Asp Arg Ile
1               5                   10

<210> SEQ ID NO 318
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 318

Xaa Ala Phe Xaa Leu Xaa Xaa Asp Arg Ile
1               5                   10

<210> SEQ ID NO 319
<211> LENGTH: 10
<212> TYPE: PRT
<213> ORGANISM: Artificial
<220> FEATURE:
<223> OTHER INFORMATION: synthetic
<220> FEATURE:

```
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 319

Xaa Xaa Phe Xaa Leu Xaa Xaa Asp Arg Ile
1               5                   10

<210> SEQ ID NO 320
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (S)-alpha-tert-butylglycine

<400> SEQUENCE: 320

Xaa Ala Phe Leu Leu Xaa Xaa Asp Arg Xaa
1               5                   10

<210> SEQ ID NO 321
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
```

```
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = 1-aminocyclohexanecarboxylic acid

<400> SEQUENCE: 321

Xaa Ala Phe Leu Leu Xaa Xaa Asp Arg Xaa
1               5                   10

<210> SEQ ID NO 322
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = 1-aminocyclohexanecarboxylic acid

<400> SEQUENCE: 322

Xaa Ala Phe Arg Leu Xaa Xaa Asp Arg Xaa
1               5                   10

<210> SEQ ID NO 323
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
```

```
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-norleucine

<400> SEQUENCE: 323

Xaa Ala Phe Leu Leu Xaa Xaa Asp Xaa Ile
1               5                   10

<210> SEQ ID NO 324
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-norleucine

<400> SEQUENCE: 324

Xaa Ala Phe Arg Leu Xaa Xaa Asp Xaa Ile
1               5                   10

<210> SEQ ID NO 325
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
```

```
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 325

Xaa Ala Phe Arg Leu Xaa Xaa Ile Arg Ile
1               5                   10

<210> SEQ ID NO 326
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 326

Xaa Ala Phe Leu Leu Xaa Xaa Ile Arg Ile
1               5                   10

<210> SEQ ID NO 327
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (2S,3aS,7aS)-octahydro-1H-indole-2-
      carboxylic acid

<400> SEQUENCE: 327
```

Xaa Ala Phe Arg Leu Xaa Xaa Asp Arg Ile
1               5                   10

<210> SEQ ID NO 328
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-pipecolinic acid

<400> SEQUENCE: 328

Xaa Ala Phe Arg Leu Xaa Xaa Asp Arg Ile
1               5                   10

<210> SEQ ID NO 329
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-pipecolinic acid

<400> SEQUENCE: 329

Xaa Ala Phe Leu Leu Xaa Xaa Asp Arg Ile
1               5                   10

<210> SEQ ID NO 330
<211> LENGTH: 10
<212> TYPE: PRT
<213> ORGANISM: Artificial
<220> FEATURE:
<223> OTHER INFORMATION: synthetic
<220> FEATURE:

```
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-2-amino-3-(dimethylamino)propanoic
      acid

<400> SEQUENCE: 330

Xaa Ala Phe Leu Leu Xaa Xaa Asp Arg Ile
1               5                   10

<210> SEQ ID NO 331
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-2-amino-3-(dimethylamino)propanoic
      acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 331

Xaa Ala Phe Leu Xaa Xaa Xaa Asp Arg Ile
1               5                   10

<210> SEQ ID NO 332
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
```

```
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 332

Xaa Xaa Phe Xaa Leu Xaa Xaa Asp Arg Ile
1               5                   10

<210> SEQ ID NO 333
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(bis(2-
      aminoethyl)amino)propanoic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 333

Xaa Xaa Phe Xaa Leu Xaa Xaa Asp Arg Ile
1               5                   10

<210> SEQ ID NO 334
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
```

<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(2-aminoethylamino)pyrrolidine-
    2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 334

Xaa Xaa Phe Leu Leu Xaa Xaa Asp Arg Ile
1               5                   10

<210> SEQ ID NO 335
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = 4-(3-amino-propylamino)-pyrrolidine-2-
    carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 335

Xaa Xaa Phe Leu Leu Xaa Xaa Asp Arg Ile
1               5                   10

<210> SEQ ID NO 336
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-hexyloxy-isoxazole-5-carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (6)..(6)
<223> OTHER INFORMATION: Xaa = (S)-N-methyl-leucine

```
<400> SEQUENCE: 336

Xaa Phe Leu Leu Xaa Xaa Asp Arg Ile
1               5

<210> SEQ ID NO 337
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-hexylamino-oxazole-4-carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 337

Xaa Phe Leu Leu Xaa Xaa Asp Arg Ile
1               5

<210> SEQ ID NO 338
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-(4-butyl-thiazol-2-ylamino) benzoic
      acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 338

Xaa Phe Leu Leu Xaa Xaa Asp Arg Ile
1               5

<210> SEQ ID NO 339
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5-pentylsulfanylmethyl-oxazole-2-
      carboxylic acid
<220> FEATURE:
```

```
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 339

Xaa Phe Leu Leu Xaa Xaa Asp Arg Ile
1               5

<210> SEQ ID NO 340
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5-pentylsulfanylmethyl-oxazole-2-
      carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 340

Xaa Phe Arg Leu Xaa Xaa Asp Arg Ile
1               5

<210> SEQ ID NO 341
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-octylsulfanyl-propionic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 341

Xaa Phe Leu Leu Xaa Xaa Asp Arg Ile
1               5
```

```
<210> SEQ ID NO 342
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-octylsulfanyl-propionic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 342

Xaa Phe Arg Leu Xaa Xaa Asp Arg Ile
1               5

<210> SEQ ID NO 343
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-(5-butyl-thizol-2-ylamino)-benzoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 343

Xaa Phe Leu Leu Xaa Xaa Asp Arg Ile
1               5

<210> SEQ ID NO 344
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-(5-butyl-thiazol-2-ylamino)-benzoic
      acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
```

```
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 344

Xaa Phe Arg Leu Xaa Xaa Asp Arg Ile
1               5

<210> SEQ ID NO 345
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5-butyl-thiazole
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 345

Xaa Xaa Phe Leu Leu Xaa Xaa Asp Arg Ile
1               5                   10

<210> SEQ ID NO 346
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-butyl-thiazole
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 346

Xaa Xaa Phe Leu Leu Xaa Xaa Asp Arg Ile
1               5                   10
```

```
<210> SEQ ID NO 347
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (2S,3aS,7aS)-octahydro-1H-indole-2-
      carboxylic acid

<400> SEQUENCE: 347

Xaa Ala Phe Leu Leu Xaa Xaa Asp Arg Ile
1               5                   10

<210> SEQ ID NO 348
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 348

Xaa Ala Phe Arg Leu Xaa Pro Asp Arg Ile
1               5                   10

<210> SEQ ID NO 349
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
```

<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic acid
<220> FEATURE:
<221> NAME/KEY: MISC_FEATURE
<222> LOCATION: (7)..(7)
<223> OTHER INFORMATION: Xaa = (S)-azetidin-2-carboxylic acid

<400> SEQUENCE: 349

Xaa Ala Phe Arg Leu Xaa Xaa Asp Arg Ile
1               5                   10

<210> SEQ ID NO 350
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic acid
<220> FEATURE:
<221> NAME/KEY: MISC_FEATURE
<222> LOCATION: (7)..(7)
<223> OTHER INFORMATION: Xaa = 2,3-dihydro-1H-indole-2-carboxylic acid

<400> SEQUENCE: 350

Xaa Ala Phe Arg Leu Xaa Xaa Asp Arg Ile
1               5                   10

<210> SEQ ID NO 351
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic acid

```
<220> FEATURE:
<221> NAME/KEY: MISC_FEATURE
<222> LOCATION: (7)..(7)
<223> OTHER INFORMATION: Xaa = (R)-thiazolidine-4-carboxylic acid

<400> SEQUENCE: 351

Xaa Ala Phe Arg Leu Xaa Xaa Asp Arg Ile
1               5                   10

<210> SEQ ID NO 352
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-1,2,3,4-tetrahydroisoquinoline-3-
      carboxylic acid

<400> SEQUENCE: 352

Xaa Ala Phe Arg Leu Xaa Xaa Asp Arg Ile
1               5                   10

<210> SEQ ID NO 353
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 353

Xaa Xaa Phe Leu Leu Xaa Xaa Val Arg Ile
1               5                   10
```

```
<210> SEQ ID NO 354
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 354

Xaa Xaa Phe Leu Leu Xaa Xaa Val Arg Ile
1               5                   10

<210> SEQ ID NO 355
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)--2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 355

Xaa Xaa Phe Xaa Leu Xaa Xaa Val Arg Ile
1               5                   10

<210> SEQ ID NO 356
<211> LENGTH: 10
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 356

Xaa Xaa Phe Leu Leu Xaa Xaa Val Arg Ile
1               5                   10

<210> SEQ ID NO 357
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 357

Xaa Xaa Phe Xaa Leu Xaa Xaa Val Arg Ile
1               5                   10

<210> SEQ ID NO 358
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
```

```
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 358

Xaa Xaa Phe Xaa Leu Xaa Xaa Val Arg Ile
1               5                   10

<210> SEQ ID NO 359
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 359

Xaa Xaa Phe Leu Leu Xaa Xaa Val Arg Ile
1               5                   10

<210> SEQ ID NO 360
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
```

```
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 360

Xaa Xaa Phe Xaa Leu Xaa Xaa Val Arg Ile
1               5                   10

<210> SEQ ID NO 361
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 4-amino-1-methyl-piperidine-4-carboxylic
      acid
<220> FEATURE:
<221> NAME/KEY: MISC_FEATURE
<222> LOCATION: (6)..(6)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (9)..(9)
<223> OTHER INFORMATION: Xaa = (S)-N-methyl-leucine

<400> SEQUENCE: 361

Xaa Ala Phe Xaa Met Glu Leu Xaa Xaa Asp Arg Ile
1               5                   10

<210> SEQ ID NO 362
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 4-amino-1-ethyl-piperidine-4-carboxylic
```

```
                               acid
<220> FEATURE:
<221> NAME/KEY: MISC_FEATURE
<222> LOCATION: (6)..(6)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (2S,4R)-4-hydroxypyrrolidine-2-carboxylic
                               acid
<220> FEATURE:
<221> NAME/KEY: MISC_FEATURE
<222> LOCATION: (9)..(9)
<223> OTHER INFORMATION: Xaa = (S)-N-methyl-leucine

<400> SEQUENCE: 362

Xaa Ala Phe Xaa Glu Thr Leu Xaa Xaa Asp Arg Ile
1               5                   10

<210> SEQ ID NO 363
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 4-amino-1-(2-amino-ethyl)-piperidine-4-
       carboxylic acid
<220> FEATURE:
<221> NAME/KEY: MISC_FEATURE
<222> LOCATION: (6)..(6)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (2S,4R)-4-hydroxypyrrolidine-2-carboxylic
       acid
<220> FEATURE:
<221> NAME/KEY: MISC_FEATURE
<222> LOCATION: (9)..(9)
<223> OTHER INFORMATION: Xaa = (S)-N-methyl-leucine

<400> SEQUENCE: 363

Xaa Ala Phe Xaa Ala Glu Leu Xaa Xaa Asp Arg Ile
1               5                   10

<210> SEQ ID NO 364
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
```

```
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = 2-aminoisobutyric acid

<400> SEQUENCE: 364

Xaa Ala Phe Leu Leu Xaa Xaa Asp Arg Xaa
1               5                   10

<210> SEQ ID NO 365
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = rac-alpha-methyl-leucine

<400> SEQUENCE: 365

Xaa Ala Phe Leu Leu Xaa Xaa Asp Arg Xaa
1               5                   10

<210> SEQ ID NO 366
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
```

```
            acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = 2-amino-2-ethyl-butyric acid

<400> SEQUENCE: 366

Xaa Ala Phe Leu Leu Xaa Xaa Asp Arg Xaa
1               5                  10

<210> SEQ ID NO 367
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-N-methyl-arginine

<400> SEQUENCE: 367

Xaa Ala Phe Leu Leu Xaa Xaa Asp Xaa Ile
1               5                  10

<210> SEQ ID NO 368
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
```

```
<222> LOCATION: (7)..(7)
<223> OTHER INFORMATION: Xaa = (S)-N-methyl-leucine

<400> SEQUENCE: 368

Xaa Ala Phe Leu Leu Xaa Xaa Asp Pro Ile
1               5                   10

<210> SEQ ID NO 369
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-terg-butylglycine

<400> SEQUENCE: 369

Xaa Ala Phe Leu Leu Xaa Xaa Xaa Arg Ile
1               5                   10

<210> SEQ ID NO 370
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-cyclohexylglycine
```

```
<400> SEQUENCE: 370

Xaa Ala Phe Leu Leu Xaa Xaa Xaa Arg Ile
1               5                   10

<210> SEQ ID NO 371
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-amino-2-cyclopropylacetic acid

<400> SEQUENCE: 371

Xaa Ala Phe Leu Leu Xaa Xaa Xaa Arg Ile
1               5                   10

<210> SEQ ID NO 372
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 372
```

```
Xaa Xaa Phe Xaa Leu Xaa Xaa Asp Arg Ile
1               5                   10

<210> SEQ ID NO 373
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (S)-4-hydroxy-3-iodo-phenylalanine
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 373

Xaa Xaa Ala Phe Arg Leu Xaa Xaa Asp Arg Ile
1               5                   10

<210> SEQ ID NO 374
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (S)-4-hydroxy-3-iodo-phenylalanine
<220> FEATURE:
<221> NAME/KEY: MISC_FEATURE
<222> LOCATION: (2)..(2)
<223> OTHER INFORMATION: Xaa = 4-aminobutyric acid
<220> FEATURE:
<221> NAME/KEY: MISC_FEATURE
<222> LOCATION: (3)..(3)
<223> OTHER INFORMATION: Xaa = (S)-2-aminooctanoic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine
<220> FEATURE:
<221> NAME/KEY: misc_feature
```

<222> LOCATION: (9)..(9)
<223> OTHER INFORMATION: Xaa can be any naturally occurring amino acid

<400> SEQUENCE: 374

Xaa Xaa Xaa Ala Phe Arg Leu Xaa Xaa Asp Arg Ile
1               5                   10

<210> SEQ ID NO 375
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Ac-(S)-4-hydroxy-3-iodo-phenylalanine
<220> FEATURE:
<221> NAME/KEY: MISC_FEATURE
<222> LOCATION: (2)..(2)
<223> OTHER INFORMATION: Xaa = 4-aminobutyric acid
<220> FEATURE:
<221> NAME/KEY: MISC_FEATURE
<222> LOCATION: (3)..(3)
<223> OTHER INFORMATION: Xaa = (S)-2-aminooctanoic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine
<220> FEATURE:
<221> NAME/KEY: misc_feature
<222> LOCATION: (9)..(9)
<223> OTHER INFORMATION: Xaa can be any naturally occurring amino acid

<400> SEQUENCE: 375

Xaa Xaa Xaa Ala Phe Arg Leu Xaa Xaa Asp Arg Ile
1               5                   10

<210> SEQ ID NO 376
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:

```
<221> NAME/KEY: MISC_FEATURE
<222> LOCATION: (7)..(7)
<223> OTHER INFORMATION: Xaa = (S)-N-methyl-leucine

<400> SEQUENCE: 376

Xaa Ala Phe Arg Leu Xaa Xaa Asp Pro Ile
1               5                   10

<210> SEQ ID NO 377
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 377

Xaa Ala Phe Xaa Leu Xaa Xaa Asp Pro Ile
1               5                   10

<210> SEQ ID NO 378
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 378

Xaa Xaa Phe Leu Leu Xaa Xaa Asp Pro Ile
1               5                   10

<210> SEQ ID NO 379
```

```
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-azetidin-2-carboxylic acid

<400> SEQUENCE: 379

Xaa Ala Phe Leu Leu Xaa Xaa Asp Xaa Ile
1               5                   10

<210> SEQ ID NO 380
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-pipecolinic acid

<400> SEQUENCE: 380

Xaa Ala Phe Leu Leu Xaa Xaa Asp Xaa Ile
1               5                   10

<210> SEQ ID NO 381
<211> LENGTH: 10
<212> TYPE: PRT
<213> ORGANISM: Artificial
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (2S,4R)-4-hydroxypyrrolidine-2-carboxylic
      acid

<400> SEQUENCE: 381

Xaa Ala Phe Leu Leu Xaa Xaa Asp Xaa Ile
1               5                   10

<210> SEQ ID NO 382
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (R)-thiazolidine-4-carboxylic acid

<400> SEQUENCE: 382

Xaa Ala Phe Leu Leu Xaa Xaa Asp Xaa Ile
1               5                   10

<210> SEQ ID NO 383
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = rac-(3R,4S)-cis-methanoproline

<400> SEQUENCE: 383

Xaa Ala Phe Leu Leu Xaa Xaa Asp Xaa Ile
1               5                   10

<210> SEQ ID NO 384
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 384

Xaa Ala Phe Leu Leu Xaa Xaa Asp Pro Ile
1               5                   10

<210> SEQ ID NO 385
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
```

-continued

```
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 385

Xaa Ala Phe Xaa Leu Xaa Xaa Asp Pro Ile
1               5                   10

<210> SEQ ID NO 386
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 386

Xaa Ala Phe Xaa Leu Xaa Xaa Asp Pro Ile
1               5                   10

<210> SEQ ID NO 387
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
```

```
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 387

Xaa Ala Phe Xaa Leu Xaa Xaa Asp Pro Ile
1               5                   10

<210> SEQ ID NO 388
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = 1-aminocyclohanecarboxylic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 388

Xaa Ala Phe Xaa Leu Xaa Xaa Asp Arg Ile
1               5                   10

<210> SEQ ID NO 389
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (2S,4S)-4-phenylpyrrolidine-2-carboxylic
      acid

<400> SEQUENCE: 389
```

```
Xaa Ala Phe Leu Leu Xaa Xaa Asp Xaa Ile
1               5                   10

<210> SEQ ID NO 390
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = 1-aminocyclohexanecarboxylic acid

<400> SEQUENCE: 390

Xaa Ala Phe Leu Leu Xaa Xaa Asp Xaa Ile
1               5                   10

<210> SEQ ID NO 391
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = 4-amino-piperidine-4-carboxylic acid

<400> SEQUENCE: 391

Xaa Ala Phe Leu Leu Xaa Xaa Asp Xaa Ile
1               5                   10
```

<210> SEQ ID NO 392
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (2S,4R)-4-aminopyrrolidine-2-carboxylic
      acid

<400> SEQUENCE: 392

Xaa Ala Phe Leu Leu Xaa Xaa Asp Xaa Ile
1               5                   10

<210> SEQ ID NO 393
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-3-(bis(piperidin-4-
      ylmethylamino))propanoic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 393

Xaa Ala Phe Xaa Leu Xaa Xaa Asp Arg Ile
1               5                   10

```
<210> SEQ ID NO 394
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-3-(piperidin-4-
     ylmethylamino)propanoic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
     acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 394

Xaa Ala Phe Xaa Leu Xaa Xaa Asp Arg Ile
1               5                   10

<210> SEQ ID NO 395
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-3-(bis((1H-imidazol-2-
     yl)methyl)amino)propanoic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
     acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 395

Xaa Ala Phe Xaa Leu Xaa Xaa Asp Arg Ile
1               5                   10
```

```
<210> SEQ ID NO 396
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (R)-2-amino-3-(neopentylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 396

Xaa Ala Phe Xaa Leu Xaa Xaa Asp Arg Ile
1               5                   10

<210> SEQ ID NO 397
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cyclohexylamine

<400> SEQUENCE: 397

Xaa Xaa Phe Leu Leu Xaa Xaa Asp Pro Xaa
1               5                   10

<210> SEQ ID NO 398
<211> LENGTH: 10
```

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = Isoleucine-OH

<400> SEQUENCE: 398

Xaa Xaa Phe Leu Leu Xaa Xaa Asp Pro Xaa
1               5                   10

<210> SEQ ID NO 399
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = Isoleucine-(NH-CH3)
<220> FEATURE:
<221> NAME/KEY: MISC_FEATURE
<222> LOCATION: (14)..(4)
<223> OTHER INFORMATION: D form of amino acid at this position

<400> SEQUENCE: 399

Xaa Xaa Phe Leu Leu Xaa Xaa Asp Pro Xaa
1               5                   10

<210> SEQ ID NO 400
<211> LENGTH: 10
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (2S,4S)-4-hydroxypyrrolidine-2-carboxylic
      acid

<400> SEQUENCE: 400

Xaa Ala Phe Leu Leu Xaa Xaa Asp Xaa Ile
1               5                   10

<210> SEQ ID NO 401
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (2S,3S)-3-hydroxypyrrolidine-2-carboxylic
      acid

<400> SEQUENCE: 401

Xaa Ala Phe Leu Leu Xaa Xaa Asp Xaa Ile
1               5                   10

<210> SEQ ID NO 402
<211> LENGTH: 10
<212> TYPE: PRT
<213> ORGANISM: Artificial
<220> FEATURE:
<223> OTHER INFORMATION: synthetic
```

```
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-2,5-dihydro-1H-pyrrole-2-carboxylic
      acid

<400> SEQUENCE: 402

Xaa Ala Phe Leu Leu Xaa Xaa Asp Xaa Ile
1               5                   10

<210> SEQ ID NO 403
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-2,3-diamino-propionic acid

<400> SEQUENCE: 403

Xaa Ala Phe Leu Leu Xaa Xaa Asp Xaa Ile
1               5                   10

<210> SEQ ID NO 404
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
```

```
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-beta-homolysine

<400> SEQUENCE: 404

Xaa Ala Phe Leu Leu Xaa Xaa Asp Xaa Ile
1               5                   10

<210> SEQ ID NO 405
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-para-nitro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 405

Xaa Xaa Xaa Leu Leu Xaa Xaa Asp Arg Ile
1               5                   10

<210> SEQ ID NO 406
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
```

<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-para-fluoro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 406

Xaa Xaa Xaa Leu Leu Xaa Xaa Asp Arg Ile
1               5                   10

<210> SEQ ID NO 407
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-para-methyoxy-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 407

Xaa Xaa Xaa Leu Leu Xaa Xaa Asp Arg Ile
1               5                   10

<210> SEQ ID NO 408
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid

```
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (74)..(4)
<223> OTHER INFORMATION: D form of amino acid at this position

<400> SEQUENCE: 408

Xaa Xaa Tyr Leu Leu Xaa Xaa Asp Arg Ile
1               5                   10

<210> SEQ ID NO 409
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = rac-2-amino-3-phenyl-butyric acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 409

Xaa Xaa Xaa Leu Leu Xaa Xaa Asp Arg Ile
1               5                   10

<210> SEQ ID NO 410
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (2S,4S)-4-phenylpyrrolidine-2-carboxylic
      acid
<220> FEATURE:
<221> NAME/KEY: MISC_FEATURE
```

```
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 410

Xaa Xaa Xaa Leu Leu Xaa Xaa Asp Arg Ile
1               5                   10

<210> SEQ ID NO 411
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-para-amino-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 411

Xaa Xaa Xaa Leu Leu Xaa Xaa Asp Arg Ile
1               5                   10

<210> SEQ ID NO 412
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-para-chloro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
```

```
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 412

Xaa Xaa Xaa Leu Leu Xaa Xaa Asp Arg Ile
1               5                   10

<210> SEQ ID NO 413
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-para-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 413

Xaa Xaa Xaa Leu Leu Xaa Xaa Asp Arg Ile
1               5                   10

<210> SEQ ID NO 414
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-3,4-dichloro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
```

```
            acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 414

Xaa Xaa Xaa Leu Leu Xaa Xaa Asp Arg Ile
1               5                   10

<210> SEQ ID NO 415
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (S)-1,2,3,4-tetrahydronaphthalen-1-amine

<400> SEQUENCE: 415

Xaa Xaa Phe Leu Leu Xaa Xaa Asp Pro Xaa
1               5                   10

<210> SEQ ID NO 416
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
```

-continued

```
<222> LOCATION: (10)..(10)
<223> OTHER INFORMATION: Xaa = cyclobutyl-amine

<400> SEQUENCE: 416

Xaa Xaa Phe Leu Leu Xaa Xaa Asp Pro Xaa
1               5                   10

<210> SEQ ID NO 417
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (S)-3,3-dimethylbutan-2-amine

<400> SEQUENCE: 417

Xaa Xaa Phe Leu Leu Xaa Xaa Asp Pro Xaa
1               5                   10

<210> SEQ ID NO 418
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (S)-3,3-dimethylbutan-2-amine
```

<400> SEQUENCE: 418

Xaa Xaa Phe Leu Leu Xaa Xaa Asp Pro Xaa
1               5                   10

<210> SEQ ID NO 419
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (1R,2R)-2-methylcyclohexanamine

<400> SEQUENCE: 419

Xaa Xaa Phe Leu Leu Xaa Xaa Asp Pro Xaa
1               5                   10

<210> SEQ ID NO 420
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (1R,2R,4R)-bicyclo[2.2.1]heptan-2-amine

<400> SEQUENCE: 420

Xaa Xaa Phe Leu Leu Xaa Xaa Asp Pro Xaa 1               5                    10

<210> SEQ ID NO 421
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 421

Xaa Xaa Phe Leu Leu Xaa Xaa Asp Pro Xaa
1               5                   10

<210> SEQ ID NO 422
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = 1-propyl-butyl-amine

<400> SEQUENCE: 422

Xaa Xaa Phe Leu Leu Xaa Xaa Asp Pro Xaa
1               5                   10

```
<210> SEQ ID NO 423
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 423

Xaa Xaa Phe Ala Leu Xaa Xaa Asp Arg Ile
1               5                   10

<210> SEQ ID NO 424
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 424

Xaa Xaa Phe Leu Leu Xaa Xaa Asp Arg Ile
1               5                   10

<210> SEQ ID NO 425
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
```

```
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 425

Xaa Xaa Phe Xaa Leu Xaa Xaa Asp Arg Ile
1               5                   10

<210> SEQ ID NO 426
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-amino-cyclopentyl-acetic acid

<400> SEQUENCE: 426

Xaa Ala Phe Leu Leu Xaa Xaa Xaa Arg Ile
1               5                   10

<210> SEQ ID NO 427
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
```

```
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (R)-amino-thiophen-2-yl-acetic acid

<400> SEQUENCE: 427

Xaa Ala Phe Leu Leu Xaa Xaa Xaa Arg Ile
1               5                   10

<210> SEQ ID NO 428
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-amino-thiophen-2-yl-acetic acid

<400> SEQUENCE: 428

Xaa Ala Phe Leu Leu Xaa Xaa Xaa Arg Ile
1               5                   10

<210> SEQ ID NO 429
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 429
```

```
Xaa Xaa Phe Leu Leu Xaa Xaa Asp Pro Ile
1               5                   10

<210> SEQ ID NO 430
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 430

Xaa Xaa Phe Gly Leu Xaa Xaa Asp Pro Ile
1               5                   10

<210> SEQ ID NO 431
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 431

Xaa Xaa Phe Xaa Leu Xaa Xaa Asp Pro Ile
1               5                   10

<210> SEQ ID NO 432
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
     acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cyclopentyl-amine

<400> SEQUENCE: 432

Xaa Xaa Phe Leu Leu Xaa Xaa Asp Pro Xaa
1               5                   10

<210> SEQ ID NO 433
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
     acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (S)-N-methyl-isoleucine

<400> SEQUENCE: 433

Xaa Xaa Phe Leu Leu Xaa Xaa Asp Arg Xaa
1               5                   10

<210> SEQ ID NO 434
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
```

```
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-N-methyl-arginine

<400> SEQUENCE: 434

Xaa Xaa Phe Leu Leu Xaa Xaa Asp Xaa Ile
1               5                   10

<210> SEQ ID NO 435
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-N-methyl-leucine
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 435

Xaa Xaa Phe Leu Xaa Xaa Xaa Asp Arg Ile
1               5                   10

<210> SEQ ID NO 436
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
```

```
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 436

Xaa Xaa Xaa Leu Leu Xaa Xaa Asp Arg Ile
1               5                   10

<210> SEQ ID NO 437
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = N-methyl-leucine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 437

Xaa Xaa Phe Xaa Leu Xaa Xaa Asp Arg Ile
1               5                   10

<210> SEQ ID NO 438
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
```

```
-continued

<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = (S)-N-methyl-isoleucine

<400> SEQUENCE: 438

Xaa Xaa Phe Xaa Leu Xaa Xaa Asp Arg Xaa
1               5                   10

<210> SEQ ID NO 439
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (S)-N-methyl-arginine

<400> SEQUENCE: 439

Xaa Xaa Phe Xaa Leu Xaa Xaa Asp Xaa Ile
1               5                   10

<210> SEQ ID NO 440
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
```

```
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-N-methyl-aspartic acid

<400> SEQUENCE: 440

Xaa Xaa Phe Xaa Leu Xaa Xaa Xaa Arg Ile
1               5                   10

<210> SEQ ID NO 441
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-N-methyl-leucine
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 441

Xaa Xaa Phe Xaa Xaa Xaa Xaa Asp Arg Ile
1               5                   10

<210> SEQ ID NO 442
<211> LENGTH: 10
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 442

Xaa Xaa Xaa Xaa Leu Xaa Xaa Asp Arg Ile
1               5                   10

<210> SEQ ID NO 443
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 443

Xaa Xaa Phe Xaa Leu Xaa Xaa Asp Pro Ile
1               5                   10

<210> SEQ ID NO 444
<211> LENGTH: 10
```

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 444

Xaa Xaa Phe Leu Leu Xaa Xaa Val Pro Xaa
1               5                   10

<210> SEQ ID NO 445
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-2-amino-4,4-dimethylpentanoic acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 445

Xaa Xaa Phe Leu Leu Xaa Xaa Asp Pro Xaa
1               5                   10

<210> SEQ ID NO 446
<211> LENGTH: 10
<212> TYPE: PRT
<213> ORGANISM: Artificial
<220> FEATURE:
```

<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 446

Xaa Xaa Phe Leu Leu Xaa Ile Asp Pro Xaa
1               5                   10

<210> SEQ ID NO 447
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 447

Xaa Xaa Xaa Leu Leu Xaa Xaa Asp Pro Xaa
1               5                   10

<210> SEQ ID NO 448
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE

```
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-N-methyl-leucine
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 448

Xaa Xaa Phe Leu Xaa Xaa Xaa Asp Pro Xaa
1               5                   10

<210> SEQ ID NO 449
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-3,4-dichloro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 449

Xaa Xaa Xaa Leu Leu Xaa Xaa Asp Pro Xaa
1               5                   10

<210> SEQ ID NO 450
<211> LENGTH: 10
<212> TYPE: PRT
```

```
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 450

Xaa Xaa Phe Gly Leu Xaa Xaa Asp Pro Xaa
1               5                   10

<210> SEQ ID NO 451
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 451

Xaa Xaa Phe Xaa Leu Xaa Xaa Asp Pro Xaa
1               5                   10

<210> SEQ ID NO 452
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 4-amino-piperidine-4-carboxylic acid
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 452

Xaa Xaa Phe Xaa Leu Xaa Xaa Asp Pro Xaa
1               5                   10

<210> SEQ ID NO 453
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 453

Xaa Xaa Phe Xaa Leu Xaa Xaa Asp Pro Xaa
1               5                   10

<210> SEQ ID NO 454
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
```

```
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 454

Xaa Xaa Phe Xaa Leu Xaa Xaa Asp Pro Xaa
1               5                   10

<210> SEQ ID NO 455
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-phenyl-butyric acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 455

Xaa Xaa Phe Leu Leu Xaa Xaa Asp Arg Ile
1               5                   10

<210> SEQ ID NO 456
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 5-phenyl-pentanoic acid
```

```
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 456

Xaa Xaa Phe Leu Leu Xaa Xaa Asp Arg Ile
1               5                   10

<210> SEQ ID NO 457
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 4-(4-methoxy-phenyl)-butyric acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 457

Xaa Xaa Phe Leu Leu Xaa Xaa Asp Arg Ile
1               5                   10

<210> SEQ ID NO 458
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (4-butoxy-phenyl)-acetic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
```

```
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 458

Xaa Xaa Phe Leu Leu Xaa Xaa Asp Arg Ile
1               5                   10

<210> SEQ ID NO 459
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-(4-bromo-phenyl)-propionic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 459

Xaa Xaa Phe Leu Leu Xaa Xaa Asp Arg Ile
1               5                   10

<210> SEQ ID NO 460
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-pentyl-benzooxazole-5-carboxylic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 460

Xaa Xaa Phe Leu Leu Xaa Xaa Asp Arg Ile
1               5                   10
```

```
<210> SEQ ID NO 461
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Hexanoic acid
<220> FEATURE:
<221> NAME/KEY: MISC_FEATURE
<222> LOCATION: (2)..(2)
<223> OTHER INFORMATION: Xaa = 3-amino-4-hydroxy-benzoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 461

Xaa Xaa Xaa Phe Leu Leu Xaa Xaa Asp Arg Ile
1               5                   10

<210> SEQ ID NO 462
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = piperidine-1,2-dicarboxylic acid 1-benzyl
      ester
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 462

Xaa Xaa Phe Leu Leu Xaa Xaa Asp Arg Ile
1               5                   10

<210> SEQ ID NO 463
<211> LENGTH: 10
<212> TYPE: PRT
<213> ORGANISM: Artificial
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-meta-chloro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 463

Xaa Xaa Xaa Leu Leu Xaa Xaa Asp Arg Ile
1               5                   10

<210> SEQ ID NO 464
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-para-bromo-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 464

Xaa Xaa Xaa Leu Leu Xaa Xaa Asp Arg Ile
1               5                   10

<210> SEQ ID NO 465
<211> LENGTH: 10
<212> TYPE: PRT
<213> ORGANISM: Artificial
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: Xaa = octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-3-thienyl-alinine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 465

Xaa Xaa Xaa Leu Leu Xaa Xaa Asp Arg Ile
1               5                   10

<210> SEQ ID NO 466
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-meta-trifluoromethyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 466

Xaa Xaa Xaa Leu Leu Xaa Xaa Asp Arg Ile
1               5                   10

<210> SEQ ID NO 467
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-ortho-trifluoro-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-alanine

<400> SEQUENCE: 467

Xaa Xaa Xaa Leu Leu Xaa Xaa Asp Arg Ile
1               5                   10

<210> SEQ ID NO 468
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (S)-2-amino-3-(tert-butylthio)propanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 468

Xaa Xaa Phe Xaa Leu Xaa Xaa Asp Arg Ile
1               5                   10

<210> SEQ ID NO 469
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
```

<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-norleucine
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 469

Xaa Xaa Phe Leu Xaa Xaa Xaa Asp Arg Ile
1               5                   10

<210> SEQ ID NO 470
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

<400> SEQUENCE: 470

Xaa Xaa Phe Leu Leu Xaa Ile Asp Arg Ile
1               5                   10

<210> SEQ ID NO 471
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid

```
<220> FEATURE:
<221> NAME/KEY: MISC_FEATURE
<222> LOCATION: (7)..(7)
<223> OTHER INFORMATION: Xaa = (S)-2-amino-2-cyclopentylacetic acid

<400> SEQUENCE: 471

Xaa Xaa Phe Leu Leu Xaa Xaa Asp Arg Ile
1               5                   10

<210> SEQ ID NO 472
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-cyclohexylglycine

<400> SEQUENCE: 472

Xaa Xaa Phe Leu Leu Xaa Xaa Asp Arg Ile
1               5                   10

<210> SEQ ID NO 473
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = benzylamino-acetic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 473
```

```
Xaa Xaa Xaa Leu Leu Xaa Xaa Asp Arg Ile
1               5                   10
```

<210> SEQ ID NO 474
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = phenethylamino-acetic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 474

```
Xaa Xaa Xaa Leu Leu Xaa Xaa Asp Arg Ile
1               5                   10
```

<210> SEQ ID NO 475
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-2-((R)-3-amino-2-oxopyrrolidin-1-yl)-
      3-phenylpropanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 475

```
Xaa Xaa Leu Leu Xaa Xaa Asp Arg Ile
1               5
```

<210> SEQ ID NO 476
<211> LENGTH: 9

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-2-((R)-3-amino-2-oxopyrrolidin-1-yl)-
      3-phenylpropanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 476

Xaa Xaa Leu Leu Xaa Xaa Asp Arg Ile
1               5

<210> SEQ ID NO 477
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (R)-thiazolidine-4-carboxylic acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 477

Xaa Xaa Phe Leu Leu Xaa Xaa Asp Xaa Xaa
1               5                   10

<210> SEQ ID NO 478
<211> LENGTH: 10
<212> TYPE: PRT
<213> ORGANISM: Artificial
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = rac-imidazolidine-2-carboxylic acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 478

Xaa Xaa Phe Leu Leu Xaa Xaa Asp Xaa Xaa
1               5                   10

<210> SEQ ID NO 479
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa - Octanoic acid
<220> FEATURE:
<221> NAME/KEY: MISC_FEATURE
<222> LOCATION: (2)..(2)
<223> OTHER INFORMATION: Xaa - (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa - (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa - (S)-N-methyl-leucine
<220> FEATURE:
<221> NAME/KEY: MISC_FEATURE
<222> LOCATION: (9)..(9)
<223> OTHER INFORMATION: Xaa - cycloheptyl-pyrrolidin-2-ylmethyl-amine

<400> SEQUENCE: 479

Xaa Xaa Phe Leu Leu Xaa Xaa Asp Xaa
1               5

<210> SEQ ID NO 480
<211> LENGTH: 10
<212> TYPE: PRT
```

```
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 480

Xaa Xaa Phe Leu Leu Xaa Xaa Glu Pro Xaa
1               5                   10

<210> SEQ ID NO 481
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 481

Xaa Xaa Phe Leu Leu Xaa Xaa Val Pro Xaa
1               5                   10

<210> SEQ ID NO 482
<211> LENGTH: 10
<212> TYPE: PRT
<213> ORGANISM: Artificial
<220> FEATURE:
<223> OTHER INFORMATION: synthetic
```

```
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (S)-norleucine
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 482

Xaa Xaa Phe Leu Xaa Xaa Xaa Asp Pro Xaa
1               5                   10

<210> SEQ ID NO 483
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-((1S,2R,4R)-bicylco[2.2.1]heptan-2-
      yl)acetic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 483

Xaa Xaa Phe Leu Leu Xaa Xaa Asp Arg Ile
1               5                   10

<210> SEQ ID NO 484
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
```

```
<222> LOCATION: (1)..(1)
<223> OTHER INFORMATION: Xaa = 2-phenethyl-benzoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 484

Xaa Xaa Phe Leu Leu Xaa Xaa Asp Arg Ile
1               5                   10

<210> SEQ ID NO 485
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-phenyl-propionic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 485

Xaa Xaa Phe Leu Leu Xaa Xaa Asp Arg Ile
1               5                   10

<210> SEQ ID NO 486
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (S)-2-cyclopentylhexanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
```

```
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 486

Xaa Xaa Phe Leu Leu Xaa Xaa Asp Arg Ile
1               5                   10

<210> SEQ ID NO 487
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (2-butoxy-ethoxy)-acetic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 487

Xaa Xaa Phe Leu Leu Xaa Xaa Asp Arg Ile
1               5                   10

<210> SEQ ID NO 488
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = decanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 488
```

```
Xaa Xaa Phe Leu Leu Xaa Xaa Asp Arg Ile
1               5                   10

<210> SEQ ID NO 489
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-phenyl-propionic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 489

Xaa Gly Xaa Phe Leu Leu Xaa Xaa Asp Arg Ile
1               5                   10

<210> SEQ ID NO 490
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 3-phenyl-propionic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 490

Xaa Xaa Xaa Phe Leu Leu Xaa Xaa Asp Arg Ile
1               5                   10

<210> SEQ ID NO 491
<211> LENGTH: 9
<212> TYPE: PRT
```

-continued

```
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-2-((S)-3-amino-2-oxopyrrolidin-1-yl)-
      3-phenylpropanoic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 491

Xaa Xaa Leu Leu Xaa Xaa Asp Arg Ile
1               5

<210> SEQ ID NO 492
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = 4-amino-peperidine-4-carboxylic acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 492

Xaa Xaa Phe Leu Leu Xaa Xaa Asp Xaa Xaa
1               5                   10

<210> SEQ ID NO 493
<211> LENGTH: 9
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = benzylamino-acetic acid
<220> FEATURE:
<221> NAME/KEY: MISC_FEATURE
<222> LOCATION: (9)..(9)
<223> OTHER INFORMATION: Xaa = cycloheptyl-amine

<400> SEQUENCE: 493

Xaa Xaa Phe Leu Leu Xaa Xaa Xaa Xaa
1               5

<210> SEQ ID NO 494
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (R)-amino-thiophen-2-yl-acetic acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 494

Xaa Xaa Phe Leu Leu Xaa Xaa Xaa Pro Xaa
1               5                   10
```

```
<210> SEQ ID NO 495
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (2S,3R)-3-aminopyrrolidine-2-carboxylic
      acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 495

Xaa Xaa Phe Leu Leu Xaa Xaa Asp Xaa Xaa
1               5                   10

<210> SEQ ID NO 496
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 496

Xaa Xaa Phe Leu Leu Xaa Xaa Asp Arg Xaa
1               5                   10
```

```
<210> SEQ ID NO 497
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(2-aminoethylamino)pyrrolidine-
      2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 497

Xaa Xaa Phe Leu Leu Xaa Xaa Asp Arg Xaa
1               5                   10

<210> SEQ ID NO 498
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 498

Xaa Xaa Phe Leu Leu Xaa Xaa Asp Arg Xaa
1               5                   10

<210> SEQ ID NO 499
```

```
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = )2S,4R)-4-(2-aminoethylamino)pyrrolidine-
      2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa cycloheptyl-amine

<400> SEQUENCE: 499

Xaa Xaa Phe Leu Leu Xaa Xaa Val Arg Xaa
1               5                   10

<210> SEQ ID NO 500
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = 4-amino-1-(2-amino-acetyl)-piperidine-4-
      carboxylic acid
<220> FEATURE:
<221> NAME/KEY: MISC_FEATURE
<222> LOCATION: (9)..(9)
<223> OTHER INFORMATION: Xaa = 4-amino-1-carbamimidoyl-piperidine-4-
      carboxylic acid
<220> FEATURE:
<221> NAME/KEY: MISC_FEATURE
<222> LOCATION: (10)..(10)
<223> OTHER INFORMATION: Xaa = cycloheptyl-amine
```

```
<400> SEQUENCE: 500

Xaa Xaa Phe Leu Leu Xaa Xaa Asp Xaa Xaa
1               5                   10

<210> SEQ ID NO 501
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = 4-amino-1-(2-amino-acetyl)-piperidine-4-
      carboxylic acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 501

Xaa Xaa Phe Leu Leu Xaa Xaa Asp Xaa Xaa
1               5                   10

<210> SEQ ID NO 502
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
```

```
<223> OTHER INFORMATION: Xaa = (S)-2,3-diamino-propionic acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 502

Xaa Xaa Phe Leu Leu Xaa Xaa Asp Xaa Xaa
1               5                   10

<210> SEQ ID NO 503
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (9)..(9)
<223> OTHER INFORMATION: Xaa = (2S,4S)-4-amino-pyrrolidine-2-caroboxylic
      acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 503

Xaa Xaa Phe Leu Leu Xaa Xaa Asp Xaa Xaa
1               5                   10

<210> SEQ ID NO 504
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (3)..(3)
<223> OTHER INFORMATION: Xaa = (S)-homo-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
```

```
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 504

Xaa Xaa Xaa Leu Leu Xaa Xaa Asp Arg Ile
1               5                   10

<210> SEQ ID NO 505
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-N-methyl-phenylalanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 505

Xaa Ala Xaa Leu Leu Xaa Xaa Asp Arg Ile
1               5                   10

<210> SEQ ID NO 506
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
```

```
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 506

Xaa Xaa Phe Leu Leu Xaa Xaa Val Arg Xaa
1               5                   10

<210> SEQ ID NO 507
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 507

Xaa Xaa Phe Leu Leu Xaa Xaa Val Arg Xaa
1               5                   10

<210> SEQ ID NO 508
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
```

<223> OTHER INFORMATION: Xaa = cycloheptyl-amine

<400> SEQUENCE: 508

Xaa Xaa Phe Leu Leu Xaa Xaa Asp Arg Xaa
1               5                   10

<210> SEQ ID NO 509
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 509

Xaa Xaa Phe Leu Leu Xaa Xaa Asn Arg Xaa
1               5                   10

<210> SEQ ID NO 510
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 510

```
Xaa Xaa Phe Leu Leu Xaa Xaa Ser Arg Xaa
1               5                   10
```

<210> SEQ ID NO 511
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 511

```
Xaa Xaa Phe Leu Leu Xaa Xaa Thr Arg Xaa
1               5                   10
```

<210> SEQ ID NO 512
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-norleucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 512

Xaa Xaa Phe Leu Leu Xaa Xaa Xaa Arg Xaa
1               5                   10

<210> SEQ ID NO 513
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
     acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (R)-beta-homoleucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 513

Xaa Xaa Phe Leu Leu Xaa Xaa Xaa Arg Xaa
1               5                   10

<210> SEQ ID NO 514
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
    acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-thienyl-alanine

```
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 514

Xaa Xaa Phe Leu Leu Xaa Xaa Xaa Arg Xaa
1               5                   10

<210> SEQ ID NO 515
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
     acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-cyclohexylglycine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 515

Xaa Xaa Phe Leu Leu Xaa Xaa Xaa Arg Xaa
1               5                   10

<210> SEQ ID NO 516
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-(7-octanoyl-1-oxo-2,7-diaza-
     spiro[4,5]dec-2-yl)-3-phenyl-propionic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (2S,4R)-4-hydroxypyrrolidine-2-carboxylic
     acid
<220> FEATURE:
<221> NAME/KEY: MISC_FEATURE
<222> LOCATION: (5)..(5)
<223> OTHER INFORMATION: Xaa = (S)-N-methyl-leucine

<400> SEQUENCE: 516
```

```
Xaa Leu Leu Xaa Xaa Asp Arg Ile
1               5
```

<210> SEQ ID NO 517
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (S,S)-2-(3-methyl-3-octanoylamino-2-oxo-
      pyrrolidin-1-yl)-3-phenyl-propionic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (5)..(5)
<223> OTHER INFORMATION: Xaa = (S)-N-methyl-leucine

<400> SEQUENCE: 517

```
Xaa Leu Leu Xaa Xaa Asp Arg Ile
1               5
```

<210> SEQ ID NO 518
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 518

```
Xaa Xaa Phe Xaa Leu Xaa Xaa Asp Arg Xaa
1               5                   10
```

```
<210> SEQ ID NO 519
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-6-(dimethylamino)hexanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 519

Xaa Xaa Phe Xaa Leu Xaa Xaa Asp Arg Xaa
1               5                   10

<210> SEQ ID NO 520
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine
```

<400> SEQUENCE: 520

Xaa Xaa Phe Xaa Leu Xaa Xaa Val Arg Xaa
1               5                   10

<210> SEQ ID NO 521
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-6-(dimethylamino)hexanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 521

Xaa Xaa Phe Xaa Leu Xaa Xaa Val Arg Xaa
1               5                   10

<210> SEQ ID NO 522
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-6-(dimethylamino)hexanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:

```
<221> NAME/KEY: MISC_FEATURE
<222> LOCATION: (7)..(7)
<223> OTHER INFORMATION: Xaa = (S)-N-methyl-leucine

<400> SEQUENCE: 522

Xaa Xaa Phe Xaa Leu Xaa Xaa Asp Arg Ile
1               5                   10

<210> SEQ ID NO 523
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 523

Xaa Xaa Phe Xaa Leu Xaa Xaa Val Arg Ile
1               5                   10

<210> SEQ ID NO 524
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-6-(dimethylamino)hexanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
```

<222> LOCATION: (7)..(7)
<223> OTHER INFORMATION: Xaa = (S)-N-methyl-leucine

<400> SEQUENCE: 524

Xaa Xaa Phe Xaa Leu Xaa Xaa Val Arg Ile
1               5                   10

<210> SEQ ID NO 525
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = ((R)-2-amino-4-(dimethylamino)butanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 525

Xaa Xaa Phe Xaa Leu Xaa Xaa Val Arg Xaa
1               5                   10

<210> SEQ ID NO 526
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = ((R)-2-amino-4-(dimethylamino)butanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic

```
           acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 526

Xaa Xaa Phe Xaa Leu Xaa Xaa Asp Arg Ile
1               5                   10

<210> SEQ ID NO 527
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = ((R)-2-amino-4-(dimethylamino)butanoic
       acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
       acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 527

Xaa Xaa Phe Xaa Leu Xaa Xaa Val Arg Ile
1               5                   10

<210> SEQ ID NO 528
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (3-hydroxy-propylamino)acetic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
       acid
<220> FEATURE:
<221> NAME/KEY: MISC_FEATURE
<222> LOCATION: (7)..(7)
<223> OTHER INFORMATION: Xaa = (S)-N-methyl-leucine
```

<400> SEQUENCE: 528

Xaa Xaa Phe Leu Leu Xaa Xaa Asp Arg Ile
1               5                   10

<210> SEQ ID NO 529
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = rac-(2,3-dihydroxy-propylamino)-acetic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 529

Xaa Xaa Phe Leu Leu Xaa Xaa Asp Arg Ile
1               5                   10

<210> SEQ ID NO 530
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 530

Xaa Ser Phe Leu Leu Xaa Xaa Asp Arg Ile
1               5                   10

<210> SEQ ID NO 531
<211> LENGTH: 10
<212> TYPE: PRT
<213> ORGANISM: Artificial

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (R)-homo-serine
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 531

Xaa Xaa Phe Leu Leu Xaa Xaa Asp Arg Ile
1               5                   10

<210> SEQ ID NO 532
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (2,3,4,5,6-pentahydroxy-
      hexylidenaminooxy)-acetic acid
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 532

Xaa Xaa Xaa Phe Leu Leu Xaa Xaa Asp Arg Ile
1               5                   10

<210> SEQ ID NO 533
<211> LENGTH: 11
<212> TYPE: PRT
<213> ORGANISM: Artificial
<220> FEATURE:
<223> OTHER INFORMATION: synthetic
```

```
<220> FEATURE:
<221> NAME/KEY: MISC_FEATURE
<222> LOCATION: (1)..(1)
<223> OTHER INFORMATION: Xaa = (2,3,4,5,6-pentahydroxy-
      hexylidenaminooxy)-acetic acid
<220> FEATURE:
<221> NAME/KEY: MISC_FEATURE
<222> LOCATION: (2)..(2)
<223> OTHER INFORMATION: Xaa = (R)-2-aminooctanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 533

Xaa Xaa Xaa Phe Leu Leu Xaa Xaa Asp Arg Ile
1               5                   10

<210> SEQ ID NO 534
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (2-methoxy-ethoxy)-acetyl chloride
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 534

Xaa Xaa Xaa Phe Leu Leu Xaa Xaa Asp Arg Ile
1               5                   10

<210> SEQ ID NO 535
<211> LENGTH: 11
<212> TYPE: PRT
<213> ORGANISM: Artificial
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = hexyl chloroformate
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 535

Xaa Xaa Xaa Phe Leu Leu Xaa Xaa Asp Arg Ile
1               5                   10

<210> SEQ ID NO 536
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-(2-methoxy-ethoxy)-ethoxy-acetic acid
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 536

Xaa Xaa Xaa Phe Leu Leu Xaa Xaa Asp Arg Ile
1               5                   10

<210> SEQ ID NO 537
<211> LENGTH: 11
<212> TYPE: PRT
<213> ORGANISM: Artificial
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 537

Xaa Xaa Xaa Phe Leu Leu Xaa Xaa Asp Arg Ile
1               5                   10

<210> SEQ ID NO 538
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = H-8-amino-3,6-dioxaoctanoic acid
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 538

Xaa Xaa Xaa Phe Leu Leu Xaa Xaa Asp Arg Ile
1               5                   10

<210> SEQ ID NO 539
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-(2-methoxy-ethoxy)-ethoxy-acetic acid
```

```
<220> FEATURE:
<221> NAME/KEY: MISC_FEATURE
<222> LOCATION: (2)..(2)
<223> OTHER INFORMATION: Xaa = (R)-2-aminooctanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 539

Xaa Xaa Xaa Phe Leu Leu Xaa Xaa Asp Arg Ile
1               5                   10

<210> SEQ ID NO 540
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = H-8-amino-3,6-dioxaoctanoic acid
<220> FEATURE:
<221> NAME/KEY: MISC_FEATURE
<222> LOCATION: (2)..(2)
<223> OTHER INFORMATION: Xaa = (R)-2-aminooctanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 540

Xaa Xaa Xaa Phe Leu Leu Xaa Xaa Asp Arg Ile
1               5                   10

<210> SEQ ID NO 541
<211> LENGTH: 10
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 541

Xaa Xaa Phe Leu Leu Xaa Xaa Asp Arg Xaa
1               5                   10

<210> SEQ ID NO 542
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 542

Xaa Xaa Phe Leu Leu Xaa Xaa Val Pro Xaa
1               5                   10

<210> SEQ ID NO 543
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
```

```
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 543

Xaa Xaa Phe Xaa Leu Xaa Xaa Val Pro Xaa
1               5                   10

<210> SEQ ID NO 544
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 544

Xaa Xaa Phe Xaa Leu Xaa Xaa Val Pro Xaa
1               5                   10

<210> SEQ ID NO 545
```

```
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 545

Xaa Xaa Phe Xaa Leu Xaa Xaa Val Pro Xaa
1               5                   10

<210> SEQ ID NO 546
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 546

Xaa Xaa Phe Leu Leu Xaa Xaa Val Arg Xaa
1               5                   10
```

```
<210> SEQ ID NO 547
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa =(S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 547

Xaa Xaa Phe Leu Leu Xaa Xaa Val Arg Xaa
1               5                   10

<210> SEQ ID NO 548
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S.4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 548

Xaa Xaa Phe Xaa Leu Xaa Xaa Val Arg Xaa
```

```
1               5                  10
```

```
<210> SEQ ID NO 549
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octane
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 549

Xaa Xaa Phe Xaa Leu Xaa Xaa Val Arg Xaa
1               5                  10

<210> SEQ ID NO 550
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = rac-2-amino-3-phenyl-butyric acid

<400> SEQUENCE: 550
```

```
Xaa Xaa Phe Leu Leu Xaa Xaa Xaa Arg Ile
1               5                   10

<210> SEQ ID NO 551
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-phenylglycine

<400> SEQUENCE: 551

Xaa Xaa Phe Leu Leu Xaa Xaa Xaa Arg Ile
1               5                   10

<210> SEQ ID NO 552
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-amino-2-cyclopentylacetic acid

<400> SEQUENCE: 552

Xaa Xaa Phe Leu Leu Xaa Xaa Xaa Arg Ile
1               5                   10
```

```
<210> SEQ ID NO 553
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-amino-3-(2H-tetrazol-5-yl)propanoic
      acid

<400> SEQUENCE: 553

Xaa Xaa Phe Leu Leu Xaa Xaa Xaa Arg Ile
1               5                   10

<210> SEQ ID NO 554
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = rac (1R,2S)-2-octylcarbamoyl)cyclohexane
      carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 554

Xaa Phe Leu Leu Xaa Xaa Asp Arg Ile
1               5

<210> SEQ ID NO 555
<211> LENGTH: 9
<212> TYPE: PRT
<213> ORGANISM: Artificial
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: Xaa = rac (1S,2S)-2-(hexylcarbamoyl)cyclohexane
      carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 555

Xaa Phe Leu Leu Xaa Xaa Asp Arg Ile
1               5

<210> SEQ ID NO 556
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = rac (1S,2S)-2-(octylcarbamoyl)cyclohexane
      carboxylic acid
<220> FEATURE:
<221> NAME/KEY: MISC_FEATURE
<222> LOCATION: (3)..(3)
<223> OTHER INFORMATION: D form of amino acid at this position
<220> FEATURE:
<221> NAME/KEY: MISC_FEATURE
<222> LOCATION: (5)..(5)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (6)..(6)
<223> OTHER INFORMATION: Xaa = (S)-N-methyl-leucine

<400> SEQUENCE: 556

Xaa Phe Leu Leu Xaa Xaa Asp Arg Ile
1               5

<210> SEQ ID NO 557
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (S)-2-(6-hexanamido-1-oxoisoindolin-2-
      yl)-3-phenylpropanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (5)..(5)
<223> OTHER INFORMATION: Xaa = (S)-N-methyl-leucine
```

```
<400> SEQUENCE: 557

Xaa Leu Leu Xaa Xaa Asp Arg Ile
1               5

<210> SEQ ID NO 558
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = (S)-2-(4-octanamido-1,3-dioxoisoindolin-
      2-yl)-3-phenylpropanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (5)..(5)
<223> OTHER INFORMATION: Xaa = (S)-N-methyl-leucine

<400> SEQUENCE: 558

Xaa Leu Leu Xaa Xaa Asp Arg Ile
1               5

<210> SEQ ID NO 559
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 2-amino-4-pyrrolidin-1-yl-butyric acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 559

Xaa Xaa Phe Xaa Leu Xaa Xaa Asp Arg Ile
1               5                   10

<210> SEQ ID NO 560
<211> LENGTH: 10
<212> TYPE: PRT
<213> ORGANISM: Artificial
<220> FEATURE:
<223> OTHER INFORMATION: synthetic
<220> FEATURE:
```

-continued

```
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-homo-serine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 560

Xaa Xaa Phe Xaa Leu Xaa Xaa Asp Arg Ile
1               5                   10

<210> SEQ ID NO 561
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-4-(piperidin-1-yl)butanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 561

Xaa Xaa Phe Xaa Leu Xaa Xaa Asp Arg Ile
1               5                   10

<210> SEQ ID NO 562
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: Xaa = (S)-2-(5-hexanamido-1,3-dioxoisoindolin-
      2-yl)-3-phenylpropanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (4)..(4)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (5)..(5)
<223> OTHER INFORMATION: Xaa = (S)-N-methyl-leucine

<400> SEQUENCE: 562

Xaa Leu Leu Xaa Xaa Asp Arg Ile
1               5

<210> SEQ ID NO 563
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (S)-2-amino-2-(piperidin-4-yl)acetic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 563

Xaa Xaa Phe Xaa Leu Xaa Xaa Asp Arg Ile
1               5                   10

<210> SEQ ID NO 564
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = amino-piperidin-3-yl-acetic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
```

```
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 564

Xaa Xaa Phe Xaa Leu Xaa Xaa Asp Arg Ile
1               5                   10

<210> SEQ ID NO 565
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = Hyp
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 565

Xaa Xaa Phe Thr Leu Xaa Xaa Asp Arg Ile
1               5                   10

<210> SEQ ID NO 566
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 566

Xaa Xaa Phe His Leu Xaa Xaa Asp Arg Ile
1               5                   10

<210> SEQ ID NO 567
```

```
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-4-(methylsulfonyl)butanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 567

Xaa Xaa Phe Xaa Leu Xaa Xaa Asp Arg Ile
1               5                   10

<210> SEQ ID NO 568
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = rac-2-amino-4-morpholinobutanoic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 568

Xaa Xaa Phe Xaa Leu Xaa Xaa Asp Arg Ile
1               5                   10

<210> SEQ ID NO 569
<211> LENGTH: 10
<212> TYPE: PRT
<213> ORGANISM: Artificial
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-3--(2-pyridyl)-alanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 569

Xaa Xaa Phe Xaa Leu Xaa Xaa Asp Arg Ile
1               5                   10

<210> SEQ ID NO 570
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-3-(3-pyridyl)-alanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 570

Xaa Xaa Phe Xaa Leu Xaa Xaa Asp Arg Ile
1               5                   10

<210> SEQ ID NO 571
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-3-(4-pyridyl)-alanine
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 571

Xaa Xaa Phe Xaa Leu Xaa Xaa Asp Arg Ile
1               5                   10

<210> SEQ ID NO 572
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 2-amino-3-piperidin-4-yl-propionic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 572

Xaa Xaa Phe Xaa Leu Xaa Xaa Asp Arg Ile
1               5                   10

<210> SEQ ID NO 573
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
```

```
<223> OTHER INFORMATION: Xaa = rac-1-amino-2,3-dihydro-1H-indene-1-
      carboxylic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 573

Xaa Xaa Phe Xaa Leu Xaa Xaa Asp Arg Ile
1               5                   10

<210> SEQ ID NO 574
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 2-aminoindan-2-carboxylic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 574

Xaa Xaa Phe Xaa Leu Xaa Xaa Asp Arg Ile
1               5                   10

<210> SEQ ID NO 575
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
```

```
             acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 575

Xaa Xaa Phe Xaa Leu Xaa Xaa Ser Arg Xaa
1               5                   10

<210> SEQ ID NO 576
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
             acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
             acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 576

Xaa Xaa Phe Xaa Leu Xaa Xaa Thr Arg Xaa
1               5                   10

<210> SEQ ID NO 577
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = H-(S)-2-aminooctanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
```

<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 577

Xaa Xaa Phe Leu Leu Xaa Xaa Asp Arg Ile
1               5                   10

<210> SEQ ID NO 578
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = H-(R)-2-aminooctanoic acid
<220> FEATURE:
<221> NAME/KEY: MISC_FEATURE
<222> LOCATION: (1)..(1)
<223> OTHER INFORMATION: D form of amino acid at this position
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 578

Xaa Xaa Phe Leu Leu Xaa Xaa Asp Arg Ile
1               5                   10

<210> SEQ ID NO 579
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = H-Lys
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid

```
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 579

Xaa Xaa Xaa Phe Leu Leu Xaa Xaa Asp Arg Ile
1               5                   10

<210> SEQ ID NO 580
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = H-Lys
<220> FEATURE:
<221> NAME/KEY: MISC_FEATURE
<222> LOCATION: (2)..(2)
<223> OTHER INFORMATION: Xaa = (R)-2aminooctanoic acid
<220> FEATURE:
<221> NAME/KEY: MISC_FEATURE
<222> LOCATION: (2)..(2)
<223> OTHER INFORMATION: D form of amino acid at this position
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 580

Xaa Xaa Xaa Phe Leu Leu Xaa Xaa Asp Arg Ile
1               5                   10

<210> SEQ ID NO 581
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = H-Lys
<220> FEATURE:
<221> NAME/KEY: MISC_FEATURE
<222> LOCATION: (3)..(3)
<223> OTHER INFORMATION: Xaa = (S)-2-aminooctanoic acid
<220> FEATURE:
<221> NAME/KEY: MISC_FEATURE
<222> LOCATION: (4)..(4)
<223> OTHER INFORMATION: Xaa = (S)-nipecotic acid
<220> FEATURE:
<221> NAME/KEY: MISC_FEATURE
<222> LOCATION: (6)..(6)
<223> OTHER INFORMATION: D form of amino acid at this position
<220> FEATURE:
<221> NAME/KEY: MISC_FEATURE
<222> LOCATION: (8)..(8)
<223> OTHER INFORMATION: Xaa = (2S,4R)-4-hydroxypyrrolidine-2-carboxylic
```

```
            acid
<220> FEATURE:
<221> NAME/KEY: MISC_FEATURE
<222> LOCATION: (9)..(9)
<223> OTHER INFORMATION: Xaa = (S)-N-methyl-leucine

<400> SEQUENCE: 581

Xaa Pro Xaa Xaa Phe Leu Leu Xaa Xaa Asp Arg Ile
1               5                   10

<210> SEQ ID NO 582
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-(2S,3R,4R,5R)-2,3,4,5,6-
      pentahydroxyhexylamino)acetic acid
<220> FEATURE:
<221> NAME/KEY: MISC_FEATURE
<222> LOCATION: (2)..(2)
<223> OTHER INFORMATION: Xaa = (S)-2-aminooctanoic acid
<220> FEATURE:
<221> NAME/KEY: MISC_FEATURE
<222> LOCATION: (3)..(3)
<223> OTHER INFORMATION: Xaa = (S)-nipecotic acid
<220> FEATURE:
<221> NAME/KEY: MISC_FEATURE
<222> LOCATION: (5)..(5)
<223> OTHER INFORMATION: D form of amino acid at this position
<220> FEATURE:
<221> NAME/KEY: MISC_FEATURE
<222> LOCATION: (7)..(7)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (8)..(8)
<223> OTHER INFORMATION: Xaa = (S)-N-methyl-leucine

<400> SEQUENCE: 582

Xaa Xaa Xaa Phe Leu Leu Xaa Xaa Asp Arg Ile
1               5                   10

<210> SEQ ID NO 583
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = 2-(hexylamino)acetic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
```

```
<400> SEQUENCE: 583

Xaa Xaa Phe Leu Leu Xaa Xaa Asp Arg Ile
1               5                   10

<210> SEQ ID NO 584
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-3-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-((S)-3-amino-2,5-dioxopyrrolidin-1-
      yl)-5-guanidinopentanoic acid

<400> SEQUENCE: 584

Xaa Xaa Phe Xaa Leu Xaa Xaa Xaa Ile
1               5

<210> SEQ ID NO 585
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
```

```
<222> LOCATION: (8)..(8)
<223> OTHER INFORMATION: Xaa = (S)-2-amino-3-(phosphonooxy)propanoic
      acid

<400> SEQUENCE: 585

Xaa Xaa Phe Leu Leu Xaa Xaa Xaa Arg Ile
1               5                   10

<210> SEQ ID NO 586
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (2S,3R)-2-amino-3-(phosphonooxy)butanoic
      acid

<400> SEQUENCE: 586

Xaa Xaa Phe Xaa Leu Xaa Xaa Xaa Arg Ile
1               5                   10

<210> SEQ ID NO 587
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = 2-aminoacrylic acid
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
```

<222> LOCATION: (7)..(7)
<223> OTHER INFORMATION: Xaa = (S)-N-methyl-leucine

<400> SEQUENCE: 587

Xaa Xaa Phe Xaa Leu Xaa Xaa Asp Arg Ile
1               5                   10

<210> SEQ ID NO 588
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-amino-3-(phosphonooxy)propanoic
      acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 588

Xaa Xaa Phe Xaa Leu Xaa Xaa Xaa Arg Xaa
1               5                   10

<210> SEQ ID NO 589
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic

```
          acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-amino-3-(phosphonooxy)propanoic
      acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 589

Xaa Xaa Phe Leu Leu Xaa Xaa Xaa Arg Xaa
1               5                   10

<210> SEQ ID NO 590
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (2S,3R)-2-amino-3-(phosphonooxy)butanoic
      acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 590

Xaa Xaa Phe Xaa Leu Xaa Xaa Xaa Arg Xaa
1               5                   10

<210> SEQ ID NO 591
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
```

```
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (2S,3R)-2-amino-3-(phosphonooxy)propanoic
      acid
<220> FEATURE:
<221> NAME/KEY: MISC_FEATURE
<222> LOCATION: (10)..(10)
<223> OTHER INFORMATION: Xaa = cycloheptyl-amine

<400> SEQUENCE: 591

Xaa Xaa Phe Leu Leu Xaa Xaa Xaa Arg Xaa
1               5                   10

<210> SEQ ID NO 592
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 592

Xaa Xaa Phe Leu Leu Xaa Xaa Ser Arg Ile
1               5                   10

<210> SEQ ID NO 593
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
```

```
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 593

Xaa Xaa Phe Xaa Leu Xaa Xaa Ser Arg Ile
1               5                   10

<210> SEQ ID NO 594
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-amino-3-sulfopropanoic acid

<400> SEQUENCE: 594

Xaa Xaa Phe Leu Leu Xaa Xaa Xaa Arg Ile
1               5                   10

<210> SEQ ID NO 595
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
```

```
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (8)..(8)
<223> OTHER INFORMATION: Xaa = (S)-2-amino-3-sulfopropanoic acid

<400> SEQUENCE: 595

Xaa Xaa Phe Xaa Leu Xaa Xaa Xaa Arg Ile
1               5                   10

<210> SEQ ID NO 596
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 596

Xaa Xaa Phe Xaa Leu Xaa Xaa Thr Arg Ile
1               5                   10

<210> SEQ ID NO 597
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
```

```
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = Hyp(Asp(-))
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 597

Xaa Xaa Phe Leu Leu Xaa Xaa Asp Arg Ile
1               5                   10

<210> SEQ ID NO 598
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = Hyp(2581)
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 598

Xaa Xaa Phe Leu Leu Xaa Xaa Asp Arg Ile
1               5                   10

<210> SEQ ID NO 599
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
```

<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = Ile-OH

<400> SEQUENCE: 599

Xaa Xaa Phe Leu Leu Xaa Xaa Asp Arg Xaa
1               5                   10

<210> SEQ ID NO 600
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine
<220> FEATURE:
<221> NAME/KEY: MISC_FEATURE
<222> LOCATION: (10)..(10)
<223> OTHER INFORMATION: Xaa = Ile-OH

<400> SEQUENCE: 600

Xaa Xaa Phe Xaa Leu Xaa Xaa Asp Arg Xaa
1               5                   10

<210> SEQ ID NO 601
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position

```
<220> FEATURE:
<221> NAME/KEY: MISC_FEATURE
<222> LOCATION: (6)..(6)
<223> OTHER INFORMATION: Xaa = (2S,4R)-4-hydroxypyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 601

Xaa Xaa Phe Leu Leu Xaa Xaa Thr Arg Ile
1               5                   10

<210> SEQ ID NO 602
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: D form of amino acid at this position
<220> FEATURE:
<221> NAME/KEY: MISC_FEATURE
<222> LOCATION: (6)..(6)
<223> OTHER INFORMATION: Xaa = (2S,4R)-4-(S)-3-amino-3-
      carboxypropaneamido)pyrrolidine-2-carboxylic acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 602

Xaa Xaa Phe Leu Leu Xaa Xaa Asp Arg Ile
1               5                   10

<210> SEQ ID NO 603
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Octanoic acid
<220> FEATURE:
<221> NAME/KEY: MISC_FEATURE
<222> LOCATION: (2)..(2)
<223> OTHER INFORMATION: Xaa = (S)-nipecotic acid
<220> FEATURE:
<221> NAME/KEY: MISC_FEATURE
<222> LOCATION: (4)..(4)
<223> OTHER INFORMATION: Xaa = (R)-2-amino-5-(dimethylamino)pentanoic
      acid
<220> FEATURE:
<221> NAME/KEY: MISC_FEATURE
<222> LOCATION: (4)..(4)
<223> OTHER INFORMATION: D form of amino acid at this position
```

```
<220> FEATURE:
<221> NAME/KEY: MISC_FEATURE
<222> LOCATION: (6)..(6)
<223> OTHER INFORMATION: Xaa = (2S,4R)-4-aminopyrrolidine-2-carboxylic
      acid
<220> FEATURE:
<221> NAME/KEY: MISC_FEATURE
<222> LOCATION: (7)..(7)
<223> OTHER INFORMATION: Xaa = (S)-N-methyl-leucine

<400> SEQUENCE: 603

Xaa Xaa Phe Xaa Leu Xaa Xaa Asp Arg Ile
1               5               10
```